US009982039B2

(12) United States Patent
Carroll et al.

(10) Patent No.: US 9,982,039 B2
(45) Date of Patent: May 29, 2018

(54) MYCOBACTERIAL ANTIGEN COMPOSITION

(71) Applicant: The Secretary of State of Health, London (GB)

(72) Inventors: Miles Carroll, Salisbury (GB); Yper Hall, Salisbury (GB); Ann Williams, Salisbury (GB)

(73) Assignee: The Secretary of State for Health, London (GB)

( * ) Notice: Subject to any disclaimer, the term of this patent is extended or adjusted under 35 U.S.C. 154(b) by 0 days. days.

(21) Appl. No.: 15/098,949

(22) Filed: Apr. 14, 2016

(65) Prior Publication Data

US 2016/0251415 A1 Sep. 1, 2016

Related U.S. Application Data

(63) Continuation of application No. 13/699,394, filed as application No. PCT/GB2011/050972 on May 23, 2011, now Pat. No. 9,339,534.

(30) Foreign Application Priority Data

May 21, 2010 (GB) .................................. 1008512.4

(51) Int. Cl.

| | |
|---|---|
| ***A61K 39/04*** | (2006.01) |
| ***A61K 39/00*** | (2006.01) |
| ***A61K 39/38*** | (2006.01) |
| ***C07K 16/12*** | (2006.01) |
| ***G01N 33/68*** | (2006.01) |
| ***C07K 14/35*** | (2006.01) |
| ***G01N 33/569*** | (2006.01) |

(52) U.S. Cl.

CPC .......... *C07K 16/1289* (2013.01); *A61K 39/04* (2013.01); *C07K 14/35* (2013.01); *G01N 33/5695* (2013.01); *G01N 33/6893* (2013.01); *A61K 2039/507* (2013.01); *A61K 2039/53* (2013.01); *A61K 2039/57* (2013.01); *A61K 2039/70* (2013.01); *C07K 2317/34* (2013.01); *C07K 2317/76* (2013.01); *G01N 2333/35* (2013.01); *G01N 2469/10* (2013.01)

(58) Field of Classification Search

CPC ............................... A61K 39/00; A61K 39/04

USPC .................... 424/184.1, 185.1, 234.1, 248.1

See application file for complete search history.

(56) References Cited

U.S. PATENT DOCUMENTS

| | | | |
|---|---|---|---|
| 2004/0241826 | A1 | 12/2004 | James et al. |
| 2004/0253711 | A1 | 12/2004 | James et al. |

FOREIGN PATENT DOCUMENTS

| | | | |
|---|---|---|---|
| GB | 2389364 | A | 12/2003 |
| RU | 2266753 | | 12/2005 |
| WO | 03/004520 | A2 | 1/2003 |
| WO | 03/035681 | A2 | 5/2003 |
| WO | 2006/053871 | A2 | 5/2006 |

OTHER PUBLICATIONS

Vipond, J., et al., Selection of novel TB vaccine candidates and their evaluation as DNA vaccines against aerosol challenge, VACCINE, Sep. 11, 2006, vol. 24, No. 37-39, pp. 6340-6350.

Morris, S., et al., The immunogenicity of single and combination DNA vaccines against tuberculosis, VACCINE, Apr. 14, 2000, vol. 18, No. 20, pp. 2155-2163.

Vipond, J., et al., Immunogenicity and Protective Efficacy of the *Mycobacterium tuberculosis* Gene Rv0111 in Guinea Pugs and Mice Following Various Prime-Boost Immunisation Strategies, Abs General Meeting Amer Soc Microbiology, 2007, vol. 107, p. 277.

*Primary Examiner* — Rodney P Swartz

(74) *Attorney, Agent, or Firm* — Hodgson Russ LLP

(57) ABSTRACT

There is provided an antigenic composition comprising (a) a first mycobacterial antigenic polypeptide or a first mycobacterial polynucleotide; and (b) a second mycobacterial antigenic polypeptide or a second mycobacterial polynucleotide; wherein: (i) said first mycobacterial antigenic polypeptide comprises a polypeptide sequence having at least 70% amino acid sequence identity to the amino acid sequence of SEQ ID NO: 1 or 7, or a fragment thereof having at least 7 consecutive amino acids thereof; (ii) said first mycobacterial polynucleotide comprises a polynucleotide sequence encoding said first mycobacterial antigenic polypeptide; (iii) said second mycobacterial antigenic polypeptide comprises a polypeptide sequence having at least 70% amino acid sequence identity to the amino acid sequence of SEQ ID NO: 5, or a fragment thereof having at least 7 consecutive amino acids thereof; and (iv) said second mycobacterial polynucleotide comprises a polynucleotide sequence encoding said second mycobacterial polypeptide.

9 Claims, 7 Drawing Sheets

MYCOBACTERIAL ANTIGEN COMPOSITION

This application is a continuation of U.S. patent application Ser. No. 13/699,394, filed Feb. 11, 2013, now U.S. Pat. No. 9,339,534, which is a National Phase of International patent application no. PCT/GB2011/050972, filed May 23, 2011, which claims priority to United Kingdom patent application no. GB 1008512.4, filed May 21, 2010, the disclosures of each of which are incorporated herein by reference.

The present invention relates to mycobacterial polynucleotides and polypeptides, to fragments or variants thereof, to inhibitors thereof, to antibodies that bind thereto, to vectors and microbial carriers, to therapeutic compositions such as vaccines against mycobacterial infections, and to compositions and methods for detecting the presence of a mycobacterial infection.

Microorganisms such as species of *Salmonella, Yersinia, Shigella, Campylobacter, Chlamydia* and *Mycobacteria* are capable of forming intracellular infections. These infections may be exclusively intracellular, or may contain both intracellular and extracellular components. Generally, these microorganisms do not circulate freely in the body, for example, in the bloodstream, and as such are often not amenable to drug treatment regimes.

The difficulties associated with treating intracellular infection have been exacerbated by the development of multiple drug-resistant microorganisms. Due to the accumulation of mutations over time and the subsequent horizontal and vertical transfer of the mutated genes to other organisms, entire classes of antibiotics have been rendered inactive. For similar reasons, vaccine therapies have not proved effective against intracellular microorganisms.

*Mycobacterium tuberculosis* (MTB) and closely related species make up a small group of mycobacteria known as the *Mycobacterium tuberculosis* complex (MTC). This group comprises five distinct species: *M. tuberculosis, M. microti, M. bovis, M. caneti*, and *M. africanum.*

Other mycobacteria are also pathogenic in man and animals, for example *M. avium* subsp. paratuberculosis which causes Johne's disease in ruminants, *M. bovis* which causes tuberculosis in cattle, *M. avium* and *M. intracellulare* which cause tuberculosis in immunocompromised patients (eg. AIDS patients, and bone marrow transplant patients) and *M. leprae* which causes leprosy in humans. Another important mycobacterial species is *M. vaccae.*

As the aetiological agent of tuberculosis infection (TB), *Mycobacterium tuberculosis* (*M. tuberculosis*) is the leading cause of death by bacterial infectious disease worldwide—latent infection affecting as much as one third of the world's population. The World Health Organisation (WHO) estimates that nearly nine million new cases of TB, and nearly two million deaths, occur globally each year. The largest number of new TB cases in 2005 occurred in South-East Asia (34% of incident cases globally), and the estimated incidence rate in sub-Saharan Africa is nearly 350 cases per 100,000 population. However, TB infection is not limited to the developing world: the UK has seen a resurgence of tuberculosis since the late 1980s and there are currently over 8000 new cases each year—a rate of 14.0 per 100,000 population. About 40% of these new cases occur in the London region, where the rate of infection is 44.8 per 100,000 population.

Optimal patient management requires early initiation of drug therapy and isolation of infectious individuals as soon as possible. Left untreated, each person with active TB disease will infect on average between 10 and 15 people every year. TB infection can normally be treated by a 6 month course of antibiotics; however, patient compliance to long-term drug treatment is varied, with patients often stopping therapy when their symptoms cease. Failure to complete the treatment can promote the development of multiple drug-resistant mycobacteria.

The term 'latency' is synonymous with 'persistence', and describes a reversible state of low metabolic activity in which mycobacterial cells can survive for extended periods with limited or no cell division. During latency (ie. latent infection), the clinical symptoms associated with a mycobacterial infection do not become manifest.

However, re-activation of latent mycobacteria may be induced by environmental stimuli—eg. an increase in nutrient availability and/or the local dissolved oxygen concentration. During active infection, mycobacteria (eg. *M. tuberculosis*) demonstrate high metabolic activity and replicate rapidly, resulting in the development of active mycobacterial infection with the associated clinical symptoms.

In vitro studies have demonstrated that mycobacteria such as *M. tuberculosis* are able to adapt to and survive under nutrient- and oxygen-depleted conditions, and can grow over a range of nutrient availabilities and oxygen tensions. Adaptation to carbon starvation and/or to a low dissolved oxygen tension in vitro triggers transition to a non-replicating persistent state that may be analogous to latency in vivo.

Intracellular survival and multiplication of mycobacteria is suspected to be a main supportive factor for mycobacterial disease progression. The presence of a large reservoir of asymptomatic individuals latently-infected with mycobacteria is a major problem for the control of mycobacterial infections, especially *M. tuberculosis* infections. In addition, conventional methods for the detection of a latent mycobacterial infection by skin testing may be compromised by BCG vaccination and by exposure to environmental mycobacteria.

The effectiveness of vaccine prevention against *M. tuberculosis* has varied widely. The current *M. tuberculosis* vaccine, BCG, is an attenuated strain of *M. bovis*. It is effective against severe complications of TB in children, but it varies greatly in its effectiveness in adults, particularly across ethnic groups. BCG vaccination has been used to prevent tuberculous meningitis and helps prevent the spread of *M. tuberculosis* to extra-pulmonary sites, but does not prevent infection. The limited efficacy of BCG and the global prevalence of TB has led to an international effort to generate new, more effective vaccines.

WO 03/004520 (in the name of the present Applicant, incorporated herein by reference) describes the identification of a distinct sub-set of mycobacterial genes, the expression of which is induced or up-regulated during mycobacterial latency. Specifically, expression of this defined subgroup of mycobacterial genes is induced or up-regulated during culture of mycobacteria under nutrient-starving culture conditions, as compared with culture conditions that are not nutrient-starving and which support exponential growth of said mycobacterium.

WO 03/035681 (in the name of the present Applicant, incorporated herein by reference) describes the identification of a distinct sub-set of mycobacterial genes, the expression of which is down-regulated during mycobacterial latency. Specifically, expression of this defined sub-group of mycobacterial genes is down-regulated under nutrient-starving culture conditions, as compared with culture conditions that are not nutrient-starving and which support exponential growth of said mycobacteria.

WO 03/000721 (in the name of the present Applicant, incorporated herein by reference) describes the identification of a distinct sub-set of mycobacterial genes, the expression of which is induced or up-regulated during continuous culture of mycobacteria under growth conditions defined by a low dissolved oxygen tension (up to 10% air saturation measured at 37° C.), as compared with a dissolved oxygen tension of at least 40% air saturation measured at 37° C.

In view of the increasing threat and global prevalence of mycobacterial infection, new strategies are required for more effective prevention, treatment, and diagnosis of mycobacterial infection.

The invention provides an antigenic composition comprising a first mycobacterial antigen and a second mycobacterial antigen;

wherein said first mycobacterial antigen comprises:

(i) a polypeptide sequence having at least 70% amino acid sequence identity to the amino acid sequence of a latency-regulated polypeptide selected from SEQ ID NOs: 1, 3, 5, 7 and 56, or a fragment thereof having at least 7 consecutive amino acids thereof; or (ii) a polynucleotide sequence encoding a polypeptide sequence according to (i); or a polynucleotide sequence having at least 70% nucleotide sequence identity to the nucleic acid sequence of a latency-regulated polynucleotide selected from SEQ ID NOs: 2, 4, 6, 8 and 57, or a fragment thereof having at least 21 consecutive nucleotides thereof;

and wherein said second mycobacterial antigen is different from said first mycobacterial antigen.

As used herein, the term "mycobacterial" or "*mycobacterium*" embraces the species *M. phlei, M. smegmatis, M. africanum, M. caneti, M. fortuitum, M. marinum, M. ulcerans, M. tuberculosis, M. bovis, M. microti, M. avium, M. paratuberculosis, M. leprae, M. lepraemurium, M. intracellulare, M. scrofulaceum, M. xenopi, M. genavense, M. kansasii, M. simiae, M. szulgai, M. haemophilum, M. asiaticum, M. malmoense, M. vaccae, M. caneti*, and *M. shimoidei*. Of particular interest are the members of the MTC, such as *M. tuberculosis.*

The term antigen means any substance that can be recognized by the immune system and/or that stimulates an immune response. For example, an antigen may stimulate a cell mediated immune response and/or may stimulate the generation of antibodies.

In one embodiment, a mycobacterial antigen of the invention provides a cell mediated response to infection involving immune cells such as T cells (CD4+ and/or CD8+ T cells) and/or the ability to respond with Th1-type cytokines such as IFN-γ. In one embodiment, a mycobacterial antigen induces IFN-γ-secreting cells (eg. predominantly CD4+ T cells). In this regard, recent studies suggest that immune cell responses (particularly T cell immune responses in, for example, the lung mucosa) may be critical for protection against pulmonary mycobacterial disease.

In one embodiment, a mycobacterial antigen of the invention provides protection (such as long term protection) against challenge by mycobacteria such as *M. tuberculosis.*

By way of example, a mycobacterial antigen of the invention may induce 'memory T cells', which can continue to stimulate protective immunity in the long term (eg. for decades). Memory immune responses have been attributed to the reactivation of long-lived, antigen-specific T lymphocytes that arise directly from differentiated effector T-cells and persist in a quiescent state. Memory T cells are heterogeneous; at least two subsets have been identified, having different migratory capacity and effector function. Memory T cells of the first subset are known as 'effector memory T cells' (TEM) because they resemble the effector T cells generated in the primary response, in that they lack the lymph node-homing receptors for migration into inflamed tissues. Upon re-encounter with antigen, the TEM rapidly produce IFN-γ or IL-4, or release pre-stored perforin. Memory T cells of the second subset (known as 'central memory cells' (TCM)) express L-selectin and CCR7 and lack immediate effector function. The TCM have a low activation threshold and proliferate and differentiate to effectors when re-stimulated in secondary lymphoid organs.

In one embodiment, a mycobacterial antigen provides a neutralizing antibody response to mycobacterial (eg. *M. tuberculosis*) infection.

In one embodiment, each antigen in the antigenic composition of the present invention independently induces an effective immune response (eg. a cell mediated immune response or antibody response). Thus, in accordance with this embodiment, following administration of the antigenic composition to a subject, an immune response is induced in the subject to each antigen in the antigenic composition.

In this regard, the present inventors have identified that (in one embodiment) the antigenic composition of the present invention advantageously avoids "antigenic competition", or is associated with low levels of "antigenic competition", as compared with the competitive effect that might have been expected in view of known multivalent vaccine compositions.

"Antigenic competition" is a phenomenon by which an immune response to one antigen suppresses an immune response to a second, unrelated antigen (see Eidinger, D. et al., J Exp Med, 1968. 128(5): pages 1183-1200). By way of example, immune cells (eg. T-cells) responding to one antigen may actively interfere with other immune cells (eg. T-cells) responding to another antigen (see Kerbel, R. S. and Eidinger, D., Nat New Biol, 1971. 232(27): pages 26-28).

WO 00/47227 describes (in Example 2) immunization of guinea pigs either with DNA encoding mycobacterial antigen 85A alone (Group A); or with DNA encoding both mycobacterial antigen 85A and mycobacterial antigen MPT32 (Group B). Following challenge with *M. tuberculosis*, vaccine efficacy was assessed by determining mycobacterial loads in the lungs and spleen. FIGS. 11A and 11B illustrate that the combination of antigens 85A and MPT32 (Group B) was less effective against *M. tuberculosis* than antigen 85A alone (Group A).

Thus, pooling effective vaccine candidates into a multivalent vaccine has been known to suppress or even completely abrogate vaccine efficacy. Such is the prevalence of antigenic competition, that a multivalent vaccine achieving improved efficacy above its most efficacious component is considered beneficial.

It is therefore surprising that the antigenic composition of the present invention combines antigens that are individually capable of eliciting an immune response and yet results in an improved/enhanced immune response as compared with the immune response to each individual antigen.

In one embodiment, a mycobacterial antigen comprises a polypeptide sequence. A mycobacterial antigen may be a polypeptide. Alternatively, or in addition, a mycobacterial antigen comprises a polynucleotide sequence. For example, a mycobacterial antigen may be a polynucleotide, such as a DNA or RNA.

The first mycobacterial antigen comprises:

(i) a polypeptide sequence having at least 70% amino acid sequence identity to the amino acid sequence of a latency-regulated polypeptide selected from SEQ ID NOs: 1, 3, 5, 7 and 56, or a fragment thereof having at least 7 consecutive amino acids thereof; or (ii) a polynucleotide sequence encoding a polypeptide sequence according to (i); or a polynucleotide sequence having at least 70% nucleotide sequence identity to the nucleic acid sequence of a latency-regulated polynucleotide selected from SEQ ID NOs: 2, 4, 6, 8 and 57, or a fragment thereof having at least 21 consecutive nucleotides thereof.

In one embodiment, the first mycobacterial antigen comprises:

(i) polypeptide sequence having at least 70% amino acid sequence identity to the amino acid sequence of SEQ ID NO: 1, or a fragment thereof having at least 7 consecutive amino acids thereof; or (ii) a polynucleotide sequence encoding a polypeptide sequence according to (i); or a polynucleotide sequence having at least 70% nucleotide sequence identity to the nucleic acid sequence of SEQ ID NO: 2, or a fragment thereof having at least 21 consecutive nucleotides thereof.

The specific sub-set of mycobacterial polypeptides represented by SEQ ID NOs: 1, 3, 5, 7 and 56 are 'latency-regulated polypeptides'. The specific subset of mycobacterial polynucleotides represented by SEQ ID NOs: 2, 4, 6, 8 and 57 are 'latency-regulated polynucleotides'.

In one embodiment, a 'latency-regulated polypeptide' is encoded by a 'latency-regulated polynucleotide'. By way of example, the latency-regulated polypeptide SEQ ID NO: 1 is encoded by latency-regulated polynucleotide SEQ ID NO: 2; SEQ ID NO: 3 is encoded by SEQ ID NO: 4; SEQ ID NO: 5 is encoded by SEQ ID NO: 6; SEQ ID NO: 7 is encoded by SEQ ID NO: 8; and SEQ ID NO: 56 is encoded by SEQ ID NO: 57.

The expression or activity of a latency-regulated polypeptide or polynucleotide is modulated in response to mycobacterial latency—eg. in response to culture of mycobacteria (eg. *M. tuberculosis*) under culture conditions that induce or maintain mycobacterial latency.

In one embodiment, "modulation" of expression or activity of the latency-regulated polypeptide or polynucleotide in response to conditions of mycobacterial latency means that the expression or activity is induced or upregulated in response to latency. Thus, the latency-regulated polypeptide or polynucleotide may be a 'latency-induced' or 'latency-up-regulated' polypeptide or polynucleotide.

For example, the expression or activity of a latency-upregulated polypeptide or polynucleotide may be up-regulated by at least 1.5-fold, 2-fold, 5-fold, 10-fold, 20-fold or 50-fold under latency conditions as compared to non-latency conditions.

The expression or activity of latency-induced and latency-upregulated polypeptides and polynucleotides may be induced or upregulated in vivo during latency in the mycobacterium's natural environment. As such, latency-induced or latency-up-regulated mycobacterial polypeptides and polynucleotides represent good vaccine candidates and good therapeutic targets for preventing the establishment, spread and reactivation of disease and/or make good diagnostic tools for latent infection.

In one embodiment, "modulation" of the expression or activity of a latency-regulated polypeptide in response to conditions of mycobacterial latency means that the expression or activity is repressed or down-regulated in response to latency. Thus, in one embodiment, the latency-regulated polypeptide or polynucleotide is a 'latency-repressed' or 'latency-down-regulated' polypeptide or polynucleotide.

The expression or activity of a latency-downregulated polypeptide or polynucleotide may be down-regulated by at least 1.5-fold, 2-fold, 5-fold, 10-fold, 20-fold or 50-fold under latency conditions as compared to non-latency conditions. Reference to "down-regulated" embraces 'switched off', which means that there is substantially no detectable activity and/or expression of the polypeptide or polynucleotide.

The expression or activity of latency-repressed or latency-down-regulated polypeptides and polynucleotides may be induced or down-regulated in vivo during active mycobacterial infection, or during/following re-activation of mycobacteria from a latent state. Latency-repressed and latency-down-regulated mycobacterial polypeptides and polynucleotides may play an early role in the development of an effective immune response against replicating bacilli during the active stages of disease, and consequently represent good vaccine candidates and good therapeutic targets for preventing the establishment, spread and reactivation of disease.

The expression or activity of a latency-regulated polypeptide or polynucleotide may be modulated (such as induced, up-regulated, repressed or down-regulated) under nutrient-starving culture conditions, as compared with culture conditions that are not nutrient starving. Under nutrient starving culture conditions, the concentration of the primary energy source (eg. carbon) is insufficient to support exponential growth of the mycobacteria, with the result that mycobacteria become metabolically stressed and enter a latent state.

The expression or activity of a latency-regulated polypeptide or polynucleotide may alternatively (or additionally) be modulated (eg. induced, up-regulated, repressed or down-regulated) under conditions of oxygen limitation (low dissolved oxygen tension), as compared with culture conditions that are not oxygen-limiting.

In one embodiment, the first mycobacterial antigen comprises a polypeptide sequence having at least 70% amino acid sequence identity (such as at least 75, 80, 82, 84, 86, 88, 90, 92, 94, 96, 98, 99 or 100% amino acid sequence identity) to the amino acid sequence of a latency-regulated polypeptide selected from SEQ ID NOs: 1, 3, 5, 7 and 56, or a fragment thereof having at least 7 consecutive amino acids thereof.

In one embodiment, the first mycobacterial antigen consists of a polypeptide sequence having at least 70% amino acid sequence identity (such as at least 75, 80, 82, 84, 86, 88, 90, 92, 94, 96, 98, 99 or 100% amino acid sequence identity) to the amino acid sequence of a latency-regulated polypeptide selected from SEQ ID NOs: 1, 3, 5, 7 and 56, or a fragment thereof having at least 7 consecutive amino acids thereof.

Thus, in one embodiment, the first mycobacterial antigen is a 'first mycobacterial polypeptide' (or fragment), as defined above.

In one embodiment, said first mycobacterial antigenic polypeptide comprises (or consists of) a polypeptide sequence having at least 70% amino acid sequence identity to the amino acid sequence of SEQ ID NO: 1, or a fragment thereof having at least 7 consecutive amino acids thereof.

SEQ ID NOs: 1, 3, 5, 7 and 56 are defined in Table 1, below:

TABLE 1

| SEQ ID NO: | Polypeptide name |
|---|---|
| 1 | Rv0111 |
| 3 | Rv1806 |
| 5 | Rv0198 |
| 7 | Rv3812 |
| 56 | Rv1807 |

Thus, in the context of the present application, a "Rv0111 polypeptide antigen" comprises or consists of SEQ ID NO:

1 (or a sequence 'variant' or 'fragment' thereof as defined herein); a "Rv1806 polypeptide antigen" comprises or consists of SEQ ID NO: 3 (or a sequence 'variant' or 'fragment' thereof as defined herein); a "Rv0198 polypeptide antigen" comprises or consists of SEQ ID NO: 5 (or a sequence 'variant' or 'fragment' thereof as defined herein); a "Rv3812 polypeptide antigen" comprises or consists of SEQ ID NO: 7 (or a sequence 'variant' or 'fragment' thereof as defined herein); and a "RV1807 polypeptide antigen" comprises or consists of SEQ ID NO: 56 (or a sequence 'variant' or 'fragment' thereof as defined herein).

In one embodiment, the amino acid sequence identity exists over a region of the polypeptide sequences that is at least 7 consecutive amino acid residues in length (eg. at least 10, 15, 25, 50, 75, 100, 150, 200, 250, 300, 350, 400, 450, 500, 550, 600 or 650 consecutive amino acid residues in length).

Conventional methods for determining amino acid sequence identity are discussed in more detail later in the specification.

In the context of the first mycobacterial antigen, a fragment of a polypeptide comprises (or consists of) at least 7 consecutive amino acid residues of said polypeptide (eg. at least 10, 15, 25, 50, 75, 100, 125, 150, 175, 200, 225, 250, 275, 300, 325, 350, 375, 400, 425, 450, 475, 500, 525, 550, 575, 600, 625, 650 or 675 consecutive amino acid residues of said polypeptide).

In one embodiment, a fragment of a polypeptide has a sequence length that is at least 5%, 10%, 25%, 50%, 60%, 70%, 80%, or 90% of that of the sequence of the full-length polypeptide.

A fragment of a polypeptide may include at least one epitope of the polypeptide.

In one embodiment, in the context of the first mycobacterial antigen, a fragment of a polypeptide comprises (or consists of) a truncated form of said polypeptide. For example, a fragment of a polypeptide may have a N-terminal truncation (as compared with the polypeptide), or a fragment of a polypeptide may have a C-terminal truncation (as compared with the polypeptide).

In one embodiment, in the context of the first mycobacterial antigen, a fragment of a polypeptide comprises (or consists of) a mature form of the polypeptide. For example, the polypeptide may comprise a signal sequence (ie. a secretion/targeting sequence) (eg. at the N-terminus), and a fragment of the polypeptide may lack this signal sequence. In one embodiment, the fragment is formed by cleavage of a signal sequence from the polypeptide.

In one embodiment, a fragment of polypeptide SEQ ID NO: 1 is a N-terminally truncated form of SEQ ID NO: 1. In one embodiment, a fragment of polypeptide SEQ ID NO: 1 has a N-terminal truncation of at least 50, 100, 150, 200, 250, 300, or 350 amino acid residues as compared with the amino acid sequence of SEQ ID NO: 1. In one embodiment, a fragment of SEQ ID NO: 1 comprises at least the C-terminal 50, 100, 150, 200, 250 or 300 amino acid sequence of SEQ ID NO: 1.

In one embodiment, a fragment of polypeptide SEQ ID NO: 7 is a N-terminally truncated form of SEQ ID NO: 7. In one embodiment, a fragment of SEQ ID NO: 7 is a mature polypeptide sequence, which differs from the sequence of SEQ ID NO: 7 by removal of a N-terminal signal sequence. In one embodiment, a fragment of polypeptide SEQ ID NO: 7 has a N-terminal truncation of at least 5, 10, 15, 20, 25, 30, 35 or 40 amino acid residues as compared with the amino acid sequence of SEQ ID NO: 7. In one embodiment, a fragment of SEQ ID NO: 7 comprises at least the C-terminal 50, 100, 150, 200, 250, 300, 350, 400 or 450 amino acid sequence of SEQ ID NO: 7.

In one embodiment, the first mycobacterial antigen comprises a polypeptide or fragment thereof that has a common antigenic cross-reactivity and/or substantially the same in vivo biological activity as a latency-regulated polypeptide selected from SEQ ID NOs: 1, 3, 5, 7 and 56.

As used herein, 'common antigenic cross-reactivity' means that the first mycobacterial polypeptide or fragment, and the latency-regulated polypeptide selected from SEQ ID NOs: 1, 3, 5, 7 and 56, share a common ability to induce a "recall response" of an immune cell such as a T-lymphocyte (eg. CD4+, CD8+, effector T cell or memory T cell such as a TEM or TCM), which has been previously exposed to an antigenic component of a mycobacterial infection.

New immunological assays for measuring and quantifying immune cell responses (eg. T cell responses) have been established over the last 10 years. For example, the interferon-gamma (IFN-γ) ELISPOT assay is useful as an immunological readout because the secretion of IFN-γ from antigen-specific immune cells such as T cells is a good correlate of protection against *M. tuberculosis*. Furthermore, the ELISPOT assay is a very reproducible and sensitive method of quantifying the number of IFN-γ secreting antigen-specific immune cells such as T cells.

Alternatively, or in addition, 'common antigenic cross-reactivity' means that an antibody capable of binding to the first mycobacterial polypeptide or fragment would also be capable of binding to the latency-regulated polypeptide.

In one embodiment, the first mycobacterial antigen comprises, or consists of, a polynucleotide sequence that encodes a first mycobacterial polypeptide as defined above.

Thus, in one embodiment, the first mycobacterial antigen comprises (or consists of) a polynucleotide sequence that encodes a polypeptide that comprises (or consists of) an amino acid sequence having at least 70% amino acid sequence identity (such as at least 75, 80, 82, 84, 86, 88, 90, 92, 94, 96, 98, 99 or 100% amino acid sequence identity) to the amino acid sequence of a latency-regulated polypeptide selected from SEQ ID NOs: 1, 3, 5, 7 and 56, or a fragment thereof having at least 7 consecutive amino acids thereof (eg. as defined above).

In one embodiment, the first mycobacterial antigen comprises a polynucleotide sequence having at least 70% nucleotide sequence identity (such as at least 75, 80, 82, 84, 86, 88, 90, 92, 94, 96, 98, 99 or 100% nucleotide sequence identity) to the nucleic acid sequence of a latency-regulated polynucleotide selected from SEQ ID NOs: 2, 4, 6, 8 and 57, or a fragment thereof having at least 21 consecutive nucleotides thereof.

In one embodiment, the first mycobacterial antigen consists of a polynucleotide sequence having at least 70% nucleotide sequence identity (such as at least 75, 80, 82, 84, 86, 88, 90, 92, 94, 96, 98, 99 or 100% nucleotide sequence identity) to the nucleic acid sequence of a latency-regulated polynucleotide selected from SEQ ID NOs: 2, 4, 6, 8 and 57, or a fragment thereof having at least 21 consecutive nucleotides thereof.

Thus, in one embodiment, the first mycobacterial antigen is a 'first mycobacterial polynucleotide' (or fragment), as defined above.

In one embodiment, said first mycobacterial polynucleotide comprises (or consists of) a polynucleotide sequence encoding a first mycobacterial antigenic polypeptide of the invention, as defined above. In one embodiment, said first mycobacterial polynucleotide comprises (or consists of) a polynucleotide sequence having at least 70% nucleotide sequence identity to the nucleic acid sequence of SEQ ID NO: 2, or a fragment thereof having at least 21 consecutive nucleotides thereof.

SEQ ID NOs: 2, 4, 6, 8 and 57 are defined in Table 2, below:

TABLE 2

| SEQ ID NO: | Polynucleotide name |
|---|---|
| 2 | Rv0111 |
| 4 | Rv1806 |
| 6 | Rv0198 |
| 8 | Rv3812 |
| 57 | Rv1807 |

Thus, in the context of the present application, a "Rv0111 polynucleotide antigen" comprises or consists of SEQ ID NO: 2 (or a sequence 'variant' or 'fragment' thereof as defined herein); a "Rv1806 polynucleotide antigen" comprises or consists of SEQ ID NO: 4 (or a sequence 'variant' or 'fragment' thereof as defined herein); a "Rv0198 polynucleotide antigen" comprises or consists of SEQ ID NO: 6 (or a sequence 'variant' or 'fragment' thereof as defined herein); a "Rv3812 polynucleotide antigen" comprises or consists of SEQ ID NO: 8 (or a sequence 'variant' or 'fragment' thereof as defined herein); and a "RV1807 polynucleotide antigen" comprises or consists of SEQ ID NO: 57 (or a sequence 'variant' or 'fragment' thereof as defined herein).

In one embodiment, the nucleotide sequence identity exists over a region of the polynucleotide sequences that is at least 21 consecutive nucleotide residues in length (eg. at least 25, 50, 75, 100, 150, 200, 250, 300, 350, 400, 450, 500, 550, 600, 650, 700, 750, 800, 850, 900 or 1000 consecutive nucleotide residues in length).

Conventional methods for determining nucleotide sequence identity are discussed in more detail later in the specification.

In the context of the first mycobacterial antigen, a fragment of said polynucleotide comprises (or consists of) at least 21 consecutive nucleotide residues of said polynucleotide (eg. at least 25, 50, 75, 100, 125, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950 or 2000 consecutive nucleotide residues of said polynucleotide).

In one embodiment, the length of the sequence of the polynucleotide fragment is at least 5%, 10%, 25%, 50%, 60%, 70%, 80%, or 90% that of the polynucleotide.

In one embodiment, in the context of the first mycobacterial antigen, a fragment of a polynucleotide comprises (or consists of) a truncated form of said polynucleotide. In one embodiment, a fragment of a polynucleotide is truncated at the 5' end and/or the 3' end, as compared with the full-length polynucleotide sequence. In one embodiment, a fragment of a polynucleotide encodes a truncated form of said polypeptide. For example, a fragment of a polynucleotide may encode a polypeptide that is N-terminally truncated and/or C-terminally truncated polypeptide (as compared with the polypeptide encoded by the full-length polynucleotide).

In one embodiment, in the context of the first mycobacterial antigen, a fragment of a polynucleotide encodes a polypeptide that comprises (or consists of) a mature polypeptide. For example, the full-length polypeptide comprises a signal sequence (ie. a secretion/targeting sequence) (eg. at the N-terminus), and the polynucleotide fragment encodes a mature polypeptide that lacks this signal sequence.

In one embodiment, a fragment of polynucleotide SEQ ID NO: 2 is a 5' truncated form of SEQ ID NO: 2. In one embodiment, a fragment of polynucleotide SEQ ID NO: 2 has a 5' truncation of at least 100, 200, 300, 400, 500, 600, 700, 800, 900 or 1000 nucleotide residues as compared with the nucleotide sequence of SEQ ID NO: 2. In one embodiment, a fragment of polynucleotide SEQ ID NO: 2 encodes a N-terminally truncated form of SEQ ID NO: 1. In one embodiment, a fragment of polynucleotide SEQ ID NO: 2 encodes a polypeptide having an N-terminal truncation of at least 50, 100, 150, 200, 250, 300, or 350 amino acid residues as compared with the amino acid sequence of SEQ ID NO: 1. In one embodiment, a fragment of SEQ ID NO: 2 comprises the 3' terminal 100, 200, 300, 400, 500, 600, 700, 800 or 900 nucleotide residues as compared with the nucleotide sequence of SEQ ID NO: 2. In one embodiment, a fragment of polynucleotide SEQ ID NO: 2 encodes a polypeptide comprising at least the C-terminal 50, 100, 150, 200, 250 or 300 amino acid sequence of SEQ ID NO: 1.

In one embodiment, a fragment of polynucleotide SEQ ID NO: 8 is a 5' truncated form of SEQ ID NO: 8. In one embodiment, a fragment of polynucleotide SEQ ID NO: 8 has a 5' truncation of at least 25, 50, 75, 100 or 125 nucleotide residues as compared with the nucleotide sequence of SEQ ID NO: 8. In one embodiment, a fragment of polynucleotide SEQ ID NO: 8 encodes a N-terminally truncated form of SEQ ID NO: 7. In one embodiment, a fragment of polynucleotide SEQ ID NO: 8 encodes a mature polypeptide sequence, which differs from the sequence of SEQ ID NO: 7 by removal of a N-terminal signal sequence. In one embodiment, a fragment of polynucleotide SEQ ID NO: 8 encodes a polypeptide that has a N-terminal truncation of at least 5, 10, 15, 20, 25, 30, 35 or 40 amino acid residues as compared with the amino acid sequence of SEQ ID NO: 7. In one embodiment, a fragment of SEQ ID NO: 8 comprises the 3' terminal 150, 300, 450, 600, 750, 900, 1050, 1200 or 1350 nucleotide residues as compared with the nucleotide sequence of SEQ ID NO: 8. In one embodiment, a fragment of SEQ ID NO: 8 encodes a polypeptide that comprises at least the C-terminal 50, 100, 150, 200, 250, 300, 350, 400 or 450 amino acid sequence of SEQ ID NO: 7.

In one embodiment, said first mycobacterial polynucleotide, or fragment thereof, encodes a polypeptide that has a common antigenic cross-reactivity and/or substantially the same in vivo biological activity as a latency-regulated polypeptide selected from SEQ ID NOs: 1, 3, 5, 7 and 56.

For example, said first mycobacterial antigen may comprise (or consist of) a polynucleotide sequence that encodes a polypeptide sequence that is capable of evoking a protective immune cell response (eg. T-cell response) against mycobacterial infection.

By way of example, the polypeptide encoded by the first mycobacterial polynucleotide or fragment shares, with the latency-regulated polypeptide, a common ability to induce a "recall response" of an immune cell such as a T-lymphocyte (eg. CD4+, CD8+, effector T cell or memory T cell such as TEM or TCM) that has previously been exposed to an antigenic component of a mycobacterial infection. In this regard, the secretion of IFN-γ from antigen-specific immune cells such as T cells is a good correlate of protection against *M. tuberculosis*. Accordingly, the interferon-gamma (IFN-γ) ELISPOT assay is a useful immunological readout, and enables reproducible and sensitive quantification of IFN-γ secreting antigen-specific immune cells such as T cells.

Alternatively, or in addition, an antibody capable of binding to a polypeptide encoded by the first mycobacterial polynucleotide or fragment would also be capable of binding to the latency-regulated polypeptide.

The antigenic composition of the invention comprises at least a second mycobacterial antigen, in addition to the first mycobacterial antigen.

In one embodiment, the second mycobacterial antigen is capable of evoking a protective immune response (eg. a T-cell response) against mycobacterial infection.

In one embodiment, the second mycobacterial antigen comprises (eg. consists of) a polypeptide sequence. In one embodiment, the second mycobacterial antigen comprises (eg. consists of) a polynucleotide sequence such as a DNA or RNA sequence.

In one embodiment, the second mycobacterial antigen comprises (eg. consists of) a mycobacterial glycolipid, such as a mycobacterial sulphoglycolipid.

In one embodiment, the second mycobacterial antigen comprises (eg. consists of) a mycobacterial carbohydrate antigen such as a mycobacterial saccharide or polysaccharide.

Optionally, the saccharide may be linked (eg. chemically conjugated) to a carrier (eg. a polypeptide) to enhance immunogenicity.

The second mycobacterial antigen is different from the first mycobacterial antigen.

In one embodiment, the ‘difference’ between the second mycobacterial antigen and the first mycobacterial antigen is defined by the specificity of the immune response to the first and second mycobacterial antigens. For example, in one embodiment, each of the first and second antigens induces an immune response that is substantially specific to that antigen.

The ‘difference’ between the second mycobacterial antigen and the first mycobacterial antigen may be defined in terms of a substantial lack (eg. an absence) of common antigenic cross-reactivity between the first and second mycobacterial antigens.

The ‘difference’ between the second mycobacterial antigen and the first mycobacterial antigen may be alternatively (or in addition) be defined as a substantial lack (eg. an absence) of common in vivo biological activity between the first and second mycobacterial antigens.

For example, in one embodiment, the first and second mycobacterial antigens may exhibit (substantially) no common antigenic cross-reactivity. In one embodiment, the first and second mycobacterial antigens may exhibit (substantially) no common in vivo biological activity. For example, the first and second mycobacterial antigens induce different immune responses and/or have different in vivo biological activities.

In one embodiment, the first and second mycobacterial antigens comprise polypeptides (as defined herein), and the second mycobacterial antigen has substantially no common antigenic cross-reactivity with the first mycobacterial antigen and/or has a substantially different in vivo biological activity from the first mycobacterial antigen.

In one embodiment, the first and second mycobacterial antigens comprise polynucleotides (as defined herein), and the second mycobacterial antigen encodes a polypeptide that has substantially no common antigenic cross-reactivity with the polypeptide encoded by the first mycobacterial antigen.

In one embodiment, the first and second mycobacterial antigens comprise polynucleotides (as defined herein), and the second mycobacterial antigen has a substantially different in vivo biological activity from the first mycobacterial antigen and/or encodes a polypeptide that has a substantially different in vivo biological activity from the polypeptide encoded by the first mycobacterial antigen.

In one embodiment, the first mycobacterial antigen comprises a polypeptide and the second mycobacterial antigen comprises a polynucleotide (as defined herein), and the second mycobacterial antigen or polypeptide encoded thereby has substantially no common antigenic cross-reactivity with the first mycobacterial antigen and/or has a substantially different in vivo biological activity from the first mycobacterial antigen.

In one embodiment, the first mycobacterial antigen comprises a polynucleotide and the second mycobacterial antigen comprises a polypeptide (as defined herein), and the second mycobacterial antigen has substantially no common antigenic cross-reactivity with the first mycobacterial antigen or polypeptide encoded thereby, and/or has a substantially different in vivo biological activity from the first mycobacterial antigen or polypeptide encoded thereby.

By way of example, in one embodiment, the first and second mycobacterial antigens (or polypeptides encoded thereby) do not share a common ability to induce a “recall response” of an immune cell such as a T-lymphocyte (eg. CD4+, CD8+, effector T cell or memory T cell such as TEM or TCM) that has previously been exposed to an antigenic component of a mycobacterial infection.

In other words, in one embodiment, the first and second mycobacterial antigens (or polypeptides encoded thereby) are ‘different’ because they induce recall responses in different immune cells (eg. different T cells).

In one embodiment, the first and second mycobacterial antigens are expressed by the mycobacteria under different culture conditions and/or infection states. The present Applicant has identified that an antigenic composition comprising first and second antigens of the invention that are representative of different mycobacterial infection states advantageously elicits an immune response against different stages of mycobacterial infection and thus protects against multiple stages of mycobacterial disease. This is particularly advantageous because mycobacteria infection occurs in distinct acute, latent and reactivation phases.

Thus, in one embodiment, the expression or activity of first mycobacterial antigen is up-regulated during conditions of mycobacterial latency, whereas the expression or activity of the second mycobacterial antigen is up-regulated during active mycobacterial infection or upon re-activation from a latent state (and/or down-regulated during conditions of mycobacterial latency).

In an alternative embodiment, the expression or activity of first mycobacterial antigen is down-regulated during conditions of mycobacterial latency, whereas the expression or activity of the second mycobacterial antigen is down-regulated during active mycobacterial infection or upon re-activation from a latent state (and/or up-regulated during conditions of mycobacterial latency).

The second mycobacterial antigen may comprise a polypeptide sequence. For example, the second mycobacterial antigen may comprise or consist of a polypeptide.

In one embodiment, the second mycobacterial polypeptide comprises (or consists of) an antigenic mycobacterial polypeptide—ie. a mycobacterial polypeptide that is capable of evoking a protective T-cell response against mycobacterial infection.

Thus, in one embodiment, the second mycobacterial antigen is a ‘second mycobacterial polypeptide’ (or fragment).

In one embodiment, the second mycobacterial antigen comprises a polypeptide that is selected from the same group of polypeptides as discussed above in connection with the first mycobacterial antigen (so long as the second mycobacterial polypeptide is different from the first mycobacterial polypeptide, as discussed above).

Thus, in one embodiment, the second mycobacterial antigen comprises (or consists of) a polypeptide sequence having at least 70% amino acid sequence identity (such as at least 75, 80, 82, 84, 86, 88, 90, 92, 94, 96, 98, 99 or 100% amino acid sequence identity) to the amino acid sequence of a latency-regulated polypeptide selected from SEQ ID NOs: 1, 3, 5, 7 and 56, or a fragment thereof having at least 7 consecutive amino acids thereof (such as at least 10, 15, 25, 50, 75, 100, 125, 150, 175, 200, 225, 250, 275, 300, 325, 350, 375, 400, 425, 450, 475, 500, 525, 550, 575, 600, 625, 650 or 675 consecutive amino acid residues thereof.

In one embodiment, the second mycobacterial antigenic polypeptide comprises a polypeptide sequence having at least 70% amino acid sequence identity to the amino acid sequence of SEQ ID NO: 5, or a fragment thereof having at least 7 consecutive amino acids thereof.

In one embodiment, the limitations discussed above with respect to the first mycobacterial polypeptide apply equally to this embodiment of the second mycobacterial polypeptide.

In one embodiment, the second mycobacterial antigen comprises a polypeptide that is not selected from the same group of polypeptides as discussed above in connection with the first mycobacterial antigen.

For example, in one embodiment, the second mycobacterial antigen comprises a polypeptide sequence having at least 70% amino acid sequence identity (such as at least 75, 80, 82, 84, 86, 88, 90, 92, 94, 96, 98, 99 or 100% amino acid sequence identity) to an amino acid sequence selected from SEQ ID NOs: 9-20 and 34-44, or a fragment thereof having at least 7 consecutive amino acids thereof.

In one embodiment, the second mycobacterial antigen consists of a polypeptide sequence having at least 70% amino acid sequence identity (such as at least 75, 80, 82, 84, 86, 88, 90, 92, 94, 96, 98, 99 or 100% amino acid sequence identity) to an amino acid sequence selected from SEQ ID NOs: 9-20 and 34-44, or a fragment thereof having at least 7 consecutive amino acids thereof.

SEQ ID NOs: 9-20 and 34-44 are illustrated in Table 3, below:

TABLE 3

| SEQ ID NO: | Polypeptide name: |
|---|---|
| 9 | Ag85A/Rv3804c |
| 10 | Ag85B/Rv1886c |
| 11 | ESAT-6/Rv3875 |
| 12 | TB10.4/Rv0288 |
| 13 | Rv0125 |
| 14 | PPE18/Rv1196 |
| 15 | P27/Rv1411c |
| 16 | Hsp65/Rv0440 |
| 17 | HBHA/Rv0475 |
| 18 | Rv2659c |
| 19 | Rv2660c |
| 20 | HspX/Rv2031c |
| 34 | RPFA/Rv0867c |
| 35 | RPFB/Rv1009 |
| 36 | RPFC/Rv1884c |
| 37 | RPFD/Rv2389c |
| 38 | RPFE/Rv2450c |
| 39 | Rv1733 |
| 40 | Rv2029c |
| 41 | Rv2032 |
| 42 | Rv2626c |
| 43 | Rv2627c |
| 44 | Rv2628 |

The polypeptide "Ag85A" represented by SEQ ID NO: 9 of the present application (Accession Nos. CAA17868 and BX842584) is a member of a family of proteins ("the Ag85 complex"), which also comprises Ag85B (SEQ ID NO: 10 of the present application) and Ag85C. This family of proteins is secreted by *M. tuberculosis*, BCG, and many other species of mycobacteria. Ag85A is highly conserved amongst all mycobacterial species and is immunodominant in animal and human studies.

The polypeptides represented by SEQ ID NOs: 20 and 39-44 are comprised within the DosR regulon (also known as the DevR regulon), which includes the polypeptides represented by Rv2623-2631 and Rv3126-3134. The expression of these polypeptides is regulated via DosR (DevR).

The polypeptides represented by SEQ ID NOs: 34-38 are members of the RPF family of polypeptides (RPFA, RPFB, RPFC, RPFD and RPFE, respectively).

In one embodiment, the amino acid sequence identity exists over a region of the polypeptide sequences that is at least 7 consecutive amino acid residues in length (eg. at least 10, 15, 25, 50, 75, 100, 125, 150, 175, 200, 225, 250, 275, 300, 325, 350, 375, 400, 425, 450, 475, 500 or 525 consecutive amino acid residues in length).

Conventional methods for determining amino acid sequence identity are discussed in more detail later in the specification.

In one embodiment, in the context of the second mycobacterial antigen, a fragment of said polypeptide comprises at least 7 consecutive amino acid residues of said polypeptide sequence. In one embodiment, the fragment comprises (or consists of) at least 10, 15, 25, 50, 75, 100, 125, 150, 175, 200, 225, 250, 275, 300, 325, 350, 375, 400, 425, 450, 475, 500 or 525 consecutive amino acid residues of said polypeptide sequence.

In one embodiment, a fragment of a polypeptide is at least 5%, 10%, 20%, 30%, 40%, 50%, 60%, 70%, 80%, or 90% of the length of the mycobacterial polypeptide.

A fragment of a polypeptide may include at least one epitope of the polypeptide.

In one embodiment, in the context of the second mycobacterial antigen, a fragment of a polypeptide comprises (or consists of) a truncated form of said polypeptide. For example, a fragment of a polypeptide may have a N-terminal truncation (as compared with the polypeptide), or a fragment of a polypeptide may have a C-terminal truncation (as compared with the polypeptide).

In one embodiment, in the context of the second mycobacterial antigen, a fragment of a polypeptide comprises (or consists of) a mature form of the polypeptide. For example, the polypeptide may comprise a signal sequence (ie. a secretion/targeting sequence) (eg. at the N-terminus), and a fragment of the polypeptide may lack this signal sequence. In one embodiment, the fragment is formed by cleavage of a signal sequence from the polypeptide.

In one embodiment, a fragment of polypeptide SEQ ID NO: 9 is a N-terminally truncated form of SEQ ID NO: 9. In one embodiment, a fragment of SEQ ID NO: 9 is a mature polypeptide sequence, which differs from the sequence of SEQ ID NO: 9 by removal of a N-terminal signal sequence. In one embodiment, a fragment of polypeptide SEQ ID NO: 9 has a N-terminal truncation of at least 10, 20, 30 or 40 amino acid residues as compared with the amino acid sequence of SEQ ID NO: 9. In one embodiment, a fragment of SEQ ID NO: 9 comprises at least the C-terminal 50, 100, 150, 200 or 250 amino acid sequence of SEQ ID NO: 9.

In one embodiment, the second mycobacterial polypeptide or fragment thereof has a common antigenic cross-reactivity and/or substantially the same in vivo biological activity as the polypeptide selected from SEQ ID NOs: 9-20 and 34-44.

In one embodiment, 'common antigenic cross-reactivity' means that the second mycobacterial polypeptide, or fragment, shares a common ability, with the polypeptide selected from SEQ ID NOs: 9-20 and 34-44, to induce a "recall response" of an immune cell such as a T-lymphocyte which has been previously exposed to an antigenic component of a mycobacterial infection. For example, the interferon-gamma (IFN-γ) ELISPOT assay is useful as an immunological readout because the secretion of IFN-γ from antigen-specific immune cells such as T cells is a good correlate of protection against *M. tuberculosis*. Furthermore, the ELISPOT assay is a very reproducible and sensitive method of quantifying the number of IFN-γ secreting antigen-specific immune cells such as T cells.

Alternatively, or in addition, 'common antigenic cross-reactivity' means that an antibody capable of binding to the second mycobacterial polypeptide, or fragment, would also be capable of binding to the polypeptide selected from SEQ ID NOs: 9-20 and 34-44.

The second mycobacterial antigen may comprise a polynucleotide sequence. For example, the second mycobacterial antigen may comprise or consist of a polynucleotide.

In one embodiment, the second mycobacterial polynucleotide comprises (or consists of) an antigenic mycobacterial polynucleotide—ie. a polynucleotide that is capable of evoking a protective immune cell response (eg. T-cell response) against mycobacterial infection. In one embodiment, the second mycobacterial polynucleotide encodes an antigenic mycobacterial polypeptide—ie. a mycobacterial polypeptide that is capable of evoking a protective immune cell response (eg. T-cell response) against mycobacterial infection.

Thus, in one embodiment, the second mycobacterial antigen is a 'second mycobacterial polynucleotide' (or fragment), as defined above.

In one embodiment, the second mycobacterial antigen comprises a polynucleotide that is selected from the same group of polynucleotides as discussed above in connection with the first mycobacterial antigen (so long as the second mycobacterial polynucleotide is different from the first mycobacterial polynucleotide).

Thus, in one embodiment, the second mycobacterial antigen comprises (or consists of) a polynucleotide sequence that encodes a polypeptide selected from the same group of polypeptides as discussed above in connection with the first mycobacterial antigen (so long as the second mycobacterial polynucleotide is different from the first mycobacterial polynucleotide, and so long as the polypeptide encoded by the second mycobacterial polynucleotide is different from the polypeptide encoded by the first mycobacterial polynucleotide).

Thus, said second mycobacterial polynucleotide comprises a polynucleotide sequence encoding a second mycobacterial polypeptide of the invention, as defined above.

In one embodiment, said encoded second mycobacterial polypeptide comprises a polypeptide sequence having at least 70% amino acid sequence identity to the amino acid sequence of SEQ ID NO: 5, or a fragment thereof having at least 7 consecutive amino acids thereof.

In one embodiment, the second mycobacterial antigen comprises (or consists of) a polynucleotide sequence having at least 70% nucleotide sequence identity (such as at least 75, 80, 82, 84, 86, 88, 90, 92, 94, 96, 98, 99 or 100% nucleotide sequence identity) to the nucleic acid sequence of a latency-regulated polynucleotide selected from SEQ ID NOs: 2, 4, 6, 8 and 57, or a fragment thereof having at least 21 consecutive nucleotides thereof (such as at least 25, 50, 75, 100, 125, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950 or 2000 consecutive amino acid residues thereof).

In one embodiment, the second mycobacterial polypeptide comprises (or consists of) a polynucleotide sequence having at least 70% nucleotide sequence identity to the nucleic acid sequence of SEQ ID NO: 6, or a fragment thereof having at least 21 consecutive nucleotides thereof.

In one embodiment, the limitations discussed above with respect to the first mycobacterial polypeptide apply equally to this embodiment of the second mycobacterial polypeptide.

In one embodiment, the second mycobacterial antigen comprises a polynucleotide that is not selected from the same group of polynucleotides as discussed above in connection with the first mycobacterial antigen.

In one embodiment, the second mycobacterial antigen comprises a polynucleotide that encodes a polypeptide that is not selected from the same group of polypeptides as discussed above in connection with the first mycobacterial antigen.

In one embodiment, the second mycobacterial antigen comprises a polynucleotide sequence that encodes a second mycobacterial polypeptide as defined above.

Thus, in one embodiment, the second mycobacterial antigen comprises (or consists of) a polynucleotide sequence, wherein said polynucleotide sequence encodes a polypeptide that comprises (or consists of) an amino acid sequence having at least 70% amino acid sequence identity (such as at least 75, 80, 82, 84, 86, 88, 90, 92, 94, 96, 98, 99 or 100% amino acid sequence identity) to an amino acid sequence selected from SEQ ID NOs: 9-20 and 34-44, or a fragment thereof having at least 7 consecutive amino acid residues thereof.

In one embodiment, the second mycobacterial antigen comprises (or consists of) a polynucleotide sequence having at least 70% nucleotide sequence identity (such as at least 75, 80, 82, 84, 86, 88, 90, 92, 94, 96, 98, 99 or 100% nucleotide sequence identity) to a nucleic acid sequence selected from SEQ ID NOs: 21-32 and 45-55, or a fragment thereof having at least 21 consecutive nucleotides thereof.

SEQ ID NOs: 21-32 and 45-55 are illustrated in Table 4, below:

TABLE 4

| SEQ ID NO: | Polynucleotide name: |
|---|---|
| 21 | Ag85A/Rv3804c |
| 22 | Ag85B/Rv1886c |
| 23 | ESAT-6/Rv3875 |
| 24 | TB10.4/Rv0288 |
| 25 | Rv0125 |
| 26 | PPE18/Rv1196 |
| 27 | P27/Rv1411c |
| 28 | Hsp65/Rv0440 |
| 29 | HBHA/Rv0475 |
| 30 | Rv2659c |
| 31 | Rv2660c |
| 32 | HspX/Rv2031c |
| 45 | RPFA/Rv0867c |
| 46 | RPFB/Rv1009 |
| 47 | RPFC/Rv1884c |
| 48 | RPFD/Rv2389c |
| 49 | RPFE/Rv2450c |

TABLE 4-continued

| SEQ ID NO: | Polynucleotide name: |
|---|---|
| 50 | Rv1733 |
| 51 | Rv2029c |
| 52 | Rv2032 |
| 53 | Rv2626c |
| 54 | Rv2627c |
| 55 | Rv2628 |

The polynucleotide "Ag85A" represented by SEQ ID NO: 21 of the present application (Accession Nos. CAA17868 and BX842584) is a member of a family of genes ("the Ag85 complex"), which also comprises Ag85B (SEQ ID NO: 22 of the present application) and Ag85C. This family of genes encodes proteins that are secreted by *M. tuberculosis*, BCG, and many other species of mycobacteria. Ag85A is highly conserved amongst all mycobacterial species and is immunodominant in animal and human studies.

The polynucleotides represented by SEQ ID NOs: 32 and 50-55 are comprised within the DosR regulon (also known as the DevR regulon), which includes the polynucleotides represented by Rv2623-2631 and Rv3126-3134. The expression of these polynucleotides is regulated via DosR (DevR).

The polynucleotides represented by SEQ ID NOs: 45-49 are members of the RPF family of polynucleotides (RPFA, RPFB, RPFC, RPFD and RPFE, respectively).

In one embodiment, the nucleotide sequence identity exists over a region of the polynucleotide sequences that is at least 21 consecutive nucleotide residues in length (eg. at least 25, 50, 75, 100, 125, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550 or 1600 consecutive nucleotide residues in length).

Conventional methods for determining nucleotide sequence identity are discussed in more detail later in the specification.

In one embodiment, in the context of the second mycobacterial antigen, a fragment of a polynucleotide comprises at least 21 consecutive nucleotide residues of said polynucleotide sequence. In one embodiment, the fragment comprises (or consists of) at least 25, 50, 75, 100, 125, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550 or 1600 consecutive nucleotide residues of said polynucleotide sequence.

In one embodiment, a fragment of said polynucleotide is at least 5%, 10%, 20%, 30%, 40%, 50%, 60%, 70%, 80%, or 90% of the length of the polynucleotide.

In one embodiment, in the context of the second mycobacterial antigen, a fragment of a polynucleotide comprises (or consists of) a truncated form of said polynucleotide. For example, a fragment of a polynucleotide may have a 5' truncation and/or 3' truncation as compared with the polynucleotide. In one embodiment, in the context of the second mycobacterial antigen, a fragment of a polynucleotide encodes a polypeptide that is truncated as compared with the polypeptide sequence encoded by the full-length polynucleotide. For example, the polynucleotide fragment may encode a polypeptide that is N-terminally truncated and/or C-terminally truncated, as compared with the polypeptide encoded by the full-length polynucleotide.

In one embodiment, in the context of the second mycobacterial antigen, a fragment of a polynucleotide encodes a mature polypeptide. For example, the polypeptide may comprise a signal sequence (ie. a secretion/targeting sequence) (eg. at the N-terminus), and the polynucleotide fragment may encode a polypeptide fragment that lacks this signal sequence.

In one embodiment, a fragment of polynucleotide SEQ ID NO: 21 is a 5' truncated form of SEQ ID NO: 21. In one embodiment, a fragment of polynucleotide SEQ ID NO: 21 has a N-terminal truncation of at least 25, 50, 75, 100 or 125 nucleotide residues as compared with the nucleotide sequence of SEQ ID NO: 21. In one embodiment, a fragment of polynucleotide SEQ ID NO: 21 comprises at least the C-terminal 150, 300, 450, 600, 750 or 850 nucleotide residues of SEQ ID NO: 21. In one embodiment, a fragment of polynucleotide SEQ ID NO: 21 encodes a N-terminally truncated form of SEQ ID NO: 9. In one embodiment, a fragment of polynucleotide SEQ ID NO: 21 encodes a mature polypeptide sequence, which differs from the sequence of SEQ ID NO: 9 by removal of a N-terminal signal sequence. In one embodiment, a fragment of polynucleotide SEQ ID NO: 21 encodes a polypeptide fragment of SEQ ID NO: 9 that has a N-terminal truncation of at least 10, 20, 30 or 40 amino acid residues as compared with the amino acid sequence of SEQ ID NO: 9. In one embodiment, a fragment of polynucleotide SEQ ID NO: 21 encodes a polypeptide fragment of SEQ ID NO: 9 that comprises at least the C-terminal 50, 100, 150, 200, 250 or 275 amino acid residues of SEQ ID NO: 9.

In one embodiment, a polypeptide encoded by the second mycobacterial polynucleotide or fragment has a common antigenic cross-reactivity and/or substantially the same in vivo biological activity as the polypeptide selected from SEQ ID NOs: 9-20 and 34-44.

By way of example, the polypeptide encoded by the second mycobacterial polynucleotide, or fragment, shares a common ability, with the polypeptide selected from SEQ ID NOs: 9-20 and 34-44, to induce a "recall response" of an immune cell such as a T-lymphocyte which has been previously exposed to an antigenic component of a mycobacterial infection. For example, the interferon-gamma (IFN-γ) ELISPOT assay is useful as an immunological readout because the secretion of IFN-γ from antigen-specific immune cells such as T cells is a good correlate of protection against *M. tuberculosis*. Furthermore, the ELISPOT assay is a very reproducible and sensitive method of quantifying the number of IFN-γ secreting antigen-specific immune cells such as T cells.

Alternatively, or in addition, an antibody capable of binding to a polypeptide encoded by the second mycobacterial polynucleotide, or fragment, would also be capable of binding to the polypeptide selected from SEQ ID NOs: 9-20 and 34-44.

In one embodiment, the antigenic composition comprises both a Rv0111 antigen (antigenic polypeptide or polynucleotide) and a Rv0198 antigen (antigenic polypeptide or polynucleotide).

In one embodiment, the antigenic composition comprises either:

(i) a first mycobacterial antigenic polypeptide, wherein said first mycobacterial antigenic polypeptide comprises a polypeptide sequence having at least 70% amino acid sequence identity to the amino acid sequence of SEQ ID NO: 1, or a fragment thereof having at least 7 consecutive amino acids thereof; or (ii) a first mycobacterial polynucleotide, wherein said first mycobacterial polynucleotide comprises a polynucleotide sequence encoding said first mycobacterial antigenic polypeptide;

and further comprises either:

(iii) a second mycobacterial antigenic polypeptide, wherein said second mycobacterial antigenic polypeptide comprises a polypeptide sequence having at least 70% amino acid sequence identity to the amino acid sequence of SEQ ID NO: 5, or a fragment thereof having at least 7 consecutive amino acids thereof; or (iv) a second mycobacterial polynucleotide, wherein said second mycobacterial polynucleotide comprises a polynucleotide sequence encoding said second mycobacterial polypeptide.

By way of example, the Rv0111/Rv0198 antigenic composition may comprise:

(i) a first mycobacterial antigenic polypeptide, wherein said first mycobacterial antigenic polypeptide comprises a polypeptide sequence having at least 70% amino acid sequence identity to the amino acid sequence of SEQ ID NO: 1, or a fragment thereof having at least 7 consecutive amino acids thereof; and (ii) a second mycobacterial antigenic polypeptide, wherein said second mycobacterial antigenic polypeptide comprises a polypeptide sequence having at least 70% amino acid sequence identity to the amino acid sequence of SEQ ID NO: 5, or a fragment thereof having at least 7 consecutive amino acids thereof.

Alternatively, the Rv0111/Rv0198 antigenic composition may comprise:

(i) a first mycobacterial polynucleotide, wherein said first mycobacterial polynucleotide comprises a polynucleotide sequence encoding a first mycobacterial antigenic polypeptide, wherein said first mycobacterial antigenic polypeptide comprises a polypeptide sequence having at least 70% amino acid sequence identity to the amino acid sequence of SEQ ID NO: 1, or a fragment thereof having at least 7 consecutive amino acids thereof; and (ii) a second mycobacterial polynucleotide, wherein said second mycobacterial polynucleotide comprises a polynucleotide sequence encoding a second mycobacterial antigenic polypeptide, wherein said second mycobacterial antigenic polypeptide comprises a polypeptide sequence having at least 70% amino acid sequence identity to the amino acid sequence of SEQ ID NO: 5, or a fragment thereof having at least 7 consecutive amino acids thereof.

Alternatively, the Rv0111/Rv0198 antigenic composition may comprise:

(i) a first mycobacterial antigenic polypeptide, wherein said first mycobacterial antigenic polypeptide comprises a polypeptide sequence having at least 70% amino acid sequence identity to the amino acid sequence of SEQ ID NO: 1, or a fragment thereof having at least 7 consecutive amino acids thereof; and (ii) a second mycobacterial polynucleotide, wherein said second mycobacterial polynucleotide comprises a polynucleotide sequence encoding a second mycobacterial antigenic polypeptide, wherein said second mycobacterial antigenic polypeptide comprises a polypeptide sequence having at least 70% amino acid sequence identity to the amino acid sequence of SEQ ID NO: 5, or a fragment thereof having at least 7 consecutive amino acids thereof.

Alternatively, the Rv0111/Rv0198 antigenic composition may comprise:

(i) a first mycobacterial polynucleotide, wherein said first mycobacterial polynucleotide comprises a polynucleotide sequence encoding a first mycobacterial antigenic polypeptide, wherein said first mycobacterial antigenic polypeptide comprises a polypeptide sequence having at least 70% amino acid sequence identity to the amino acid sequence of SEQ ID NO: 1, or a fragment thereof having at least 7 consecutive amino acids thereof; and (ii) a second mycobacterial antigenic polypeptide, wherein said second mycobacterial antigenic polypeptide comprises a polypeptide sequence having at least 70% amino acid sequence identity to the amino acid sequence of SEQ ID NO: 5, or a fragment thereof having at least 7 consecutive amino acids thereof.

In accordance with this embodiment, in the Rv0111/Rv0198 antigenic composition of the invention, the first mycobacterial polynucleotide may comprise (or consist of) a polynucleotide sequence having at least 70% nucleotide sequence identity to the nucleic acid sequence of SEQ ID NO: 2, or a fragment thereof having at least 21 consecutive nucleotides thereof.

In accordance with this embodiment, in the Rv0111/Rv0198 antigenic composition of the invention, the second mycobacterial polynucleotide may comprise (or consist of) a polynucleotide sequence having at least 70% nucleotide sequence identity to the nucleic acid sequence of SEQ ID NO: 6, or a fragment thereof having at least 21 consecutive nucleotides thereof.

In one embodiment, the antigenic composition does not comprise both a Rv1806 antigen and a Rv1807 antigen.

Thus, in one embodiment, if the first mycobacterial antigen is a Rv1806 polypeptide antigen, the second mycobacterial antigen is not a Rv1807 polypeptide antigen. In one embodiment, if the first mycobacterial antigen is a Rv1806 polynucleotide antigen, the second mycobacterial antigen is not a Rv1807 polynucleotide antigen. In one embodiment, if the first mycobacterial antigen is a Rv1806 polypeptide antigen, the second mycobacterial antigen is not a Rv1807 polynucleotide antigen. In one embodiment, if the first mycobacterial antigen is a Rv1806 polynucleotide antigen, the second mycobacterial antigen is not a Rv1807 polypeptide antigen.

In one embodiment, if the first mycobacterial antigen is a Rv1807 polypeptide antigen, the second mycobacterial antigen is not a Rv1806 polypeptide antigen. In one embodiment, if the first mycobacterial antigen is a Rv1807 polynucleotide antigen, the second mycobacterial antigen is not a Rv1806 polynucleotide antigen. In one embodiment, if the first mycobacterial antigen is a Rv1807 polypeptide antigen, the second mycobacterial antigen is not a Rv1806 polynucleotide antigen. In one embodiment, if the first mycobacterial antigen is a Rv1807 polynucleotide antigen, the second mycobacterial antigen is not a Rv1806 polynucleotide antigen.

In one embodiment, if the first mycobacterial antigen comprises:

(i) a polypeptide sequence having at least 70% amino acid sequence identity to the amino acid sequence of SEQ ID NO: 3, or a fragment thereof having at least 7 consecutive amino acids thereof;

the second mycobacterial antigen does not comprise:

(ii) a polypeptide sequence having at least 70% amino acid sequence identity to the amino acid sequence of SEQ ID NO: 56, or a fragment thereof having at least 7 consecutive amino acids thereof.

In one embodiment, if the first mycobacterial antigen comprises:

(i) a polynucleotide sequence encoding a polypeptide sequence having at least 70% amino acid sequence identity to the amino acid sequence of SEQ ID NO: 3, or a fragment thereof having at least 7 consecutive amino acids thereof; or a polynucleotide sequence having at least 70% nucleotide sequence identity to the nucleic acid sequence of SEQ ID NO: 4, or a fragment thereof having at least 21 consecutive nucleotides thereof;

the second mycobacterial antigen does not comprise:

(ii) a polynucleotide sequence encoding a polypeptide sequence having at least 70% amino acid sequence identity to the amino acid sequence of SEQ ID NO: 56, or a fragment thereof having at least 7 consecutive amino acids thereof; or a polynucleotide sequence having at least 70% nucleotide sequence identity to the nucleic acid sequence of SEQ ID NO: 57, or a fragment thereof having at least 21 consecutive nucleotides thereof.

In one embodiment, if the first mycobacterial antigen comprises:

(i) a polypeptide sequence having at least 70% amino acid sequence identity to the amino acid sequence of SEQ ID NO: 3, or a fragment thereof having at least 7 consecutive amino acids thereof; or (ii) a polynucleotide sequence encoding a polypeptide sequence according to (i); or a polynucleotide sequence having at least 70% nucleotide sequence identity to the nucleic acid sequence of SEQ ID NO: 4, or a fragment thereof having at least 21 consecutive nucleotides thereof;

the second mycobacterial antigen does not comprise:

(iii) a polypeptide sequence having at least 70% amino acid sequence identity to the amino acid sequence of SEQ ID NO: 56, or a fragment thereof having at least 7 consecutive amino acids thereof; or (iv) a polynucleotide sequence encoding a polypeptide sequence according to (iii); or a polynucleotide sequence having at least 70% nucleotide sequence identity to the nucleic acid sequence of SEQ ID NO: 57, or a fragment thereof having at least 21 consecutive nucleotides thereof.

In one embodiment, if the first mycobacterial antigen comprises:

(i) a polypeptide sequence having at least 70% amino acid sequence identity to the amino acid sequence of SEQ ID NO: 56, or a fragment thereof having at least 7 consecutive amino acids thereof;

the second mycobacterial antigen does not comprise:

(ii) a polypeptide sequence having at least 70% amino acid sequence identity to the amino acid sequence of SEQ ID NO: 3, or a fragment thereof having at least 7 consecutive amino acids thereof.

In one embodiment, if the first mycobacterial antigen comprises:

(i) a polynucleotide sequence encoding a polypeptide sequence having at least 70% amino acid sequence identity to the amino acid sequence of SEQ ID NO: 56, or a fragment thereof having at least 7 consecutive amino acids thereof; or a polynucleotide sequence having at least 70% nucleotide sequence identity to the nucleic acid sequence of SEQ ID NO: 57, or a fragment thereof having at least 21 consecutive nucleotides thereof;

the second mycobacterial antigen does not comprise:

(ii) a polynucleotide sequence encoding a polypeptide sequence having at least 70% amino acid sequence identity to the amino acid sequence of SEQ ID NO: 3, or a fragment thereof having at least 7 consecutive amino acids thereof; or a polynucleotide sequence having at least 70% nucleotide sequence identity to the nucleic acid sequence of SEQ ID NO: 4, or a fragment thereof having at least 21 consecutive nucleotides thereof.

In one embodiment, if the first mycobacterial antigen comprises:

(i) a polypeptide sequence having at least 70% amino acid sequence identity to the amino acid sequence of SEQ ID NO: 56, or a fragment thereof having at least 7 consecutive amino acids thereof; or (ii) a polynucleotide sequence encoding a polypeptide sequence according to (i); or a polynucleotide sequence having at least 70% nucleotide sequence identity to the nucleic acid sequence of SEQ ID NO: 57, or a fragment thereof having at least 21 consecutive nucleotides thereof;

the second mycobacterial antigen does not comprise:

(iii) a polypeptide sequence having at least 70% amino acid sequence identity to the amino acid sequence of SEQ ID NO: 3, or a fragment thereof having at least 7 consecutive amino acids thereof; or (iv) a polynucleotide sequence encoding a polypeptide sequence according to (iii); or a polynucleotide sequence having at least 70% nucleotide sequence identity to the nucleic acid sequence of SEQ ID NO: 4, or a fragment thereof having at least 21 consecutive nucleotides thereof.

In one embodiment, the antigenic composition comprises both a Rv3812 antigen (antigenic polypeptide or polynucleotide) and a Rv0198 antigen (antigenic polypeptide or polynucleotide).

In one embodiment, the antigenic composition comprises either:

(i) a first mycobacterial antigenic polypeptide, wherein said first mycobacterial antigenic polypeptide comprises a polypeptide sequence having at least 70% amino acid sequence identity to the amino acid sequence of SEQ ID NO: 7, or a fragment thereof having at least 7 consecutive amino acids thereof; or (ii) a first mycobacterial polynucleotide, wherein said first mycobacterial polynucleotide comprises a polynucleotide sequence encoding said first mycobacterial antigenic polypeptide;

and further comprises either:

(iii) a second mycobacterial antigenic polypeptide, wherein said second mycobacterial antigenic polypeptide comprises a polypeptide sequence having at least 70% amino acid sequence identity to the amino acid sequence of SEQ ID NO: 5, or a fragment thereof having at least 7 consecutive amino acids thereof; or (iv) a second mycobacterial polynucleotide, wherein said second mycobacterial polynucleotide comprises a polynucleotide sequence encoding said second mycobacterial polypeptide.

By way of example, the Rv3812/Rv0198 antigenic composition may comprise:

(i) a first mycobacterial antigenic polypeptide, wherein said first mycobacterial antigenic polypeptide comprises a polypeptide sequence having at least 70% amino acid sequence identity to the amino acid sequence of SEQ ID NO: 7, or a fragment thereof having at least 7 consecutive amino acids thereof; and (ii) a second mycobacterial antigenic polypeptide, wherein said second mycobacterial antigenic polypeptide comprises a polypeptide sequence having at least 70% amino acid sequence identity to the amino acid sequence of SEQ ID NO: 5, or a fragment thereof having at least 7 consecutive amino acids thereof.

Alternatively, the Rv3812/Rv0198 antigenic composition may comprise:

(i) a first mycobacterial polynucleotide, wherein said first mycobacterial polynucleotide comprises a polynucleotide sequence encoding a first mycobacterial antigenic polypeptide, wherein said first mycobacterial antigenic polypeptide comprises a polypeptide sequence having at least 70% amino acid sequence identity to the amino acid sequence of SEQ ID NO: 7, or a fragment thereof having at least 7 consecutive amino acids thereof; and (ii) a second mycobacterial polynucleotide, wherein said second mycobacterial polynucleotide comprises a polynucleotide sequence encoding a second mycobacterial antigenic polypeptide, wherein said second mycobacterial antigenic polypeptide comprises a polypeptide sequence having at least 70% amino acid sequence identity to the amino acid sequence of SEQ ID NO: 5, or a fragment thereof having at least 7 consecutive amino acids thereof.

Alternatively, the Rv3812/Rv0198 antigenic composition may comprise:

(i) a first mycobacterial antigenic polypeptide, wherein said first mycobacterial antigenic polypeptide comprises a polypeptide sequence having at least 70% amino acid sequence identity to the amino acid sequence of SEQ ID NO: 7, or a fragment thereof having at least 7 consecutive amino acids thereof; and (ii) a second mycobacterial polynucleotide, wherein said second mycobacterial polynucleotide comprises a polynucleotide sequence encoding a second mycobacterial antigenic polypeptide, wherein said second mycobacterial antigenic polypeptide comprises a polypeptide sequence having at least 70% amino acid sequence identity to the amino acid sequence of SEQ ID NO: 5, or a fragment thereof having at least 7 consecutive amino acids thereof.

Alternatively, the Rv3812/Rv0198 antigenic composition may comprise:

(i) a first mycobacterial polynucleotide, wherein said first mycobacterial polynucleotide comprises a polynucleotide sequence encoding a first mycobacterial antigenic polypeptide, wherein said first mycobacterial antigenic polypeptide comprises a polypeptide sequence having at least 70% amino acid sequence identity to the amino acid sequence of SEQ ID NO: 7, or a fragment thereof having at least 7 consecutive amino acids thereof; and (ii) a second mycobacterial antigenic polypeptide, wherein said second mycobacterial antigenic polypeptide comprises a polypeptide sequence having at least 70% amino acid sequence identity to the amino acid sequence of SEQ ID NO: 5, or a fragment thereof having at least 7 consecutive amino acids thereof.

The antigenic composition of the invention may further comprise, in addition to the first and second mycobacterial antigens discussed above, at least one further mycobacterial antigen, which is different from the first and/or second mycobacterial antigens. In one embodiment, the at least one further mycobacterial antigen is different from both the first mycobacterial antigen and the second mycobacterial antigen.

In one embodiment, the antigenic composition of the invention further comprises at least one additional mycobacterial antigenic polypeptide, which is different from said first mycobacterial antigenic polypeptide and/or said second mycobacterial antigenic polypeptide. In one embodiment, the antigenic composition of the invention further comprises at least one additional mycobacterial polynucleotide, which is different from said first mycobacterial polynucleotide and/or said second mycobacterial polynucleotide.

In one embodiment, where there are multiple additional mycobacterial antigens (eg. 2 or more additional mycobacterial antigens, as well as the first and second mycobacterial antigens), each of said additional mycobacterial antigens is different from each other.

In one embodiment, the 'difference' between the additional mycobacterial antigen(s) and the first and second mycobacterial antigens is defined by the specificity of the immune response to the mycobacterial antigens. For example, in one embodiment, each of the first, second and additional antigens induces an immune response that is substantially specific to that antigen.

The 'difference' between the first, second and additional mycobacterial antigens may be defined in terms of a substantial lack (eg. an absence) of common antigenic cross-reactivity between the mycobacterial antigens.

The 'difference' between the first, second and additional mycobacterial antigens may be alternatively (or in addition) be defined as a substantial lack (eg. an absence) of common in vivo biological activity between the mycobacterial antigens.

For example, in one embodiment, the first, second and additional mycobacterial antigens (eg. first, second and additional mycobacterial antigenic polypeptides, or first, second and additional mycobacterial antigenic polynucleotides or polypeptide encoded thereby) may exhibit (substantially) no common antigenic cross-reactivity.

In one embodiment, the first, second and additional mycobacterial antigens (eg. first, second and additional mycobacterial antigenic polypeptides, or first, second and additional mycobacterial antigenic polynucleotides or polypeptide encoded thereby) exhibit (substantially) no common in vivo biological activity.

For example, the first, second and additional mycobacterial antigens (eg. first, second and additional mycobacterial antigenic polypeptides, or first, second and additional mycobacterial antigenic polynucleotides or polypeptide encoded thereby) may each induce different immune responses and/or each have different in vivo biological activities.

By way of example, in one embodiment, the first, second and additional mycobacterial antigens (eg. first, second and additional mycobacterial antigenic polypeptides, or first, second and additional mycobacterial antigenic polynucleotides or polypeptide encoded thereby) do not share a common ability to induce a "recall response" of an immune cell such as a T-lymphocyte (eg. CD4+, CD8+, effector T cell or memory T cell such as a TEM or TCM) that has previously been exposed to an antigenic component of a mycobacterial infection.

In other words, in one embodiment, the first, second and additional mycobacterial antigens are 'different' because they induce recall responses in different immune cells (eg. different T cells).

In one embodiment, the one or more additional mycobacterial antigen(s) is expressed or up-regulated under different culture conditions and/or mycobacterial infection states as compared with the first and/or second mycobacterial antigens. In one embodiment, the activity of the one or more additional mycobacterial antigen(s) is up-regulated under different culture conditions and/or mycobacterial infection states as compared with the first and/or second mycobacterial antigens.

In this regard, the present Applicant has identified that an antigenic composition comprising first and second and additional mycobacterial antigens of the invention that are representative of different mycobacterial infection states advantageously elicits an immune response against different stages of mycobacterial infection and thus protects against multiple stages of mycobacterial disease. This is particularly advantageous because mycobacteria infection occurs in distinct acute, latent and reactivation phases.

Thus, in one embodiment, the expression or activity of first mycobacterial antigen is up-regulated during conditions of mycobacterial latency, whereas the expression or activity of the second and/or additional mycobacterial antigen is up-regulated during active mycobacterial infection or upon re-activation from a latent state (and/or down-regulated during conditions of mycobacterial latency).

In an alternative embodiment, the expression or activity of first mycobacterial antigen is down-regulated during conditions of mycobacterial latency, whereas the expression or activity of the second and/or additional mycobacterial antigen is down-regulated during active mycobacterial infection or upon re-activation from a latent state (and/or up-regulated during conditions of mycobacterial latency).

In one embodiment, where there are multiple additional mycobacterial antigens (eg. 2 or more additional mycobacterial antigens, as well as the first and second mycobacterial antigens), each additional mycobacterial antigen is expressed/up-regulated at different stages of mycobacterial infection, or the activity of each additional mycobacterial antigen is up-regulated at different stages of mycobacterial infection.

In one embodiment, the one or more additional mycobacterial antigens are from a mycobacterium other than *M. tuberculosis*. For example, the one or more additional mycobacterial antigens may be from another member of the MTC, such as *M. microti, M. bovis, M. canetti* or *M. africanum*, or a non-MTC mycobacterium such as *M. avium-intracellulare, M. kansasii, M. marinum* or *M. ulcerans.*

In one embodiment, the antigenic composition comprises at least 1, 2, 3, 4 or 5 further mycobacterial antigens, in addition to the first and second mycobacterial antigens discussed above. In one embodiment, each of said at least 1, 2, 3, 4 or 5 additional mycobacterial antigens is different from each other and from the first and second mycobacterial antigens. In one embodiment, the antigenic composition comprises up to about 10 different mycobacterial antigens (eg. including the first and second mycobacterial antigens discussed above).

In one embodiment, the antigenic composition comprises 1 additional mycobacterial antigen, and thus comprises a total of 3 different mycobacterial antigens (ie. the antigenic composition is trimeric). In one embodiment, the antigenic composition comprises 2 additional mycobacterial antigens, and thus comprises a total of 4 different mycobacterial antigens (ie. the antigenic composition is tetrameric). In one embodiment, the antigenic composition comprises 3 additional mycobacterial antigens, and thus comprises a total of 4 different mycobacterial antigens (ie. the antigenic composition is pentameric). In one embodiment, the antigenic composition comprises up to 8 additional mycobacterial antigens, and thus comprises up to a total of 10 different mycobacterial antigens (ie. the antigenic composition is up to decameric).

The one or more additional mycobacterial antigens may comprise (or consist of) a polypeptide sequence.

In one embodiment, the one or more additional mycobacterial antigens comprises (or consists of) a polypeptide sequence having at least 70% amino acid sequence identity to the amino acid sequence of a latency-regulated polypeptide selected from SEQ ID NOs: 1, 3, 5, 7 and 56, or a fragment thereof having at least 7 consecutive amino acids thereof, as defined above with respect to the first mycobacterial antigen (so long as the one or more additional mycobacterial antigens is different from the first mycobacterial antigen).

Alternatively, or in addition, the one or more additional mycobacterial antigens may comprise (or consist of) a polypeptide sequence having at least 70% amino acid sequence identity to an amino acid sequence selected from SEQ ID NOs: 9-20 and 34-44, or a fragment thereof having at least 7 consecutive amino acids thereof, as defined above with respect to the second mycobacterial antigen (so long as the one or more additional mycobacterial antigens is different from the second mycobacterial antigen).

The one or more additional mycobacterial antigens may comprise (or consist of) a polynucleotide sequence.

In one embodiment, the one or more additional mycobacterial antigens comprises (or consists of) a polynucleotide sequence that encodes a polypeptide sequence as described above with respect to the first mycobacterial antigenic polypeptide (so long as the one or more additional mycobacterial antigens is different from the first mycobacterial antigen).

In one embodiment, the one or more additional mycobacterial antigens comprises (or consists of) a polynucleotide sequence that encodes a polypeptide sequence as described above with respect to the second mycobacterial antigenic polypeptide (so long as the one or more additional mycobacterial antigens is different from the second mycobacterial antigen).

In one embodiment, the one or more additional mycobacterial antigens comprises (or consists of) a polynucleotide sequence having at least 70% nucleotide sequence identity to the nucleic acid sequence of a latency-regulated polynucleotide selected from SEQ ID NOs: 2, 4, 6, 8 and 57, or a fragment thereof having at least 21 consecutive nucleotides thereof, as described above with respect to the first mycobacterial antigen (so long as the one or more additional mycobacterial antigens is different from the first mycobacterial antigen).

Alternatively, or in addition, the one or more additional mycobacterial antigens may comprise (or consist of) a polynucleotide sequence having at least 70% nucleotide sequence identity to a nucleic acid sequence selected from SEQ ID NOs: 21-32 and 45-55, or a fragment thereof having at least 21 consecutive nucleotides thereof, as described above with respect to the second mycobacterial antigen (so long as the one or more additional mycobacterial antigens is different from the second mycobacterial antigen).

In one embodiment, the antigenic composition comprises:

(i) a first mycobacterial antigenic polypeptide, wherein said first mycobacterial antigenic polypeptide comprises a polypeptide sequence having at least 70% amino acid sequence identity to the amino acid sequence of SEQ ID NO: 1 or 7, or a fragment thereof having at least 7 consecutive amino acids thereof; or (ii) a first mycobacterial polynucleotide, wherein said first mycobacterial polynucleotide comprises a polynucleotide sequence encoding said first mycobacterial antigenic polypeptide;

and further comprises:

(iii) a second mycobacterial antigenic polypeptide, wherein said second mycobacterial antigenic polypeptide comprises a polypeptide sequence having at least 70% amino acid sequence identity to the amino acid sequence of SEQ ID NO: 5, or a fragment thereof having at least 7 consecutive amino acids thereof; or (iv) a second mycobacterial polynucleotide, wherein said second mycobacterial polynucleotide comprises a polynucleotide sequence encoding said second mycobacterial polypeptide;

and further comprises:

(v) at least one additional mycobacterial antigenic polypeptide, which is different from said first mycobacterial antigenic polypeptide and/or said second mycobacterial antigenic polypeptide; or at least one additional mycobacterial polynucleotide, which is different from said first mycobacterial polynucleotide and/or said second mycobacterial polynucleotide.

In one embodiment, the antigenic composition does not comprise both a Rv1806 antigen and a Rv1807 antigen.

Thus, in one embodiment, if the first mycobacterial antigen is a Rv1806 polypeptide antigen, said additional mycobacterial antigen in the antigenic composition is not a Rv1807 polypeptide antigen. In one embodiment, if the first mycobacterial antigen is a Rv1806 polynucleotide antigen, said additional mycobacterial antigen in the antigenic composition is not a Rv1807 polynucleotide antigen. In one embodiment, if the first mycobacterial antigen is a Rv1806 polypeptide antigen, said additional mycobacterial antigen in the antigenic composition is not a Rv1807 polynucleotide antigen. In one embodiment, if the first mycobacterial antigen is a Rv1806 polynucleotide antigen, said additional mycobacterial antigen in the antigenic composition is not a Rv1807 polypeptide antigen.

In one embodiment, if the first mycobacterial antigen is a Rv1807 polypeptide antigen, said additional mycobacterial antigen in the antigenic composition is not a Rv1806 polypeptide antigen. In one embodiment, if the first mycobacterial antigen is a Rv1807 polynucleotide antigen, said additional mycobacterial antigen in the antigenic composition is not a Rv1806 polynucleotide antigen. In one embodiment, if the first mycobacterial antigen is a Rv1807 polypeptide antigen, said additional mycobacterial antigen in the antigenic composition is not a Rv1806 polynucleotide antigen. In one embodiment, if the first mycobacterial antigen is a Rv1807 polynucleotide antigen, said additional mycobacterial antigen in the antigenic composition is not a Rv1806 polypeptide antigen.

In one embodiment, the antigenic composition does not comprise an Rv0111 antigen, an Rv0198 antigen and an Rv3812 antigen. Thus, if the antigenic composition comprises an Rv0111 antigen and an Rv0198 antigen, the antigenic composition does not also comprise an Rv3812 antigen.

By way of example, if the first mycobacterial antigenic polypeptide or the first mycobacterial polypeptide comprises an Rv0111 antigen and if the second mycobacterial antigenic polypeptide or the second mycobacterial polynucleotide comprises an Rv0198 antigen, the one or more additional antigenic polypeptides or polynucleotides in the antigenic composition does not comprise (or consist of) an Rv3812 antigen. Alternatively, if the first mycobacterial antigenic polypeptide or the first mycobacterial polypeptide comprises an Rv0198 antigen and if the second mycobacterial antigenic polypeptide or the second mycobacterial polynucleotide comprises an Rv0111 antigen, the one or more additional antigenic polypeptides or polynucleotides in the antigenic composition does not comprise (or consist of) an Rv3812 antigen.

By way of example, in one embodiment, the antigenic composition comprises:

(i) a first mycobacterial antigenic polypeptide, wherein said first mycobacterial antigenic polypeptide comprises a polypeptide sequence having at least 70% amino acid sequence identity to the amino acid sequence of SEQ ID NO: 1, or a fragment thereof having at least 7 consecutive amino acids thereof; or (ii) a first mycobacterial polynucleotide, wherein said first mycobacterial polynucleotide comprises a polynucleotide sequence encoding said first mycobacterial antigenic polypeptide;

and further comprises:

(iii) a second mycobacterial antigenic polypeptide, wherein said second mycobacterial antigenic polypeptide comprises a polypeptide sequence having at least 70% amino acid sequence identity to the amino acid sequence of SEQ ID NO: 5, or a fragment thereof having at least 7 consecutive amino acids thereof; or (iv) a second mycobacterial polynucleotide, wherein said second mycobacterial polynucleotide comprises a polynucleotide sequence encoding said second mycobacterial polypeptide;

and yet further comprises at least one additional mycobacterial antigenic polypeptide, which is different from said first mycobacterial antigenic polypeptide and/or said second mycobacterial antigenic polypeptide; wherein said at least one additional mycobacterial antigenic polypeptide is not an Rv3812 polypeptide antigen.

As discussed above, a "Rv3812 polypeptide antigen" comprises or consists of SEQ ID NO: 7 (or a sequence 'variant' or 'fragment' thereof as defined herein). Thus, in accordance with this embodiment of the invention, the at least one additional mycobacterial antigenic polypeptide may comprise or consist of a polypeptide sequence that has less than 50% amino acid sequence identity to the amino acid sequence of SEQ ID NO: 7, or a fragment thereof having fewer than 7 consecutive amino acids thereof.

In an alternative embodiment, the antigenic composition comprises:

(i) a first mycobacterial antigenic polypeptide, wherein said first mycobacterial antigenic polypeptide comprises a polypeptide sequence having at least 70% amino acid sequence identity to the amino acid sequence of SEQ ID NO: 1, or a fragment thereof having at least 7 consecutive amino acids thereof; or (ii) a first mycobacterial polynucleotide, wherein said first mycobacterial polynucleotide comprises a polynucleotide sequence encoding said first mycobacterial antigenic polypeptide;

and further comprises:

(iii) a second mycobacterial antigenic polypeptide, wherein said second mycobacterial antigenic polypeptide comprises a polypeptide sequence having at least 70% amino acid sequence identity to the amino acid sequence of SEQ ID NO: 5, or a fragment thereof having at least 7 consecutive amino acids thereof; or (iv) a second mycobacterial polynucleotide, wherein said second mycobacterial polynucleotide comprises a polynucleotide sequence encoding said second mycobacterial polypeptide;

and yet further comprises at least one additional mycobacterial polynucleotide, which is different from said first mycobacterial polynucleotide and/or said second mycobacterial polynucleotide; wherein said at least one additional mycobacterial polynucleotide is not an Rv3812 polynucleotide antigen.

As discussed above, a "Rv3812 polynucleotide antigen" comprises or consists of SEQ ID NO: 8 (or a sequence 'variant' or 'fragment' thereof as defined herein). Thus, in accordance with this embodiment of the invention, the at least one additional mycobacterial polynucleotide may comprise or consist of a polynucleotide sequence that has less than 50% nucleotide sequence identity to the nucleic acid sequence of SEQ ID NO: 8, or a fragment thereof having fewer than 21 consecutive nucleotides thereof.

In one embodiment, the antigenic composition does not comprise SEQ ID NO: 1 (or a sequence 'variant' or 'fragment' thereof as defined herein) and SEQ ID NO: 5 (or a sequence 'variant' or 'fragment' thereof as defined herein) and SEQ ID NO: 7 (or a sequence 'variant' or 'fragment' thereof as defined herein).

In one embodiment, the antigenic composition does not comprise SEQ ID NO: 2 (or a sequence 'variant' or 'fragment' thereof as defined herein) and SEQ ID NO: 6 (or a sequence 'variant' or 'fragment' thereof as defined herein) and SEQ ID NO: 8 (or a sequence 'variant' or 'fragment' thereof as defined herein).

In one embodiment, at least two of the mycobacterial antigens in the antigenic composition comprise (or consist of) a polypeptide sequence, and said at least two polypeptide sequences are joined together to form a fusion protein.

By way of example, in one embodiment, the first mycobacterial antigen and second mycobacterial antigen each comprise (or consist of) a polypeptide sequence, as defined above, and said first and second polypeptide sequences are joined together to form a fusion protein.

In one embodiment, said fusion protein is an Rv0111-Rv0198 fusion protein, wherein said Rv0111-Rv0198 fusion protein comprises or consists of (in any order from the N- to C-terminus):

(i) a first mycobacterial antigenic polypeptide, wherein said first mycobacterial antigenic polypeptide comprises (or consists of) a polypeptide sequence having at least 70% amino acid sequence identity to the amino acid sequence of SEQ ID NO: 1, or a fragment thereof having at least 7 consecutive amino acids thereof; and (ii) a second mycobacterial antigenic polypeptide, wherein said second mycobacterial antigenic polypeptide comprises (or consists of) a polypeptide sequence having at least 70% amino acid sequence identity to the amino acid sequence of SEQ ID NO: 5, or a fragment thereof having at least 7 consecutive amino acids thereof.

In one embodiment, said fusion protein is an Rv3812-Rv0198 fusion protein, wherein said Rv3812-Rv0198 fusion protein comprises or consists of (in any order from the N- to C-terminus):

(i) a first mycobacterial antigenic polypeptide, wherein said first mycobacterial antigenic polypeptide comprises (or consists of) a polypeptide sequence having at least 70% amino acid sequence identity to the amino acid sequence of SEQ ID NO: 7, or a fragment thereof having at least 7 consecutive amino acids thereof; and (ii) a second mycobacterial antigenic polypeptide, wherein said second mycobacterial antigenic polypeptide comprises (or consists of) a polypeptide sequence having at least 70% amino acid sequence identity to the amino acid sequence of SEQ ID NO: 5, or a fragment thereof having at least 7 consecutive amino acids thereof.

In one embodiment, said fusion protein further comprises at least one additional mycobacterial antigenic polypeptide sequence, joined to said first and/or second polypeptide sequences, wherein each of said further mycobacterial antigens is different from each other and from the first and second mycobacterial antigens. For example, the fusion protein may comprise at least 1, 2, 3, 4 or 5 further mycobacterial antigens, in addition to said first and second mycobacterial antigens, wherein each of said further mycobacterial antigens is different from each other and from the first and second mycobacterial antigens. In one embodiment, the fusion protein may comprise up to about 10 different mycobacterial antigens (eg. including the first and second mycobacterial antigens).

In one embodiment, the antigenic composition comprises at least one additional mycobacterial antigen (eg. at least 1, 2, 3, 4, 5, 6, 7, 8, 9 or 10 additional mycobacterial antigens) and the first mycobacterial antigen and said at least one additional mycobacterial antigen each comprise (or consist of) a polypeptide sequence, as defined above, and said polypeptide sequences are joined together to form a fusion protein.

In one embodiment, the antigenic composition comprises at least one additional mycobacterial antigen (eg. at least 1, 2, 3, 4, 5, 6, 7, 8, 9 or 10 additional mycobacterial antigens), and the second mycobacterial antigen and said at least one additional mycobacterial antigen each comprise (or consist of) a polypeptide sequence, as defined above, and said polypeptide sequences are joined together to form a fusion protein.

Alternatively, in one embodiment, the antigenic composition comprises at least two additional mycobacterial antigens (eg. at least 2, 3, 4, 5, 6, 7, 8, 9 or 10 additional mycobacterial antigens), and said at least two additional mycobacterial antigens each comprise (or consist of) a polypeptide sequence, as defined above, and said polypeptide sequences are joined together to form a fusion protein.

In one embodiment, the antigenic composition does not comprise a fusion protein comprising both a Rv1806 antigen and a Rv1807 antigen. Thus, in one embodiment, the antigenic composition does not comprise a fusion protein comprising both SEQ ID NO: 3 (or a sequence 'variant' or 'fragment' thereof as defined herein) and SEQ ID NO: 56 (or a sequence 'variant' or 'fragment' thereof as defined herein).

In one embodiment, the antigenic composition does not comprise a fusion protein consisting of a Rv1806 antigen and a Rv1807 antigen. Thus, in one embodiment, the antigenic composition does not comprise a fusion protein consisting of both SEQ ID NO: 3 (or a sequence 'variant' or 'fragment' thereof as defined herein) and SEQ ID NO: 56 (or a sequence 'variant' or 'fragment' thereof as defined herein).

In one embodiment, if the antigenic composition comprises an Rv0111 antigen and an Rv1098 antigen (eg. separately, or in the form of a fusion protein), the antigenic composition (or fusion protein) does not also comprise an Rv3821 antigen.

Thus, in one embodiment, the antigenic composition does not comprise a fusion protein comprising or consisting of: SEQ ID NO: 1 (or a sequence 'variant' or 'fragment' thereof as defined herein) and SEQ ID NO: 5 (or a sequence 'variant' or 'fragment' thereof as defined herein) and SEQ ID NO: 7 (or a sequence 'variant' or 'fragment' thereof as defined herein).

The order of the polypeptide sequences in the fusion protein is not important.

Techniques for preparing fusion proteins are well known in the art.

In one embodiment, a recombinant fusion protein may be generated by expression of a recombinant polynucleotide sequence that encodes said fusion protein. By way of example, polynucleotide sequences encoding mycobacterial antigenic polypeptides of the invention may be positioned in the same reading frame downstream of a promoter in an expression vector, thereby allowing transcription through the polynucleotide sequences and translation as one protein product.

In one embodiment, intervening 'linker' sequences are located between the polynucleotide sequence for each polypeptide antigen, arising from the inclusion of restriction sites. In general, the amino acids encoded by these linker sequences are not deleterious to the immunogenicity of the resultant fusion protein, and may even be beneficial to immunogenicity. Alternatively, a fusion protein of the invention may be produced as an epitope string, by expression of polynucleotide sequences that are linked without intervening nucleotides. The absence of intervening linker sequence avoids the presence of unnecessary nucleic acid and/or amino acid material.

Alternatively, a fusion protein of the invention may be prepared by chemically conjugating the mycobacterial antigenic polypeptides of the invention. By way of example, the first and/or second and/or additional mycobacterial polypeptides of the invention may be coupled to each other using conventional chemical conjugation techniques.

In one embodiment, at least two of the mycobacterial antigens in the antigenic composition comprise (or consist of) a polynucleotide sequence, and said at least two polynucleotide sequences are joined together to form a polycistronic nucleic acid sequence.

By way of example, in one embodiment, the first mycobacterial antigen and second mycobacterial antigen each comprise (or consist of) a polynucleotide sequence, as defined above, and said first and second polynucleotide sequences are joined together to form a polycistronic nucleic acid sequence.

In one embodiment, said polycistronic nucleic acid sequence comprises or consists of (in any order from the 5' to 3' end):

(i) a first mycobacterial polynucleotide, wherein said first mycobacterial polynucleotide comprises (or consists of) a polynucleotide sequence encoding a first mycobacterial antigenic polypeptide, wherein said first mycobacterial antigenic polypeptide comprises (or consists of) a polypeptide sequence having at least 70% amino acid sequence identity to the amino acid sequence of SEQ ID NO: 1, or a fragment thereof having at least 7 consecutive amino acids thereof; and (ii) a second mycobacterial polynucleotide, wherein said second mycobacterial polynucleotide comprises (or consists of) a polynucleotide sequence encoding a second mycobacterial antigenic polypeptide, wherein said second mycobacterial antigenic polypeptide comprises (or consists of) a polypeptide sequence having at least 70% amino acid sequence identity to the amino acid sequence of SEQ ID NO: 5, or a fragment thereof having at least 7 consecutive amino acids thereof.

In one embodiment, said first mycobacterial polynucleotide comprises (or consists of) a polynucleotide sequence having at least 70% nucleotide sequence identity to the nucleic acid sequence of SEQ ID NO: 2, or a fragment thereof having at least 21 consecutive nucleotides thereof. In one embodiment, said second mycobacterial polynucleotide comprises (or consists of) a polynucleotide sequence having at least 70% nucleotide sequence identity to the nucleic acid sequence of SEQ ID NO: 6, or a fragment thereof having at least 21 consecutive nucleotides thereof.

In one embodiment, said polycistronic nucleic acid sequence comprises or consists of (in any order from the 5' to 3' end):

(i) a first mycobacterial polynucleotide, wherein said first mycobacterial polynucleotide comprises (or consists of) a polynucleotide sequence encoding a first mycobacterial antigenic polypeptide, wherein said first mycobacterial antigenic polypeptide comprises (or consists of) a polypeptide sequence having at least 70% amino acid sequence identity to the amino acid sequence of SEQ ID NO: 7, or a fragment thereof having at least 7 consecutive amino acids thereof; and (ii) a second mycobacterial polynucleotide, wherein said second mycobacterial polynucleotide comprises (or consists of) a polynucleotide sequence encoding a second mycobacterial antigenic polypeptide, wherein said second mycobacterial antigenic polypeptide comprises (or consists of) a polypeptide sequence having at least 70% amino acid sequence identity to the amino acid sequence of SEQ ID NO: 5, or a fragment thereof having at least 7 consecutive amino acids thereof.

In one embodiment, said first mycobacterial polynucleotide comprises (or consists of) a polynucleotide sequence having at least 70% nucleotide sequence identity to the nucleic acid sequence of SEQ ID NO: 8, or a fragment thereof having at least 21 consecutive nucleotides thereof. In one embodiment, said second mycobacterial polynucleotide comprises (or consists of) a polynucleotide sequence having at least 70% nucleotide sequence identity to the nucleic acid sequence of SEQ ID NO: 6, or a fragment thereof having at least 21 consecutive nucleotides thereof.

In one embodiment, said polycistronic sequence further comprises at least one additional mycobacterial antigenic polynucleotide sequence, joined to said first and second polynucleotide sequences.

Alternatively, in one embodiment, the antigenic composition comprises at least one additional mycobacterial antigen, and the first mycobacterial antigen and at least one additional mycobacterial antigen each comprise (or consist of) a polynucleotide sequence, as defined above, and said polynucleotide sequences are joined together to form a polycistronic nucleic acid sequence.

Alternatively, in one embodiment, the antigenic composition comprises at least one additional mycobacterial antigen, and the second mycobacterial antigen and at least one additional mycobacterial antigen each comprise (or consist of) a polynucleotide sequence, as defined above, and said polynucleotide sequences are joined together to form a polycistronic nucleic acid sequence.

Alternatively, in one embodiment, the antigenic composition comprises at least two additional mycobacterial antigens, and said at least two additional mycobacterial antigens each comprise (or consist of) a polynucleotide sequence, as defined above, and said polynucleotide sequences are joined together to form a polycistronic nucleic acid sequence.

In one embodiment, the polycistronic sequence does not comprise both a Rv1806 antigen and a Rv1807 antigen. In one embodiment, the polycistronic sequence does not consist of a Rv1806 antigen and a Rv1807 antigen.

Thus, in one embodiment, the polycistronic sequence does not comprise both SEQ ID NO: 3 (or a sequence 'variant' or 'fragment' thereof as defined herein) and SEQ ID NO: 56 (or a sequence 'variant' or 'fragment' thereof as defined herein). In one embodiment, the antigenic composition does not consist of both SEQ ID NO: 3 (or a sequence 'variant' or 'fragment' thereof as defined herein) and SEQ ID NO: 56 (or a sequence 'variant' or 'fragment' thereof as defined herein).

In one embodiment, if the antigenic composition comprises a Rv0111 antigen and a Rv0198 antigen (eg. in the form of a polycistronic sequence comprising or consisting of a Rv0111 polynucleotide and a Rv0198 polynucleotide), the antigenic composition (or polycistronic sequence) does not also comprise a Rv3812 antigen. Thus, in one embodiment, if the antigenic composition comprises a polycistronic sequence comprising or consisting of SEQ ID NO: 2 (or a sequence 'variant' or 'fragment' thereof as defined herein) and SEQ ID NO: 6 (or a sequence 'variant' or 'fragment' thereof as defined herein), the antigenic composition does not also comprise SEQ ID NO: 8 (or a sequence 'variant' or 'fragment' thereof as defined herein).

In one embodiment, the polycistronic sequence does not comprise or consist of a Rv0111 antigen, a Rv0198 antigen and a Rv3812 antigen. Thus, in one embodiment, the polycistronic sequence does not comprise or consist of SEQ ID NO: 2 (or a sequence 'variant' or 'fragment' thereof as defined herein) and SEQ ID NO: 6 (or a sequence 'variant' or 'fragment' thereof as defined herein) and SEQ ID NO: 8 (or a sequence 'variant' or 'fragment' thereof as defined herein).

The order of the polynucleotide sequences in the polycistronic sequence from 5' to 3' is not important.

Techniques for preparing polycistronic nucleic acid sequences are known in the art and typically involve preparing a recombinant molecule comprising the individual polynucleotide sequences in the same reading frame.

In one embodiment, the polycistronic nucleic acid sequence of the invention is positioned downstream of a promoter in frame in a vector (eg. an expression vector or viral vector as discussed below), thereby allowing transcription through the polynucleotide sequences and optional translation as one 'fusion protein' product.

Accordingly, in one embodiment, the polycistronic nucleic acid sequence encodes a fusion protein as discussed above. Alternatively, in one embodiment, the polycistronic nucleic acid sequence encodes separate mycobacterial antigenic polypeptide sequences, as discussed above.

In one embodiment, the polycistronic nucleic acid sequence is operably linked to a nucleic acid sequence encoding a tag polypeptide, such that the encoded tag is covalently linked to the encoded antigenic polypeptide(s) upon translation.

The tag may facilitate detection of antigenic polypeptide expression, or detection of clones that express the antigen, and/or may lead to increases in antigen efficacy. Suitable tag polypeptides include a PK tag, FLAG tag, MYC tag, polyhistidine tag or any detectable tag (eg. a tag that can be detected by an antibody such as a monoclonal antibody). Other examples of tags will be clear to skilled persons in the art. A PK tag may have the sequence Pro-Asn-Pro-Leu-Gly-Leu-Asp (SEQ ID NO: 33).

The nucleic acid sequence encoding the tag polypeptide may be positioned such that, following translation, the tag is located at the C-terminus of the expressed antigenic polypeptide (ie. in the order: antigenic polypeptide-tag). Alternatively, the nucleic acid sequence encoding the tag polypeptide may be positioned such that, following translation, the tag is located at the N-terminus of the expressed antigenic polypeptide (ie. in the order: tag—antigenic polypeptide). Alternatively, the nucleic acid sequence encoding the tag polypeptide may be positioned such that, following translation, the tag is located internally to the expressed antigenic polypeptide, or between the expressed antigenic polypeptides of an encoded fusion protein.

Nucleotides encoding a linker sequence may be inserted between the polycistronic nucleic acid sequence encoding the antigenic polypeptide(s) and the nucleic acid sequence encoding the tag polypeptide. In one embodiment, the linker sequence encodes the amino acid sequence Gly-Ser-Ile.

In one embodiment, the encoded linker sequence is located between an expressed antigenic polypeptide and a tag polypeptide (ie. in the order: antigenic polypeptide-linker-tag, or tag-linker-antigenic polypeptide). In one embodiment, the nucleic acid sequence encoding the tag polypeptide and the nucleotides encoding the linker sequence are positioned such that, following translation, the linker sequence (eg. Gly-Ser-Ile) is located at the C-terminus of the expressed antigenic polypeptide and the tag is located at the C-terminus of the expressed linker sequence (ie. in the order antigenic polypeptide-linker-tag).

Intervening 'linker' sequences (eg. encoding Gly-Ser-Ile) may alternatively (or additionally) be located between the mycobacterial polynucleotide sequences of the polycistronic sequence, arising from the inclusion of restriction sites (eg. in the form: mycobacterial polynucleotide-linker-mycobacterial polynucleotide). However, to avoid the presence of unnecessary nucleic acid and/or amino acid material, the polynucleotide sequences may be linked without intervening nucleotides.

In one embodiment, the polycistronic nucleic acid sequence is operably linked to a leader sequence. For example, the leader sequence may be fused to the N-terminus of the polycistronic sequence (ie. in the form: leader—polycistronic sequence) or to the C-terminus of the polycistronic sequence (ie. in the form: polycistronic sequence—leader).

A leader sequence may affect processing of a primary DNA transcript to mRNA, and/or may affect mRNA stability or translation efficiency. In one embodiment, a leader sequence ensures that the encoded polypeptide antigen is directed to the secretory machinery of a host cell. In one embodiment, a leader sequence enhances expression and/or immunogenicity of the antigen. Enhanced expression may be determined by a conventional assay, such as using an antibody (eg. monoclonal antibody) to detect the amount of protein produced. Enhanced immunogenicity may be determined using a conventional assay such as a cultured or ex vivo ELISPOT assay. In one embodiment, the presence of a leader sequence enhances the expression and/or immunogenicity of the mycobacterial antigenic polypeptide by 2-fold, 3-fold or more when compared with antigenic polypeptide expressed without the leader sequence.

An example of a suitable leader sequence is t-PA (tissue plasminogen activator).

Accordingly, in one embodiment, the polycistronic nucleic acid sequence encoding said mycobacterial antigenic polypeptides is operably linked to a leader sequence and a tag sequence. For example, the leader sequence may be fused to the N-terminus of the polycistronic sequence and the tag sequence may be fused to the C-terminus of the polycistronic sequence (ie. in the form: leader-polycistronic sequence-tag. In one embodiment, a linker sequence (eg. Gly-Ser-Ile) is located between the polycistronic sequence and the nucleic acid sequence encoding the tag (ie. in the form leader-polycistronic sequence-linker-tag).

In one embodiment, the leader sequence is a t-PA leader sequence and/or the tag sequence is a PK tag sequence (ie. in the form: t-PA leader-polycistronic sequence-PK tag). In one embodiment, a linker sequence (eg. Gly-Ser-Ile) is located between the polycistronic sequence and the nucleic acid sequence encoding the tag (ie. in the form t-PA leader-polycistronic sequence-linker-PK tag).

In one embodiment, intervening leader sequences are located between one or more of the mycobacterial polynucleotide sequences of the polycistronic sequence (ie. in the form: mycobacterial polynucleotide-leader-mycobacterial polynucleotide).

In one embodiment, the polycistronic nucleic acid sequence encoding the mycobacterial antigenic polypeptides is operably linked to an N-terminal leader sequence, internal leader sequence and a tag sequence (ie. in the form: leader-first mycobacterial polynucleotide-leader-second mycobacterial polynucleotide-tag). In one embodiment, a linker sequence (eg. Gly-Ser-Ile) is located between the polycistronic sequence and the nucleic acid sequence encoding the tag (ie. in the form: leader-first mycobacterial polynucleotide-leader-second mycobacterial polynucleotide-linker-tag).

In one embodiment, the leader sequence is a t-PA leader sequence and/or the tag sequence is a PK tag sequence (ie. in the form: t-PA leader-first mycobacterial polynucleotide-t-PA leader-second mycobacterial polynucleotide-PK tag).

In one embodiment, a linker sequence (eg. Gly-Ser-Ile) is located between the polycistronic sequence and the nucleic acid sequence encoding the tag (ie. in the form t-PA leader-first mycobacterial polynucleotide-t-PA leader-second mycobacterial polynucleotide-linker-PK tag).

In one embodiment, the polycistronic nucleic acid sequence further comprises a polyadenylation signal, such as a bovine growth hormone (BGH) polyadenylation signal.

In one embodiment, the antigenic composition comprises one or more cells, wherein said cells comprise at least one of the mycobacterial antigens.

In one embodiment, said one or more cells comprise a first mycobacterial antigen, as defined above. In one embodiment, said first mycobacterial antigen comprises a polypeptide sequence as defined above, such as an Rv0111 or Rv3812 polypeptide sequence as defined above. In one embodiment, said first mycobacterial antigen comprises a polynucleotide sequence as defined above, such as an Rv0111 or Rv3812 polynucleotide sequence as defined above.

In one embodiment, said one or more cells comprise a second mycobacterial antigen, as defined above. In one embodiment, said second mycobacterial antigen comprises a polypeptide sequence as defined above, such as an Rv0198 polypeptide sequence as defined above. In one embodiment, said second mycobacterial antigen comprises a polynucleotide sequence as filed above, such as an Rv0198 polynucleotide sequence as defined above.

In one embodiment, said one or more cells comprises one or more of said additional mycobacterial antigens, as defined above. In one embodiment, one or more of said additional mycobacterial antigens comprises a polypeptide sequence as defined above. In one embodiment, one or more of said additional mycobacterial antigens comprises a polynucleotide sequence as filed above.

In one embodiment, the limitations discussed above with respect to an antigenic composition comprising first and second mycobacterial antigens apply equally to an antigenic composition comprising one or more cells, wherein said cells comprise at least one of the mycobacterial antigens.

In one embodiment, said at least one mycobacterial antigen (eg. polypeptide) is at least partially exposed at the surface of the cell(s).

In an alternative embodiment, the cell becomes degraded in vivo so that at least part of the mycobacterial antigen (eg. polypeptide) becomes exposed to a host's immune system. In an alternative embodiment, the cell at least partially releases (eg. secretes or exports) the mycobacterial antigen (eg. polypeptide) to the outside of the cell, so that it is exposed to a host's immune system.

In one embodiment, said antigenic composition comprises an individual cell, wherein said cell comprises at least two of said mycobacterial antigens.

By way of example, in one embodiment, said antigenic composition comprises an individual cell, wherein said cell comprises both said first mycobacterial antigen and said second mycobacterial antigen. In one embodiment, said individual cell comprises an Rv0111 polypeptide or polynucleotide antigen or an Rv3812 polypeptide or polynucleotide antigen as defined herein, and also comprises an Rv0198 polypeptide or polynucleotide antigen as defined herein. In one embodiment, said individual cell further comprises one or more of said additional mycobacterial antigens.

In one embodiment, said antigenic composition comprises an individual cell, wherein said cell comprises said first mycobacterial antigen and said one or more additional mycobacterial antigens. In one embodiment, said antigenic composition comprises an individual cell, wherein said cell comprises said second mycobacterial antigen and said one more additional mycobacterial antigens. In one embodiment, said antigenic composition comprises an individual cell, wherein said cell comprises said at least two of said additional mycobacterial antigens.

In an alternative embodiment, the antigenic composition comprises at least first and second cells, wherein said first cell comprises said first mycobacterial antigen (as defined above) and wherein said second cell comprises said second mycobacterial antigen (as defined above). In this embodiment, the first and second mycobacterial antigens are not present in the same cell; rather, the first and second mycobacterial antigens are in different cells.

In one embodiment, said antigenic composition further comprises at least a third cell, wherein said cell comprises an additional mycobacterial antigen, as defined above.

In one embodiment, if said antigenic composition comprises an Rv0111 polypeptide or polynucleotide antigen as defined herein, and an Rv0198 polypeptide or polynucleotide antigen as defined herein (eg. in the same or different cells), said antigenic composition (or said cell) does not also comprise an Rv3812 polypeptide or polynucleotide antigen as defined herein.

In one embodiment, said at least one cell is an attenuated microbial carrier. An attenuated carrier is a cell (such as a bacterial cell) that is incapable of causing a significant pathological effect in an animal subject, typically a mammalian subject such as a human, bovine, porcine or equine subject.

Suitable examples of attenuated microbial carriers include attenuated salmonella, attenuated *M. tuberculosis*, or attenuated *M. bovis* (eg. BCG strain).

In one embodiment, the antigenic composition comprises one or more vectors, wherein said vectors comprise at least one of the mycobacterial antigens.

In one embodiment, said one or more vectors comprises a first mycobacterial antigen, as defined above. In one embodiment, said first mycobacterial antigen comprises a polypeptide sequence as defined above, such as a Rv0111 polypeptide antigen or Rv3812 polypeptide antigen, as defined herein. In one embodiment, said first mycobacterial antigen comprises a polynucleotide sequence as filed above, such as a Rv0111 polynucleotide antigen or Rv3812 polynucleotide antigen, as defined herein.

In one embodiment, said one or more vectors comprises a second mycobacterial antigen, as defined above. In one embodiment, said second mycobacterial antigen comprises a polypeptide sequence as defined above, such as a Rv0198 polypeptide antigen, as defined herein. In one embodiment, said second mycobacterial antigen comprises a polynucleotide sequence as filed above, such as a Rv0198 polynucleotide antigen, as defined herein.

In one embodiment, said vector comprises said first mycobacterial antigen and said second mycobacterial antigen. By way of example, said vector may comprise a first mycobacterial polynucleotide as defined herein and a second mycobacterial polynucleotide as defined herein.

In one embodiment, said vector comprises:

(i) a first mycobacterial polynucleotide, wherein said first mycobacterial polynucleotide comprises (or consists of) a polynucleotide sequence encoding a first mycobacterial antigenic polypeptide, wherein said first mycobacterial antigenic polypeptide comprises (or consists of) a polypeptide sequence having at least 70% amino acid sequence identity to the amino acid sequence of SEQ ID NO: 1, or a fragment thereof having at least 7 consecutive amino acids thereof; and (ii) a second mycobacterial polynucleotide, wherein said second mycobacterial polynucleotide comprises (or consists of) a polynucleotide sequence encoding a second mycobacterial antigenic polypeptide, wherein said second mycobacterial antigenic polypeptide comprises (or consists of) a polypeptide sequence having at least 70% amino acid sequence identity to the amino acid sequence of SEQ ID NO: 5, or a fragment thereof having at least 7 consecutive amino acids thereof.

In one embodiment, said first mycobacterial polynucleotide comprises (or consists of) a polynucleotide sequence having at least 70% nucleotide sequence identity to the nucleic acid sequence of SEQ ID NO: 2, or a fragment thereof having at least 21 consecutive nucleotides thereof. In one embodiment, said second mycobacterial polynucleotide comprises (or consists of) a polynucleotide sequence having at least 70% nucleotide sequence identity to the nucleic acid sequence of SEQ ID NO: 6, or a fragment thereof having at least 21 consecutive nucleotides thereof.

In one embodiment, said vector comprises or consists of:

(i) a first mycobacterial polynucleotide, wherein said first mycobacterial polynucleotide comprises (or consists of) a polynucleotide sequence encoding a first mycobacterial antigenic polypeptide, wherein said first mycobacterial antigenic polypeptide comprises (or consists of) a polypeptide sequence having at least 70% amino acid sequence identity to the amino acid sequence of SEQ ID NO: 7, or a fragment thereof having at least 7 consecutive amino acids thereof; and (ii) a second mycobacterial polynucleotide, wherein said second mycobacterial polynucleotide comprises (or consists of) a polynucleotide sequence encoding a second mycobacterial antigenic polypeptide, wherein said second mycobacterial antigenic polypeptide comprises (or consists of) a polypeptide sequence having at least 70% amino acid sequence identity to the amino acid sequence of SEQ ID NO: 5, or a fragment thereof having at least 7 consecutive amino acids thereof.

In one embodiment, said first mycobacterial polynucleotide comprises (or consists of) a polynucleotide sequence having at least 70% nucleotide sequence identity to the nucleic acid sequence of SEQ ID NO: 8, or a fragment thereof having at least 21 consecutive nucleotides thereof. In one embodiment, said second mycobacterial polynucleotide comprises (or consists of) a polynucleotide sequence having at least 70% nucleotide sequence identity to the nucleic acid sequence of SEQ ID NO: 6, or a fragment thereof having at least 21 consecutive nucleotides thereof.

In one embodiment, said one or more vectors comprises one or more of said additional mycobacterial antigens, as defined above. In one embodiment, one or more of said additional mycobacterial antigens comprises a polypeptide sequence as defined above. In one embodiment, one or more of said additional mycobacterial antigens comprises a polynucleotide sequence as filed above.

In one embodiment, if said antigenic composition comprises an Rv0111 polypeptide or polynucleotide antigen as defined herein, and an Rv0198 polypeptide or polynucleotide antigen as defined herein (eg. in the same or different vectors), said antigenic composition (or said vector) does not also comprise an Rv3812 polypeptide or polynucleotide antigen as defined herein.

In one embodiment, the limitations discussed above with respect to an antigenic composition comprising first and second mycobacterial antigens apply equally to an antigenic composition one or more vectors, wherein said vectors comprise at least one of the mycobacterial antigens.

Examples of vectors include DNA vectors and RNA vectors. The term 'vector' embraces expression vectors (which may be useful for preparation of mycobacterial antigens of the invention), and viral vectors (which may be useful for replication and/or delivery of mycobacterial antigens of the invention).

The vectors optionally include appropriate control sequences such as a promoter and/or terminator. Expression control sequences for such vectors are known to those skilled in the art and may be selected depending upon the host cells. Further discussion of conventional vector components is provided later in the specification.

In one embodiment, the vector comprises one or more polynucleotide sequence(s) encoding said mycobacterial antigen(s). Said polynucleotide sequence may be operably linked to a nucleic acid sequence encoding a tag polypeptide, such that the encoded tag is covalently linked to the antigen upon translation. The tag may facilitate detection of antigen expression, or of clones that express the antigen, and/or may lead to increases in antigen efficacy.

Suitable tag polypeptides include a PK tag, FLAG tag, MYC tag, polyhistidine tag or any detectable tag (eg. a tag that can be detected by an antibody such as a monoclonal antibody). Other examples of tags will be clear to skilled persons in the art. A PK tag may have the sequence Pro-Asn-Pro-Leu-Gly-Leu-Asp (SEQ ID NO: 33).

The nucleic acid sequence encoding the tag polypeptide may be positioned such that, following translation, the tag is located at the C-terminus of the expressed antigen. Alternatively, the nucleic acid sequence encoding the tag polypeptide may be positioned such that, following translation, the tag is located at the N-terminus of the expressed antigen. Alternatively, the nucleic acid sequence encoding the tag polypeptide may be positioned such that, following translation, the tag is located internally to the expressed antigen.

Nucleotides encoding a linker sequence may be inserted between the polynucleotide encoding the expressed antigen and the nucleic acid sequence encoding the tag polypeptide. In one embodiment, the encoded linker sequence is located between an expressed antigen polypeptide and a tag polypeptide. In one embodiment, the linker sequence encodes the amino acid sequence Gly-Ser-Ile.

In one embodiment, the nucleic acid sequence encoding the tag polypeptide and the nucleotides encoding the linker sequence are be positioned such that, following translation, the linker sequence (eg. Gly-Ser-Ile) is located at the C-terminus of the expressed antigen and the tag is located at the C-terminus of the expressed linker sequence.

In one embodiment, the vector comprises one or more polynucleotide sequences encoding mycobacterial antigenic polypeptide(s), wherein said polynucleotide sequence is operably linked to a leader sequence. A leader sequence may affect processing of the primary transcript to mRNA, and/or may affect mRNA stability or translation efficiency. In one embodiment, a leader sequence ensures that the encoded polypeptide antigen is directed to the secretory machinery of a host cell. In one embodiment, a leader sequence enhances expression and/or immunogenicity of the antigen. Enhanced immunogenicity may be determined using a conventional assay such as a cultured or ex vivo ELISPOT assay. Enhanced expression may be determined by a conventional assay, such as using an antibody (eg. monoclonal antibody) to detect the amount of protein produced. In one embodiment, the presence of a leader sequence enhances the expression and/or immunogenicity of the mycobacterial antigen by 2-fold, 3-fold or more when compared with antigen expressed without the leader sequence.

An example of a suitable leader sequence is t-PA (tissue plasminogen activator).

In one embodiment, the vector comprises a C-terminally truncated polynucleotide encoding said mycobacterial antigen fused to a t-PA leader sequence. In one embodiment, the vector comprises a C-terminally truncated polynucleotide encoding said mycobacterial antigen fused to a t-PA leader sequence and a PK tag sequence. For example, the leader sequence may be fused to the N-terminus of the polynucleotide encoding the antigen and the tag sequence may be fused to the C-terminus of the polynucleotide encoding the antigen. In one embodiment, a linker sequence (eg. Gly-Ser-Ile) is located between the polynucleotide encoding the antigen and the nucleic acid sequence encoding the tag.

In one embodiment, said antigenic composition comprises an individual vector, wherein said vector comprises both said first mycobacterial antigen and said second mycobacterial antigen. In one embodiment, said individual vector further comprises one or more of said additional mycobacterial antigens.

In one embodiment, said antigenic composition comprises an individual vector, wherein said vector comprises said first mycobacterial antigen and said one or more additional mycobacterial antigens. In one embodiment, said antigenic composition comprises an individual vector, wherein said vector comprises said second mycobacterial antigen and said one more additional mycobacterial antigens. In one embodiment, said antigenic composition comprises an individual vector, wherein said cell comprises said one or more additional mycobacterial antigens.

In an alternative embodiment, the antigenic composition comprises at least first and second vectors, wherein said first vector comprises said first mycobacterial antigen (as defined above) and wherein said second vector comprises said second mycobacterial antigen (as defined above). In this embodiment, the first and second mycobacterial antigens are not present in the same vector; rather, first and second mycobacterial antigens are in different vectors.

In one embodiment, said antigenic composition further comprises at least a third vector, wherein said third vector comprises an (one or more) additional mycobacterial antigen(s), as defined above.

In one embodiment, the vector (or at least one of said vectors) is a viral vector.

Viral vectors are usually non-replicating or replication-impaired vectors, which means that the viral vector cannot replicate to any significant extent in normal cells (eg. normal human cells), as measured by conventional means—eg. via measuring DNA synthesis and/or viral titre. Non-replicating or replication-impaired vectors may have become so naturally (ie. they have been isolated as such from nature) or artificially (eg. by breeding in vitro or by genetic manipulation). There will generally be at least one cell-type in which the replication-impaired viral vector can be grown—for example, modified vaccinia Ankara (MVA) can be grown in CEF cells.

Typically, the viral vector is incapable of causing a significant infection in an animal subject, typically in a mammalian subject such as a human, bovine, porcine or equine patient.

Examples of viral vectors that are useful in this context include attenuated vaccinia virus vectors such as modified vaccinia Ankara (MVA) and NYVAC, or strains derived therefrom.

Other suitable viral vectors include poxvirus vectors, such as avipox vectors, for example attenuated fowlpox vectors (eg. FP9) or canarypox vectors (eg. ALVAC and strains derived therefrom). Alternative viral vectors useful in the present invention include adenoviral vectors (eg. non-human adenovirus vectors), alphavirus vectors, flavivirus vectors, herpes viral vectors, influenza virus vectors and retroviral vectors.

In one embodiment, the vector (or at least one of said vectors) is an expression vector.

Expression vectors are nucleic acid molecules (linear or circular) that comprise one or more polynucleotide sequences encoding a polypeptide(s) of interest, operably linked to additional regulatory elements required for its expression.

In this regard, expression vectors generally include promoter and terminator sequences, and optionally one or more enhancer sequences, polyadenylation signals, and the like. Expression vectors may also include suitable translational regulatory elements, including ribosomal binding sites, and translation initiation and termination sequences. The transcriptional and translational regulatory elements employed in the expression vectors of the invention are functional in the host cell used for expression, and may include those naturally associated with mycobacterial genes.

The selection of suitable promoters, terminators, selectable markers and other elements is a matter of routine design within the level of ordinary skill in the art.

Promoters such as the trp, lac and phage promoters, tRNA promoters and glycolytic enzyme promoters may be used in prokaryotic hosts. Useful yeast promoters include the promoter regions for metallothionein, 3-phosphoglycerate kinase or other glycolytic enzymes such as enolase or glyceraldehyde-3-phosphate dehydrogenase, enzymes responsible for maltose and galactose utilization, and others. Appropriate non-native mammalian promoters may include the early and late promoters from SV40 or promoters derived from murine moloney leukemia virus, mouse mammary tumour virus, avian sarcoma viruses, adenovirus II, bovine papilloma virus or polyoma. In one embodiment, the expression vector comprises a CMV promoter.

Generally, "operably linked" means that the nucleic acid sequences being linked are contiguous and arranged so that they function in concert for their intended purposes—for example, transcription initiates in the promoter and proceeds through the coding polynucleotide segment to the terminator. Where necessary to join two protein coding regions, the polynucleotide coding sequences should be contiguous and in reading frame. In one embodiment, the invention provides a host cell comprising an antigenic composition of the invention, as defined above. The host cell thus comprises the first mycobacterial antigen and second mycobacterial antigen of the invention, wherein said mycobacterial antigens may comprise polypeptide and/or polynucleotide sequences, as discussed above.

Accordingly, in one embodiment, a host cell comprises an antigenic composition comprising a first mycobacterial antigen and a second mycobacterial antigen; wherein said first mycobacterial antigen comprises:

(i) a polypeptide sequence having at least 70% amino acid sequence identity to the amino acid sequence of a latency-regulated polypeptide selected from SEQ ID NOs: 1, 3, 5, 7 and 56, or a fragment thereof having at least 7 consecutive amino acids thereof; or (ii) a polynucleotide sequence encoding a polypeptide sequence according to (i); or a polynucleotide sequence having at least 70% nucleotide sequence identity to the nucleic acid sequence of a latency-regulated polynucleotide selected from SEQ ID NOs: 2, 4, 6, 8 and 57, or a fragment thereof having at least 21 consecutive nucleotides thereof;

and wherein said second mycobacterial antigen is different from said first mycobacterial antigen.

In one embodiment, said host cell comprises either:

(i) a first mycobacterial antigenic polypeptide, wherein said first mycobacterial antigenic polypeptide comprises a polypeptide sequence having at least 70% amino acid sequence identity to the amino acid sequence of SEQ ID NO: 1 or 7, or a fragment thereof having at least 7 consecutive amino acids thereof; or (ii) a first mycobacterial polynucleotide, wherein said first mycobacterial polynucleotide comprises a polynucleotide sequence encoding said first mycobacterial antigenic polypeptide;

and also comprises either:

(iii) a second mycobacterial antigenic polypeptide, wherein said second mycobacterial antigenic polypeptide comprises a polypeptide sequence having at least 70% amino acid sequence identity to the amino acid sequence of SEQ ID NO: 5, or a fragment thereof having at least 7 consecutive amino acids thereof; or (iv) a second mycobacterial polynucleotide, wherein said second mycobacterial polynucleotide comprises a polynucleotide sequence encoding said second mycobacterial polypeptide.

The antigenic compositions, polynucleotides or polypeptides of the present invention may be prepared by expressing the polynucleotide sequences of the invention in vectors or other expression vehicles in compatible prokaryotic or eukaryotic host cells using standard molecular biology methods (e.g., Sambrook et al. 1989, Molecular Cloning a Laboratory Manual, Second Edition, Cold Spring Harbor Laboratory Press, Cold Spring Harbor, N.Y.; incorporated herein by reference).

The most commonly used prokaryotic hosts are strains of *E. coli*, although other prokaryotes, such as *B. subtilis* or *Pseudomonas* may be used. Mammalian or other eukaryotic host cells, such as those of yeast, filamentous fungi, plant, insect, amphibian or avian species, may also be useful in the present invention. Propagation of mammalian cells in culture is per se well known. Examples of commonly used mammalian host cell lines are VERO and HeLa cells, Chinese hamster ovary (CHO) cells, and WI38, BHK, and COS cell lines, although other cell lines may be appropriate, e.g., to provide higher expression.

As used herein, "recombinant host cells", "host cells", "cells", "cell lines", "cell cultures", and other such terms denoting microorganisms or higher eukaryotic cell lines cultured as unicellular entities refer to cells which can be, or have been, used as recipients for recombinant vector or other transfer DNA, and include the progeny of the original cell which has been transformed. It is understood that the progeny of a single parental cell may not necessarily be completely identical in morphology or in genomic or total DNA complement as the original parent, due to natural, accidental or deliberate mutation.

Polynucleotide sequences of interest can be transcribed in vitro and the resulting RNA introduced into the host cell (eg. by injection), or the polynucleotide sequences can be introduced directly into host cells by methods which vary depending on the type of cellular host, including electroporation; transfection employing calcium chloride, rubidium chloride, calcium phosphate, DEAE-dextran, or other substances; microprojectile bombardment; lipofection; infection (where the vector is an infectious agent, such as a retroviral genome). "Transformation" refers to the insertion of an exogenous polynucleotide into a host cell, irrespective of the method used for the insertion, for example, direct uptake, transduction, f-mating or electroporation.

Vectors may replicate autonomously, or may replicate by being inserted into the genome of a host cell, in which case they include an insertion sequence.

Expression and cloning vectors may contain a selectable marker, a gene encoding a protein necessary for the survival or growth of a host cell transformed with the vector. This gene ensures the growth of only those host cells which express the inserts. Conventional selection genes encode proteins that (a) confer resistance to antibiotics or other toxic substances, eg. ampicillin, neomycin, methotrexate, etc.; (b) complement auxotrophic deficiencies; or (c) supply critical nutrients not available from complex media, e.g. the gene encoding D-alanine racemase for Bacilli. The choice of appropriate selectable marker will depend on the host cell.

The transformed host cell can be cultured in accordance with known methods, and the expressed polypeptide may be recovered and isolated (eg. from the culture medium) using conventional protocols.

In one aspect, the present invention provides a method for producing an antigenic composition comprising (at least) a first mycobacterial antigen and a second mycobacterial antigen, as defined above; said method comprising:

(a) expressing polynucleotide sequences as defined above that encode said at least first and second mycobacterial antigens; or (b) culturing a host cell as described above, whereby said cell produces said at least first and second mycobacterial antigens;

and recovering the expressed antigens.

In one embodiment, the limitations discussed above with respect to an antigenic composition comprising first and second mycobacterial antigens apply equally to the above-mentioned method for producing an antigenic composition comprising at least first and second mycobacterial antigens.

The invention also relates to antibodies that bind a first mycobacterial antigen (eg. polypeptide) as defined above and a second mycobacterial antigen (eg. polypeptide) as defined above.

Thus, in one embodiment, the invention provides an immunogenic composition comprising a first antibody and a second antibody, wherein said first antibody binds a first mycobacterial antigen and said second antibody binds a second mycobacterial antigen;

wherein said first mycobacterial antigen comprises:

(i) a polypeptide sequence having at least 70% amino acid sequence identity to the amino acid sequence of a latency-regulated polypeptide selected from SEQ ID NOs: 1, 3, 5, 7 and 56, or a fragment thereof having at least 7 consecutive amino acids thereof; or (ii) a polynucleotide sequence encoding a polypeptide sequence according to (i); or a polynucleotide sequence having at least 70% nucleotide sequence identity to the nucleic acid sequence of a latency-regulated polynucleotide selected from SEQ ID NOs: 2, 4, 6, 8 and 57, or a fragment thereof having at least 21 consecutive nucleotides thereof;

and wherein said second mycobacterial antigen is different from said first mycobacterial antigen.

In one embodiment, said first mycobacterial antigen comprises or consists of an antigenic polypeptide of the invention, such as an Rv0111 polypeptide antigen or an Rv3812 polypeptide antigen as defined herein.

In one embodiment, said second mycobacterial antigen comprises or consists of an antigenic polypeptide of the invention, such as an Rv0198 polypeptide antigen as defined herein.

In one embodiment, the immunogenic composition comprises a first antibody and a second antibody, wherein said first antibody binds a first mycobacterial antigenic polypeptide and said second antibody binds a second mycobacterial antigenic polypeptide;

wherein said first mycobacterial antigenic polypeptide comprises a polypeptide sequence having at least 70% amino acid sequence identity to the amino acid sequence of SEQ ID NO: 1, or a fragment thereof having at least 7 consecutive amino acids thereof; and wherein said second mycobacterial antigenic polypeptide comprises a polypeptide sequence having at least 70% amino acid sequence identity to the amino acid sequence of SEQ ID NO: 5, or a fragment thereof having at least 7 consecutive amino acids thereof.

In one embodiment, the immunogenic composition comprises a first antibody and a second antibody, wherein said first antibody binds a first mycobacterial antigenic polypeptide and said second antibody binds a second mycobacterial antigenic polypeptide;

wherein said first mycobacterial antigenic polypeptide comprises a polypeptide sequence having at least 70% amino acid sequence identity to the amino acid sequence of SEQ ID NO: 7, or a fragment thereof having at least 7 consecutive amino acids thereof; and wherein said second mycobacterial antigenic polypeptide comprises a polypeptide sequence having at least 70% amino acid sequence identity to the amino acid sequence of SEQ ID NO: 5, or a fragment thereof having at least 7 consecutive amino acids thereof.

Optionally, said immunogenic composition further comprises at least a third antibody (eg. at least a 3, 4, 5, 6, 7, 8 additional antibodies), wherein said third antibody binds a third mycobacterial antigen that is different from the first and second mycobacterial antigens.

In one embodiment, if the immunogenic composition comprises (i) an antibody that binds an Rv0111 antigen as defined herein (eg. comprising or consisting of a polypeptide sequence having at least 70% amino acid sequence identity to the amino acid sequence of SEQ ID NO: 1, or a fragment thereof having at least 7 consecutive amino acids thereof); and (ii) an antibody that binds an Rv0198 antigen as defined herein (eg. comprising or consisting of a polypeptide sequence having at least 70% amino acid sequence identity to the amino acid sequence of SEQ ID NO: 5, or a fragment thereof having at least 7 consecutive amino acids thereof); the composition does not comprise an antibody that binds an Rv3812 antigen as defined herein (eg. comprising or consisting of a polypeptide sequence having at least 70% amino acid sequence identity to the amino acid sequence of SEQ ID NO: 7, or a fragment thereof having at least 7 consecutive amino acids thereof).

In one embodiment, the limitations discussed above with respect to an antigenic composition comprising at least first and second mycobacterial antigens apply equally to the mycobacterial antigens to which the at least first and second antibodies of the above-described antigenic composition bind.

The term 'antibody' encompasses any polypeptide that comprises an antigen binding fragment or an antigen-binding domain. Examples include, but are not limited to, polyclonal, monoclonal, specific, monospecific, polyspecific, non specific, humanized, human, single chain, chimeric, synthetic, recombinant, hybrid, mutated, grafted, and in vitro generated antibodies.

Unless preceded by the word "intact", the term "antibody" includes antibody fragments such as Fab, F(ab')2, Fv, scFv, Fd, dAb, and other antibody fragments that retain antigen binding function.

In one embodiment the antibody belongs to the IgG, IgM or IgA isotype families. Reference to the IgA isotype includes the secretory form of this antibody (ie. sIgA). The secretory component (SC) of sIgA may be added in vitro or in vivo. In the latter case, the use of a patient's natural SC labeling machinery may be employed.

In one embodiment, the antibody specifically binds the mycobacterial antigen in question. "Specific binding" is intended to mean the formation of a complex between two or more molecules that is relatively stable under physiologic conditions. Specific binding is characterized by a high affinity and a low to moderate capacity, as distinguished from non-specific binding which usually has a low affinity with a moderate to high capacity. Typically, binding between an antibody and an antigen is considered to be specific when the association constant KA is higher than 106 M 1. If necessary, nonspecific binding can be reduced without substantially affecting specific binding by varying the binding conditions.

The appropriate binding conditions, such as antibody concentration, ionic strength of the solution, temperature, time allowed for binding, concentration of a blocking agent (e.g., serum albumin, milk casein), etc., may be optimized by a skilled person using routine techniques.

In one embodiment, said first and second antibodies have been raised against the first and second mycobacterial antigens of the invention, as described herein, respectively. In one embodiment, said first and second antibodies have been raised against the first and second mycobacterial antigenic polypeptides of the invention, as described herein, respectively.

In one embodiment, the invention provides antisera isolated from animals that have been immunized with an antigenic composition of the invention. As used herein, the term 'antisera' refers to antibodies in serum that possess detectable binding, e.g., by ELISA or flow cytometry, for a particular antigen.

Methods of preparing immune sera are known in the art. For example, the first and second antibodies (and optional additional antibodies) of the invention, or immunogenic composition of the invention, can be administered to an animal (such as a mammal—eg. a horse or a human) until an antibody response (for instance, neutralizing antibody response) is generated to the first and second mycobacterial antigens.

General methodology for making monoclonal antibodies by hybridomas involves, for example, preparation of immortal antibody-producing cell lines by cell fusion, or other techniques such as direct transformation of B lymphocytes with oncogenic DNA, or transfection with Epstein-Barr virus may be employed.

Antibodies raised against antigenic fragments disclosed herein (eg. polypeptide fragments) may have the property of recognizing the full-length antigen (eg. full-length polypeptide) from which they are derived. In this regard, polypeptide fragments bear antigenic determinants that are detectable by conventional immunoassays. One or more antigenic determinants is shared by full-length antigens of the invention and fragments thereof, thus antibodies raised against an antigenic fragment may also bind corresponding full-length antigens of the invention.

In one embodiment, the antibodies are provided in an isolated form.

The antibodies may be tagged with a detectable or functional label. These labels include radiolabels (eg. 131I or 99Tc), enzymatic labels (eg. horseradish peroxidase or alkaline phosphatase), and other chemical moieties (eg. biotin).

The above-described antibodies may provide improved survival when administered to a mammal, such as a human, prior to or shortly after exposure to mycobacteria such as *M. tuberculosis*. Accordingly, the first and second antibodies (and optional additional antibodies) of the invention (or immunogenic, antibody-containing composition of the invention) can be used as a passive immune serum to prevent mycobacterial infection, or to treat patients exposed to mycobacteria (such as *M. tuberculosis*).

In one embodiment, binding of the antibodies to the mycobacterial antigens of the invention may initiate coating of a mycobacterium expressing said antigen. Coating of the *mycobacterium* preferably leads to opsonization thereof, which leads to the bacterium being destroyed. Opsonization by antibodies may influence cellular entry and spread of mycobacteria in phagocytic and non-phagocytic cells by preventing or modulating receptor-mediated entry and replication in macrophages.

Without being bound by any theory, it is possible that following mycobacterial infection of a macrophage, the macrophage is killed and the bacilli are released. It is at this stage that the mycobacteria are considered to be most vulnerable to antibody attack. Thus, it is possible that the antibodies of the present invention act on released bacilli following macrophage death, and thereby exert a post-infection effect.

It is possible that the passive protection aspect (ie. delivery of antibodies) of the present invention is facilitated by enhanced accessibility of the antibodies of the present invention to antigens on mycobacterial bacilli. It is also possible that antibody binding may block macrophage infection by steric hindrance or disruption of its oligomeric structure. Thus, antibodies acting on mycobacterial bacilli released from killed, infected macrophages may interfere with the spread of re-infection to fresh macrophages. This hypothesis involves a synergistic action between antibodies and cytotoxic T cells, acting early after infection, eg. □NK T cells, but could later involve also CD8 and CD4 cytotoxic T cells.

In another embodiment, compositions comprising antibodies (eg. monoclonal antibodies) of the invention may be used to raise anti-idiotype antibodies. Anti-idiotype antibodies are immunoglobulins which carry an "internal image" of the antigen of the infectious mycobacterial agent against which protection is desired. These anti-idiotype antibodies may also be useful for treatment, vaccination and/or diagnosis of mycobacterial infections. The first and second mycobacterial antigens of the invention stimulate an immune response against mycobacteria, such as *M. tuberculosis.*

In the context of the therapeutic uses and methods discussed below, a 'subject' is any animal subject that would benefit from stimulation of an immune response against mycobacteria, such as *M. tuberculosis*. Typical animal subjects are mammals, for example, human, bovine, porcine, ovine, caprine, equine, corvine, canine or feline subjects. In one embodiment, the subject is human, bovine, porcine or equine.

According to one aspect of the present invention, there is provided the use of a first mycobacterial antigen and a second mycobacterial antigen for the manufacture of a medicament for stimulating an immune response in a subject, such as a mammalian subject, (eg. a human, bovine, porcine or equine subject); wherein said first mycobacterial antigen comprises:

(i) a polypeptide sequence having at least 70% amino acid sequence identity to the amino acid sequence of a latency-regulated polypeptide selected from SEQ ID NOs: 1, 3, 5, 7 and 56, or a fragment thereof having at least 7 consecutive amino acids thereof; or (ii) a polynucleotide sequence encoding a polypeptide sequence according to (i); or a polynucleotide sequence having at least 70% nucleotide sequence identity to the nucleic acid sequence of a latency-regulated polynucleotide selected from SEQ ID NOs: 2, 4, 6, 8 and 57, or a fragment thereof having at least 21 consecutive nucleotides thereof; and wherein said second mycobacterial antigen is different from said first mycobacterial antigen.

The invention also provides a first mycobacterial antigen and a second mycobacterial antigen for use in stimulating an immune response in a subject, such as a mammalian subject, (eg. a human, bovine, porcine or equine subject); wherein said first mycobacterial antigen comprises:

(i) a polypeptide sequence having at least 70% amino acid sequence identity to the amino acid sequence of a latency-regulated polypeptide selected from SEQ ID NOs: 1, 3, 5, 7 and 56, or a fragment thereof having at least 7 consecutive amino acids thereof; or (ii) a polynucleotide sequence encoding a polypeptide sequence according to (i); or a polynucleotide sequence having at least 70% nucleotide sequence identity to the nucleic acid sequence of a latency-regulated polynucleotide selected from SEQ ID NOs: 2, 4, 6, 8 and 57, or a fragment thereof having at least 21 consecutive nucleotides thereof; and wherein said second mycobacterial antigen is different from said first mycobacterial antigen.

In one embodiment, said second mycobacterial antigen comprises or consists of a mycobacterial antigenic polypeptide or polynucleotide sequence, such as a mycobacterial antigenic polypeptide or polynucleotide sequence as defined in (i) or (ii) (wherein said second mycobacterial antigen is different from said first mycobacterial antigen).

In one embodiment, the invention provides (a) a first mycobacterial antigenic polypeptide or a first mycobacterial polynucleotide, and (b) a second mycobacterial antigenic polypeptide or a second mycobacterial polynucleotide, for use in stimulating an immune response in a subject; wherein (i) said first mycobacterial antigenic polypeptide comprises a polypeptide sequence having at least 70% amino acid sequence identity to the amino acid sequence of SEQ ID NO: 1, or a fragment thereof having at least 7 consecutive amino acids thereof;

(ii) said first mycobacterial polynucleotide sequence comprises a polynucleotide sequence encoding said first mycobacterial antigenic polypeptide;

(iii) said second mycobacterial antigenic polypeptide comprises a polypeptide sequence having at least 70% amino acid sequence identity to the amino acid sequence of SEQ ID NO: 5, or a fragment thereof having at least 7 consecutive amino acids thereof; and (iv) said second mycobacterial polynucleotide sequence comprises a polynucleotide sequence encoding said second mycobacterial antigenic polypeptide.

In one embodiment, said first mycobacterial polynucleotide comprises a polynucleotide sequence having at least 70% nucleotide sequence identity to the nucleic acid sequence of SEQ ID NO: 2, or a fragment thereof having at least 21 consecutive nucleotides thereof. In one embodiment, said second mycobacterial polynucleotide comprises a polynucleotide sequence having at least 70% nucleotide sequence identity to the nucleic acid sequence of SEQ ID NO: 6, or a fragment thereof having at least 21 consecutive nucleotides thereof.

In one embodiment, the invention provides (a) a first mycobacterial antigenic polypeptide or a first mycobacterial polynucleotide, and (b) a second mycobacterial antigenic polypeptide or a second mycobacterial polynucleotide, for use in stimulating an immune response in a subject; wherein (i) said first mycobacterial antigenic polypeptide comprises a polypeptide sequence having at least 70% amino acid sequence identity to the amino acid sequence of SEQ ID NO: 7, or a fragment thereof having at least 7 consecutive amino acids thereof;

(ii) said first mycobacterial polynucleotide sequence comprises a polynucleotide sequence encoding said first mycobacterial antigenic polypeptide;

(iii) said second mycobacterial antigenic polypeptide comprises a polypeptide sequence having at least 70% amino acid sequence identity to the amino acid sequence of SEQ ID NO: 5, or a fragment thereof having at least 7 consecutive amino acids thereof; and (iv) said second mycobacterial polynucleotide sequence comprises a polynucleotide sequence encoding said second mycobacterial antigenic polypeptide.

In one embodiment, said first mycobacterial polynucleotide comprises a polynucleotide sequence having at least 70% nucleotide sequence identity to the nucleic acid sequence of SEQ ID NO: 8, or a fragment thereof having at least 21 consecutive nucleotides thereof. In one embodiment, said second mycobacterial polynucleotide comprises a polynucleotide sequence having at least 70% nucleotide sequence identity to the nucleic acid sequence of SEQ ID NO: 6, or a fragment thereof having at least 21 consecutive nucleotides thereof.

In one embodiment, immune stimulation is measured by a protective effect in an in vivo survival assay. In one embodiment, immune stimulation is measured by an increased frequency in immune cells such as T lymphocytes specific for the antigen in the vaccine—ie. an immune cell response (eg. T cell immune response). In one embodiment, the immune stimulation is a memory T cell immune response, such as a central memory T cell response (eg. a CCR7+ response). In one embodiment, immune stimulation is measured by an increase in antibody titer that is specific for the antigen in the vaccine.

In one embodiment, said medicament further comprises one or more additional mycobacterial antigens, as described herein. In one embodiment, one or more additional mycobacterial antigens, as described herein, are also for use with said first and second mycobacterial antigens. In one embodiment, if said first mycobacterial antigen comprises or consists of an Rv0111 antigen (as defined herein) and if said second mycobacterial antigen comprises or consists of an Rv1098 antigen (as defined herein), said one or more additional mycobacterial antigen does not comprise or consist of an Rv3812 antigen (as defined herein).

In one embodiment of this therapeutic use, said first and second (and optional additional mycobacterial antigen(s)) are provided in the form of an antigenic composition as described herein. In one embodiment, one or more of said first, second and/or optional additional mycobacterial antigens may be comprised within one or more vectors or cells as described herein.

In one embodiment of this therapeutic use, any of the limitations described herein with respect to said first and/or second mycobacterial antigens (and optional additional mycobacterial antigens) apply equally to the therapeutic uses thereof.

In one embodiment of this therapeutic use, said first and second mycobacterial antigens (and optional additional mycobacterial antigen(s)) are for administration to the subject substantially simultaneously, or sequentially. Simultaneous and sequential administration regimes are discussed in more detail below.

The present invention also provides the use of a first mycobacterial antigen and a second mycobacterial antigen for the manufacture of a medicament for treating or preventing a mycobacterial infection (eg. *M. tuberculosis* infection) in a subject, such as a mammalian subject (eg. a human, bovine, porcine or equine subject); wherein said first mycobacterial antigen comprises:

(i) a polypeptide sequence having at least 70% amino acid sequence identity to the amino acid sequence of a latency-regulated polypeptide selected from SEQ ID NOs: 1, 3, 5, 7 and 56, or a fragment thereof having at least 7 consecutive amino acids thereof; or (ii) a polynucleotide sequence encoding a polypeptide sequence according to (i); or a polynucleotide sequence having at least 70% nucleotide sequence identity to the nucleic acid sequence of a latency-regulated polynucleotide selected from SEQ ID NOs: 2, 4, 6, 8 and 57, or a fragment thereof having at least 21 consecutive nucleotides thereof; and wherein said second mycobacterial antigen is different from said first mycobacterial antigen.

The invention also provides a first mycobacterial antigen and a second mycobacterial antigen for use in treating or preventing a mycobacterial infection (eg. *M. tuberculosis* infection) in a subject, such as a mammalian subject (eg. a human, bovine, porcine or equine subject); wherein said first mycobacterial antigen comprises:

(i) a polypeptide sequence having at least 70% amino acid sequence identity to the amino acid sequence of a latency-regulated polypeptide selected from SEQ ID NOs: 1, 3, 5, 7 and 56, or a fragment thereof having at least 7 consecutive amino acids thereof; or (ii) a polynucleotide sequence encoding a polypeptide sequence according to (i); or a polynucleotide sequence having at least 70% nucleotide sequence identity to the nucleic acid sequence of a latency-regulated polynucleotide selected from SEQ ID NOs: 2, 4, 6, 8 and 57, or a fragment thereof having at least 21 consecutive nucleotides thereof; and wherein said second mycobacterial antigen is different from said first mycobacterial antigen.

In one embodiment, said second mycobacterial antigen comprises or consists of a mycobacterial antigenic polypeptide or polynucleotide sequence, such as a mycobacterial antigenic polypeptide or polynucleotide sequence as defined in (i) or (ii) (wherein said second mycobacterial antigen is different from said first mycobacterial antigen).

In one embodiment, the invention provides (a) a first mycobacterial antigenic polypeptide or a first mycobacterial polynucleotide, and (b) a second mycobacterial antigenic polypeptide or a second mycobacterial polynucleotide, for use in treating or preventing a mycobacterial infection (eg. *M. tuberculosis* infection) in a subject; wherein:

(i) said first mycobacterial antigenic polypeptide comprises a polypeptide sequence having at least 70% amino acid sequence identity to the amino acid sequence of SEQ ID NO: 1 or 7, or a fragment thereof having at least 7 consecutive amino acids thereof;

(ii) said first mycobacterial polynucleotide sequence comprises a polynucleotide sequence encoding said first mycobacterial antigenic polypeptide;

(iii) said second mycobacterial antigenic polypeptide comprises a polypeptide sequence having at least 70% amino acid sequence identity to the amino acid sequence of SEQ ID NO: 5, or a fragment thereof having at least 7 consecutive amino acids thereof; and (iv) said second mycobacterial polynucleotide sequence comprises a polynucleotide sequence encoding said second mycobacterial antigenic polypeptide.

In one embodiment, said first mycobacterial polynucleotide comprises a polynucleotide sequence having at least 70% nucleotide sequence identity to the nucleic acid sequence of SEQ ID NO: 2 or 8, or a fragment thereof having at least 21 consecutive nucleotides thereof. In one embodiment, said second mycobacterial polynucleotide comprises a polynucleotide sequence having at least 70% nucleotide sequence identity to the nucleic acid sequence of SEQ ID NO: 6, or a fragment thereof having at least 21 consecutive nucleotides thereof.

For example, said use or medicament may protect the subject against infection with mycobacteria, such as *M. tuberculosis*. For example, said use or medicament may be useful for treating TB in a subject, typically a mammalian subject such as a human, bovine, porcine or equine subject.

In one embodiment, said use or medicament may protect the subject against an early stage infection with mycobacteria, such as *M. tuberculosis*. The term ‘early stage infection’ refers to the initial period after infection in which mycobacteria proliferate in the lung, having overcome the host subject’s innate defenses (the non-specific immune system). During early stage infection, mycobacterial proliferation stimulates an increasing immune response in the infected subject. The subject’s immune system attempts to control bacterial growth so that it may be slowed, be restricted to within a granuloma, and then decline to a persistent low level. Dissemination to other organs, such as the spleen, may occur during this period. The period during which early stage infection occurs in humans is not clearly defined; however, in experimental models such as the guinea pig, this period is approximately 3-4 weeks.

Early stage infection is thus distinct from latent infection. During latent infection, due to the presence of a continued successful immune response, the level of mycobacteria is held at a low level within the granuloma, in which the mycobacteria may exhibit ‘dormancy’ (otherwise known as ‘non-replicating persistence’).

In one embodiment, said medicament further comprises one or more additional mycobacterial antigens, as described herein. In one embodiment, one or more additional mycobacterial antigens, as described herein, are also for use with said first and second mycobacterial antigens. In one embodiment, if said first mycobacterial antigen comprises or consists of an Rv0111 antigen (as defined herein) and if said second mycobacterial antigen comprises or consists of an Rv1098 antigen (as defined herein), said one or more additional mycobacterial antigen does not comprise or consist of an Rv3812 antigen (as defined herein).

In one embodiment of this therapeutic use, said first and second (and optional additional mycobacterial antigen(s)) are provided in the form of an antigenic composition as described herein. In one embodiment, one or more of said first, second and/or optional additional mycobacterial antigens may be comprised within one or more vectors or cells as described herein.

In one embodiment of this therapeutic use, any of the limitations described herein with respect to said first and/or second mycobacterial antigens (and/or optional additional mycobacterial antigens) apply equally to the therapeutic uses thereof.

In one embodiment of this therapeutic use, said first and second mycobacterial antigens (and optional additional mycobacterial antigen(s)) are for administration to the subject substantially simultaneously, or sequentially. Simultaneous and sequential administration regimes are discussed in more detail below.

A related aspect includes a method for stimulating an immune response in a subject, comprising administering to a subject, such as a mammal (eg. a human, bovine, porcine or equine subject) an effective amount of a first mycobacterial antigen and a second mycobacterial antigen;

wherein said first mycobacterial antigen comprises:

(i) a polypeptide sequence having at least 70% amino acid sequence identity to the amino acid sequence of a latency-regulated polypeptide selected from SEQ ID NOs: 1, 3, 5, 7 and 56, or a fragment thereof having at least 7 consecutive amino acids thereof; or (ii) a polynucleotide sequence encoding a polypeptide sequence according to (i); or a polynucleotide sequence having at least 70% nucleotide sequence identity to the nucleic acid sequence of a latency-regulated polynucleotide selected from SEQ ID NOs: 2, 4, 6, 8 and 57, or a fragment thereof having at least 21 consecutive nucleotides thereof; and wherein said second mycobacterial antigen is different from said first mycobacterial antigen.

In one embodiment, said second mycobacterial antigen comprises or consists of a mycobacterial antigenic polypeptide or polynucleotide sequence, such as a mycobacterial antigenic polypeptide or polynucleotide sequence as defined in (i) or (ii) (wherein said second mycobacterial antigen is different from said first mycobacterial antigen).

In one embodiment, the invention provides a method of stimulating an immune response in a subject, comprising administrating to said subject: (a) a first mycobacterial antigenic polypeptide or a first mycobacterial polynucleotide, and (b) a second mycobacterial antigenic polypeptide or a second mycobacterial polynucleotide; wherein:

(i) said first mycobacterial antigenic polypeptide comprises a polypeptide sequence having at least 70% amino acid sequence identity to the amino acid sequence of SEQ ID NO: 1 or 7, or a fragment thereof having at least 7 consecutive amino acids thereof;

(ii) said first mycobacterial polynucleotide comprises a polynucleotide sequence encoding said first mycobacterial antigenic polypeptide;

(iii) said second mycobacterial antigenic polypeptide comprises a polypeptide sequence having at least 70% amino acid sequence identity to the amino acid sequence of SEQ ID NO: 5, or a fragment thereof having at least 7 consecutive amino acids thereof; and (iv) said second mycobacterial polynucleotide comprises a polynucleotide sequence encoding said second mycobacterial polypeptide.

In one embodiment, immune stimulation is measured by a protective effect in an in vivo survival assay. In one embodiment, immune stimulation is measured by an increased frequency in immune cells such as T lymphocytes specific for the antigen in the vaccine—ie. an immune cell response (eg. a T cell immune response). In one embodiment, the immune stimulation is a memory T cell immune response, such as a central memory T cell response (eg. a CCR7+ response). In one embodiment, immune stimulation is measured by an increase in antibody titer that is specific for the antigen in the vaccine.

In one embodiment, said method further comprises administering one or more additional mycobacterial antigens, as described herein. In one embodiment, if said first mycobacterial antigen comprises or consists of an Rv0111 antigen (as defined herein) and if said second mycobacterial antigen comprises or consists of an Rv1098 antigen (as defined herein), said one or more additional mycobacterial antigen does not comprise or consist of an Rv3812 antigen (as defined herein).

In one embodiment of this therapeutic method, said first and second (and optional additional mycobacterial antigen(s)) are provided in the form of an antigenic composition or formulation as described herein. In one embodiment, one or more of said first, second and/or optional additional mycobacterial antigens may be comprised within one or more vectors or cells as described herein.

In one embodiment of this therapeutic method, any of the limitations described herein with respect to said first and/or second mycobacterial antigens (and/or optional additional mycobacterial antigens) apply equally to the therapeutic uses thereof.

In one embodiment, the method comprises administering said first and second mycobacterial antigens to the subject substantially simultaneously, or sequentially. Simultaneous and sequential administration regimes are discussed in more detail below.

In a related aspect, there is provided a method of treating or preventing a mycobacterial infection (eg. an *M. tuberculosis* infection), comprising administering to a subject, such as a mammal (eg. a human, bovine, porcine or equine subject) an effective amount of a first mycobacterial antigen and a second mycobacterial antigen;

wherein said first mycobacterial antigen comprises:

(i) a polypeptide sequence having at least 70% amino acid sequence identity to the amino acid sequence of a latency-regulated polypeptide selected from SEQ ID NOs: 1, 3, 5, 7 and 56, or a fragment thereof having at least 7 consecutive amino acids thereof; or (ii) a polynucleotide sequence encoding a polypeptide sequence according to (i); or a polynucleotide sequence having at least 70% nucleotide sequence identity to the nucleic acid sequence of a latency-regulated polynucleotide selected from SEQ ID NOs: 2, 4, 6, 8 and 57, or a fragment thereof having at least 21 consecutive nucleotides thereof;

and wherein said second mycobacterial antigen is different from said first mycobacterial antigen.

In one embodiment, said second mycobacterial antigen comprises or consists of a mycobacterial antigenic polypeptide or polynucleotide sequence, such as a mycobacterial antigenic polypeptide or polynucleotide sequence as defined in (i) or (ii) (wherein said second mycobacterial antigen is different from said first mycobacterial antigen).

In one embodiment, the invention provides a method of treating or preventing a mycobacterial infection (eg. *M. tuberculosis* infection) in a subject; comprising administering to said subject: (a) a first mycobacterial antigenic polypeptide or a first mycobacterial polynucleotide, and (b) a second mycobacterial antigenic polypeptide or a second mycobacterial polynucleotide; wherein:

(i) said first mycobacterial antigenic polypeptide comprises a polypeptide sequence having at least 70% amino acid sequence identity to the amino acid sequence of SEQ ID NO: 1 or 7, or a fragment thereof having at least 7 consecutive amino acids thereof;

(ii) said first mycobacterial polynucleotide comprises a polynucleotide sequence encoding said first mycobacterial antigenic polypeptide;

(iii) said second mycobacterial antigenic polypeptide comprises a polypeptide sequence having at least 70% amino acid sequence identity to the amino acid sequence of SEQ ID NO: 5, or a fragment thereof having at least 7 consecutive amino acids thereof; and (iv) said second mycobacterial polynucleotide comprises a polynucleotide sequence encoding said second mycobacterial polypeptide.

For example, said method may protect the subject against infection with mycobacteria, such as *M. tuberculosis*. For example, said method may treat TB in the subject. In one embodiment, said method may protect the subject against an early stage infection with mycobacteria, such as *M. tuberculosis*. Early stage mycobacterial infection is defined above.

In one embodiment, said method further comprises administering one or more additional mycobacterial antigens, as described herein. In one embodiment, if said first mycobacterial antigen comprises or consists of an Rv0111 antigen (as defined herein) and if said second mycobacterial antigen comprises or consists of an Rv1098 antigen (as defined herein), said one or more additional mycobacterial antigen does not comprise or consist of an Rv3812 antigen (as defined herein).

In one embodiment of this therapeutic method, said first and second (and optional additional mycobacterial antigen(s)) are provided in the form of an antigenic composition as described herein. In one embodiment, one or more of said first, second and/or optional additional mycobacterial antigens may be comprised within one or more vectors or cells as described herein.

In one embodiment of this therapeutic method, any of the limitations described herein with respect to said first and/or second mycobacterial antigens (and/or optional additional mycobacterial antigens) apply equally to the therapeutic uses thereof.

In one embodiment, the method comprises administering said first and second mycobacterial antigens to the subject substantially simultaneously, or sequentially. Simultaneous and sequential administration regimes are discussed in more detail below.

The first and second antibodies of the invention are also useful for stimulating an immune response against mycobacteria, such as *M. tuberculosis*.

Accordingly, the invention also provides therapeutic uses and methods involving a first antibody and a second antibody, wherein said first antibody binds a first mycobacterial antigen and said second antibody binds a second mycobacterial antigen;

wherein said first mycobacterial antigen comprises:

(i) a polypeptide sequence having at least 70% amino acid sequence identity to the amino acid sequence of a latency-regulated polypeptide selected from SEQ ID NOs: 1, 3, 5, 7 and 56, or a fragment thereof having at least 7 consecutive amino acids thereof; or (ii) a polynucleotide sequence encoding a polypeptide sequence according to (i); or a polynucleotide sequence having at least 70% nucleotide sequence identity to the nucleic acid sequence of a latency-regulated polynucleotide selected from SEQ ID NOs: 2, 4, 6, 8 and 57, or a fragment thereof having at least 21 consecutive nucleotides thereof;

and wherein said second mycobacterial antigen is different from said first mycobacterial antigen.

In one embodiment, said first mycobacterial antigen comprises or consists of a mycobacterial antigenic polypeptide sequence as defined in (i). In one embodiment, said second mycobacterial antigen comprises or consists of a mycobacterial antigenic polypeptide sequence such as a mycobacterial antigenic polypeptide sequence as defined in (i) (wherein said second mycobacterial antigen is different from said first mycobacterial antigen).

In one embodiment, said first antibody and second antibody are provided in the form of an immunogenic antibody-containing composition, or a formulation, as described herein.

By way of example, the invention provides the use of the first and second antibodies of the invention (eg. in the form of an immunogenic antibody-containing composition of the invention), for the manufacture of a medicament for stimulating an immune response in a subject (typically a mammal—eg. a human, bovine, porcine or equine subject); or for the manufacture of a medicament for treating or preventing a mycobacterial infection (eg. TB), or suspected infection, in a subject (such as a mammal—eg. a human, bovine, porcine or equine subject).

The invention also provides the first and second antibodies of the invention (eg. in the form of an immunogenic antibody-containing composition of the invention), for use in stimulating an immune response in a subject (typically a mammal—eg. a human, bovine, porcine or equine subject); or for the manufacture of a medicament for treating or preventing a mycobacterial infection (eg. TB), or suspected infection, in a subject (such as a mammal—eg. a human, bovine, porcine or equine subject).

In one embodiment, the invention provides a first antibody and a second antibody for use in stimulating an immune response in a subject;

wherein said first antibody binds a first mycobacterial antigenic polypeptide, wherein said first mycobacterial antigenic polypeptide comprises a polypeptide sequence having at least 70% amino acid sequence identity to the amino acid sequence of SEQ ID NO: 1 or 7, or a fragment thereof having at least 7 consecutive amino acids thereof; and wherein said second antibody binds a second mycobacterial antigenic polypeptide, wherein said second mycobacterial antigenic polypeptide comprises a polypeptide sequence having at least 70% amino acid sequence identity to the amino acid sequence of SEQ ID NO: 5, or a fragment thereof having at least 7 consecutive amino acids thereof.

The invention also provides a method for stimulating an immune response in a subject (such as a mammal—eg. a human, bovine, porcine or equine subject) or for treating or preventing a mycobacterial infection (eg. *M. tuberculosis* infection, TB) in a subject (such as a mammal—eg. a human, bovine, porcine or equine subject), comprising administering to said subject (pre- or post-infection) the first and second antibodies (and optional additional antibodies) of the invention (eg. in the form of an immunogenic, antibody-containing composition of the invention).

In one embodiment, the invention provides a method of stimulating an immune response in a subject, comprising administrating to said subject:

(a) a first antibody, wherein said first antibody binds a first mycobacterial antigenic polypeptide; wherein said first mycobacterial antigenic polypeptide comprises a polypeptide sequence having at least 70% amino acid sequence identity to the amino acid sequence of SEQ ID NO: 1 or 7, or a fragment thereof having at least 7 consecutive amino acids thereof; and (b) a second antibody, wherein said second antibody binds a second mycobacterial antigenic polypeptide; wherein said second mycobacterial antigen comprises a polypeptide sequence having at least 70% amino acid sequence identity to the amino acid sequence of SEQ ID NO: 5, or a fragment thereof having at least 7 consecutive amino acids thereof.

In one embodiment of said uses and methods, said first antibody and second antibody are provided in the form of an immunogenic antibody-containing composition or formulation, as described herein.

In one embodiment, said use or method further comprises administration of one or more additional antibodies that bind one or more additional mycobacterial antigens, as described herein. In one embodiment, if said first antibody binds a first mycobacterial antigen that comprises or consists of an Rv0111 antigen (as defined herein) and if said second antibody binds a second mycobacterial antigen that comprises or consists of an Rv1098 antigen (as defined herein), said one or more additional antibodies does not bind a mycobacterial antigen that comprises or consists of an Rv3812 antigen (as defined herein).

In one embodiment, any of the limitations described herein with respect to said first and/or second antibodies (and/or the antigens to which the antibodies bind) apply equally to the therapeutic methods and uses thereof.

Said method or use may be for simultaneous or sequential administration of said first and second antibodies (and/or optional additional antibodies). In one embodiment, the first and second mycobacterial antibodies are for administration to the subject substantially simultaneously, or sequentially. Simultaneous and sequential administration regimes are discussed in more detail below.

In one embodiment, said use or method may protect the subject against an early stage infection with mycobacteria, such as *M. tuberculosis*. Early stage mycobacterial infection is defined above.

In a related aspect, the first and second (and optional additional) mycobacterial antigens, antigenic composition, antibodies, immunogenic composition or medicament of the present invention, as defined herein, may be useful in therapies (including preventative treatments) for a range of mycobacterial diseases not limited to tuberculosis (TB), leprosy, *M. avium* infection, *M. bovis* infection, *M. paratuberculosis* infection, *M. ulcerans* infection (eg. Buruli ulcer), or other non-tuberculosis mycobacterial infection.

The first and second (and optional additional) mycobacterial antigens, antigenic composition, antibodies, immunogenic composition or medicament of the present invention may be useful for inducing a range of immune responses and may therefore be useful in methods for treating a range of diseases.

In one embodiment, the first and second (and optional additional) mycobacterial antigens, antigenic composition or medicament of the present invention is useful for treating or preventing a range of non-mycobacterial diseases in which mycobacteria are implicated. For example, diseases that may benefit from the medicament of the invention include inflammatory diseases such as autoimmune disease, cancer (eg. bladder cancer), inflammatory bowel disease, Crohn's Disease, Johne's Disease, Hansen's Disease, osteomyelitis, lymphadenitis, smallpox or monkeypox.

As used herein, the term "treatment" or "treating" embraces therapeutic or preventative/prophylactic measures, and includes post-infection therapy and amelioration of a mycobacterial infection.

As used herein, the term "preventing" includes preventing the initiation of a mycobacterial infection and/or reducing the severity or intensity of a mycobacterial infection.

In one embodiment, the antigenic composition or medicament of the invention comprises mycobacterial antigens that represent different mycobacterial infection states (eg. latency, re-activation or active infection). In one embodiment the antigenic composition or medicament of the invention comprises at least one mycobacterial antigen that is expressed during latency and at least one mycobacterial antigen that is down-regulated during latency.

This mixture of antigens is therefore useful for preventing and/or for treating multiple stages of mycobacterial infection, because the antigens elicit responses in a subject against different disease stages (eg. the early-stage, latent, re-activation or acute phases of mycobacterial disease).

As used herein, the term "vaccine efficacy" describes the ability of a vaccine to protect a subject (typically a mammalian subject eg. a human, bovine, porcine or equine subject) from challenge with mycobacteria such as *M. tuberculosis*. By way of example, "vaccine efficacy" may refer to the efficacy of a vaccine in preventing the initiation of a mycobacterial infection and/or reducing the severity/intensity of a mycobacterial infection.

A therapeutic/prophylactic composition or medicament may be administered to a subject (typically a mammalian subject such as a human, bovine, porcine or equine subject) already having a mycobacterial infection, condition or symptoms associated with a mycobacterial infection, to treat or prevent said mycobacterial infection. In one embodiment, the subject is suspected of having come in contact with mycobacteria, or has had known contact with mycobacteria, but is not yet showing symptoms of exposure. In one embodiment, the subject has an early-stage infection.

When administered to a subject (eg. a mammal such as a human, bovine, porcine or equine subject) that already has a mycobacterial infection or disease, or is showing symptoms associated with a mycobacterial infection, the therapeutic composition/medicament can cure, delay, reduce the severity of, or ameliorate one or more symptoms, and/or prolong the survival of a subject beyond that expected in the absence of such treatment.

Alternatively, a therapeutic/prophylactic composition or medicament may be administered to a subject (eg. a mammal such as a human, bovine, porcine or equine subject) who ultimately may acquire a mycobacterial infection, in order to prevent, cure, delay, reduce the severity of, or ameliorate one or more symptoms of said mycobacterial infection, or in order to prolong the survival of a subject beyond that expected in the absence of such treatment.

In one embodiment, the subject has previously been exposed to mycobacteria. For example, the subject may have had a mycobacterial infection in the past (but is optionally not currently infected with mycobacteria). The subject may be latently infected with mycobacteria. Alternatively, or in addition, the subject may have been vaccinated against mycobacterial infection in the past (eg. the subject has previously received a BCG vaccination).

The treatments and preventative therapies of the present invention are applicable to a variety of different subjects of different ages. In the context of humans, the therapies are applicable to children (eg. infants, children under 5 years old, older children or teenagers) and adults. In the context of other animal subjects (eg. mammals such as bovine, porcine or equine subjects), the therapies are applicable to immature subjects (eg. calves, piglets, foals) and mature/adult subjects. The treatments and preventative therapies of the present invention are applicable to subjects who are immunocompromised or immunosuppressed (eg. human patients who have HIV or AIDS, or other animal patients with comparable immunodeficiency diseases), subjects who have undergone an organ transplant, bone marrow transplant, or who have genetic immuno-deficiencies.

The invention provides therapeutic formulations, medicaments and prophylactic formulations (eg. vaccines) comprising pharmaceutically acceptable carrier, a first mycobacterial antigen of the invention as defined above, and a second mycobacterial antigen of the invention, as defined above (and optionally one or more additional mycobacterial antigens of the invention, as described above).

In one embodiment, the invention provides a therapeutic or prophylactic formulation (eg. vaccine), comprising pharmaceutically acceptable carrier and:

(a) a first mycobacterial antigen, wherein said first mycobacterial antigen comprises:
   (i) a polypeptide sequence having at least 70% amino acid sequence identity to the amino acid sequence of a latency-regulated polypeptide selected from SEQ ID NOs: 1, 3, 5, 7 and 56, or a fragment thereof having at least 7 consecutive amino acids thereof; or
   (ii) a polynucleotide sequence encoding a polypeptide sequence according to (i) or a polynucleotide sequence having at least 70% nucleotide sequence identity to the nucleic acid sequence of a latency-regulated polynucleotide selected from SEQ ID NOs: 2, 4, 6, 8 and 57, or a fragment thereof having at least 21 consecutive nucleotides thereof;

and (b) a second mycobacterial antigen, wherein said second mycobacterial antigen is different from said first mycobacterial antigen;

wherein said formulation is for simultaneous or sequential administration of said first and second mycobacterial antigens.

In one embodiment, said second mycobacterial antigen comprises or consists of a mycobacterial antigenic polypeptide or polynucleotide sequence, such as a mycobacterial antigenic polypeptide or polynucleotide sequence as defined in (i) or (ii) (wherein said second mycobacterial antigen is different from said first mycobacterial antigen).

In one embodiment, said therapeutic or prophylactic formulation (eg. vaccine), comprises (a) pharmaceutically acceptable carrier; (b) a first mycobacterial antigenic polypeptide or a first mycobacterial polynucleotide; and (c) a second mycobacterial antigenic polypeptide or a second mycobacterial polynucleotide; wherein:

(i) said first mycobacterial antigenic polypeptide comprises a polypeptide sequence having at least 70% amino acid sequence identity to the amino acid sequence of SEQ ID NO: 1 or 7, or a fragment thereof having at least 7 consecutive amino acids thereof;

(ii) said first mycobacterial polynucleotide comprises a polynucleotide sequence encoding said first mycobacterial antigenic polypeptide;

(iii) said second mycobacterial antigenic polypeptide comprises a polypeptide sequence having at least 70% amino acid sequence identity to the amino acid sequence of SEQ ID NO: 5, or a fragment thereof having at least 7 consecutive amino acids thereof; and (iv) said second mycobacterial polynucleotide comprises a polynucleotide sequence encoding said second mycobacterial polypeptide;

wherein said formulation is for simultaneous or sequential administration of said first mycobacterial antigenic polypeptide or polynucleotide and said second mycobacterial antigenic polypeptide or polynucleotide.

In one embodiment, said first mycobacterial polynucleotide comprises a polynucleotide sequence having at least 70% nucleotide sequence identity to the nucleic acid sequence of SEQ ID NO: 2 or 8, or a fragment thereof having at least 21 consecutive nucleotides thereof. In one embodiment, said second mycobacterial polynucleotide comprises a polynucleotide sequence having at least 70% nucleotide sequence identity to the nucleic acid sequence of SEQ ID NO: 6, or a fragment thereof having at least 21 consecutive nucleotides thereof.

In one embodiment, said therapeutic formulation, medicament or prophylactic formulation (eg. vaccine) of the invention comprises an antigenic composition of the invention, as defined above.

In one embodiment, said therapeutic formulation, medicament or prophylactic formulation (eg. vaccine) comprises an antigenic composition comprising one or more vectors or cells, as described above, wherein said vectors or cells comprise at least one of the mycobacterial antigens.

In one embodiment of said therapeutic formulation, medicament or prophylactic formulation (eg. vaccine), any of the limitations described herein with respect to said first and/or second (or additional) mycobacterial antigens apply equally to said therapeutic formulation, medicament or prophylactic formulation (eg. vaccine).

In one embodiment, a vaccine of the invention is a "vectored vaccine" comprising one or more vectors as described above.

In one embodiment, the therapeutic formulations, medicaments or prophylactic formulations (eg. vaccines) of the invention are for simultaneous administration of said first and second (and/or optional additional) mycobacterial antigens. In an alternative embodiment, the therapeutic formulations, medicaments or prophylactic formulations (eg. vaccines) of the invention are for sequential administration of said first and second (and/or optional additional) mycobacterial antigens. Simultaneous and sequential administration regimes are discussed in more detail below.

The invention also provides therapeutic formulations, medicaments and prophylactic formulations (eg. vaccines) comprising pharmaceutically acceptable carrier, a first antibody, wherein said first antibody binds a first mycobacterial antigen of the invention as defined above; and a second antibody, wherein said second antibody binds a second mycobacterial antigen of the invention as defined above (and optionally one or more additional antibodies of the invention, as described above).

In one embodiment, the invention provides a therapeutic or prophylactic formulation (eg. vaccine), comprising pharmaceutically acceptable carrier and:

(a) a first antibody, wherein said first antibody binds a first mycobacterial antigen;

wherein said first mycobacterial antigen comprises:

(i) a polypeptide sequence having at least 70% amino acid sequence identity to the amino acid sequence of a latency-regulated polypeptide selected from SEQ ID NOs: 1, 3, 5, 7 and 56, or a fragment thereof having at least 7 consecutive amino acids thereof; or (ii) a polynucleotide sequence encoding a polypeptide sequence according to (i) or a polynucleotide sequence having at least 70% nucleotide sequence identity to the nucleic acid sequence of a latency-regulated polynucleotide selected from SEQ ID NOs: 2, 4, 8 and 57, or a fragment thereof having at least 21 consecutive nucleotides thereof;

and (b) a second antibody, wherein said second antibody binds a second mycobacterial antigen that is different from said first mycobacterial antigen;

wherein said formulation is for simultaneous or sequential administration of said first and second antibodies.

In one embodiment, said first antibody binds a first mycobacterial antigen comprising a mycobacterial antigenic polypeptide sequence as defined in (i). In one embodiment, said second antibody binds a second mycobacterial antigen comprising a mycobacterial antigenic polypeptide sequence as defined in (i) (wherein said second mycobacterial antigenic polypeptide is different from said first mycobacterial antigenic polypeptide).

In one embodiment, the invention provides a therapeutic or prophylactic formulation (eg. vaccine), comprising pharmaceutically acceptable carrier and:

(a) a first antibody, wherein said first antibody binds a first mycobacterial antigenic polypeptide; wherein said first mycobacterial antigenic polypeptide comprises a polypeptide sequence having at least 70% amino acid sequence identity to the amino acid sequence of SEQ ID NO: 1 or 7, or a fragment thereof having at least 7 consecutive amino acids thereof; and (b) a second antibody, wherein said second antibody binds a second mycobacterial antigenic polypeptide; wherein said second mycobacterial antigen comprises a polypeptide sequence having at least 70% amino acid sequence identity to the amino acid sequence of SEQ ID NO: 5, or a fragment thereof having at least 7 consecutive amino acids thereof;

wherein said formulation is for simultaneous or sequential administration of said first and second antibodies.

In one embodiment, said therapeutic formulation, medicament or prophylactic formulation (eg. vaccine) of the invention comprises an immunogenic antibody-containing composition of the invention, as defined above.

In one embodiment of said therapeutic formulation, medicament or prophylactic formulation (eg. vaccine), any of the limitations described herein with respect to said first and/or second (or additional) antibodies (or the mycobacterial antigens to which they bind) apply equally to said therapeutic formulation, medicament or prophylactic formulation (eg. vaccine).

In one embodiment, the therapeutic formulations, medicaments or prophylactic formulations (eg. vaccines) of the invention are for simultaneous administration of said first and second (and/or optional additional) antibodies. In an alternative embodiment, the therapeutic formulations, medicaments or prophylactic formulations (eg. vaccines) of the invention are for sequential administration of said first and second (and/or optional additional) antibodies. Simultaneous and sequential administration regimes are discussed in more detail below.

Therapeutic formulations, medicaments and prophylactic formulations (eg. vaccines) of the invention comprise a pharmaceutically acceptable carrier, and optionally one or more of a salt, excipient, diluent and/or adjuvant.

In one embodiment, the therapeutic formulation, medicament or prophylactic formulation (eg. vaccine) of the invention may comprise one or more immunoregulatory agents selected from, for example, immunoglobulins, antibiotics, interleukins (eg. IL-2, IL-12), and/or cytokines (eg. IFNγ).

In one embodiment, the therapeutic formulation, medicament or prophylactic formulation (eg. vaccine) of the invention may comprise one or more antimicrobial compounds, such as conventional anti-tuberculosis drugs (eg. rifampicin, isoniazid, ethambutol or pyrizinamide).

Accordingly, in one aspect, the invention provides a method for producing a therapeutic or prophylactic formulation (eg. vaccine), the method comprising combining pharmaceutically acceptable carrier with a first mycobacterial antigen of the invention, as defined above; and a second mycobacterial antigen of the invention, as defined above (and optionally one or more additional mycobacterial antigens, as defined above).

Thus, in one embodiment, the invention provides a method for producing a therapeutic or prophylactic formulation (eg. vaccine), the method comprising combining pharmaceutically acceptable carrier with:

(a) a first mycobacterial antigen, wherein said first mycobacterial antigen comprises:
  (i) a polypeptide sequence having at least 70% amino acid sequence identity to the amino acid sequence of a latency-regulated polypeptide selected from SEQ ID NOs: 1, 3, 5, 7 and 56, or a fragment thereof having at least 7 consecutive amino acids thereof; or
  (ii) a polynucleotide sequence encoding a polypeptide sequence according to (i) or a polynucleotide sequence having at least 70% nucleotide sequence identity to the nucleic acid sequence of a latency-regulated polynucleotide selected from SEQ ID NOs: 2, 4, 6, 8 and 57, or a fragment thereof having at least 21 consecutive nucleotides thereof;

and (b) a second mycobacterial antigen, wherein said second mycobacterial antigen is different from said first mycobacterial antigen.

In one embodiment, said second mycobacterial antigen comprises or consists of a mycobacterial antigenic polypeptide or polynucleotide sequence, such as a mycobacterial antigenic polypeptide or polynucleotide sequence as defined in (i) or (ii) (wherein said second mycobacterial antigen is different from said first mycobacterial antigen).

In one embodiment, the invention provides a method for producing a therapeutic or prophylactic formulation (eg. vaccine), the method comprising:

(i) combining pharmaceutically acceptable carrier with either:

a first mycobacterial antigenic polypeptide, wherein said first mycobacterial antigenic polypeptide comprises a polypeptide sequence having at least 70% amino acid sequence identity to the amino acid sequence of SEQ ID NO: 1 or 7, or a fragment thereof having at least 7 consecutive amino acids thereof; or (ii) a first mycobacterial polynucleotide, wherein said first mycobacterial polynucleotide comprises a polynucleotide sequence encoding said first mycobacterial antigenic polypeptide;

and with either:

(iii) a second mycobacterial antigenic polypeptide, wherein said second mycobacterial antigenic polypeptide comprises a polypeptide sequence having at least 70% amino acid sequence identity to the amino acid sequence of SEQ ID NO: 5, or a fragment thereof having at least 7 consecutive amino acids thereof; or (iv) a second mycobacterial polynucleotide, wherein said second mycobacterial polynucleotide comprises a polynucleotide sequence encoding said second mycobacterial polypeptide.

In one embodiment, said mycobacterial antigens are in the form of an antigenic composition of the invention, as defined above.

In one embodiment of said method, any of the limitations described herein with respect to said first and/or second (or additional) mycobacterial antigens apply equally to said method.

In one embodiment, the method further comprises combining said pharmaceutically acceptable carrier and mycobacterial antigens (or antigenic composition) with one or more of a salt, excipient, diluent, adjuvant, immunoregulatory agent and/or antimicrobial compound.

The invention also provides a method for producing a therapeutic or prophylactic formulation (eg. vaccine), the method comprising combining pharmaceutically acceptable carrier with a first antibody, wherein said first antibody binds a first mycobacterial antigen of the invention, as defined above; and a second antibody, wherein said second antibody binds a second mycobacterial antigen of the invention, as defined above (and optionally one or more additional mycobacterial antibodies of the invention, as defined above).

Thus, in one embodiment, the invention provides a method for producing a therapeutic or prophylactic formulation (eg. vaccine), the method comprising combining pharmaceutically acceptable carrier with:

(a) a first antibody, wherein said first antibody binds a first mycobacterial antigen; wherein said first mycobacterial antigen comprises:
  (i) a polypeptide sequence having at least 70% amino acid sequence identity to the amino acid sequence of a latency-regulated polypeptide selected from SEQ ID NOs: 1, 3, 5, 7 and 56, or a fragment thereof having at least 7 consecutive amino acids thereof; or
  (ii) a polynucleotide sequence encoding a polypeptide sequence according to (i) or a polynucleotide sequence having at least 70% nucleotide sequence identity to the nucleic acid sequence of a latency-regulated polynucleotide selected from SEQ ID NOs: 2, 4, 6, 8 and 57, or a fragment thereof having at least 21 consecutive nucleotides thereof;

and (b) a second antibody, wherein said second antibody binds a second mycobacterial antigen that is different from said first mycobacterial antigen.

In one embodiment, said first antibody binds a first mycobacterial antigen comprising a mycobacterial antigenic polypeptide sequence as defined in (i). In one embodiment, said second antibody binds a second mycobacterial antigen comprising a mycobacterial antigenic polypeptide sequence as defined in (i) (wherein said second mycobacterial antigenic polypeptide is different from said first mycobacterial antigenic polypeptide).

In one embodiment, the invention provides a method for producing a therapeutic or prophylactic formulation (eg. vaccine), the method comprising combining pharmaceutically acceptable carrier with a first antibody and a second antibody;

wherein said first antibody binds a first mycobacterial antigenic polypeptide, wherein said first mycobacterial antigenic polypeptide comprises a polypeptide sequence having at least 70% amino acid sequence identity to the amino acid sequence of SEQ ID NO: 1 or 7, or a fragment thereof having at least 7 consecutive amino acids thereof; and wherein said second antibody binds a second mycobacterial antigenic polypeptide, wherein said second mycobacterial antigenic polypeptide comprises a polypeptide sequence having at least 70% amino acid sequence identity to the amino acid sequence of SEQ ID NO: 5, or a fragment thereof having at least 7 consecutive amino acids thereof.

In one embodiment, said first and second antibodies are in the form of an immunogenic composition of the invention, as defined above.

In one embodiment of said method, any of the limitations described herein with respect to said first and/or second (or additional) antibodies (or mycobacterial antigens to which they bind) apply equally to said method.

In one embodiment, the method further comprises combining said pharmaceutically acceptable carrier and antibodies (or immunogenic composition) with one or more of a salt, excipient, diluent, adjuvant, immunoregulatory agent and/or antimicrobial compound.

As used, herein, a “vaccine” is a formulation that, when administered to an animal subject such as a mammal (eg. a human, bovine, porcine, ovine, caprine, equine, corvine, canine or feline subject) stimulates a protective immune response against mycobacterial infection. The immune response may be a humoral and/or cell-mediated immune response (eg. a T cell response). A vaccine of the invention can be used, for example, to protect an animal from the effects of mycobacterial invention (eg. *M. tuberculosis* infection), such as an early-stage infection.

The immunogenicity of the epitopes of the first and second mycobacterial antigens (eg. polypeptides) of the invention may be enhanced by preparing them in mammalian or yeast systems fused with or assembled with particle-forming proteins such as, for example, that associated with hepatitis B surface antigen. In one embodiment, the vaccine comprises at least one mycobacterial polypeptide that has been treated with a chemical modifying agent (such as formaldehyde) to give a vaccine of improved efficacy.

The polypeptides (including antibodies) and/or polynucleotides of the invention may be formulated into a vaccine as neutral or salt forms. Pharmaceutically acceptable salts include acid addition salts formed with inorganic acids such as, for example, hydrochloric or phosphoric acids, or with organic acids such as acetic, oxalic, tartaric, maleic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Administration of therapeutic formulations, medicaments and prophylactic formulations (eg. vaccines) is generally by conventional routes e.g. intravenous, subcutaneous, intraperitoneal, or mucosal routes. The administration may be by parenteral injection, for example, a subcutaneous or intramuscular injection. Formulations comprising neutralizing antibodies may be particularly suited to administration intravenously, intramuscularly, intradermally, or subcutaneously.

Accordingly, the therapeutic formulations, medicaments and prophylactic formulations (eg. vaccines) of the invention are typically prepared as injectables, either as liquid solutions or suspensions. Solid forms suitable for solution in, or suspension in, liquid prior to injection may alternatively be prepared. The preparation may also be emulsified, or the peptide encapsulated in liposomes or microcapsules.

The active immunogenic ingredients are often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, and/or adjuvants which enhance the effectiveness of the vaccine.

Generally, the carrier is a pharmaceutically-acceptable carrier. Non-limiting examples of pharmaceutically acceptable carriers include water, saline, and phosphate-buffered saline. In some embodiments, however, the composition is in lyophilized form, in which case it may include a stabilizer, such as BSA. In some embodiments, it may be desirable to formulate the composition with a preservative, such as thiomersal or sodium azide, to facilitate long term storage.

Examples of adjuvants which may be effective include but are not limited to: complete Freunds adjuvant (CFA), Incomplete Freunds adjuvant (IVA), Saponin, a purified extract fraction of Saporin such as Quil A, a derivative of Saporin such as QS-21, lipid particles based on Saponin such as ISCOM/ISCOMATIX, *E. coli* heat labile toxin (LT) mutants such as LTK63 and/or LTK72, aluminium hydroxide, N-acetyl-muramyl-L-threonyl-D-isoglutamine (thr-M DP), N-acetyl-nor-muramyl-L-alanyl-D-isoglutamine (CGP 11637, referred to as nor-M DP), N-acetylmuramyl-L-alanyl-D-isoglutaminyl-L-alanine-2-(1'-2'-dipalmitoyl-sn-glycero-3-hydroxyphosphoryl oxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

Examples of buffering agents include, but are not limited to, sodium succinate (pH 6.5), and phosphate buffered saline (PBS; pH 6.5 and 7.5).

Additional formulations which are suitable for other modes of administration include suppositories and, in some cases, oral formulations or formulations suitable for distribution as aerosols. For suppositories, traditional binders and carriers may include, for example, polyalkylene glycols or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders.

In the case of a mycobacterial respiratory infection (eg. a *M. tuberculosis* infection), efficient transmission of the therapeutic/prophylactic composition or medicament to the site of infection in the lungs may be achieved by oral or intra-nasal administration (i.n.). These modes of delivery correspond to the route of delivery of a *M. tuberculosis* infection. In the case of antibody-based compositions, these modes of delivery ensure that antibodies are present at the site of infection to combat the bacterium before it becomes intracellular and also during the period when it spreads between cells.

Formulations for intranasal administration may in the form of nasal droplets or a nasal spray. An intranasal formulation may comprise droplets having approximate diameters in the range of 100-5000 μm, such as 500-4000 μm, 1000-3000 μm or 100-1000 μm. Alternatively, in terms of volume, the droplets may be in the range of about 0.001-100 μl, such as 0.1-50 μl or 1.0-25 μl, or such as 0.001-1 μl.

Alternatively, the therapeutic/prophylactic formulation or medicament may be an aerosol formulation. The aerosol formulation may take the form of a powder, suspension or solution. The size of aerosol particles is relevant to the delivery capability of an aerosol. Smaller particles may travel further down the respiratory airway towards the alveoli than would larger particles. In one embodiment, the aerosol particles have a diameter distribution to facilitate delivery along the entire length of the bronchi, bronchioles, and alveoli. Alternatively, the particle size distribution may be selected to target a particular section of the respiratory airway, for example the alveoli. In the case of aerosol delivery of the medicament, the particles may have diameters in the approximate range of 0.1-50 μm, preferably 1-25 μm, more preferably 1-5 μm.

Aerosol particles may be for delivery using a nebulizer (eg. via the mouth) or nasal spray. An aerosol formulation may optionally contain a propellant and/or surfactant.

It is possible that, following i.n. delivery of mycobacterial antigens or antibodies, their passage to the lungs is facilitated by a reverse flow of mucosal secretions, although mucociliary action in the respiratory tract is thought to take particles within the mucus out of the lungs. The relatively long persistence in lung lavage, fast clearance from the bile and lack of transport to the saliva of some antibodies suggests the role of mucosal site-specific mechanisms.

By controlling the size of the droplets/particles to within the defined range of the present invention, it is possible to avoid (or minimize) inadvertent antigen delivery to the alveoli and thus avoid alveoli-associated pathological problems such as inflammation and fibrotic scarring of the lungs.

I.n. vaccination engages both T and B cell mediated effector mechanisms in nasal and bronchus associated mucosal tissues, which differ from other mucosae-associated lymphoid tissues. The protective mechanisms invoked by the intranasal route of administration may include: the activation of T lymphocytes with preferential lung homing; up-regulation of co-stimulatory molecules (eg. B7.2); and/or activation of macrophages or secretory IgA antibodies.

Intranasal delivery of antigens may facilitate the invoking of a mucosal antibody response, which is favoured by a shift in the T cell response toward the Th2 phenotype which helps antibody production. A mucosal response is characterised by enhanced IgA production, and a Th2 response is characterised by enhanced IL-4 production.

Intranasal delivery of mycobacterial antigens of the invention allows targeting of the antigens to sub-mucosal B cells of the respiratory system. These B cells are the major local IgA-producing cells in mammals and intranasal delivery facilitates a rapid increase in IgA production by these cells against the mycobacterial antigens.

In one embodiment, the therapeutic/prophylactic formulation or medicament of the invention stimulates a mucosal and/or Th2 immune response. In another embodiment, IgA antibody production is stimulated, and the IgA antibody binds to the mycobacterial antigen.

In one embodiment, the first and second (and optional additional) mycobacterial antigens or antibodies of the invention are for simultaneous administration.

Thus, in one embodiment, the methods/uses of the invention comprise simultaneous administration of the first and second (and optional additional) mycobacterial antigens. In one embodiment, the methods/uses of the invention comprise simultaneous administration of the first and second (and optional additional) mycobacterial antibodies.

Simultaneous administration means administration at (substantially) the same time. For example, in one embodiment the first and second (and optional additional) mycobacterial antigens are administered to the subject within 5 minutes of each other, such as within 4, 3, 2 or 1 minute of each other, for example within 30 seconds of each other.

In one embodiment of 'simultaneous administration', the at least two components (ie. antigens or antibodies) of the invention are combined into one composition (eg. a single antigenic composition or immunogenic composition of the invention as defined herein). This composition is administered to the subject (such as a mammal—eg. a human, bovine, porcine, ovine, caprine, equine, corvine, canine or feline subject) thereby providing both components to the subject simultaneously.

In an alternative embodiment of 'simultaneous administration', at least two of the components (ie. antigens or antibodies) of the invention are provided separately from each other, but are administered to the subject (such as a mammal—eg. a human, bovine, porcine, ovine, caprine, equine, corvine, canine or feline subject) at (substantially) the same time. The concurrent/parallel administration of said separate compositions provides both components to the subject at (substantially) the same time. By way of example, the therapeutic or prophylactic formulation (eg. vaccine) of the invention may comprise a first mycobacterial antigen or antibody in a first composition and the second mycobacterial antigen or antibody in a second composition.

In one embodiment, the first and second (and optional additional) mycobacterial antigens or antibodies of the invention are for simultaneous administration at (substantially) the same site. Thus, in one embodiment, the methods/uses of the invention comprise simultaneous administration of the first and second (and optional additional) mycobacterial antigens at (substantially) the same site. In one embodiment, the methods/uses of the invention comprise simultaneous administration of the first and second (and optional additional) mycobacterial antibodies at (substantially) the same site.

In this regard, it is considered advantageous to administer each different antigenic component of conventional multivalent vaccines at different sites of the subject's body, in order to stimulate different lymph nodes. Administration of different antigenic components of conventional multivalent vaccines at different sites is also considered advantageous in order to reduce or avoid undesirable antigenic competition.

In one embodiment, the present invention advantageously avoids the need to administer each different antigenic component to different sites/locations of the subject's body. In this regard, in one embodiment, the first and second (and optional additional) antigens of the present invention (substantially) do not compete with each other, or are associated with relatively low levels of antigenic competition, as compared with the competitive effect that might have been expected in view of known multivalent vaccine compositions.

If the at least two components (ie. antigens or antibodies) of the invention are combined into a single composition (eg. a single antigenic composition or immunogenic composition of the invention as defined herein), it is evident that all components of the invention are administered to the subject at the same site.

In one embodiment, if the first and second (and optional additional) mycobacterial antigens or antibodies of the invention are provided separately from each other, for simultaneous, parallel administration to the subject at (substantially) the same time, the separate compositions are administered at the same (or substantially the same) site on/in the subject.

In one embodiment, administration at (substantially) the same site on/in the subject means that the site at which the each mycobacterial antigen or antibody of the invention is administered is in the vicinity of or in close proximity to the site at which the other mycobacterial antigens or antibodies of the invention are administered. Alternatively, administration at (substantially) the same site on/in the subject means that the site at which the each mycobacterial antigen or antibody of the invention is administered is at the precise site at which the other mycobacterial antigens or antibodies of the invention are administered.

By way of example, the first and second (and optional additional) mycobacterial antigens or antibodies of the invention may be for administration to the same vein, artery or muscle of the subject, or via the same nostril of the subject; or to the same limb (eg. arm) of the subject (eg. to the same upper arm of the subject); or the first and second (and optional additional) mycobacterial antigens or antibodies of the invention may all be for oral or sublingual administration. In one embodiment, the first and second (and optional additional) mycobacterial antigens or antibodies of the invention may all be for administration at or in close proximity to the same lymph node.

Alternatively, the mycobacterial antigens or antibodies of the invention are for administration to the subject (eg. a mammal such as a human, bovine, porcine, ovine, caprine, equine, corvine, canine or feline subject) sequentially (ie. one after the other). In this embodiment, at least two of the components (ie. antigens or antibodies) of the invention are provided separately from each other, and are administered sequentially to the subject.

By way of example, the therapeutic or prophylactic formulation (eg. vaccine) of the invention may comprise a first mycobacterial antigen or antibody in a first composition and the second mycobacterial antigen or antibody in a second composition. The sequential administration of said first and second compositions provides both components to the subject one after the other.

Thus, in one embodiment, the methods of the invention comprise administration of the first mycobacterial antigen, and then administration of the second mycobacterial antigen. Alternatively, the second mycobacterial antigen may be administered and then the first mycobacterial antigen is administered. Any additional mycobacterial antigens may be administered together with the first and/or second mycobacterial antigens. Alternatively, any additional mycobacterial antigens may be administered before or after the first and/or second mycobacterial antigens.

In one embodiment, the methods of the invention comprise administration of the first mycobacterial antibody, and then administration of the second mycobacterial antibody. Alternatively, the second mycobacterial antibody may be administered and then the first mycobacterial antibody is administered. Any additional mycobacterial antibodies may be administered together with the first and/or second mycobacterial antibodies. Alternatively, any additional mycobacterial antibodies may be administered before or after the first and/or second mycobacterial antibodies.

In one embodiment, each sequential administration of antigen/antibody is made immediately one after the other. In one embodiment, there is a time-gap or pause between one or more (eg. between each) of the administrations. A time-gap or pause between sequential administrations may be at least 5, 10, 15, or 30 minutes, or may be at least 1, 2, 5, 12, 18 or 24 hours, or may be at least 1, 2, or 5 days, or may be at least 1 or 2 weeks.

In one embodiment, the first and second (and optional additional) mycobacterial antigens or antibodies of the invention are for sequential administration at (substantially) the same site. Thus, in one embodiment, the methods/uses of the invention comprise sequential administration of the first and second (and optional additional) mycobacterial antigens at (substantially) the same site. In one embodiment, the methods/uses of the invention comprise sequential administration of the first and second (and optional additional) mycobacterial antibodies at (substantially) the same site.

In one embodiment, administration at (substantially) the same site on/in the subject means that the site at which the each mycobacterial antigen or antibody of the invention is administered is in the vicinity of or in close proximity to the site at which the other mycobacterial antigens or antibodies of the invention are administered. Alternatively, administration at (substantially) the same site on/in the subject means that the site at which the each mycobacterial antigen or antibody of the invention is administered is at the precise site at which the other mycobacterial antigens or antibodies of the invention are administered.

By way of example, the first and second (and optional additional) mycobacterial antigens or antibodies of the invention may be for administration to the same vein, artery or muscle of the subject, or via the same nostril of the subject; or to the same limb (eg. arm) of the subject (eg. to the same upper arm of the subject); or the first and second (and optional additional) mycobacterial antigens or antibodies of the invention may all be for oral or sublingual administration. In one embodiment, the first and second (and optional additional) mycobacterial antigens or antibodies of the invention may all be for administration at or in close proximity to the same lymph node.

The therapeutic formulation, medicament or prophylactic formulation (eg. a vaccine) of the invention may be given in a single dose schedule (ie. the full dose is given at substantially one time). Alternatively, the therapeutic formulation, medicament or prophylactic formulation (eg. a vaccine) of the invention may be given in a multiple dose schedule.

A multiple dose schedule is one in which a primary course of treatment (eg. vaccination) may be with 1-6 separate doses, followed by other doses given at subsequent time intervals required to maintain and or reinforce the immune response, for example (for human subjects), at 1-4 months for a second dose, and if needed, a subsequent dose(s) after a further 1-4 months.

The dosage regimen will be determined, at least in part, by the need of the individual and be dependent upon the judgment of the practitioner (eg. doctor or veterinarian).

In one embodiment, the vaccine of the present invention may be administered as part of a 'prime-boost' vaccination regime.

Prime-boost vaccination regimes involve: Priming—ie. exposing a subject to one or more antigens or a vaccine; and subsequently: Boosting—ie. exposing the subject to one or more antigens or a vaccine. The 'boost' antigens/vaccine is typically different from the 'primer' antigens/vaccine (known as "heterologous" prime-boost). In this regard, heterologous prime-boost immunization strategies have been shown to induce higher levels of immune cell responses (eg. effector T cell responses) in subjects as compared with homologous boosting with the same vaccine. For example, repeated vaccination with conventional vaccines such as BCG does not appear to further enhance protection against TB. However, incorporating BCG into a heterologous prime-boost regime may retain the protective effects of BCG.

Thus, in one embodiment the invention provides a method of vaccination against mycobacterial infection comprising 'priming' a subject's immune system by administration of a heterologous conventional vaccine (eg. BCG vaccine) and then 'boosting' the subject's immune system by administration of the vaccine of the present invention. In one embodiment, the invention provides a method of vaccination against mycobacterial infection comprising administering the vaccine of the present invention to a subject that has been pre-exposed to a heterologous conventional vaccine such as BCG.

Alternatively, a subject's immune system may be 'primed' by administration of the vaccine of the present invention, and then 'boosted' by administration of a heterologous conventional vaccine (eg. BCG vaccine). Accordingly, in one embodiment, the vaccine is administered to a subject that is subsequently to be exposed to a heterologous conventional vaccine such as BCG.

The 'priming' step may be carried out on the subject at any age—in the case of mammalian subjects (eg. human, bovine, porcine, ovine, caprine, equine, cervine, canine or feline subjects), priming with BCG is conventionally carried out neonatally, or during infancy, adolescence or adulthood. The 'boosting' step may be carried out at any time after the 'priming' step. In the case of mammalian subjects (eg. human, bovine, porcine, ovine, caprine, equine, cervine, canine or feline subjects), a boosting step may be carried out at least about 1, 2, 3, 4, 5, 6, 7, 8, 9 or 10 weeks after the priming step, or at least about 3, 6, 8 or 12 months after the priming step, or at least about 2, 5, 10, 15, 20, 25, 30, 35, or 40 or more years after the boosting step. In one embodiment, for a human subject, the priming step is carried out during infancy and the boosting step is carried out during adolescence.

In one embodiment, the therapeutic formulation, medicament or prophylactic formulation (eg. a vaccine) of the invention can be administered to a subject such as a mammal (eg. a human, bovine, porcine, ovine, caprine, equine, corvine, canine or feline subject) in conjunction with (simultaneously or sequentially) one or more immunoregulatory agents selected from, for example, immunoglobulins, antibiotics, interleukins (eg. IL-2, IL-12), and/or cytokines (eg. IFNγ).

In one embodiment, the therapeutic formulation, medicament or prophylactic formulation (eg. vaccine) of the invention can be administered to a subject such as a mammal (eg. a human, bovine, porcine, ovine, caprine, equine, corvine, canine or feline subject) in conjunction with (simultaneously or sequentially) one or more antimicrobial compounds, such as conventional anti-tuberculosis drugs (eg. rifampicin, isoniazid, ethambutol or pyrizinamide).

The therapeutic formulation, medicament or prophylactic formulation (eg. vaccine) may contain 5% to 95% of active ingredient, such as at least 10% or 25% of active ingredient, or at least 40% of active ingredient or at least 50, 55, 60, 70 or 75% active ingredient.

The therapeutic formulation, medicament or prophylactic formulation (eg. a vaccine) is administered in a manner compatible with the dosage formulation, and in such amount as will be prophylactically and/or therapeutically effective.

In this regard, as used herein, an "effective amount" is a dosage or amount that is sufficient to achieve a desired biological outcome. As used herein, a "therapeutically effective amount" is an amount which is effective, upon single or multiple dose administration to a subject (such as a mammal—eg. a human, bovine, porcine, ovine, caprine, equine, corvine, canine or feline subject) for treating, preventing, curing, delaying, reducing the severity of, ameliorating at least one symptom of a disorder or recurring disorder, or prolonging the survival of the subject beyond that expected in the absence of such treatment.

Accordingly, the quantity of active ingredient to be administered, which is generally in the range of 5 micrograms to 250 micrograms of antigen per dose (or higher if delivered orally or in the form of viral vectors), depends on the subject to be treated, capacity of the subject's immune system to generate a protective immune response, and the degree of protection desired. Precise amounts of active ingredient required to be administered may depend on the judgment of the practitioner and may be particular to each subject.

According to a further aspect of the invention, the first and second mycobacterial antigens (and optional additional mycobacterial antigens) of the invention, as described herein, are useful in immunoassays to detect the presence in a test sample of antibodies to said first and second mycobacterial antigens. In one embodiment, said first and second mycobacterial antigens (and optional additional antigens) are used in the form of an antigenic composition, as described herein.

According to another aspect of the invention, the first and second antibodies (and optional additional antibodies) of the invention, as described herein, are useful in immunoassays to detect the presence in a test sample of said first and second mycobacterial antigens. In one embodiment, said first and second antibodies (and optional additional antibodies) are used in the form of an immunogenic antibody-containing composition, as described herein.

A test sample may be a biological sample such as a clinical sample or environmental sample. As used herein, a 'clinical sample' refers to a sample of tissue or fluid isolated from an individual, including but not limited to, for example, plasma, serum, spinal fluid, lymph fluid, the external sections of the skin, respiratory, intestinal, and genitourinary tracts, tears, saliva, milk, blood cells, tumours, organs, and also samples of in vitro cell culture constituents (including but not limited to conditioned medium resulting from the growth of cells in cell culture medium, putatively infected cells, recombinant cells, and cell components).

In the context of the diagnostic methods discussed below, a 'subject' is any animal subject that would benefit from detection of mycobacterial infection, such as *M. tuberculosis* infection. Typical animal subjects are mammals, for example, human, bovine, porcine, ovine, caprine, equine, corvine, canine or feline subjects. In one embodiment, the subject is human, bovine, porcine or equine.

Design of immunoassays is subject to a great deal of variation, and many formats are known in the art. Protocols may be based, for example, upon competition, direct reaction, or sandwich type assays. Protocols may also, for example, use solid supports, or may employ immuno-precipitation. Most assays involve the use of labeled antibodies or polypeptides; the labels may be, for example, enzymatic, fluorescent, chemiluminescent, radioactive, or dye molecules. Assays that comprise signal amplification be are also known; for example, assays that utilize biotin and avidin, or enzyme-labeled and mediated immunoassays, such as ELISA assays.

In one aspect of the invention, the first and second mycobacterial antigens (or antigenic composition) of the invention are useful for detecting the presence of a T-lymphocyte that has been previously exposed to an antigenic component of a mycobacterial infection in a patient.

Accordingly, in one embodiment, the invention provides an in vitro method of diagnosing a mycobacterial infection, such as an early stage mycobacterial infection, comprising incubating ('challenging') a test sample containing an immune cell such as a T-lymphocyte from a subject (eg. a mammal such as a human, bovine, porcine or equine subject) with a first mycobacterial antigen of the invention and a second mycobacterial antigen of the invention, as defined herein; or an antigenic composition of the invention, as defined herein; and detecting activation of said immune cell (eg. T-lymphocyte). Activation of said immune cell is indicative of a mycobacterial infection in the subject.

In one embodiment of said in vitro method, said first mycobacterial antigen is selected from (i) a first mycobacterial antigenic polypeptide comprising a polypeptide sequence having at least 70% amino acid sequence identity to the amino acid sequence of SEQ ID NO: 1 or 7, or a fragment thereof having at least 7 consecutive amino acids thereof; or (ii) a first mycobacterial polynucleotide sequence comprising a polynucleotide sequence encoding said first mycobacterial antigenic polypeptide. In one embodiment of said in vitro method, said second mycobacterial antigen is selected from (iii) a second mycobacterial antigenic polypeptide comprising a polypeptide sequence having at least 70% amino acid sequence identity to the amino acid sequence of SEQ ID NO: 5, or a fragment thereof having at least 7 consecutive amino acids thereof; or (iv) a second mycobacterial polynucleotide sequence comprising a polynucleotide sequence encoding said second mycobacterial antigenic polypeptide.

An immune cell, such as a T-lymphocyte, that has been previously exposed to one or both of the first and second mycobacterial antigens will become 'activated' on subsequent challenge by the same antigen. As such, activation of said immune cell (eg. T-lymphocyte) is indicative of a mycobacterial infection in the subject, and provides a means for identifying a positive diagnosis of mycobacterial infection. In contrast, the same activation is not achieved by an immune cell (eg. T-lymphocyte) that has not been previously exposed to the particular antigen.

The above-described 'activation' of an immune cell (eg. T-lymphocyte) is sometimes referred to as a 'recall response' and may be measured, for example, by determining the release of interferon (eg. IFN-γ) from the activated immune cell (eg. T-lymphocyte).

Thus, the presence of a mycobacterial infection in a patient may be determined by detecting activation of immune cell (eg. T-lymphocyte) in response to in vitro challenge with the first and second mycobacterial antigens (or antigenic composition) of the present invention—eg. by detecting the release of a minimum concentration of interferon from immune cell (eg. T-lymphocyte) after a defined time period following the challenge.

The above immune cell (eg. T-lymphocyte) diagnostic assay may further include an antigen presenting cell (APC) expressing at least one major histocompatibility complex (MHC) class II molecule expressed by the patient in question. The APC may be inherently provided in the biological sample, or may be added exogenously. In one embodiment, the T-lymphocyte is a CD4 T-lymphocyte.

Alternative immunoassays for diagnosing mycobacterial infection depend upon detection of antibodies to the first and second mycobacterial antigens (eg. polypeptides) of the invention. Such assays may comprise the step of incubating a test sample (eg. a biological sample) suspected of containing the antibodies with said first and second antigens (or antigenic composition) of the invention.

Accordingly, the invention also provides an in vitro method of diagnosing a mycobacterial infection, such as an early stage mycobacterial infection, comprising incubating a test sample from a subject (eg. a mammal such as a human, bovine, porcine or equine subject) with a first mycobacterial antigen and a second mycobacterial antigen of the invention, as defined herein; or an antigenic composition of the invention, as defined herein; wherein said incubating is performed under conditions that allow binding of said first and second mycobacterial antigens with antibodies in the sample to form antigen-antibody complexes; and then detecting the formation of such complexes. The presence of antigen-antibody complexes is indicative of a mycobacterial infection in the subject.

In one embodiment of said in vitro method, said first mycobacterial antigen is selected from (i) a first mycobacterial antigenic polypeptide comprising a polypeptide sequence having at least 70% amino acid sequence identity to the amino acid sequence of SEQ ID NO: 1 or 7, or a fragment thereof having at least 7 consecutive amino acids thereof; or (ii) a first mycobacterial polynucleotide sequence comprising a polynucleotide sequence encoding said first mycobacterial antigenic polypeptide; and said second mycobacterial antigen is selected from (iii) a second mycobacterial antigenic polypeptide comprising a polypeptide sequence having at least 70% amino acid sequence identity to the amino acid sequence of SEQ ID NO: 5, or a fragment thereof having at least 7 consecutive amino acids thereof; and (iv) a second mycobacterial polynucleotide sequence comprising a polynucleotide sequence encoding said second mycobacterial antigenic polypeptide.

Antigen-antibody complexes (or, in the case of competitive assays, the amount of competing antibody) may be detected by any of a number of known techniques, depending on the format. For example, unlabelled antibodies in the complex may be detected using a conjugate of anti-xenogeneic Ig complexed with a label (eg. an enzyme label).

The immunoassay may be of a standard or competitive type.

In one embodiment, the first and second mycobacterial antigens are bound to one or more solid supports to facilitate separation of the sample from the antigens after incubation. Examples of solid supports that can be used are nitrocellulose (eg. in membrane or microtiter well form), polyvinyl chloride (eg. in sheets or microtiter wells), polystyrene latex (eg. in beads or microtiter plates, polyvinylidine fluoride (known as Immulon), diazotized paper, nylon membranes, activated beads, and Protein A beads. For example, Dynatech Immulon microtiter plates or 60 mm diameter polystyrene beads (Precision Plastic Ball) may be used. The solid support(s) containing the first and second mycobacterial antigens is typically washed after separating it from the test sample, and prior to detection of bound antibodies.

The invention also embraces immunoassays for detecting the presence of the first and second mycobacterial antigens (eg. polypeptides) of the invention in a test sample (eg. a biological sample). In such methods, a test sample suspected of containing said mycobacterial antigens may be incubated with antibodies directed against the first and second mycobacterial antigens.

Accordingly, the invention provides an in vitro method of diagnosing a mycobacterial infection, such as an early stage mycobacterial infection, comprising incubating a test sample from a subject (eg. a mammal such as a human, bovine, porcine or equine subject) with a first antibody and a second antibody of the invention, as defined herein; or an immunogenic composition of the invention, as defined herein; wherein said incubating is performed under conditions that allow binding of said first and second antibodies with antigens in the sample to form antigen-antibody complexes; and then detecting the formation of such complexes, wherein the presence of antigen-antibody complexes is indicative of a mycobacterial infection in the subject.

In one embodiment of said in vitro method, said first antibody binds a first mycobacterial antigenic polypeptide, wherein said first mycobacterial antigenic polypeptide comprises a polypeptide sequence having at least 70% amino acid sequence identity to the amino acid sequence of SEQ ID NO: 1 or 7, or a fragment thereof having at least 7 consecutive amino acids thereof; and said second antibody binds a second mycobacterial antigenic polypeptide, wherein said second mycobacterial antigenic polypeptide comprises a polypeptide sequence having at least 70% amino acid sequence identity to the amino acid sequence of SEQ ID NO: 5, or a fragment thereof having at least 7 consecutive amino acids thereof.

It may be desirable to treat the biological sample prior to testing, to release putative bacterial components. Various formats can be employed. For example, a "sandwich assay" may be employed, where antibodies bound to a solid support are incubated with the test sample; washed; incubated with second, labeled antibodies to the first and second antigens, and the support is washed again. The first and second mycobacterial antigens are detected by determining if the second antibody is bound to the support. In a competitive format, a test sample is usually incubated with antibodies and a labeled, competing antigen is also incubated, either sequentially or simultaneously.

In one aspect, the invention provides an immunoassay kit, comprising an antigenic composition of the invention, or antibodies to said first and second mycobacterial antigens. The immunoassay kit may further comprise a buffer.

The term "polypeptide" throughout this specification is synonymous with the terms "oligopeptide", "peptide" and "protein". These terms are used interchangeably and do not refer to a specific length of the product. These terms embrace post-translational modifications such as glycosylation, acetylation and phosphorylation.

In one embodiment, the isolated polypeptides of the invention are substantially free from other proteins with which they are co-produced as well as from other contaminants. For instance, an isolated polypeptide is substantially free of material or other proteins from the cell, bacterial, or tissue source from which it was derived.

As used herein, a "purified" molecule is substantially free of its original environment and is sufficiently pure for use in pharmaceutical compositions. A substantially pure polypeptide, as used herein, refers to a polypeptide that is at least about 50% (w/w) pure; or at least about 60%, 70%, 80%, 85%, 90% or 95% (w/w) pure; or at least about 95%, 96%, 97%, 98%, 99%, or 100% (w/w) pure.

The polypeptides of the present invention may be purified from mycobacteria, or may be purified from other cell-types that express these peptides (eg. because they are transformed with recombinant nucleic acids encoding these peptides). The expressed polypeptide may be purified by, for instance, a combination of hydrophobic interaction chromatography, ion exchange chromatography and ceramic hydroxyl apatite chromatography. Other chromatographic techniques well known to the art of protein purification, such size exclusion chromatography, may be used. Polypeptide purity or homogeneity may be indicated by, for example, polyacrylamide gel electrophoresis of a protein sample, followed by visualizing a single polypeptide band upon staining the gel, or using HPLC.

The polypeptides of the invention should generally be soluble or predominantly soluble (for instance, at least about 70%, 75%, 80%, 85%, 90%, 95%, 97%, 98%, or even 99% soluble).

The present invention encompasses polypeptides that are substantially homologous to a polypeptide based on any one of the reference SEQ ID NOs identified in this application (including fragments thereof). The terms "sequence identity" and "sequence homology" are considered synonymous in this specification.

By way of example, a polypeptide of interest may comprise an amino acid sequence having at least 70, 75, 80, 82, 84, 86, 88, 90, 92, 94, 96, 98, 99 or 100% amino acid sequence identity with the amino acid sequence of a reference polypeptide.

There are many established algorithms available to align two amino acid sequences.

Typically, one sequence acts as a reference sequence, to which test sequences may be compared. The sequence comparison algorithm calculates the percentage sequence identity for the test sequence(s) relative to the reference sequence, based on the designated program parameters. Alignment of amino acid sequences for comparison may be conducted, for example, by computer implemented algorithms (eg. GAP, BESTFIT, FASTA or TFASTA), or BLAST and BLAST 2.0 algorithms.

The BLOSUM62 table shown below is an amino acid substitution matrix derived from about 2,000 local multiple alignments of protein sequence segments, representing highly conserved regions of more than 500 groups of related proteins (Henikoff & Henikoff, Proc. Natl. Acad. Sci. USA 89:10915-10919, 1992; incorporated herein by reference). Amino acids are indicated by the standard one-letter codes. The percent identity is calculated as:

$$\frac{\text{Total number of identical matches}}{\begin{array}{c}\text{[length of the longer sequence plus the number of gaps} \\ \text{Introduced into the longer sequence} \\ \text{in order to align the two sequences]}\end{array}} \times 100$$

BLOSUM62 table

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | −1 | 5 | | | | | | | | | | | | | | | | | | |
| N | −2 | 0 | 6 | | | | | | | | | | | | | | | | | |
| D | −2 | −2 | 1 | 6 | | | | | | | | | | | | | | | | |
| C | 0 | −3 | −3 | −3 | 9 | | | | | | | | | | | | | | | |
| Q | −1 | 1 | 0 | 0 | −3 | 5 | | | | | | | | | | | | | | |
| E | −1 | 0 | 0 | 2 | −4 | 2 | 5 | | | | | | | | | | | | | |
| G | 0 | −2 | 0 | −1 | −3 | −2 | −2 | 6 | | | | | | | | | | | | |
| H | −2 | 0 | 1 | −1 | −3 | 0 | 0 | −2 | 8 | | | | | | | | | | | |
| I | −1 | −3 | −3 | −3 | −1 | −3 | −3 | −4 | −3 | 4 | | | | | | | | | | |
| L | −1 | −2 | −3 | −4 | −1 | −2 | −3 | −4 | −3 | 2 | 4 | | | | | | | | | |
| K | −1 | 2 | 0 | −1 | −3 | 1 | 1 | −2 | −1 | −3 | −2 | 5 | | | | | | | | |
| M | −1 | −1 | −2 | −3 | −1 | 0 | −2 | −3 | −2 | 1 | 2 | −1 | 5 | | | | | | | |
| F | −2 | −3 | −3 | −3 | −2 | −3 | −3 | −3 | −1 | 0 | 0 | −3 | 0 | 6 | | | | | | |
| P | −1 | −2 | −2 | −1 | −3 | −1 | −1 | −2 | −2 | −3 | −3 | −1 | −2 | −4 | 7 | | | | | |
| S | 1 | −1 | 1 | 0 | −1 | 0 | 0 | 0 | −1 | −2 | −2 | 0 | −1 | −2 | −1 | 4 | | | | |
| T | 0 | −1 | 0 | −1 | −1 | −1 | −1 | −2 | −2 | −1 | −1 | −1 | −1 | −2 | −1 | 1 | 5 | | | |
| W | −3 | −3 | −4 | −4 | −2 | −2 | −3 | −2 | −2 | −3 | −2 | −3 | −1 | 1 | −4 | −3 | −2 | 11 | | |
| Y | −2 | −2 | −2 | −3 | −2 | −1 | −2 | −3 | 2 | −1 | −1 | −2 | −1 | 3 | −3 | −2 | −2 | 2 | 7 | |
| V | 0 | −3 | −3 | −3 | −1 | −2 | −2 | −3 | −3 | 3 | 1 | −2 | 1 | −1 | −2 | −2 | 0 | −3 | −1 | 4 |

In a homology comparison, the identity may exist over a region of the sequences that is at least 7 amino acid residues in length (eg. at least 10, 20, 30, 40, 50, 75, 100, 150, 200, 250, 300, 350, 400, 450, 500, 550, 600 or 650 amino acid residues in length—eg. up to the entire length of the reference sequence.

Substantially homologous polypeptides have one or more amino acid substitutions, deletions, or additions. In many embodiments, those changes are of a minor nature, for example, involving only conservative amino acid substitutions. Conservative substitutions are those made by replacing one amino acid with another amino acid within the following groups: Basic: arginine, lysine, histidine; Acidic: glutamic acid, aspartic acid; Polar: glutamine, asparagine; Hydrophobic: leucine, isoleucine, valine; Aromatic: phenylalanine, tryptophan, tyrosine; Small: glycine, alanine, serine, threonine, methionine. Substantially homologous polypeptides also encompass those comprising other substitutions that do not significantly affect the folding or activity of the polypeptide; small deletions, typically of 1 to about 30 amino acids (such as 1-10, or 1-5 amino acids); and small amino- or carboxyl-terminal extensions, such as an amino-terminal methionine residue, a small linker peptide of up to about 20-25 residues, or an affinity tag.

The polypeptides of the present invention may also comprise non-naturally occurring amino acid residues. In this regard, in addition to the 20 standard amino acids, non-standard amino acids (such as 4-hydroxyproline, 6-N-methyl lysine, 2-aminoisobutyric acid, isovaline and α-methyl serine) may be substituted for amino acid residues of the mycobacterial polypeptides of the present invention. A limited number of non-conservative amino acids, amino acids that are not encoded by the genetic code, and unnatural amino acids may be substituted for mycobacterial polypeptide amino acid residues. Non-naturally occurring amino acids include, without limitation, trans-3-methylproline, 2,4-methano-proline, cis-4-hydroxyproline, trans-4-hydroxy-proline, N-methylglycine, allo-threonine, methyl-threonine, hydroxy-ethylcysteine, hydroxyethylhomo-cysteine, nitro-glutamine, homoglutamine, pipecolic acid, tert-leucine, norvaline, 2-azaphenylalanine, 3-azaphenyl-alanine, 4-azaphenyl-alanine, and 4-fluorophenylalanine.

Several methods are known in the art for incorporating non-naturally occurring amino acid residues into polypeptides. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations can be carried out in a cell free system comprising an *E. coli* S30 extract and commercially available enzymes and other reagents. Peptides can be, for instance, purified by chromatography. In a second method, translation is carried out in *Xenopus* oocytes by microinjection of mutated mRNA and chemically aminoacylated suppressor tRNAs. Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the polypeptide in place of its natural counterpart. Naturally occurring amino acid residues can be converted to non-naturally occurring species by in vitro chemical modification. Chemical modification can be combined with site-directed mutagenesis to further expand the range of substitutions.

Essential amino acids, such as those in the polypeptides of the present invention, can be identified according to procedures known in the art, such as site-directed mutagenesis or alanine-scanning mutagenesis. Sites of biological interaction can also be determined by physical analysis of structure, as determined by such techniques as nuclear magnetic resonance, crystallography, electron diffraction or photoaffinity labeling, in conjunction with mutation of putative contact site amino acids. The identities of essential amino acids can also be inferred from analysis of homologies with related family members of the polypeptide of interest.

Multiple amino acid substitutions can be made and tested using known methods of mutagenesis and screening. Methods are known for simultaneously randomizing two or more positions in a polypeptide, selecting for functional polypeptide, and then sequencing the mutagenized polypeptides to determine the spectrum of allowable substitutions at each position. Other methods that can be used include phage display.

Routine deletion analyses of nucleic acid molecules can be performed to obtain functional fragments of a nucleic acid molecule that encodes a polypeptide of the invention. As an illustration, DNA molecules can be digested with Bal31 nuclease to obtain a series of nested deletions. These DNA fragments are then inserted into expression vectors in proper reading frame, and the expressed polypeptides are isolated and tested for the desired activity. An alternative to exonuclease digestion is to use oligonucleotide-directed mutagenesis to introduce deletions, or stop codons to specify production of a desired fragment. Alternatively, particular polynucleotide fragments can be synthesized using the polymerase chain reaction.

A mutant of a polypeptide of the invention may contain one or more analogs of an amino acid (eg. an unnatural amino acid), or a substituted linkage, as compared with the sequence of the reference polypeptide. In a further embodiment, a polypeptide of interest may be a mimic of the reference polypeptide, which mimic reproduces at least one epitope of the reference polypeptide.

Mutants of the disclosed polynucleotide and polypeptide sequences of the invention can be generated through DNA shuffling. Briefly, mutant DNAs are generated by in vitro homologous recombination by random fragmentation of a parent DNA followed by reassembly using PCR, resulting in randomly introduced point mutations. This technique can be modified by using a family of parent DNAs, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed above can be combined with high-throughput screening methods to detect activity of cloned mutant polypeptides. Mutagenized nucleic acid molecules that encode polypeptides of the invention, or fragments thereof, can be recovered from the host cells and rapidly sequenced using modern equipment. These methods allow the rapid determination of the importance of individual amino acid residues in a polypeptide of interest, and can be applied to polypeptides of unknown structure.

A "fragment" of a polypeptide of interest comprises a series of consecutive amino acid residues from the sequence of said polypeptide. By way of example, a "fragment" of a polypeptide of interest may comprise (or consist of) at least 7 consecutive amino acid residues from the sequence of said polypeptide (eg. at least 10, 15, 25, 50, 75, 100, 125, 150, 175, 200, 225, 250, 275, 300, 325, 350, 375, 400, 425, 450, 475, 500, 525, 550, 575, 600, 625, 650 or 675 consecutive amino acid residues of said polypeptide). A fragment may include at least one epitope of the polypeptide of interest.

A polypeptide of interest, or fragment, may possess the active site of the reference polypeptide.

The polypeptide of interest, or fragment thereof, may have a common antigenic cross-reactivity and/or substantially the same in vivo biological activity as the reference peptide. For example, the polypeptides, or polypeptide fragments, and reference polypeptides share a common ability to induce a "recall response" of an immune cell such as a T-lymphocyte (eg. CD4+, CD8+, effector T cell or memory T cell such as a TEM or TCM), which has been previously exposed to an antigenic component of a mycobacterial infection.

New immunological assays for measuring and quantifying immune cell responses (eg. T cell responses) have been established over the last 10 years. For example, the interferon-gamma (IFN-γ) ELISPOT assay is useful as an immunological readout because the secretion of IFN-γ from antigen-specific T cells is a good correlate of protection against *M. tuberculosis*. Furthermore, the ELISPOT assay is a very reproducible and sensitive method of quantifying the number of IFN-γ secreting antigen-specific immune cells (eg. T cells).

Alternatively, or in addition, an antibody capable of binding to a polypeptide of interest, or fragment, may be also capable of binding to the reference peptide.

As used herein, the terms "nucleic acid sequence" and "polynucleotide" are used interchangeably and do not imply any length restriction. As used herein, the terms "nucleic acid" and "nucleotide" are used interchangeably. The terms "nucleic acid sequence" and "polynucleotide" embrace DNA (including cDNA) and RNA sequences.

The polynucleotide sequences of the present invention include nucleic acid sequences that have been removed from their naturally occurring environment, recombinant or cloned DNA isolates, and chemically synthesized analogues or analogues biologically synthesized by heterologous systems.

The polynucleotides of the present invention may be prepared by any means known in the art. For example, large amounts of the polynucleotides may be produced by replication in a suitable host cell. The natural or synthetic DNA fragments coding for a desired fragment will be incorporated into recombinant nucleic acid constructs, typically DNA constructs, capable of introduction into and replication in a prokaryotic or eukaryotic cell. Usually the DNA constructs will be suitable for autonomous replication in a unicellular host, such as yeast or bacteria, but may also be intended for introduction to and integration within the genome of a cultured insect, mammalian, plant or other eukaryotic cell lines.

The polynucleotides of the present invention may also be produced by chemical synthesis, eg. by the phosphoramidite method or the triester method, and may be performed on commercial automated oligonucleotide synthesizers. A double-stranded fragment may be obtained from the single stranded product of chemical synthesis either by synthesizing the complementary strand and annealing the strand together under appropriate conditions or by adding the complementary strand using DNA polymerase with an appropriate primer sequence.

The term "recombinant" as used herein intends a polynucleotide of genomic, cDNA, semi-synthetic, or synthetic origin which, by virtue of its origin or manipulation: (1) is not associated with all or a portion of a polynucleotide with which it is associated in nature; or (2) is linked to a polynucleotide other than that to which it is linked in nature; and (3) does not occur in nature. This artificial combination is often accomplished by via conventional chemical synthesis techniques, or by the artificial manipulation of isolated segments of nucleic acids—eg., by conventional genetic engineering techniques.

When applied to a nucleic acid sequence, the term "isolated" in the context of the present invention denotes that the polynucleotide sequence has been removed from its natural genetic milieu and is thus free of other extraneous or unwanted coding sequences (but may include naturally occurring 5' and 3' untranslated regions such as promoters and terminators), and is in a form suitable for use within genetically engineered protein production systems. Such isolated molecules are those that are separated from their natural environment.

Methods for isolating nucleic acid sequences are known in the art.

A nucleic acid sequence encoding a polypeptide of the invention can be obtained by conventional cloning procedures, such as PCR, or can be synthesized using nucleic acid synthesis machines. An alternative way to prepare a full-length polynucleotide is to synthesize a specified set of overlapping oligonucleotides (eg. 40 to 100 nucleotides), as described (for example) in Glick & Pasternak, Molecular Biotechnology, Principles & Applications of Recombinant DNA, (1994). Other sequences may be added that contain signals for proper initiation and termination of transcription and translation.

In view of the degeneracy of the genetic code, considerable sequence variation is possible among the polynucleotides of the present invention. Degenerate codons encompassing all possible codons for a given amino acid are set forth below:

| Amino Acid | Codons | Degenerate Codon |
|---|---|---|
| Cys | TGC TGT | TGY |
| Ser | AGC AGT TCA TCC TCG TCT | WSN |
| Thr | ACA ACC ACG ACT | ACN |
| Pro | CCA CCC CCG CCT | CCN |
| Ala | GCA GCC GCG GCT | GCN |
| Gly | GGA GGC GGG GGT | GGN |
| Asn | AAC AAT | AAY |
| Asp | GAC GAT | GAY |
| Glu | GAA GAG | GAR |
| Gln | CAA CAG | CAR |
| His | CAC CAT | CAY |
| Arg | AGA AGG CGA CGC CGG CGT | MGN |
| Lys | AAA AAG | AAR |
| Met | ATG | ATG |
| Ile | ATA ATC ATT | ATH |
| Leu | CTA CTC CTG CTT TTA TTG | YTN |
| Val | GTA GTC GTG GTT | GTN |
| Phe | TTC TTT | TTY |
| Tyr | TAC TAT | TAY |
| Trp | TGG | TGG |
| Ter | TAA TAG TGA | TRR |
| Asn/Asp | | RAY |
| Glu/Gln | | SAR |
| Any | | NNN |

One of ordinary skill in the art will appreciate that some ambiguity is introduced in determining a degenerate codon, representative of all possible codons encoding each amino acid. For example, some polynucleotides encompassed by the degenerate sequence may encode variant amino acid sequences, but one of ordinary skill in the art can easily identify such variant sequences by reference to the amino acid sequences of the present invention.

A "variant" nucleic acid sequence has substantial homology or substantial similarity to a reference nucleic acid sequence (or a fragment thereof). A nucleic acid sequence or fragment thereof is "substantially homologous" (or "substantially identical") to a reference sequence if, when optimally aligned (with appropriate nucleotide insertions or deletions) with the other nucleic acid (or its complementary strand), there is nucleotide sequence identity in at least about 70%, 75%, 80%, 82, 84, 86, 88, 90, 92, 94, 96, 98 or 99% of the nucleotide bases. Homology determination is performed as described supra for polypeptides.

Alternatively, a "variant" nucleic acid sequence is substantially homologous with (or substantially identical to) a reference sequence (or a fragment thereof) if the "variant" and the reference sequence they are capable of hybridizing under stringent (eg. highly stringent) hybridization conditions. Nucleic acid sequence hybridization will be affected by such conditions as salt concentration (eg. NaCl), temperature, or organic solvents, in addition to the base composition, length of the complementary strands, and the number of nucleotide base mismatches between the hybridizing nucleic acids, as will be readily appreciated by those skilled in the art. Stringent temperature conditions are preferably employed, and generally include temperatures in excess of 30° C., typically in excess of 37° C. and preferably in excess of 45° C. Stringent salt conditions will ordinarily be less than 1000 mM, typically less than 500 mM, and preferably less than 200 mM. The pH is typically between 7.0 and 8.3. The combination of parameters is much more important than any single parameter.

One of ordinary skill in the art appreciates that different species exhibit "preferential codon usage". As used herein, the term "preferential codon usage" refers to codons that are most frequently used in cells of a certain species, thus favouring one or a few representatives of the possible codons encoding each amino acid. For example, the amino acid threonine (Thr) may be encoded by ACA, ACC, ACG, or ACT, but in mammalian host cells ACC is the most commonly used codon; in other species, different Thr codons may be preferential. Preferential codons for a particular host cell species can be introduced into the polynucleotides of the present invention by a variety of methods known in the art. Introduction of preferential codon sequences into recombinant DNA can, for example, enhance production of the protein by making protein translation more efficient within a particular cell type or species.

Thus, in one embodiment of the invention, the nucleic acid sequence is codon optimized for expression in a host cell.

A "fragment" of a polynucleotide of interest comprises a series of consecutive amino acid residues from the sequence of said full-length polynucleotide. By way of example, a "fragment" of a polynucleotide of interest may comprise (or consist of) at least 21 consecutive nucleic acid residues from the sequence of said polypeptide (eg. at least 25, 50, 75, 100, 150, 200, 250, 300, 350, 400, 450, 500, 550, 600, 650, 700, 750, 800 850, 900, 950 or 1000 consecutive nucleic acid residues of said polynucleotide). A fragment may include at least one antigenic determinant and/or may encode at least one antigenic epitope of the corresponding polypeptide of interest.

A polynucleotide of interest, or variant or fragment thereof, may encode a polypeptide that has a common antigenic cross-reactivity and/or substantially the same in vivo biological activity as a reference peptide.

For example, polypeptides encoded by the polynucleotide (or fragment or variant), and the reference polynucleotide may hare a common ability to induce a "recall response" of an immune cell such as a T-lymphocyte (eg. CD4+, CD8+, effector T cell or memory T cell such as a TEM or TCM), which has been previously exposed to an antigenic component of a mycobacterial infection.

New immunological assays for measuring and quantifying immune cell responses (eg. T cell responses) have been established over the last 10 years. For example, the interferon-gamma (IFN-γ) ELISPOT assay is useful as an immunological readout because the secretion of IFN-γ from antigen-specific T cells is a good correlate of protection against *M. tuberculosis*. Furthermore, the ELISPOT assay is a very reproducible and sensitive method of quantifying the number of IFN-γ secreting antigen-specific immune cells (eg. T cells).

Alternatively, or in addition, an antibody capable of binding to a polypeptide encoded by the polynucleotide of interest, or fragment or variant, may be also capable of binding to a polypeptide encoded by the reference polynucleotide.

Key to SEQ ID NOs:

SEQ ID NO: 1 Latency-regulated peptide Rv0111
SEQ ID NO: 2 Latency-regulated gene Rv0111 (encodes SEQ ID NO: 1)
SEQ ID NO: 3 Latency-regulated peptide Rv1806
SEQ ID NO: 4 Latency-regulated gene Rv1806 (encodes SEQ NO: 3)
SEQ ID NO: 5 Latency-regulated peptide Rv0198
SEQ ID NO: 6 Latency-regulated gene Rv1098 (encodes SEQ ID NO: 5)
SEQ ID NO: 8 Latency-regulated gene Rv3812 (encodes SEQ ID NO: 7)
SEQ ID NO: 9 Mycobacterial peptide Ag85A/Rv3804c
SEQ ID NO: 10 Mycobacterial peptide Ag85B/Rv1886c
SEQ ID NO: 11 Mycobacterial peptide ESAT6/Rv3875
SEQ ID NO: 12 Mycobacterial peptide TB10.4/Rv0288
SEQ ID NO: 13 Mycobacterial peptide Rv0125
SEQ ID NO: 14 Mycobacterial peptide PPE18/Rv1196
SEQ ID NO: 15 Mycobacterial peptide P27/Rv1411c
SEQ ID NO: 16 Mycobacterial peptide HSP65/Rv0440
SEQ ID NO: 17 Mycobacterial peptide HBHA/Rv0475
SEQ ID NO: 18 Mycobacterial peptide Rv2659c
SEQ ID NO: 19 Mycobacterial peptide Rv2660c
SEQ ID NO: 20 Mycobacterial peptide HspX/Rv2031c
SEQ ID NO: 21 Mycobacterial polynucleotide encoding peptide Ag85A
SEQ ID NO: 22 Mycobacterial polynucleotide encoding peptide Ag85B
SEQ ID NO: 23 Mycobacterial polynucleotide encoding peptide ESAT6
SEQ ID NO: 24 Mycobacterial polynucleotide encoding peptide TB10.4
SEQ ID NO: 25 Mycobacterial polynucleotide encoding peptide Rv0125
SEQ ID NO: 26 Mycobacterial polynucleotide encoding peptide Rv1196
SEQ ID NO: 27 Mycobacterial polynucleotide encoding peptide Rv1411
SEQ ID NO: 28 Mycobacterial polynucleotide encoding peptide HSP65
SEQ ID NO: 29 Mycobacterial polynucleotide encoding peptide HBHA
SEQ ID NO: 30 Mycobacterial polynucleotide encoding peptide Rv2659c
SEQ ID NO: 31 Mycobacterial polynucleotide encoding peptide Rv2660c
SEQ ID NO: 32 Mycobacterial polynucleotide encoding peptide HspX/Rv2031c
SEQ ID NO: 33 PK tag sequence
SEQ ID NO: 34 Mycobacterial peptide RPFA/Rv0867c
SEQ ID NO: 35 Mycobacterial peptide RPFB/Rv1009
SEQ ID NO: 36 Mycobacterial peptide RPFC/Rv1884c
SEQ ID NO: 37 Mycobacterial peptide RPFD/Rv2389c
SEQ ID NO: 38 Mycobacterial peptide RPFE/Rv2450c
SEQ ID NO: 39 Mycobacterial peptide Rv1733c
SEQ ID NO: 40 Mycobacterial peptide Rv2029c
SEQ ID NO: 41 Mycobacterial peptide Rv2032
SEQ ID NO: 42 Mycobacterial peptide Rv2626c
SEQ ID NO: 43 Mycobacterial peptide Rv2627c
SEQ ID NO: 44 Mycobacterial peptide Rv2628
SEQ ID NO: 45 Mycobacterial polynucleotide encoding peptide RPFA/Rv0867c
SEQ ID NO: 46 Mycobacterial polynucleotide encoding peptide RPFB/Rv1009
SEQ ID NO: 47 Mycobacterial polynucleotide encoding peptide RPFC/Rv1884c
SEQ ID NO: 48 Mycobacterial polynucleotide encoding peptide RPFD/Rv2389c
SEQ ID NO: 49 Mycobacterial polynucleotide encoding peptide RPFE/Rv2450c
SEQ ID NO: 50 Mycobacterial polynucleotide encoding peptide Rv1733c
SEQ ID NO: 51 Mycobacterial polynucleotide encoding peptide Rv2029c
SEQ ID NO: 52 Mycobacterial polynucleotide encoding peptide Rv2032
SEQ ID NO: 53 Mycobacterial polynucleotide encoding peptide Rv2626c
SEQ ID NO: 54 Mycobacterial polynucleotide encoding peptide Rv2627c
SEQ ID NO: 55 Mycobacterial polynucleotide encoding peptide Rv2628
SEQ ID NO: 56 Latency-regulated peptide Rv1807
SEQ ID NO: 57 Latency-regulated gene Rv1807 (encodes SEQ ID NO: 56)

SEQ ID NO: 1

```
Val Pro Ala Arg Ser Val Pro Arg Pro Arg Trp Val Ala Pro Val Arg

Arg Val Gly Arg Leu Ala Val Trp Asp Arg Pro Glu Arg Arg Ser Gly

Ile Pro Ala Leu Asp Gly Leu Arg Ala Ile Ala Val Ala Leu Val Leu

Ala Ser His Gly Gly Ile Pro Gly Met Gly Gly Gly Phe Ile Gly Val

Asp Ala Phe Phe Val Leu Ser Gly Phe Leu Ile Thr Ser Leu Leu Leu

Asp Glu Leu Gly Arg Thr Gly Arg Ile Asp Leu Ser Gly Phe Trp Ile

Arg Arg Ala Arg Arg Leu Leu Pro Ala Leu Val Leu Met Val Leu Thr
```

-continued

Val Ser Ala Ala Arg Ala Leu Phe Pro Asp Gln Ala Leu Thr Gly Leu

Arg Ser Asp Ala Ile Ala Ala Phe Leu Trp Thr Ala Asn Trp Arg Phe

Val Ala Gln Asn Thr Asp Tyr Phe Thr Gln Gly Ala Pro Pro Ser Pro

Leu Gln His Thr Trp Ser Leu Gly Val Glu Glu Gln Tyr Tyr Val Val

Trp Pro Leu Leu Leu Ile Gly Ala Thr Leu Leu Leu Ala Ala Arg Ala

Arg Arg Arg Cys Arg Arg Ala Thr Val Gly Gly Val Arg Phe Ala Ala

Phe Leu Ile Ala Ser Leu Gly Thr Met Ala Ser Ala Thr Ala Ala Val

Ala Phe Thr Ser Ala Ala Thr Arg Asp Arg Ile Tyr Phe Gly Thr Asp

Thr Arg Ala Gln Ala Leu Leu Ile Gly Ser Ala Ala Ala Ala Leu Leu

Val Arg Asp Trp Pro Ser Leu Asn Arg Gly Trp Cys Leu Ile Arg Thr

Arg Trp Gly Arg Arg Ile Ala Arg Leu Leu Pro Phe Val Gly Leu Ala

Gly Leu Ala Val Thr Thr His Val Ala Thr Gly Ser Val Gly Glu Phe

Arg His Gly Leu Leu Ile Val Val Ala Gly Ala Ala Val Ile Val Val

Ala Ser Val Ala Met Glu Gln Arg Gly Ala Val Ala Arg Ile Leu Ala

Trp Arg Pro Leu Val Trp Leu Gly Thr Ile Ser Tyr Gly Val Tyr Leu

Trp His Trp Pro Ile Phe Leu Ala Leu Asn Gly Gln Arg Thr Gly Trp

Ser Gly Pro Ala Leu Phe Ala Ala Arg Cys Ala Ala Thr Val Val Leu

Ala Gly Ala Ser Trp Trp Leu Ile Glu Gln Pro Ile Arg Arg Trp Arg

Pro Ala Arg Val Pro Leu Leu Pro Leu Ala Ala Ala Thr Val Ala Ser

Ala Ala Ala Val Thr Met Leu Val Val Pro Val Gly Ala Gly Pro Gly

Leu Arg Glu Ile Gly Leu Pro Pro Gly Val Ser Ala Val Ala Ala Val

Ser Pro Ser Pro Pro Glu Ala Ser Gln Pro Ala Pro Gly Pro Arg Asp

Pro Asn Arg Pro Phe Thr Val Ser Val Phe Gly Asp Ser Ile Gly Trp

Thr Leu Met His Tyr Leu Pro Pro Thr Pro Gly Phe Arg Phe Ile Asp

His Thr Val Ile Gly Cys Ser Leu Val Arg Gly Thr Pro Tyr Arg Tyr

Ile Gly Gln Thr Leu Glu Gln Arg Ala Glu Cys Asp Gly Trp Pro Ala

Arg Trp Ser Ala Gln Val Asn Arg Asp Gln Pro Asp Val Ala Leu Leu

Ile Val Gly Arg Trp Glu Thr Val Asp Arg Val Asn Glu Gly Arg Trp

Thr His Ile Gly Asp Pro Thr Phe Asp Ala Tyr Leu Asn Ala Glu Leu

Gln Arg Ala Leu Ser Ile Val Gly Ser Thr Gly Val Arg Val Met Val

Thr Thr Val Pro Tyr Ser Arg Gly Gly Glu Lys Pro Asp Gly Arg Leu

Tyr Pro Glu Asp Gln Pro Glu Arg Val Asn Lys Trp Asn Ala Met Leu

His Asn Ala Ile Ser Gln His Ser Asn Val Gly Met Ile Asp Leu Asn

Lys Lys Leu Cys Pro Asp Gly Val Tyr Thr Ala Lys Val Asp Gly Ile

Lys Val Arg Ser Asp Gly Val His Leu Thr Gln Glu Gly Val Lys Trp

Leu Ile Pro Trp Leu Glu Asp Ser Val Arg Val Ala Ser

SEQ ID NO: 2 gtgccggcac gttctgttcc ccggccccgt tgggtggccc cggtgcgccg ggtcggtcgg ctggccgtat gggatcggcc ggagcggcgc agcggaattc cagcgttaga tggccttcgt gcgatagcgg tcgcgctggt actcgccagc catggcggca tccccggtat gggcggcggg ttcatcggcg tcgacgcctt cttcgtcttg agcggatttc tcatcacctc gctgctgctc -continued gacgagctgg ggcgcaccgg tcgtatcgat ctgagcgggt tctggattcg ccgtgcgcgg cggctgctgc cggcgctggt gctgatggtt ctcaccgtga gcgccgcacg cgcactattt cctgaccaag ctctcaccgg gctacggagc gatgcgatcg ccgcgttcct atggacggcg aattggcggt ttgtggccca aaataccgat tacttcaccc agggcgctcc accctcgccc ctacagcaca cctggtcgtt gggggtggag gagcagtatt acgttgtctg gccactgttg ctgatcgggg cgacgctact gttggcggcc cgggcgaggc gccgttgcag acgggccacg gtgggcgggg ttcggttcgc cgcgttcctg attgccagtc tcggcacgat ggcttccgcc accgccgcgg tcgcatttac ctcggcggcc acccgcgacc ggatttactt cggcaccgat acccgtgcgc aggcgttgct gatcggctcc gcggcagcgg ctctgctggt gcgggattgg ccatcgctga accgcgggtg gtgcctgatc cggactcgct ggggacggcg gattgcccgt ctgttgccgt tcgtcgggct ggctgggctg gcggtgacga ctcacgtcgc aacgggcagt gtgggcgagt tccgccatgg tctgctgatc gtggtggcag gtgcggccgt catcgtggtt gcctcggtag ccatggagca gcgcggagcg gtggcccgca tcctggcctg gcgaccgttg gtgtggctgg gcaccatatc gtacggcgtc tatctgtggc actggccaat ctttctggcg ctcaacggcc aacgtacggg ctggtcgggc ccggccctgt ttgccgctag gtgtgcagcc acggtggtgc tggccggtgc gtcgtggtgg ctgatcgagc aacctattcg gcgctggcga ccggcacggg ttccgctgtt gccgctggca gcggcgaccg ttgccagcgc tgccgccgtg acgatgctcg ttgttccggt cggagccgga ccggggctac gcgagatcgg ccttccgccc ggcgtttcgg cggtcgccgc ggtctcgccg tcgccgccgg aagcgagtca gcccgcgccc gggccacgag atcccaaccg gccgttcacc gtttcggtat tcggtgattc gatcgggtgg actttgatgc attacctgcc gccgactccc ggattccggt tcatcgacca caccgtcatc ggctgcagcc tggtacgcgg cacaccgtat cggtacatcg gtcaaaccct ggagcagagg gcggaatgcg acggctggcc ggccagatgg tcggcgcagg tcaaccggga ccaaccggac gttgcgttgc tgatcgtcgg ccgctgggag acggtagacc gggtcaatga ggggcggtgg acacatatcg gcgacccgac cttcgatgcg tacctcaacg ccgagctaca gcgagcgctc agcatcgttg gatccaccgg ggttcgagtg atggtcacca ccgtgcccta cagccgcggc ggcgaaaagc cggacggccg cttgtatccg gaggatcaac ccgagcgtgt gaacaaatgg aacgccatgt tacataacgc cattagccaa cactcgaacg tcggaatgat cgacctcaac aaaaagcttt gtccagacgg cgtttacacg gccaaggtcg acggcatcaa ggtccgcagt gatggtgttc atctcaccca ggaaggcgtg aagtggctga taccgtggct tgaggattcg gtgcgggtcg ccagt

SEQ ID NO: 3

Met Ala Phe Val Leu Val Cys Pro Asp Ala Leu Ala Ile Ala Ala Gly

Gln Leu Arg His Val Gly Ser Val Ile Ala Ala Arg Asn Ala Val Ala

Ala Pro Ala Thr Ala Glu Leu Ala Pro Ala Ala Ala Asp Glu Val Ser

Ala Leu Thr Ala Thr Gln Phe Asn Phe His Ala Ala Met Tyr Gln Ala

Val Gly Ala Gln Ala Ile Ala Met Asn Glu Ala Phe Val Ala Met Leu

Gly Ala Ser Ala Asp Ser Tyr Ala Ala Thr Glu Ala Ala Asn Ile Ile

Ala Val Ser

SEQ ID NO: 4 atggcgtttg ttcttgtctg tccagatgcg ctggccatcg cggccggtca gttgcgccat gttggatcgg tgatagccgc gcggaatgcg gtcgcggcac cggcaactgc cgaattggcc -continued ccggcggccg ctgacgaagt atcagctttg actgcaacac aattcaactt ccatgccgcc atgtaccaag cggtcggcgc ccaggcgatc gccatgaatg aggcgttcgt cgcgatgttg ggcgccagcg cggattctta cgcggctacc gaagccgcca acatcattgc tgtgagc

SEQ ID NO: 5

Val Thr Leu Ala Ile Pro Ser Gly Ile Asp Leu Ser His Ile Asp Ala

Asp Ala Arg Pro Gln Asp Asp Leu Phe Gly His Val Asn Gly Arg Trp

Leu Ala Glu His Glu Ile Pro Ala Asp Arg Ala Thr Asp Gly Ala Phe

Arg Ser Leu Phe Asp Arg Ala Glu Thr Gln Val Arg Asp Leu Ile Ile

Gln Ala Ser Gln Ala Gly Ala Ala Val Gly Thr Asp Ala Gln Arg Ile

Gly Asp Leu Tyr Ala Ser Phe Leu Asp Glu Glu Ala Val Glu Arg Ala

Gly Val Gln Pro Leu His Asp Glu Leu Ala Thr Ile Asp Ser Ala Ala

Asp Ala Thr Glu Leu Ala Ala Ala Leu Gly Thr Leu Gln Arg Ala Gly

Val Gly Gly Gly Ile Gly Val Tyr Val Asp Thr Asp Ser Lys Asp Ser

Thr Arg Tyr Leu Val His Phe Thr Gln Ser Gly Ile Gly Leu Pro Asp

Glu Ser Tyr Tyr Arg Asp Glu Gln His Ala Ala Val Leu Ala Ala Tyr

Pro Gly His Ile Ala Arg Met Phe Gly Leu Val Tyr Gly Gly Glu Ser

Arg Asp His Ala Lys Thr Ala Asp Arg Ile Val Ala Leu Glu Thr Lys

Leu Ala Asp Ala His Trp Asp Val Val Lys Arg Arg Asp Ala Asp Leu

Gly Tyr Asn Leu Arg Thr Phe Ala Gln Leu Gln Thr Glu Gly Ala Gly

Phe Asp Trp Val Ser Trp Val Thr Ala Leu Gly Ser Ala Pro Asp Ala

Met Thr Glu Leu Val Val Arg Gln Pro Asp Tyr Leu Val Thr Phe Ala

Ser Leu Trp Ala Ser Val Asn Val Glu Asp Trp Lys Cys Trp Ala Arg

Trp Arg Leu Ile Arg Ala Arg Ala Pro Trp Leu Thr Arg Ala Leu Val

Ala Glu Asp Phe Glu Phe Tyr Gly Arg Thr Leu Thr Gly Ala Gln Gln

Leu Arg Asp Arg Trp Lys Arg Gly Val Ser Leu Val Glu Asn Leu Met

Gly Asp Ala Val Gly Lys Leu Tyr Val Gln Arg His Phe Pro Pro Asp

Ala Lys Ser Arg Ile Asp Thr Leu Val Asp Asn Leu Gln Glu Ala Tyr

Arg Ile Ser Ile Ser Glu Leu Asp Trp Met Thr Pro Gln Thr Arg Gln

Arg Ala Leu Ala Lys Leu Asn Lys Phe Thr Ala Lys Val Gly Tyr Pro

Ile Lys Trp Arg Asp Tyr Ser Lys Leu Ala Ile Asp Arg Asp Asp Leu

Tyr Gly Asn Val Gln Arg Gly Tyr Ala Val Asn His Asp Arg Glu Leu

Ala Lys Leu Phe Gly Pro Val Asp Arg Asp Glu Trp Phe Met Thr Pro

Gln Thr Val Asn Ala Tyr Tyr Asn Pro Gly Met Asn Glu Ile Val Phe

Pro Ala Ala Ile Leu Gln Pro Pro Phe Phe Asp Pro Gln Ala Asp Glu

Ala Ala Asn Tyr Gly Gly Ile Gly Ala Val Ile Gly His Glu Ile Gly

His Gly Phe Asp Asp Gln Gly Ala Lys Tyr Asp Gly Asp Gly Asn Leu

Val Asp Trp Trp Thr Asp Asp Asp Arg Thr Glu Phe Ala Ala Arg Thr

Lys Ala Leu Ile Glu Gln Tyr His Ala Tyr Thr Pro Arg Asp Leu Val

Asp His Pro Gly Pro Pro His Val Gln Gly Ala Phe Thr Ile Gly Glu

Asn Ile Gly Asp Leu Gly Gly Leu Ser Ile Ala Leu Leu Ala Tyr Gln

Leu Ser Leu Asn Gly Asn Pro Ala Pro Val Ile Asp Gly Leu Thr Gly

-continued

Met Gln Arg Val Phe Phe Gly Trp Ala Gln Ile Trp Arg Thr Lys Ser

Arg Ala Ala Glu Ala Ile Arg Arg Leu Ala Val Asp Pro His Ser Pro

Pro Glu Phe Arg Cys Asn Gly Val Val Arg Asn Val Asp Ala Phe Tyr

Gln Ala Phe Asp Val Thr Glu Asp Asp Ala Leu Phe Leu Asp Pro Gln

Arg Arg Val Arg Ile Trp Asn

SEQ ID NO: 6 gtgacacttg ccatcccctc gggtatcgac ctgagccaca tcgacgctga tgcccgaccc caagacgacc tgttcggcca cgttaacggc cgctggctgg ctgaacacga gataccagcg gaccgagcga ccgacggcgc cttccgtagc ctgttcgacc gcgccgagac acaagtgcga gacctgatca tccaggccag ccaagcaggt gctgcggtag gcaccgatgc gcagcgcatc ggcgacctct acgccagctt cctcgacgag gaagccgtcg agcgcgcagg ggtgcaaccg ctgcacgacg aattggccac gattgacagc gcggccgacg ccaccgaatt ggccgccgcc cttggcactc tgcaacgtgc cggcgtgggc ggcggcatcg gagtctatgt cgataccgat tccaaagact cgacccgtta cttggtgcat ttcacccaat ccggcatcgg attacccgac gagtcctact accgtgacga gcaacacgcc gccgtgctag cggcctaccc ggggcacatc gcccggatgt tcggcctggt gtacgggggc gagagccgtg accatgccaa aaccgcggac cgcatcgtcg cgctggagac caaactcgcc gacgcgcatt gggatgtggt gaagcgccgc gacgccgacc ttggctacaa cctgcgcacg tttgcccagc tgcagaccga aggggcgggt ttcgactggg tcagctgggt gaccgcattg gggagcgctc cggacgccat gacggaactg gttgtgcgcc aacctgatta cctcgtcacc tttgcctcgc tgtgggcgag cgttaacgtt gaagactgga aatgctgggc gcgttggcgt ttgatccgcg cccgggcccc ctggctgacc cgcgccctgg tcgccgagga cttcgaattc tacggccgca cgcttaccgg cgcacagcag cttcgggacc gttggaagcg tggggtgtca ctggtggaga acctgatggg cgatgccgtc ggaaagctct atgtacaacg ccatttcccg ccggatgcca agtcccgcat cgacaccctg gtggacaacc tgcaggaggc gtatcggatc agcatcagcg agctggattg gatgacgccg cagacccggc aacgcgcgct agcgaagctg aacaagttca ccgccaaagt cggctatccg atcaagtggc gcgactactc gaagctggcg atcgaccgcg acgacctcta cggtaacgtc cagcgcggct acgccgtcaa ccatgaccgc gagctagcca agcttttcgg cccggtcgac cgcgacgagt ggttcatgac accacaaacc gtcaacgcct actacaaccc ggggatgaac gaaatcgtct tccccgcagc gattttacag ccaccatttt tcgatccgca ggccgacgag gccgccaact acggcgggat cggggcggtg atcgggcacg agatcgggca cggtttcgac gatcagggcg ccaaatacga cggcgacggc aatctggtcg attggtggac cgacgacgat cgcaccgagt tcgccgcccg caccaaagcg ttgatcgagc agtaccacgc ttacacgccg cgcgatctcg tcgaccaccc cggcccgcct catgtgcaag gcgcgttcac cataggcgag aacatcggcg acctgggcgg gctgtcgatc gccctgctgg cttaccagct ctcgctgaac ggcaaccccg ctccggttat cgacgggctg accggcatgc aacgggtgtt cttcggctgg gcacaaatat ggcgaaccaa atcgcgtgca gccgaagcaa tccgccggtt ggcggtcgat ccgcactccc cgccggagtt ccggtgcaac ggtgtggttc gcaacgtgga cgctttttat caggccttcg acgtcaccga ggatgacgcg ctgtttctgg acccgcagcg cagggtccgg atctggaac -continued

SEQ ID NO: 7

Val Ser Phe Val Val Thr Val Pro Glu Ala Val Ala Ala Ala Ala Gly

Asp Leu Ala Ala Ile Gly Ser Thr Leu Arg Glu Ala Thr Ala Ala Ala

Ala Gly Pro Thr Thr Gly Leu Ala Ala Ala Ala Ala Asp Asp Val Ser

Ile Ala Val Ser Gln Leu Phe Gly Arg Tyr Gly Gln Glu Phe Gln Thr

Val Ser Asn Gln Leu Ala Ala Phe His Thr Glu Phe Val Arg Thr Leu

Asn Arg Gly Ala Ala Ala Tyr Leu Asn Thr Glu Ser Ala Asn Gly Gly

Gln Leu Phe Gly Gln Ile Glu Ala Gly Gln Arg Ala Val Ser Ala Ala

Ala Ala Ala Ala Pro Gly Gly Ala Tyr Gly Gln Leu Val Ala Asn Thr

Ala Thr Asn Leu Glu Ser Leu Tyr Gly Ala Trp Ser Ala Asn Pro Phe

Pro Phe Leu Arg Gln Ile Ile Ala Asn Gln Gln Val Tyr Trp Gln Gln

Ile Ala Ala Ala Leu Ala Asn Ala Val Gln Asn Phe Pro Ala Leu Val

Ala Asn Leu Pro Ala Ala Ile Asp Ala Ala Val Gln Gln Phe Leu Ala

Phe Asn Ala Ala Tyr Tyr Ile Gln Gln Ile Ile Ser Ser Gln Ile Gly

Phe Ala Gln Leu Phe Ala Thr Thr Val Gly Gln Gly Val Thr Ser Val

Ile Ala Gly Trp Pro Asn Leu Ala Ala Glu Leu Gln Leu Ala Phe Gln

Gln Leu Leu Val Gly Asp Tyr Asn Ala Ala Val Ala Asn Leu Gly Lys

Ala Met Thr Asn Leu Leu Val Thr Gly Phe Asp Thr Ser Asp Val Thr

Ile Gly Thr Met Gly Thr Thr Ile Ser Val Thr Ala Lys Pro Lys Leu

Leu Gly Pro Leu Gly Asp Leu Phe Thr Ile Met Thr Ile Pro Ala Gln

Glu Ala Gln Tyr Phe Thr Asn Leu Met Pro Pro Ser Ile Leu Arg Asp

Met Ser Gln Asn Phe Thr Asn Val Leu Thr Thr Leu Ser Asn Pro Asn

Ile Gln Ala Val Ala Ser Phe Asp Ile Ala Thr Thr Ala Gly Thr Leu

Ser Thr Phe Phe Gly Val Pro Leu Val Leu Thr Tyr Ala Thr Leu Gly

Ala Pro Phe Ala Ser Leu Asn Ala Ile Ala Thr Ser Ala Glu Thr Ile

Glu Gln Ala Leu Leu Ala Gly Asn Tyr Leu Gly Ala Val Gly Ala Leu

Ile Asp Ala Pro Ala His Ala Leu Asp Gly Phe Leu Asn Ser Ala Thr

Val Leu Asp Thr Pro Ile Leu Val Pro Thr Gly Leu Pro Ser Pro Leu

Pro Pro Thr Val Gly Ile Thr Leu His Leu Pro Phe Asp Gly Ile Leu

Val Pro Pro His Pro Val Thr Ala Thr Ile Ser Phe Pro Gly Ala Pro

Val Pro Ile Pro Gly Phe Pro Thr Thr Val Thr Val Phe Gly Thr Pro

Phe Met Gly Met Ala Pro Leu Leu Ile Asn Tyr Ile Pro Gln Gln Leu

Ala Leu Ala Ile Lys Pro Ala Ala

SEQ ID NO: 8 gtgtcgttcg tggtcacagt gccggaggcc gtggcggctg cggcggggga tttggcggcc atcggctcga cgcttcggga agcgaccgct gcggcggcgg gccccacgac cgggctggcg gccgcggccg ccgacgacgt gtcgatcgct gtctcgcagc tgttcggcag gtacggccag gaatttcaaa ccgtgagcaa ccaactggcc gcgtttcata ccgagttcgt acgcacgttg aaccgcggcg cggcggcgta tctcaacacc gaaagcgcta acggcgggca gctgttcggt cagatcgagg cgggacagcg cgccgtttcc gcggccgcgg ccgccgctcc gggcggcgca tacggccaac tcgttgccaa cacggccacc aacctggaat ccctctacgg cgcatggtcg gccaacccgt tcccattcct ccgccagatc atcgccaacc agcaggttta ctggcagcag -continued atcgccgcgg cgctcgccaa cgccgtccag aacttccccg ccctggtggc gaatttgcca gcggccatcg acgcggccgt ccagcaattc ctggccttca acgcggcgta ctacatccaa cagattatta gctcgcagat cggcttcgcc cagctattcg ccacgacggt cggtcagggg gtcaccagcg tcattgccgg gtggcccaac cttgcggcgg agcttcagct agcgtttcaa cagcttctgg tgggtgacta caacgccgcg gtggcgaacc tgggtaaggc catgacaaac cttctggtca ccgggttcga caccagcgac gtgacgatcg gcacaatggg caccaccatt agtgtcaccg cgaaacccaa gctgctgggc ccgctgggag atctgttcac catcatgacc atcccggcac aagaggcgca gtacttcacc aacctgatgc ccccctccat cctgcgagac atgtcgcaga acttcaccaa cgtgctcacg acgctctcca acccgaacat ccaggcggtc gcttcgttcg atatcgcaac caccgccggg actttgagca ccttcttcgg ggtgccattg gtgctcactt acgccacatt gggtgcgccg ttcgcgtcac tgaacgcgat tgcgacgagc gcggaaacca tcgagcaggc cctgttggcc ggcaactacc taggggcggt gggtgcgctt atcgacgccc cggcccacgc gttagacggc ttcctcaaca gcgcaaccgt gttggatacg ccgatcctgg tgcccacggg gctcccgtcc cctctgcccc cgacggtcgg gatcacgctg cacttgcctt tcgacgggat tctcgtgccg ccgcatcccg tcaccgcgac gatcagcttc ccgggtgctc cggttcctat tcccggtttc ccaaccaccg taaccgtttt cggcacaccc ttcatgggaa tggctccgct gctgatcaac tacattcccc aacagctcgc cctggcaatc aaaccggcgg ct

SEQ ID NO: 9

MQLVDRVRGAVTGMSRRLVVGAVGAALVSGLVGAVGGTATAGAFSRPGLPVEYLQVPSPS

MGRDIKVQFQSGGANSPALYLLDGLRAQDDFSGWDINTPAFEWYDQSGLSVVMPVGGQSS

FYSDWYQPACGKAGCQTYKWETFLTSELPGWLQANRHVKPTGSAVVGLSMAASSALTLAI

YHPQQFVYAGAMSGLLDPSQAMGPTLIGLAMGDAGGYKASDMWGPKEDPAWQRNDPLLNV

GKLIANNTRVWVYCGNGKPSDLGGNNLPAKFLEGFVRTSNIKFQDAYNAGGGHNGVFDFP

DSGTHSWEYWGAQLNAMKPDLQRALGATPNTGPAPQGA

SEQ ID NO: 10

MTDVSRKIRAWGRRLMIGTAAAVVLPGLVGLAGGAATAGAFSRPGLPVEYLQVPSPSMGR

DIKVQFQSGGNNSPAVYLLDGLRAQDDYNGWDINTPAFEWYYQSGLSIVMPVGGQSSFYS

DWYSPACGKAGCQTYKWETFLTSELPQWLSANRAVKPTGSAAIGLSMAGSSAMILAAYHP

QQFIYAGSLSALLDPSQGMGPSLIGLAMGDAGGYKAADMWGPSSDPAWERNDPTQQIPKL

VANNTRLWVYCGNGTPNELGGANIPAEFLENFVRSSNLKFQDAYNAAGGHNAVFNFPPNG

THSWEYWGAQLNAMKGDLQSSLGAG

SEQ ID NO: 11

MTEQQWNFAGIEAAASAIQGNVTSIHSLLDEGKQSLTKLAAAWGGSGSEAYQGVQQKWDA

TATELNNALQNLARTISEAGQAMASTEGNVTGMFA

SEQ ID NO: 12

MSQIMYNYPAMLGHAGDMAGYAGTLQSLGAEIAVEQAALQSAWQGDTGITYQAWQAQWNQ

AMEDLVRAYHAMSSTHEANTMAMMARDTAEAAKWGG

SEQ ID NO: 13

MSNSRRRSLRWSWLLSVLAAVGLGLATAPAQAAPPALSQDRFADFPALPLDPSAMVAQVG

PQVVNINTKLGYNNAVGAGTGIVIDPNGVVLTNNHVIAGATDINAFSVGSGQTYGVDVVG

YDRTQDVAVLQLRGAGGLPSAAIGGGVAVGEPVVAMGNSGGQGGTPRAVPGRVVALGQTV

QASDSLTGAEETLNGLIQFDAAIQPGDSGGPVVNGLGQVVGMNTAASDNFQLSQGGQGFA

-continued

IPIGQAMAIAGQIRSGGGSPTVHIGPTAFLGLGVVDNNGNGARVQRVVGSAPAASLGIST

GDVITAVDGAPINSATAMADALNGHHPGDVISVTWQTKSGGTRTGNVTLAEGPPA

SEQ ID NO: 14

MVDFGALPPEINSARMYAGPGSASLVAAAQMWDSVASDLFSAASAFQSVVWGLTVGSWIG

SSAGLMVAAASPYVAWMSVTAGQAELTAAQVRVAAAAYETAYGLTVPPPVIAENRAELMI

LIATNLLGQNTPAIAVNEAEYGEMWAQDAAAMFGYAAATATATATLLPFEEAPEMTSAGG

LLEQAAAVEEASDTAAANQLMNNVPQALQQLAQPTQGTTPSSKLGGLWKTVSPHRSPISN

MVSMANNHMSMTNSGVSMTNTLSSMLKGFAPAAAAQAVQTAAQNGVRAMSSLGSSLGSSG

LGGGVAANLGRAASVGSLSVPQAWAAANQAVTPAARALPLTSLTSAAERGPGQMLGGLPV

GQMGARAGGGLSGVLRVPPRPYVMPHSPAAG

SEQ ID NO: 15

MRTPRRHCRRIAVLAAVSIAATVVAGCSSGSKPSGGPLPDAKPLVEEATAQTKALKSAHM

VLTVNGKIPGLSLKTLSGDLTTNPTAATGNVKLTLGGSDIDADFVVFDGILYATLTPNQW

SDFGPAADIYDPAQVLNPDTGLANVLANFADAKAEGRDTINGQNTIRISGKVSAQAVNQI

APPFNATQPVPATVWIQETGDHQLAQAQLDRGSGNSVQMTLSKWGEKVQVTKPPVS

SEQ ID NO: 16

MAKTIAYDEEARRGLERGLNALADAVKVTLGPKGRNVVLEKKWGAPTITNDGVSIAKEIE

LEDPYEKIGAELVKEVAKKTDDVAGDGTTTATVLAQALVREGLRNVAAGANPLGLKRGIE

KAVEKVTETLLKGAKEVETKEQIAATAAISAGDQSIGDLIAEAMDKVGNEGVITVEESNT

FGLQLELTEGMRFDKGYISGYFVTDPERQEAVLEDPYILLVSSKVSTVKDLLPLLEKVIG

AGKPLLIIAEDVEGEALSTLVVNKIRGTFKSVAVKAPGFGDRRKAMLQDMAILTGGQVIS

EEVGLTLENADLSLLGKARKVVVTKDETTIVEGAGDTDAIAGRVAQIRQEIENSDSDYDR

EKLQERLAKLAGGVAVIKAGAATEVELKERKHRIEDAVRNAKAAVEEGIVAGGGVTLLQA

APTLDELKLEGDEATGANIVKVALEAPLKQIAFNSGLEPGVVAEKVRNLPAGHGLNAQTG

VYEDLLAAGVADPVKVTRSALQNAASIAGLFLTTEAVVADKPEKEKASVPGGGDMGGMDF

SEQ ID NO: 17

MAENSNIDDIKAPLLAALGAADLALATVNELITNLRERAEETRTDTRSRVEESRARLTKL

QEDLPEQLTELREKFTAEELRKAAEGYLEAATSRYNELVERGEAALERLRSQQSFEEVSA

RAEGYVDQAVELTQEALGTVASQTRAVGERAAKLVGIELPKKAAPAKKAAPAKKAAPAKK

AAAKKAPAKKAAAKKVTQK

SEQ ID NO: 18

VTQTGKRQRRKFGRIRQFNSGRWQASYTGPDGRVYIAPKTFNAKIDAEAWLTDRRREIDR

QLWSPASGQEDRPGAPFGEYAEGWLKQRGIKDRTRAHYRKLLDNHILATFADTDLRDITP

AAVRRWYATTAVGTPTMRAHSYSLLRAIMQTALADDLIDSNPCRISGASTARRVHKIRPA

TLDELETITKAMPDPYQAFVLMAAWLAMRYGELTELRRKDIDLHGEVARVRRAVVRVGEG

FKVTTPKSDAGVRDISIPPHLIPAIEDHLHKHVNPGRESLLFPSVNDPNRHLAPSALYRM

FYKARKAAGRPDLRVHDLRHSGAVLAASTGATLAELMQRLGHSTAGAALRYQHAAKGRDR

EIAALLSKLAENQEM

SEQ ID NO: 19

VIAGVDQALAATGQASQRAAGASGGVTVGVGVGTEQRNLSVVAPSQFTFSSRSPDFVDET

AGQSWCAILGLNQFH

-continued

SEQ ID NO: 20
MATTLPVQRHPRSLFPEFSELFAAFPSFAGLRPTFDTRLMRLEDEMKEGRYEVRAELPGV

DPDKDVDIMVRDGQLTIKAERTEQKDFDGRSEFAYGSFVRTVSLPVGADEDDIKATYDKG

ILTVSVAVSEGKPTEKHIQIRSTN

SEQ ID NO: 21
atgcagcttgttgacagggttcgtggcgccgtcacgggtatgtcgcgtcgactcgtggtc ggggccgtcggcgcggccctagtgtcgggtctggtcggcgccgtcggtggcacggcgacc gcgggggcattttcccggccgggcttgccggtggagtacctgcaggtgccgtcgccgtcg atgggccgtgacatcaaggtccaattccaaagtggtggtgccaactcgcccgccctgtac ctgctcgacggcctgcgcgcgcaggacgacttcagcggctgggacatcaacaccccggcg ttcgagtggtacgaccagtcgggcctgtcggtggtcatgccggtgggtggccagtcaagc ttctactccgactggtaccagcccgcctgcggcaaggccggttgccagacttacaagtgg gagaccttcctgaccagcgagctgccggggtggctgcaggccaacaggcacgtcaagccc accggaagcgccgtcgtcggtctttcgatggctgcttcttcggcgctgacgctggcgatc tatcacccccagcagttcgtctacgcgggagcgatgtcgggcctgttggacccctcccag gcgatgggtcccaccctgatcggcctggcgatgggtgacgctggcggctacaaggcctcc gacatgtggggcccgaaggaggacccggcgtggcagcgcaacgacccgctgttgaacgtc gggaagctgatcgccaacaacacccgcgtctgggtgtactgcggcaacggcaagccgtcg gatctgggtggcaacaacctgccggccaagttcctcgagggcttcgtgcggaccagcaac atcaagttccaagacgcctacaacgccggtggcggccacaacggcgtgttcgacttcccg gacagcggtacgcacagctgggagtactggggcgcgcagctcaacgctatgaagcccgac ctgcaacgggcactgggtgccacgcccaacaccgggcccgcgccccagggcgcctag SEQ ID NO: 22
atgacagacgtgagccgaaagattcgagcttggggacgccgattgatgatcggcacggca gcggctgtagtccttccgggcctggtggggcttgccggcggagcggcaaccgcgggcgcg ttctcccggccggggctgccggtcgagtacctgcaggtgccgtcgccgtcgatgggccgc gacatcaaggttcagttccagagcggtgggaacaactcacctgcggtttatctgctcgac ggcctgcgcgcccaagacgactacaacggctgggatatcaacaccccggcgttcgagtgg tactaccagtcgggactgtcgatagtcatgccggtcggcgggcagtccagcttctacagc gactggtacagcccggcctgcggtaaggctggctgccagacttacaagtgggaaaccttc ctgaccagcgagctgccgcaatggttgtccgccaacagggccgtgaagcccaccggcagc gctgcaatcggcttgtcgatggccggctcgtcggcaatgatcttggccgcctaccacccc cagcagttcatctacgccggctcgctgtcggccctgctggacccctctcaggggatgggg cctagcctgatcggcctcgcgatgggtgacgccggcggttacaaggccgcagacatgtgg ggtccctcgagtgacccggcatgggagcgcaacgaccctacgcagcagatccccaagctg gtcgcaaacaacacccggctatgggtttattgcgggaacggcaccccgaacgagttgggc ggtgccaacatacccgccgagttcttggagaacttcgttcgtagcagcaacctgaagttc caggatgcgtacaacgccgcgggcgggcacaacgccgtgttcaacttcccgcccaacggc acgcacagctgggagtactggggcgctcagctcaacgccatgaagggtgacctgcagagt tcgttaggcgccggctga SEQ ID NO: 23
atgacagagcagcagtggaatttcgcgggtatcgaggccgcggcaagcgcaatccaggga aatgtcacgtccattcattccctccttgacgaggggaagcagtccctgaccaagctcgca -continued gcggcctggggcggtagcggttcggaggcgtaccagggtgtccagcaaaaatgggacgcc acggctaccgagctgaacaacgcgctgcagaacctggcgcggacgatcagcgaagccggt caggcaatggcttcgaccgaaggcaacgtcactgggatgttcgcatag

SEQ ID NO: 24 atgtcgcaaatcatgtacaactaccccgcgatgttgggtcacgccggggatatggccgga tatgccggcacgctgcagagcttgggtgccgagatcgccgtggagcaggccgcgttgcag agtgcgtggcagggcgataccgggatcacgtatcaggcgtggcaggcacagtggaaccag gccatggaagatttggtgcgggcctatcatgcgatgtccagcacccatgaagccaacacc atggcgatgatggcccgcgacacggccgaagccgccaaatggggcggctag

SEQ ID NO: 25 atgagcaattcgcgccgccgctcactcaggtggtcatggttgctgagcgtgctggctgcc gtcgggctgggcctggccacggcgccggcccaggcggccccgccggccttgtcgcaggac cggttcgccgacttccccgcgctgcccctcgacccgtccgcgatggtcgcccaagtgggg ccacaggtggtcaacatcaacaccaaactgggctacaacaacgccgtgggcgccgggacc ggcatcgtcatcgatcccaacggtgtcgtgctgaccaacaaccacgtgatcgcgggcgcc accgacatcaatgcgttcagcgtcggctccggccaaacctacggcgtcgatgtggtcggg tatgaccgcacccaggatgtcgcggtgctgcagctgcgcggtgccggtggcctgccgtcg gcggcgatcggtggcggcgtcgcggttggtgagcccgtcgtcgcgatgggcaacagcggt gggcagggcggaacgccccgtgcggtgcctggcagggtggtcgcgctcggccaaaccgtg caggcgtcggattcgctgaccggtgccgaagagacattgaacgggttgatccagttcgat gccgcgatccagcccggtgattcgggcgggcccgtcgtcaacggcctaggacaggtggtc ggtatgaacacggccgcgtccgataacttccagctgtcccagggtgggcagggattcgcc attccgatcgggcaggcgatggcgatcgcgggccagatccgatcgggtggggggtcaccc accgttcatatcgggcctaccgccttcctcggcttgggtgttgtcgacaacaacggcaac ggcgcacgagtccaacgcgtggtcgggagcgctccggcggcaagtctcggcatctccacc ggcgacgtgatcaccgcggtcgacggcgctccgatcaactcggccaccgcgatggcggac gcgcttaacgggcatcatcccggtgacgtcatctcggtgacctggcaaaccaagtcgggc ggcacgcgtacagggaacgtgacattggccgagggacccccggcctga

SEQ ID NO: 26 atggtggatttcggggcgttaccaccggagatcaactccgcgaggatgtacgccggcccg ggttcggcctcgctggtggccgcggctcagatgtgggacagcgtggcgagtgacctgttt tcggccgcgtcggcgtttcagtcggtggtctggggtctgacggtggggtcgtggataggt tcgtcggcgggtctgatggtggcggcggcctcgccgtatgtggcgtggatgagcgtcacc gcggggcaggccgagctgaccgccgcccaggtccgggttgctgcggcggcctacgagacg gcgtatgggctgacggtgcccccgccggtgatcgccgagaaccgtgctgaactgatgatt ctgatagcgaccaacctcttggggcaaaacaccccggcgatcgcggtcaacgaggccgaa tacggcgagatgtgggcccaagacgccgccgcgatgtttggctacgccgcggcgacggcg acggcgacggcgacgttgctgccgttcgaggaggcgccggagatgaccagcgcgggtggg ctcctcgagcaggccgccgcggtcgaggaggcctccgacaccgccgcggcgaaccagttg atgaacaatgtgccccaggcgctgcaacagctggcccagcccacgcagggcaccacgcct tcttccaagctgggtggcctgtggaagacggtctcgccgcatcggtcgccgatcagcaac atggtgtcgatggccaacaaccacatgtcgatgaccaactcgggtgtgtcgatgaccaac -continued accttgagctcgatgttgaagggctttgctccggcggcggccgcccaggccgtgcaaacc gcggcgcaaaacggggtccgggcgatgagctcgctgggcagctcgctgggttcttcgggt ctgggcggtggggtggccgccaacttgggtcgggcggcctcggtcggttcgttgtcggtg ccgcaggcctgggccgcggccaaccaggcagtcaccccggcggcgcgggcgctgccgctg accagcctgaccagcgccgcggaaagagggcccgggcagatgctgggcgggctgccggtg gggcagatgggcgccagggccggtggtgggctcagtggtgtgctgcgtgttccgccgcga ccctatgtgatgccgcattctccggcggccggctag

SEQ ID NO: 27 atgcggacccccagacgccactgccgtcgcatcgccgtcctcgccgccgttagcatcgcc gccactgtcgttgccggctgctcgtcgggctcgaagccaagcggcggaccacttccggac gcgaagccgctggtcgaggaggccaccgcgcagaccaaggctctcaagagcgcgcacatg gtgctgacggtcaacggcaagatcccgggactgtctctgaagacgctgagcggcgatctc accaccaaccccaccgccgcgacgggaaacgtcaagctcacgctgggtgggtctgatatc gatgccgacttcgtggtgttcgacgggatcctgtacgccaccctgacgcccaaccagtgg agcgatttcggtcccgccgccgacatctacgaccccgcccaggtgctgaatccggatacc ggcctggccaacgtgctggcgaatttcgccgacgcaaaagccgaagggcgggataccatc aacggccagaacaccatccgcatcagcgggaaggtatcggcacaggcggtgaaccagata gcgccgccgttcaacgcgacgcagccggtgccggcgaccgtctggattcaggagaccggc gatcatcaactggcacaggcccagttggaccgcggctcgggcaattccgtccagatgacc ttgtcgaaatggggcgagaaggtccaggtcacgaagccccccggtgagctga

SEQ ID NO: 28 atggccaagacaattgcgtacgacgaagaggcccgtcgcggcctcgagcggggcttgaac gccctcgccgatgcggtaaaggtgacattgggccccaagggccgcaacgtcgtcctggaa aagaagtggggtgcccccacgatcaccaacgatggtgtgtccatcgccaaggagatcgag ctggaggatccgtacgagaagatcggcgccgagctggtcaaagaggtagccaagaagacc gatgacgtcgccggtgacggcaccacgacggccaccgtgctggcccaggcgttggttcgc gagggcctgcgcaacgtcgcggccggcgccaacccgctcggtctcaaacgcggcatcgaa aaggccgtggagaaggtcaccgagaccctgctcaagggcgccaaggaggtcgagaccaag gagcagattgcggccaccgcagcgatttcggcgggtgaccagtccatcggtgacctgatc gccgaggcgatggacaaggtgggcaacgagggcgtcatcaccgtcgaggagtccaacacc tttgggctgcagctcgagctcaccgagggtatgcggttcgacaagggctacatctcgggg tacttcgtgaccgacccggagcgtcaggaggcggtcctggaggacccctacatcctgctg gtcagctccaaggtgtccactgtcaaggatctgctgccgctgctcgagaaggtcatcgga gccggtaagccgctgctgatcatcgccgaggacgtcgagggcgaggcgctgtccaccctg gtcgtcaacaagatccgcggcaccttcaagtcggtggcggtcaaggctcccggcttcggc gaccgccgcaaggcgatgctgcaggatatggccattctcaccggtggtcaggtgatcagc gaagaggtcggcctgacgctggagaacgccgacctgtcgctgctaggcaaggcccgcaag gtcgtggtcaccaaggacgagaccaccatcgtcgagggcgccggtgacaccgacgccatc gccggacgagtggcccagatccgccaggagatcgagaacagcgactccgactacgaccgt gagaagctgcaggagcggctggccaagctggccggtggtgtcgcggtgatcaaggccggt gccgccaccgaggtcgaactcaaggagcgcaagcaccgcatcgaggatgcggttcgcaat gccaaggccgccgtcgaggagggcatcgtcgccggtgggggtgtgacgctgttgcaagcg -continued gccccgaccctggacgagctgaagctcgaaggcgacgaggcgaccggcgccaacatcgtg aaggtggcgctggaggccccgctgaagcagatcgccttcaactccgggctggagccgggc gtggtggccgagaaggtgcgcaacctgccggctggccacggactgaacgctcagaccggt gtctacgaggatctgctcgctgccggcgttgctgacccggtcaaggtgacccgttcggcg ctgcagaatgcggcgtccatcgcggggctgttcctgaccaccgaggccgtcgttgccgac aagccggaaaaggagaaggcttccgttcccggtggcggcgacatgggtggcatggatttc tga

SEQ ID NO: 29 atggctgaaaactcgaacattgatgacatcaaggctccgttgcttgccgcgcttggagcg gccgacctggccttggccactgtcaacgagttgatcacgaacctgcgtgagcgtgcggag gagactcgtacggacacccgcagccgggtcgaggagagccgtgctcgcctgaccaagctg caggaagatctgcccgagcagctcaccgagctgcgtgagaagttcaccgccgaggagctg cgtaaggccgccgagggctacctcgaggccgcgactagccggtacaacgagctggtcgag cgcggtgaggccgctctagagcggctgcgcagccagcagagcttcgaggaagtgtcggcg cgcgccgaaggctacgtggaccaggcggtggagttgacccaggaggcgttgggtacggtc gcatcgcagacccgcgcggtcggtgagcgtgccgccaagctggtcggcatcgagctgcct aagaaggctgctccggccaagaaggccgctccggccaagaaggccgctccggccaagaag gcggcggccaagaaggcgcccgcgaagaaggcggcggccaagaaggtcacccagaagtag

SEQ ID NO: 30 gtgacgcaaaccggcaagcgtcagagacgcaaattcggtcgcatccgacagttcaactcc ggccgctggcaagccagctacaccggccccgacggccgcgtgtacatcgcccccaaaacc ttcaacgccaagatcgacgccgaagcatggctcaccgaccgccgccgcgaaatcgaccga caactatggtccccggcatcgggtcaggaagaccgccccggagccccattcggtgagtac gccgaaggatggctgaagcagcgtggaatcaaggaccgcacccgcgcccactatcgcaaa ctgctggacaaccacatcctggccaccttcgctgacaccgacctacgcgacatcaccccg gccgccgtgcgccgctggtacgccaccaccgccgtgggcacaccgaccatgcgggcacac tcctacagcttgctgcgcgcaatcatgcagaccgccttggccgacgacctgatcgactcc aacccctgccgcatctcaggcgcgtccaccgcccgccgcgtccacaagatcaggcccgcc accctcgacgagctggaaaccatcaccaaagccatgcccgacccctaccaggcgttcgtg ctgatggcggcatggctggccatgcgctacggcgagctgaccgaattacgccgcaaagac atcgacctgcacggcgaggttgcgcgggtgcggcgggctgtcgttcgggtgggcgaaggc ttcaaggtgacgacaccgaaaagcgatgcgggagtgcgcgacataagtatcccgccacat ctgatacccgccatcgaagaccaccttcacaaacacgtcaaccccggccgggagtccctg ctgttcccatcggtcaacgaccccaaccgtcacctagcaccctcggcgctgtaccgcatg ttctacaaggcccgaaaagccgccggccgaccagacttacgggtgcacgaccttcgacac tccggcgccgtgttggctgcatccaccggcgccacactggccgaactgatgcagcggcta ggacacagcacagccggcgccgcactccgctaccagcacgccgccaagggccgggaccgc gaaatcgccgcactgttaagcaaactggccgagaaccaggagatgtga

SEQ ID NO: 31 gtgatagcgggcgtcgaccaggcgcttgcagcaacaggccaggctagccagcgggcggca ggcgcatctggtggggtcaccgtcggtgtcggcgtgggcacggaacagaggaacctttcg -continued gtggttgcaccgagtcagttcacatttagttcacgcagcccagattttgtggatgaaacc gcaggtcaatcgtggtgcgcgatactgggattgaaccagtttcactag

SEQ ID NO: 32 atggccaccacccttcccgttcagcgccacccgcggtccctcttccccgagttttctgag ctgttcgcggccttcccgtcattcgccggactccggcccaccttcgacacccggttgatg cggctggaagacgagatgaaagaggggcgctacgaggtacgcgcggagcttcccggggtc gaccccgacaaggacgtcgacattatggtccgcgatggtcagctgaccatcaaggccgag cgcaccgagcagaaggacttcgacggtcgctcggaattcgcgtacggttccttcgttcgc acggtgtcgctgccggtaggtgctgacgaggacgacattaaggccacctacgacaagggc attcttactgtgtcggtggcggtttcggaagggaagccaaccgaaaagcacattcagatc cggtccaccaactga

SEQ ID NO: 33

Pro Asn Pro Leu Gly Leu Asp

SEQ ID NO: 34

MSGRHRKPTTSNVSVAKIAFTGAVLGGGGIAMAAQATAATDGEWDQVARCESGGNWSINT

GNGYLGGLQFTQSTWAAHGGGEFAPSAQLASREQQIAVGERVLATQGRGAWPVCGRGLSN

ATPREVLPASAAMDAPLDAAAVNGEPAPLAPPPADPAPPVELAANDLPAPLGEPLPAAPA

DPAPPADLAPPAPADVAPPVELAVNDLPAPLGEPLPAAPADPAPPADLAPPAPADLAPPA

PADLAPPAPADLAPPVELAVNDLPAPLGEPLPAAPAELAPPADLAPASADLAPPAPADLA

PPAPAELAPPAPADLAPPAAVNEQTAPGDQPATAPGGPVGLATDLELPEPDPQPADAPPP

GDVTEAPAETPQVSNIAYTKKLWQAIRAQDVCGNDALDSLAQPYVIG

SEQ ID NO: 35

MLRLVVGALLLVLAFAGGYAVAACKTVTLTVDGTAMRVTTMKSRVIDIVEENGFSVDDRD

DLYPAAGVQVHDADTIVLRRSRPLQISLDGHDAKQVWTTASTVDEALAQLAMTDTAPAAA

SRASRVPLSGMALPVVSAKTVQLNDGGLVRTVHLPAPNVAGLLSAAGVPLLQSDHVVPAA

TAPIVEGMQIQVTRNRIKKVTERLPLPPNARRVEDPEMNMSREVVEDPGVPGTQDVTFAV

AEVNGVETGRLPVANVVVTPAHEAVVRVGTKPGTEVPPVIDGSIWDAIAGCEAGGNWAIN

TGNGYYGGVQFDQGTWEANGGLRYAPRADLATREEQIAVAEVTRLRQGWGAWPVCAARAG

AR

SEQ ID NO: 36

VHPLPADHGRSRCNRHPISPLSLIGNASATSGDMSSMTRIAKPLIKSAMAAGLVTASMSL

STAVAHAGPSPNWDAVAQCESGGNWAANTGNGKYGGLQFKPATWAAFGGVGNPAAASREQ

QIAVANRVLAEQGLDAWPTCGAASGLPIALWSKPAQGIKQIINEIIWAGIQASIPR

SEQ ID NO: 37

MTPGLLTTAGAGRPRDRCARIVCTVFIETAVVATMFVALLGLSTISSKADDIDWDAIAQC

ESGGNWAANTGNGLYGGLQISQATWDSNGGVGSPAAASPQQQIEVADNIMKTQGPGAWPK

CSSCSQGDAPLGSLTHILTFLAAETGGCSGSRDD

SEQ ID NO: 38

LKNARTTLIAAAIAGTLVTTSPAGIANADDAGLDPNAAAGPDAVGFDPNLPPAPDAAPVD

TPPAPEDAGFDPNLPPPLAPDFLSPPAEEAPPVPVAYSVNWDAIAQCESGGNWSINTGNG

YYGGLRFTAGTWRANGGSGSAANASREEQIRVAENVLRSQGIRAWPVCGRRG

SEQ ID NO: 39

MIATTRDREGATMITFRLRLPCRTILRVFSRNPLVRGTDRLEAVVMLLAVTVSLLTIPFA

AAAGTAVQDSRSHVYAHQAQTRHPATATVIDHEGVIDSNTTATSAPPRTKITVPARWVVN

-continued

GIERSGEVNAKPGTKSGDRVGIWVDSAGQLVDEPAPPARAIADAALAALGLWLSVAAVAG

ALLALTRAILIRVRNASWQHDIDSLFCTQR

SEQ ID NO: 40

MTEPAAWDEGKPRIITLTMNPALDITTSVDVVRPTEKMRCGAPRYDPGGGGINVARIVHV

LGGCSTALFPAGGSTGSLLMALLGDAGVPFRVIPIAASTRESFTVNESRTAKQYRFVLPG

PSLTVAEQEQCLDELRGAAASAAFVVASGSLPPGVAADYYQRVADICRRSSTPLILDTSG

GGLQHISSGVFLLKASVRELRECVGSELLTEPEQLAAAHELIDRGRAEVVVVSLGSQGAL

LATRHASHRFSSIPMTAVSGVGAGDAMVAAITVGLSRGWSLIKSVRLGNAAGAAMLLTPG

TAACNRDDVERFFELAAEPTEVGQDQYVWHPIVNPEASP

SEQ ID NO: 41

MPDTMVTTDVIKSAVQLACRAPSLHNSQPWRWIAEDHTVALFLDKDRVLYATDHSGREAL

LGCGAVLDHFRVAMAAAGTTANVERFPNPNDPLHLASIDFSPADFVTEGHRLRADAILLR

RTDRLPFAEPPDWDLVESQLRTTVTADTVRIDVIADDMRPELAAASKLTESLRLYDSSYH

AELFWWTGAFETSEGIPHSSLVSAAESDRVTFGRDFPVVANTDRRPEFGHDRSKVLVLST

YDNERASLLRCGEMLSAVLLDATMAGLATCTLTHITELHASRDLVAALIGQPATPQALVR

VGLAPEMEEPPPATPRRPIDEVFHVRAKDHR

SEQ ID NO: 42

MTTARDIMNAGVTCVGEHETLTAAAQYMREHDIGALPICGDDDRLHGMLTDRDIVIKGLA

AGLDPNTATAGELARDSIYYVDANASIQEMLNVMEEHQVRRVPVISEHRLVGIVTEADIA

RHLPEHAIVQFVKAICSPMALAS

SEQ ID NO: 43

MASSASDGTHERSAFRLSPPVLSGAMGPFMHTGLYVAQSWRDYLGQQPDKLPIARPTIAL

AAQAFRDEIVLLGLKARRPVSNHRVFERISQEVAAGLEFYGNRRWLEKPSGFFAQPPPLT

EVAVRKVKDRRRSFYRIFFDSGFTPHPGEPGSQRWLSYTANNREYALLLRHPEPRPWLVC

VHGTEMGRAPLDLAVFRAWKLHDELGLNIVMPVLPMHGPRGQGLPKGAVFPGEDVLDDVH

GTAQAVWDIRRLLSWIRSQEEESLIGLNGLSLGGYIASLVASLEEGLACAILGVPVADLI

ELLGRHCGLRHKDPRRHTVKMAEPIGRMISPLSLTPLVPMPGRFIYAGIADRLVHPREQV

TRLWEHWGKPEIVWYPGGHTGFFQSRPVRRFVQAALEQSGLLDAPRTQRDRSA

SEQ ID NO: 44

MSTQRPRHSGIRAVGPYAWAGRCGRIGRWGVHQEAMMNLAIWHPRKVQSATIYQVTDRSH

DGRTARVPGDEITSTVSGWLSELGTQSPLADELARAVRIGDWPAAYAIGEHLSVEIAVAV

SEQ ID NO: 45 atgagtggacgccaccgtaagcccaccacatccaacgtcagcgtcgccaagatcgccttt accggcgcagtactcggtggcggcggcatcgccatggccgctcaggcgaccgcggccacc gacggggaatgggatcaggtggcccgctgcgagtcgggcggcaactggtcgatcaacacc ggcaacggttacctcggtggcttgcagttcactcaaagcacctgggccgcacatggtggc ggcgagttcgccccgtcggctcagctggccagccgggagcagcagattgccgtcggtgag cgggtgctggccacccagggtcgcggcgcctggccggtgtgcggccgcgggttatcgaac gcaacaccccgcgaagtgcttcccgcttcggcagcgatggacgctccgttggacgcggcc gcggtcaacggcgaaccagcaccgctggccccgccgcccgccgacccggcgccacccgtg gaacttgccgctaacgacctgcccgcaccgctgggtgaacccctcccggcagctcccgcc gacccggcaccacccgccgacctggcaccacccgcgcccgccgacgtcgcgccacccgtg gaacttgccgtaaacgacctgcccgcaccgctgggtgaacccctcccggcagctcccgcc gacccggcaccacccgccgacctggcaccacccgcgcccgccgacctggcgccacccgcg -continued cccgccgacctggcgccacccgcgcccgccgacctggcaccacccgtggaacttgccgta
aacgacctgcccgcgccgctgggtgaacccctcccggcagctcccgccgaactggcgcca
cccgccgatctggcacccgcgtccgccgacctggcgccacccgcgcccgccgacctggcg
ccacccgcgcccgccgaactggcgccacccgcgcccgccgacctggcaccacccgctgcg
gtgaacgagcaaaccgcgccgggcgatcagcccgccacagctccaggcggcccggttggc
cttgccaccgatttggaactccccgagcccgacccccaaccagctgacgcaccgccgccc
ggcgacgtcaccgaggcgcccgccgaaacgccccaagtctcgaacatcgcctatacgaag
aagctgtggcaggcgattcgggcccaggacgtctgcggcaacgatgcgctggactcgctc
gcacagccgtacgtcatcggctga

SEQ ID NO: 46 atgttgcgcctggtagtcggtgcgctgctgctggtgttggcgttcgccggtggctatgcg
gtcgccgcatgcaaaacggtgacgttgaccgtcgacggaaccgcgatgcgggtgaccacg
atgaaatcgcgggtgatcgacatcgtcgaagagaacgggttctcagtcgacgaccgcgac
gacctgtatcccgcggccggcgtgcaggtccatgacgccgacaccatcgtgctgcggcgt
agccgtccgctgcagatctcgctggatggtcacgacgctaagcaggtgtggacgaccgcg
tcgacggtggacgaggcgctggcccaactcgcgatgaccgacacggcgccggccgcggct
tctcgcgccagccgcgtcccgctgtccgggatggcgctaccggtcgtcagcgccaagacg
gtgcagctcaacgacggcgggttggtgcgcacggtgcacttgccggcccccaatgtcgcg
gggctgctgagtgcggccggcgtgccgctgttgcaaagcgaccacgtggtgcccgccgcg
acggccccgatcgtcgaaggcatgcagatccaggtgacccgcaatcggatcaagaaggtc
accgagcggctgccgctgccgccgaacgcgcgtcgtgtcgaggacccggagatgaacatg
agccgggaggtcgtcgaagacccgggggttccggggacccaggatgtgacgttcgcggta
gctgaggtcaacggcgtcgagaccggccgtttgcccgtcgccaacgtcgtggtgaccccg
gcccacgaagccgtggtgcgggtgggcaccaagcccggtaccgaggtgcccccggtgatc
gacggaagcatctgggacgcgatcgccggctgtgaggccggtggcaactgggcgatcaac
accggcaacgggtattacggtggtgtgcagtttgaccagggcacctgggaggccaacggc
gggctgcggtatgcaccccgcgctgacctcgccacccgcgaagagcagatcgccgttgcc
gaggtgacccgactgcgtcaaggttggggcgcctggccggtatgtgctgcacgagcgggt
gcgcgctga

SEQ ID NO: 47 gtgcatcctttgccggccgaccacggccggtcgcggtgcaatagacacccgatctcacca
ctctctctaatcggtaacgcttcggccacttccggcgatatgtcgagcatgacaagaatc
gccaagccgctcatcaagtccgccatggccgcaggactcgtcacggcatccatgtcgctc
tccaccgccgttgcccacgccggtcccagcccgaactgggacgccgtcgcgcagtgcgaa
tccgggggcaactgggcggccaacaccggaaacggcaaatacggcggactgcagttcaag
ccggccacctgggccgcattcggcggtgtcggcaacccagcagctgcctctcgggaacaa
caaatcgcagttgccaatcgggttctcgccgaacagggattggacgcgtggccgacgtgc
ggcgccgcctctggccttccgatcgcactgtggtcgaaacccgcgcagggcatcaagcaa
atcatcaacgagatcatttgggcaggcattcaggcaagtattccgcgctga

SEQ ID NO: 48 atgacaccgggtttgcttactactgcgggtgctggccgaccacgtgacaggtgcgccagg
atcgtatgcacggtgttcatcgaaaccgccgttgtcgcgaccatgtttgtcgcgttgttg -continued ggtctgtccaccatcagctcgaaagccgacgacatcgattgggacgccatcgcgcaatgc gaatccggcggcaattgggcggccaacaccggtaacgggttatacggtggtctgcagatc agccaggcgacgtgggattccaacggtggtgtcgggtcgccggcggccgcgagtccccag caacagatcgaggtcgcagacaacattatgaaaacccaaggcccgggtgcgtggccgaaa tgtagttcttgtagtcagggagacgcaccgctgggctcgctcacccacatcctgacgttc ctcgcggccgagactggaggttgttcggggagcagggacgattga

SEQ ID NO: 49 ttgaagaacgcccgtacgacgctcatcgccgccgcgattgccgggacgttggtgaccacg tcaccagccggtatcgccaatgccgacgacgcgggcttggacccaaacgccgcagccggc ccggatgccgtgggctttgacccgaacctgccgccggccccggacgctgcacccgtcgat actccgccggctccggaggacgcgggctttgatcccaacctcccccgccgctggccccg gacttcctgtccccgcctgcggaggaagcgcctcccgtgcccgtggcctacagcgtgaac tgggacgcgatcgcgcagtgcgagtccggtggaaactggtcgatcaacaccggtaacggt tactacggcggcctgcggttcaccgccggcacctggcgtgccaacggtggctcggggtcc gcggccaacgcgagccgggaggagcagatccgggtggctgagaacgtgctgcgttcgcag ggtatccgcgcctggccggtctgcggccgccgcggctga

SEQ ID NO: 50 atgatcgccacaacccgcgatcgtgaaggagccaccatgatcacgtttaggctgcgcttg ccgtgccggacgatactgcgggtgttcagccgcaatccgctggtgcgtgggacggatcga ctcgaggcggtcgtcatgctgctggccgtcacggtctcgctgctgactatcccgttcgcc gccgcggccggcaccgcagtccaggattcccgcagccacgtctatgcccaccaggcccag acccgccatcccgcaaccgcgaccgtgatcgatcacgaggggtgatcgacagcaacacg accgccacgtcagcgccgccgcgcacgaagatcaccgtgcctgcccgatgggtcgtgaac ggaatagaacgcagcggtgaggtcaacgcgaagccgggaaccaaatccggtgaccgcgtc ggcatttgggtcgacagtgccggtcagctggtcgatgaaccagctccgccggcccgtgcc attgcggatgcggccctggccgccttgggactctggttgagcgtcgccgcggttgcgggc gccctgctggcgctcactcgggcgattctgatccgcgttcgcaacgccagttggcaacac gacatcgacagcctgttctgcacgcagcggtga

SEQ ID NO: 51 atgacggagccagcggcgtgggacgaaggcaagccgcgaatcatcactttgaccatgaac cccgccttggacatcacgacgagcgtcgacgtggtgcgcccgaccgagaaaatgcgttgt ggcgcacctcgctacgatcccggcggcggcggtatcaatgtcgcccgcattgtgcatgtc ctcggcggttgctcgacagcactgttcccggccggcgggtcgaccgggagcctgctgatg gcgctgctcggtgatgcgggagtgccatttcgcgtcattccgatcgcggcctcgacgcgg gagagcttcacggtcaacgagtccaggaccgccaagcagtatcgtttcgtgcttccgggg ccgtcgctgaccgtcgcggagcaggagcaatgcctcgacgaactgcgcggtgcggcggct tcggccgcctttgtggtggccagtggcagcctgccgccaggtgtggctgccgactactat cagcgggttgccgacatctgccgccgatcgagcactccgctgatcctggatacatctggt ggcgggttgcagcacatttcgtccggggtgtttcttctcaaggcgagcgtgcgggaactg cgcgagtgcgtcggatccgaactgctgaccgagcccgaacaactggccgccgcacacgaa ctcattgaccgtgggcgcgccgaggtcgtggtggtctcgcttggatctcagggcgcgcta ttggccacacgacatgcgagccatcgattttcgtcgattccgatgaccgcggttagcggt -continued gtcggcgccggcgacgcgatggtggccgcgattaccgtgggcctcagccgtggctggtcg ctcatcaagtccgttcgcttgggaaacgcggcaggtgcagccatgctgctgacgccaggc accgcggcctgcaatcgcgacgatgtggagaggttcttcgagctggcggccgaacccacc gaagtcgggcaggatcaatacgtttggcacccgatcgttaacccggaagcctcgccatga

SEQ ID NO: 52 atgccggacaccatggtgaccaccgatgtcatcaagagcgcggtgcagttggcctgccgc gcaccgtcgctccacaacagccagccctggcgctggatagccgaggaccacacggttgcg ctgttcctcgacaaggatcgggtgctttacgcgaccgaccactccggccgggaagcgctg ctggggtgcggcgccgtactcgaccactttcgggtggcgatggcggccgcgggtaccacc gccaatgtggaacggtttcccaaccccaacgatcctttgcatctggcgtcaattgacttc agcccggccgatttcgtcaccgagggccaccgtctaagggcggatgcgatcctactgcgc cgtaccgaccggctgcctttcgccgagccgccggattgggacttggtggagtcgcagttg cgcacgaccgtcaccgccgacacggtgcgcatcgacgtcatcgccgacgatatgcgtccc gaactggcggcggcgtccaaactcaccgaatcgctgcggctctacgattcgtcgtatcat gccgaactcttttggtggacaggggcttttgagacttctgagggcataccgcacagttca ttggtatcggcggccgaaagtgaccgggtcaccttcggacgcgacttcccggtcgtcgcc aacaccgataggcgcccggagtttggccacgaccgctctaaggtcctggtgctctccacc tacgacaacgaacgcgccagcctactgcgctgcggcgagatgctttccgccgtattgctt gacgccaccatggctgggcttgccacctgcacgctgacccacatcaccgaactgcacgcc agccgagacctggtcgcagcgctgattgggcagcccgcaactccgcaagccttggttcgc gtcggtctggccccggagatggaagagccgccaccggcaacgcctcggcgaccaatcgat gaagtgtttcacgttcgggctaaggatcaccggtag

SEQ ID NO: 53 atgaccaccgcacgcgacatcatgaacgcaggtgtgacctgtgttggcgaacacgagacg ctaaccgctgccgctcaatacatgcgtgagcacgacatcggcgcgttgccgatctgcggg gacgacgaccggctgcacggcatgctcaccgaccgcgacattgtgatcaaaggcctggct gcgggcctagacccgaataccgccacggctggcgagttggcccgggacagcatctactac gtcgatgcgaacgcaagcatccaggagatgctcaacgtcatggaagaacatcaggtccgc cgtgttccggtcatctcagagcaccgcttggtcggaatcgtcaccgaagccgacatcgcc cgacacctgcccgagcacgccattgtgcagttcgtcaaggcaatctgctcgcccatggcc ctcgccagctag

SEQ ID NO: 54 atggcaagttctgcgagcgacggcacccacgaacgctcggcttttcgcctgagtccaccg gtcttgagcggcgccatgggaccgttcatgcacaccggtctgtacgtcgctcaatcgtgg cgcgactatctgggtcaacagcccgataaactgccgatcgcacggcccactattgcctta gcggcgcaagcctttcgagacgaaatcgtcctgctgggcctcaaggcacgacgtccggtc agcaatcatcgagtgttcgagcgcatcagccaagaagtggccgctggactggagttctat gggaatcgcagatggctggagaagcctagcggatttttttgcccagcccccaccgctcacc gaggtcgcggtccgaaaggtcaaggaccgcagacgctccttttatcgcatcttcttcgac agtgggtttacgccgcatccgggtgaaccgggcagccaacggtggctctcatacactgcg aacaatcgcgagtacgccctgttactgcggcacccagagccgcgtccctggctggtttgt gtacacggcaccgagatgggcagggccccgttggatctcgcggtgttccgcgcctggaag -continued ctgcatgacgaactcggcctgaacattgtcatgccggttcttccgatgcatggtccccgc gggcaaggtctgccgaagggcgccgtttttcccggagaagatgttctcgacgatgtgcat gggacggctcaagcggtgtgggatatccggcggctgttgtcctggatacgatcgcaggag gaggagtcgctgatcgggttgaacggtctctcgctgggcggctacatcgcgtcattggtc gccagcctcgaagaaggtctcgcctgcgcgattctcggtgtcccagtggctgatctgatc gagttgttgggccgccactgcggtcttcggcacaaagacccccgccgccacaccgtcaag atggccgaaccgatcggccgaatgatctcgccgctctcacttacgccactggtgcccatg ccgggccgctttatctacgcgggcattgccgaccgactcgtgcatccacgcgaacaggtg actcgcctctgggagcactggggcaaacccgaaatcgtgtggtatccaggcggtcacact ggcttcttccagtcgcggccggtacgacggtttgtccaggctgcgctggagcagtcgggc ctgttggacgcgccacggacacagcgcgaccgttccgcctaa

SEQ ID NO: 55 atgtccacgcaacgaccgaggcactccggtattcgggctgttggcccctacgcatgggcc ggccgatgtggtcggataggcaggtggggggtgcaccaggaggcgatgatgaatctagcg atatggcacccgcgcaaggtgcaatccgccaccatctatcaggtgaccgatcgctcgcac gacgggcgcacagcacgggtgcctggtgacgagatcactagcaccgtgtccggttggttg tcggagttgggcacccaaagcccgttggccgatgagcttgcgcgtgcggtgcggatcggc gactggcccgctgcgtacgcaatcggtgagcacctgtccgttgagattgccgttgcggtc taa

SEQ ID NO: 56

LDFATLPPEINSARMYSGAGSAPMLAAASAWHGLSAELRASALSYSSVLSTLTGEEWHGP

ASASMTAAAAPYVAWMSVTAVRAEQAGAQAEAAAAAYEAAFAATVPPPVIEANRAQLMAL

IATNVLGQNAPAIAATEAQYAEMWSQDAMAMYGYAGASAAATQLTPFTEPVQTTNASGLA

AQSAAIAHATGASAGAQQTTLSQLIAAIPSVLQGLSSSTAATFASGPSGLLGIVGSGSSW

LDKLWALLDPNSNFWNTIASSGLFLPSNTIAPFLGLLGGVAAADAAGDVLGEATSGGLGG

ALVAPLGSAGGLGGTVAAGLGNAATVGTLSVPPSWTAAAPLASPLGSALGGTPMVAPPPA

VAAGMPGMPFGTMGGQGFGRAVPQYGFRPNFVARPPAAG

SEQ ID NO: 57 cttgacttcgccacgctaccgcccgaaatcaactcggcgcgtatgtattccggcgcgggc tcggccccgatgctggccgcagcgtcagcctggcacggcttgtccgcagaactgcgcgcc agcgcactgtcatacagctcggtgctttcgacgctgaccggtgaagaatggcacggtccg gcgtcggcatcgatgacagccgcggccgcccccctacgtggcctggatgagcgtcaccgcc gtccgggccgagcaggccggggcacaggcggaggctgccgctgcagcgtacgaagccgcg ttcgcagcaacggtgcccccgccggtcatcgaggccaaccgcgcccagctcatggcgctg atcgccaccaatgtgctaggccaaaacgcccccgcgatcgcggccaccgaggcccagtac gccgaaatgtggtcccaggacgcgatggccatgtacggctacgccggcgcctcggcagcc gctacccagctgaccccgttcaccgagccggtgcagactaccaacgcgtccggcctggcg gcccagtcggctgcgattgcccacgccaccggcgcctcggctggtgctcagcaaacgacg ctgtcgcagctgatcgccgccataccgtctgtactgcaaggactttcgtcatcgactgca gccacgttcgcgtcggggccgtccggattgctgggcattgtcgggtctggatcttcctgg ctcgacaaactctgggcgttactggaccccaactccaatttctggaacacgatagcttcg tccggactgttcttgccgagtaacacgattgcgccctttttgggtctactcggcggcgtg -continued

```
gcagctgcggatgcggccggggatgtgttgggagaggccaccagtggcgggctcggtggc

gcgctggtggcgccgcttggctcagcgggcgggctaggcggcactgtcgcggccggcctg

ggcaacgcggccaccgtcggaaccttgtcggtgccgccgagctggacggcggccgcacca

ctagccagccccttgggctccgcgttgggaggcacaccgatggtggcaccgcccccagca

gtggcggccggcatgcccggaatgcctttcggcaccatgggcggtcaaggcttcgggcgt

gccgtgccccagtatggcttccgccccaacttcgtcgcacgaccgcccgccgccggg
```

The invention will be further clarified by the following examples, which are intended to be purely exemplary of the invention and in no way limiting.

EXAMPLES

Example 1—Sub-Unit Vaccines Containing Polypeptides of the Invention

To prepare sub-unit vaccines comprising polypeptides it is first of all necessary to obtain a supply of polypeptide to prepare the vaccine. This can be achieved by purifying proteins of interest from TB culture, or by cloning the gene of interest and producing a recombinant protein.

The coding sequences for the genes of interest are amplified by PCR with restriction sites inserted at the N terminus and C terminus to permit cloning in-frame into a protein expression vector such as pET-15b. The genes are inserted behind an inducible promoter such as lacZ. The vector is then transformed into *E. coli* which is grown in culture. The recombinant protein is over-expressed and is purified.

One of the common purification methods is to produce a recombinant protein with an N-terminal tag for purification—eg. a His-tag. The protein can then be purified on the basis of the affinity of the His-tag for metal ions on a Ni-NTA column after which the His-tag is cleaved. The purified protein is then administered to animals in a suitable adjuvant.

Where at least 2 mycobacterial antigens are used in combination, the 1st and 2nd mycobacterial antigens may be expressed as separate polypeptides and used in combination by mixing with adjuvant and inoculating at a single site. Alternatively, the 1st and 2nd mycobacterial antigens may be expressed as a fusion protein, mixed with adjuvant and used to inoculate at a single site.

Example 2—Use of BCG as a Microbial Carrier

The polynucleotide sequence of interest is amplified by PCR. The amplified product is purified and cloned into a plasmid (pMV306) that integrates site specifically into the mycobacterial genome at the attachment site (attB) for mycobacteriophage L5.

BCG is transformed with the plasmid by electroporation, which involves damaging the cell envelope with high voltage electrical pulses, resulting in uptake of the DNA. The plasmid integrates into the BCG chromosome at the attB site, generating stable recombinants. Recombinants are selected and are checked by PCR or Southern blotting to ensure that the gene has been integrated. The recombinant strain is then used for protection studies.

The polynucleotide sequence of interest may comprise a single mycobacterial antigen, 1st and 2nd mycobacterial antigens, or fragments thereof as defined herein.

Example 3—Viral Vectors (Eg. Attenuated Vaccinia Virus) Expressing Mycobacterial Genes Left Flanking Region—Promotor—Target gene(s)—Right Flanking Region One of the best examples of this type of approach is the use of Modified Vaccinia virus Ankara (MVA). Methodologies permitting recombination of foreign or target genes into the genome of MVA are well known in the art [1,2].

Insertion of the target gene(s) is mediated by transfer DNA with features similar to those shown above. The transfer DNA may be in the form of a plasmid that can be propagated in a bacterial strain optimized for routine cloning procedures. The target gene(s) is introduced to the cassette downstream of a promoter such as mH5, p7.5 or another. The target gene(s) may comprise one or more of the polynucleotides of the invention and/or fragments thereof. The target gene(s) may also comprise adjuvanting cofactors such as B7-1 or IL-12, as is well described in the art [3]. The target gene(s) are positioned downstream and in frame with an optimized Kozak sequence—eg. GCCACCATGG (SEQ ID NO:58). The target gene(s) may also be positioned downstream and in frame with a leader sequence—eg. tPA. The target gene(s) may be positioned upstream of an in-frame tag—eg. V5, HIS or another. Transfer of the cassette into the genome of MVA is mediated by homologous flanking regions well known in the art—eg. Del I-VI.

1. Earl P L et al. Current Protocols in Protein Science, (2001) "Generation of recombinant vaccinia viruses".
2. Earl P L et al. Current Protocols in Protein Science, (2001) "Preparation of cell cultures and vaccine virus stocks".
3. Carroll M W et al. Journal of the National Cancer Institute, (1998) "Construction and characterization of a triple-recombinant vaccine virus encoding B7-1, Interleukin 12 and a model tumor antigen".

Example 4—Plasmid DNA Vaccines Carrying Mycobacterial Polynucleotides

A polynucleotide sequence of interest is amplified by PCR, purified and inserted into specialized vectors developed for vaccine development, such as pVAX1. These vectors contain promoter sequences (eg. CMV or SV40 promoters), which direct strong expression of the introduced polynucleotide (encoding the candidate antigen) in eukaryotic cells; and polyadenylation signals (eg. SV40 or bovine growth hormone) to stabilize the mRNA transcript.

The vector is transformed into *E. coli* and transformants are selected using a marker, such as kanamycin resistance, encoded by the plasmid. The plasmid is then recovered from transformed colonies and is sequenced to check that the polynucleotide of interest is present and encoded properly without PCR generated mutations.

Large quantities of the plasmid are then produced in *E. coli* and the plasmid is recovered and purified using commercially available kits (e.g. Qiagen Endofree-plasmid preparation). The vaccine is then administered to animals (eg. by intramuscular injection) in the presence or absence of an adjuvant.

Plasmid DNA encoding the 1st mycobacterial antigens or the 2nd mycobacterial antigens separately may be mixed and inoculated at a single site of administration. A single plasmid may be constructed that expresses both the 1st and the 2nd mycobacterial antigens (and optionally the third mycobacterial antigen).

Example 5—Plasmid DNA Vaccines Carrying Multiple Mycobacterial Polynucleotides Further plasmid DNA encoding a 3rd and/or further (eg. $4^{th}$ and $5^{th}$) mycobacterial antigens separately may be prepared as described in Example 4. The separate plasmids encoding the $3^{rd}$ and/or further mycobacterial antigens may be inoculated at a single site of administration simultaneously or sequentially with plasmid DNA encoding the $1^{st}$ and $2^{nd}$ mycobacterial antigens (eg. as prepared in Example 4).

Alternatively, a single plasmid may be constructed as described in Example 4 that expresses the $3^{rd}$ and one or more further (eg. $4^{th}$ and $5^{th}$) mycobacterial antigens. This single plasmid may be inoculated at a single site of administration simultaneously or sequentially with plasmid DNA encoding the $1^{st}$ and $2^{nd}$ mycobacterial antigens separately or from a single plasmid. Alternatively, a single plasmid may be constructed as described in Example 4 that expresses the $1^{st}$, $2^{nd}$ and $3^{rd}$ (and optionally one or more further—eg. $4^{th}$ and $5^{th}$) mycobacterial antigens.

Example 6—Preparation of DNA Expression Vectors

DNA vaccines consist of a nucleic acid sequence of interest cloned into a bacterial plasmid. The plasmid vector pVAX1 is commonly used in the preparation of DNA vaccines. The vector is designed to facilitate high copy number replication in *E. coli* and high level transient expression of the peptide of interest in most mammalian cells (for details see manufacturers protocol for pVAX1 (catalog No. V260-20 www.invitrogen.com).

The vector contains the following elements:

- Human cytomegalovirus immediate-early (CMV) promoter for high-level expression in a variety of mammalian cells
- T7 promoter/priming site to allow in vitro transcription in the sense orientation and sequencing through the insert
- Bovine growth hormone (BGH) polyadenylation signal for efficient transcription termination and polyadenylation of mRNA
- Kanamycin resistance gene for selection in *E. coli*
- A multiple cloning site
- pUC origin for high-copy number replication and growth in *E. coli*
- BGH reverse priming site to permit sequencing through the insert Vectors may be prepared by means of standard recombinant techniques that are known in the art, for example Sambrook et al. (1989). Key stages in preparing the vaccine are as follows:

- The polynucleotide of interest is ligated into pVAX1 via one of the multiple cloning sites
- The ligation mixture is then transformed into a competent *E. coli* strain (e.g. TOP10) and LB plates containing 50 pg/ml kanamycin are used to select transformants.
- Clones are selected and may be sequenced to confirm the presence and orientation of the gene of interest.
- Once the presence of the gene has been verified, the vector can be used to transfect a mammalian cell line to check for protein expression. Methods for transfection are known in the art and include, for example, electroporation, calcium phosphate, and lipofection.
- Once polypeptide expression has been confirmed, large quantities of the vector can be produced and purified from the appropriate cell host, eg. *E. coli.* pVAX1 does not integrate into the host chromosome. All non-essential sequences have been removed to minimise the possibility of integration. When constructing a specific vector, a leader sequence may be included to direct secretion of the encoded protein when expressed inside the eukaryotic cell.

Other examples of vectors that can be used include V1Jns.tPA and pCMV4.

Expression vectors may be used that integrate into the genome of the host, however, it is more common and more preferable to use a vector that does not integrate. Integration would lead to the generation of a genetically modified host which raises other issues.

Example 7—Preparation of DNA Expression Vectors Containing Multiple Antigens DNA vaccines consist of a nucleic acid sequence of interest cloned into a bacterial plasmid. The plasmid vector pVAX1 is commonly used in the preparation of DNA vaccines. The vector is designed to facilitate high copy number replication in *E. coli* and high level transient expression of the peptide of interest in most mammalian cells (for details see manufacturers protocol for pVAX1 (catalog No. V260-20 www.invitrogen.com).

The vector contains the following elements:

- Human cytomegalovirus immediate-early (CMV) promoter for high-level expression in a variety of mammalian cells
- T7 promoter/priming site to allow in vitro transcription in the sense orientation and sequencing through the insert
- Bovine growth hormone (BGH) polyadenylation signal for efficient transcription termination and polyadenylation of mRNA
- Kanamycin resistance gene for selection in *E. coli*
- A multiple cloning site
- pUC origin for high-copy number replication and growth in *E. coli*
- BGH reverse priming site to permit sequencing through the insert Vectors may be prepared by means of standard recombinant techniques that are known in the art, for example Sambrook et al. (1989), Gateway® cloning (Invitrogen, UK). Key stages in preparing the vaccine are as follows:

- The polynucleotides of interest are ligated into pVAX1 via one of the multiple cloning sites or introduced via Gateway® cloning.
- Polynucleotides for more than one antigen can be expressed as a recombinant fusion.
- A competent *E. coli* strain (e.g. TOP10) is transformed and LB plates containing 50 μg/ml kanamycin are used to select transformants.
- Clones are selected and may be sequenced to confirm the presence and orientation of the genes of interest.
- Once the presence of the genes has been verified, the vector can be used to transfect a mammalian cell line to check for protein expression. Methods for transfection are known in the art and include, for example, electroporation, calcium phosphate, and lipofection.

Once polypeptide expression has been confirmed, large quantities of the vector can be produced and purified from the appropriate cell host, eg. *E. coli.* pVAX1 does not integrate into the host chromosome. All non-essential sequences have been removed to minimise the possibility of integration. When constructing a specific vector, a leader sequence may be included to direct secretion of the encoded protein when expressed inside the eukaryotic cell.

Other examples of vectors that can be used include V1Jns.tPA and pCMV4.

Expression vectors may be used that integrate into the genome of the host; however, it is more common and more preferable to use a vector that does not integrate. Integration would lead to the generation of a genetically modified host which raises other issues.

A single plasmid may be thus constructed that expresses multiple mycobacterial antigens. For example, the single plasmid may encode both the $1^{st}$ and $2^{nd}$ mycobacterial antigens. The single plasmid may additionally encode one or more further mycobacterial antigens, such as a $3^{rd}$ mycobacterial antigen (and optionally one or more further—eg. $4^{th}$ and $5^{th}$) mycobacterial antigens.

Example 8—RNA Vaccine

RNA can be introduced directly into the host. Thus, a vector construct may be used to generate RNA in vitro and the purified RNA is then injected into the host. The RNA then serves as a template for translation in the host cell. In this embodiment, integration would not normally occur.

An alternative option is to use an infectious agent such as the retroviral genome carrying RNA corresponding to the gene of interest. In this embodiment, integration into the host genome will occur.

Another option is the use of RNA replicon vaccines which can be derived from virus vectors such as Sindbis virus or Semliki Forest virus. These vaccines are self-replicating and self-limiting and may be administered as either RNA or DNA which is then transcribed into RNA replicons in vivo. The vector eventually causes lysis of the transfected cells thereby reducing concerns about integration into the host genome.

Example 9—Diagnostic Assays Based on Assessing Immune Cell Responses

For a diagnostic assay based on assessing immune cell responses (eg. T cell responses) it would be sufficient to obtain a sample of blood from the patient. Mononuclear cells (monocytes, T and B lymphocytes) can be separated from the blood using density gradients such as Ficoll gradients.

Both monocytes and B-lymphocytes are both able to present antigen, although less efficiently than professional antigen presenting cells (APCs) such as dendritic cells. The latter are more localized in lymphoid tissue.

The simplest approach would be to add antigen to the separated mononuclear cells and incubate for a week and then assess the amount of proliferation. If the individual had been exposed to the antigen previously through infection, then immune cell clones (eg. T-cell clones) specific to the antigen should be more prevalent in the sample and should respond.

It is also possible to separate the different cellular populations should it be desired to control the ratio of T cells to APCs.

Another variation of this type of assay is to measure cytokine production by the responding lymphocytes as a measure of response. The ELISPOT assay is a suitable example of this assay.

Example 10—Detection of Latent Mycobacteria

The presence of latent mycobacteria-associated antigen may be detected either by detecting antigen-specific antibody, or by detecting immune cells such as T-cells in blood samples.

A 96 well plate is coated with cytokine (e.g. interferon-□, IL-2)-specific antibody. Peripheral blood monocytes are then isolated from patient whole blood and are applied to the wells.

Antigen is added to stimulate specific immune cells (eg. T cells) that may be present and the plates are incubated for 24 h. The antigen stimulates the immune cells (eg. T-cells) to produce cytokines, which bind a specific antibody.

The plates are washed leaving a footprint where antigen-specific immune cells (eg. T cells) were present. A second antibody coupled with a suitable detection system, e.g. enzyme, is then added and the number of spots is enumerated after the appropriate substrate has been added. The number of spots, each corresponding to a single antigen-specific immune cell (eg. T cell), is related to the total number of cells originally added.

The above-described assay may also be used to distinguish TB-infected individuals from BCG-vaccinated individuals.

Example 11—Antigenic Activity of Multiple Antigens

Mice are immunized with at least a 1st and 2nd mycobacterial antigen. Delivery systems include (but are not restricted to) DNA vaccines, recombinant MVA, adjuvanted protein. Delivery routes include (but are not restricted to) sub-cutaneous, intra-dermal, intra-muscular administration. The immunization regimen may involve heterologous prime-boosting—eg. 'priming' with a DNA vaccine followed by 'boosting' with an MVA vaccine. The immunization regimen may involve multiple doses.

After vaccination (eg. about 2 weeks later), splenocytes are removed from the vaccinated animals and stimulated with a polypeptide(s) representative of the immunizing antigen or antigens. An immune response is measurable through antigen-specific induction of cytokine release—eg. IFN-γ, and is evidence of immunization against the target antigen.

Where an animal has been immunized with a vaccine comprising a 1st and 2nd mycobacterial antigen, an antigen recall response to the 1st and 2nd mycobacterial antigen in the same sample demonstrates immunogenicity of both antigens when co-administered. Immunogenicity is a prerequisite for protective efficacy.

Data generated according to this Example are illustrated in FIGS. 1-7.

FIGS. 1A and B illustrate the splenocyte response to antigens Ag85A and Rv1807 alone and in combination (FIG. 1A=intra-muscular; FIG. 1B=intra-dermal).

Figure 1A:
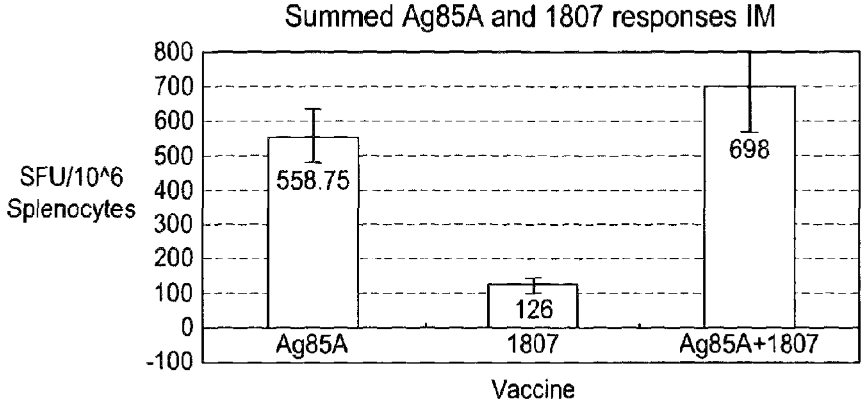
Figure 1B:
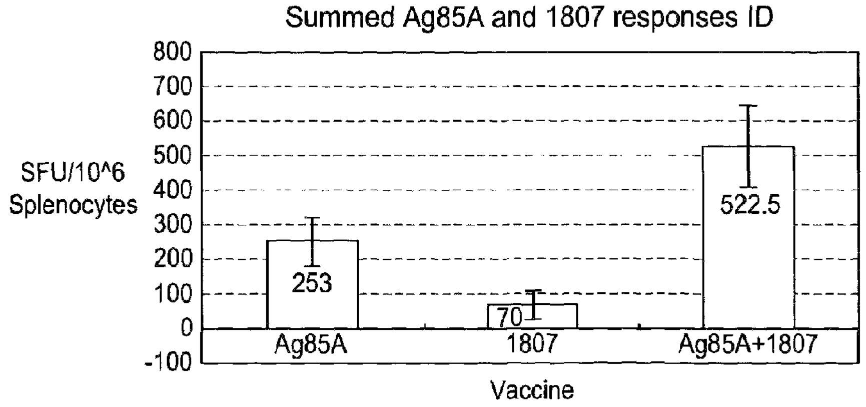
Figure 2:
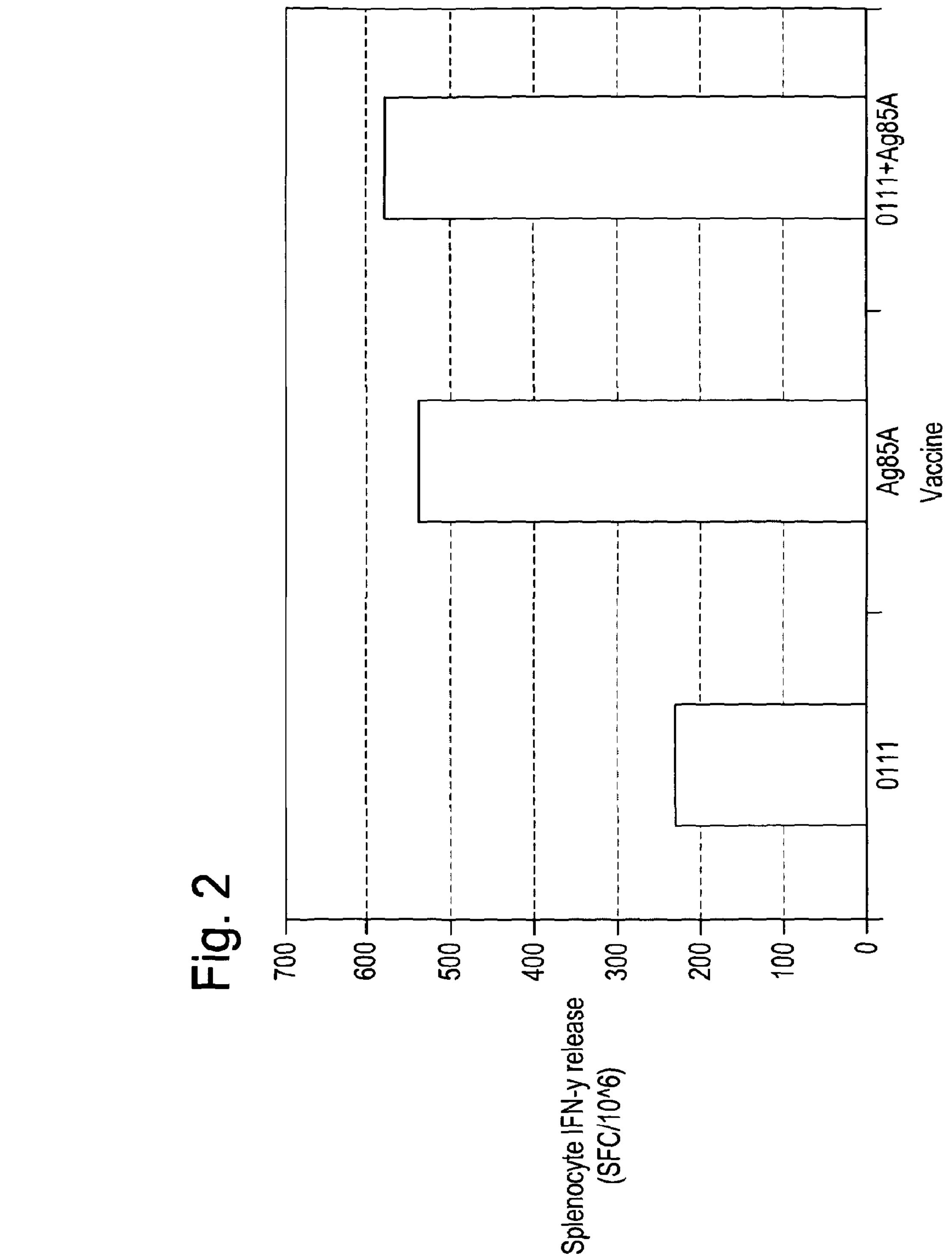
FIG. 2 illustrates the splenocyte response to antigens Ag85A and Rv0111 alone and in combination.
Figure 3:
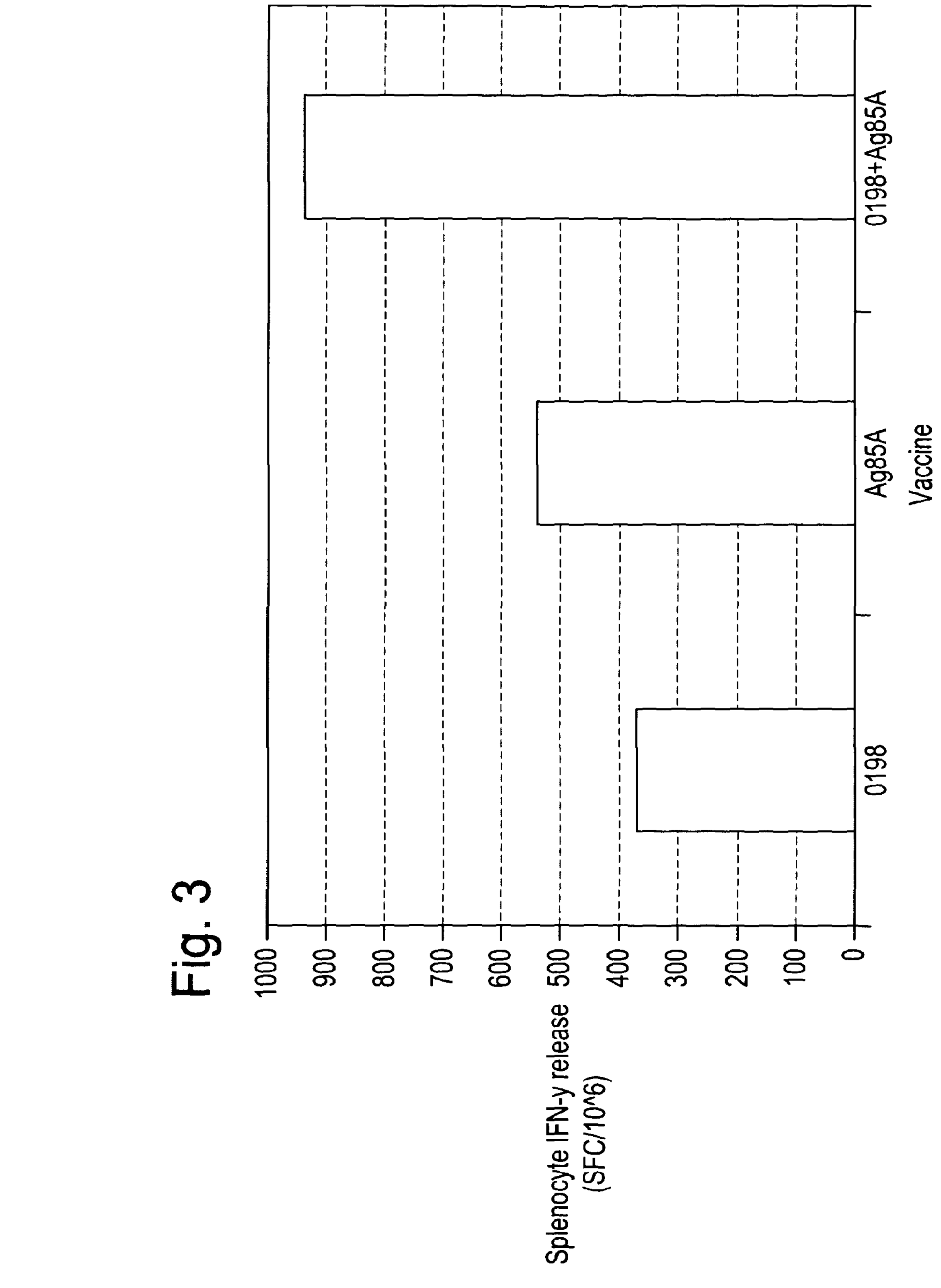
FIG. 3 illustrates the splenocyte response to antigens Ag85A and Rv0198 alone and in combination.
Figure 4:
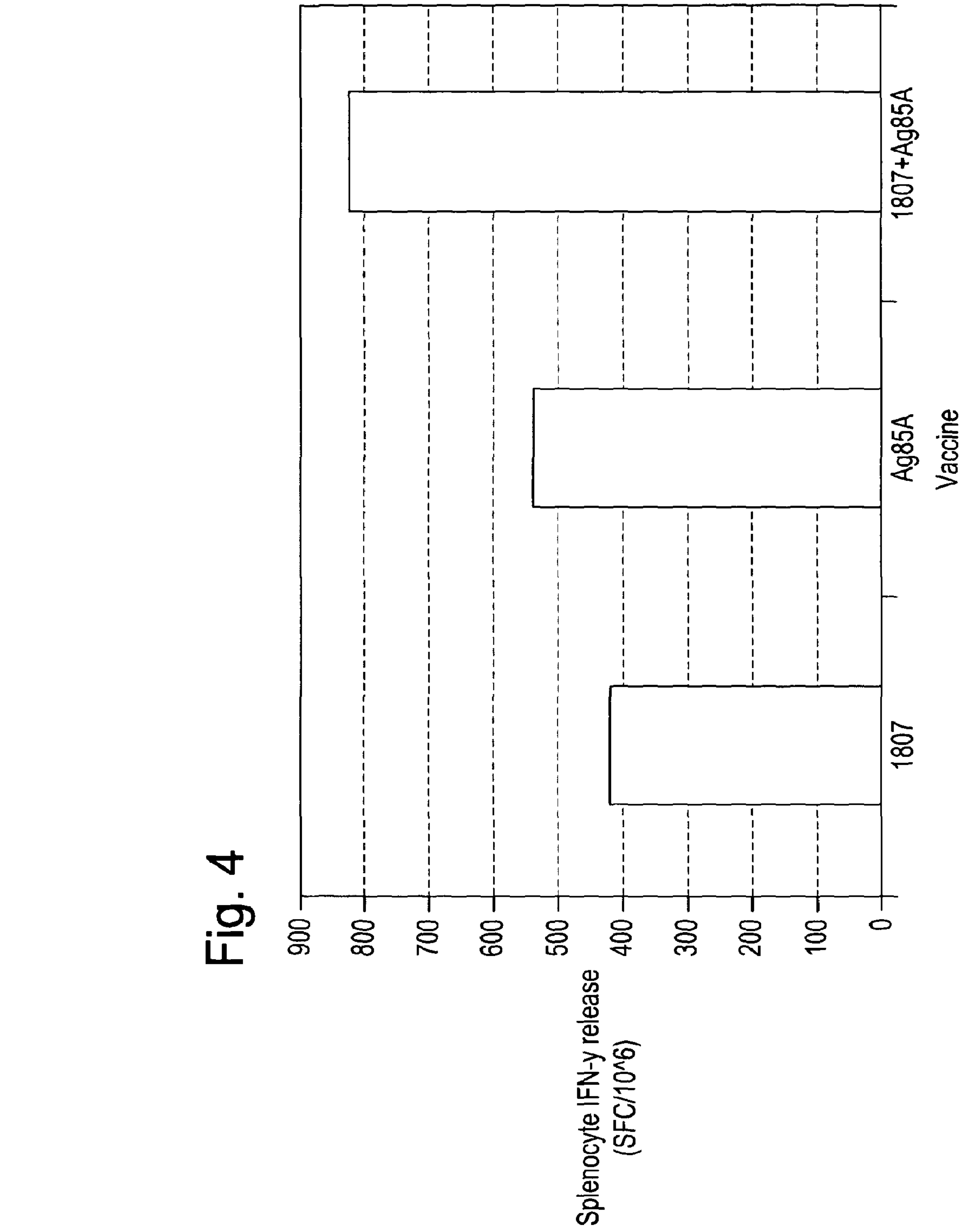
FIG. 4 illustrates the splenocyte response to antigens Ag85A and Rv1807 alone and in combination (repeat of the IM data in FIG. 1B).
Figure 5:
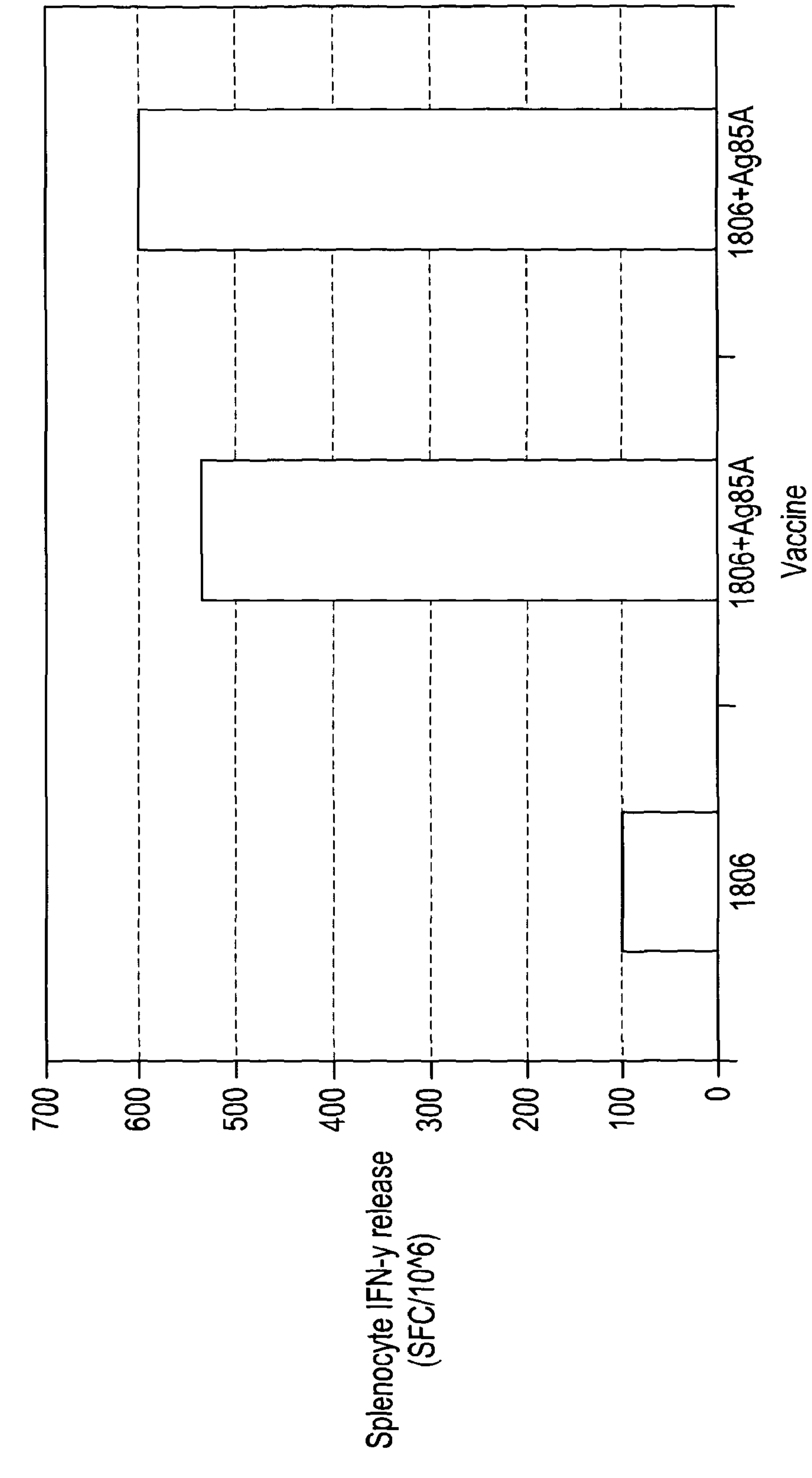
FIG. 5 illustrates the splenocyte response to antigens Ag85A and Rv1806 alone and in combination.
Figure 6:
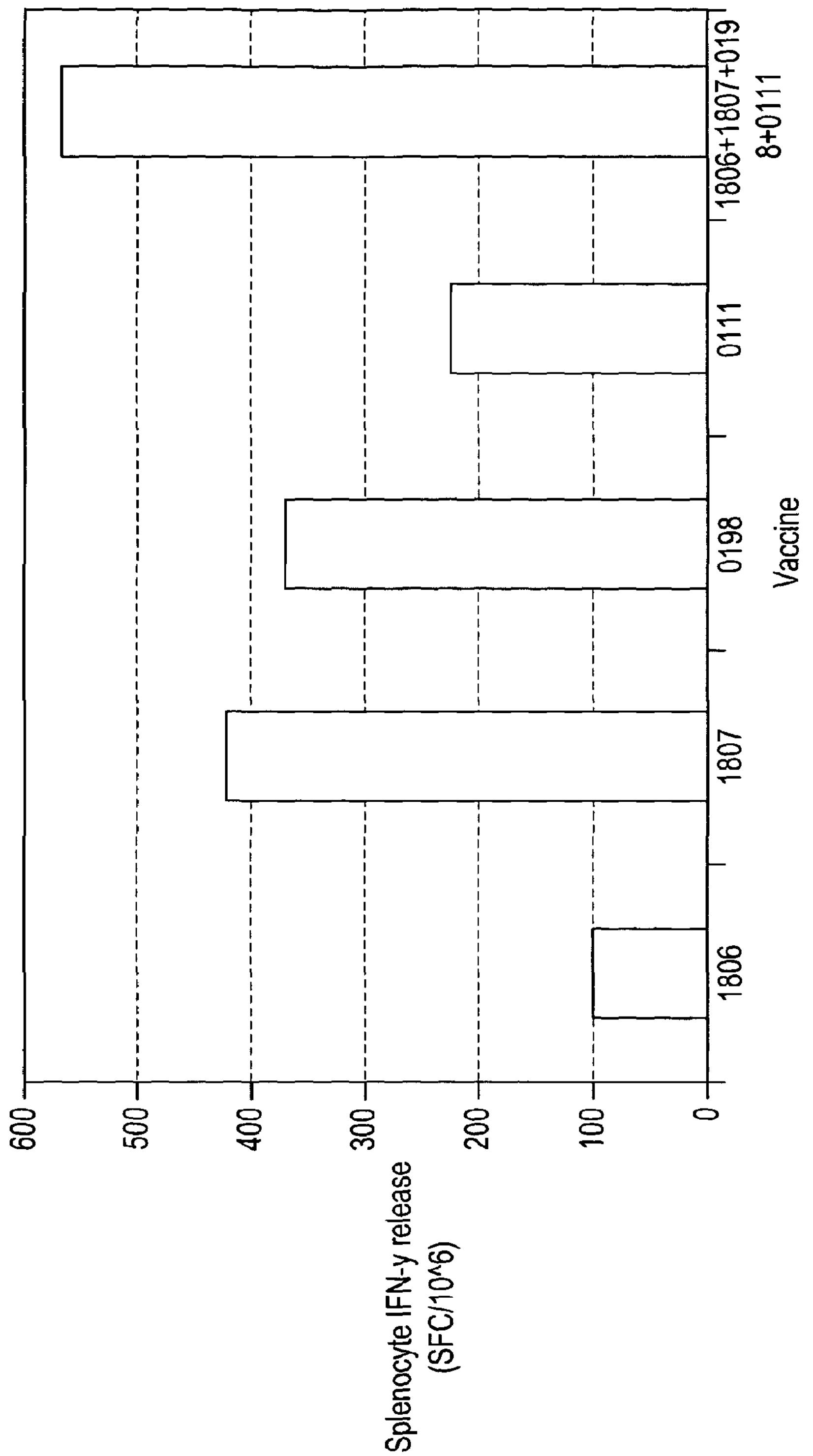
FIG. 6 illustrates the splenocyte response to antigensRv1806, Rv1807, Rv0198 and Rv0111, alone and in combination.

Example 12—Demonstrating Vaccine Efficacy in an Experimental Model

The efficacy of vaccine candidates in guinea pigs may be assessed on the basis of reducing the bacterial burden of *M. tuberculosis* in the lungs and/or spleens at 4 weeks post-aerosol challenge.

The 1st and 2nd mycobacterial antigens are delivered as sub-unit DNA vaccines or protein in a Th1-inducing adjuvant such as DDA/MPL, or by expression vectors such as recombinant viruses or BCG (see Examples 1-4). The 1st and 2nd mycobacterial antigens are delivered in a manner designed to prime the immune system, which includes all of the above. At least one 'boost' to the initial prime is given through inoculation of either DNA, polypeptide or viral vector or (less commonly) recombinant BCG. Groups of six to eight guinea pigs are immunized two or three times with a 2 to 3 week rest between each immunization. Following the final inoculation, the guinea pigs are rested for 6 weeks prior to challenge.

A group of positive control animals are inoculated subcutaneously with $5\times10^4$ colony forming units (CFU) of BCG Danish (1331), and a group of negative control animals are given saline.

Six weeks following the final vaccination, fine particle aerosols of *M. tuberculosis* (2 μm mean diameter; generated in a Collison nebuliser), are delivered directly to the animal snout using a contained Henderson apparatus. A suspension of the challenge strain, *M. tuberculosis* H37Rv (NCTC 7416), cultured under defined conditions in a chemostat is diluted to $1\times10^6$ CFU/ml in order to achieve an estimated retained, inhaled dose of approximately 10 CFU/lung.

Four weeks after aerosol challenge, the animals are humanely killed, and the lungs removed for CFU determination.

Homogenized samples are serially diluted and plated on Middlebrook 7H11 selective agar and the mean CFU for each treatment group is determined. Vaccine efficacy is assessed in terms of reduction in bacterial counts in lungs or spleens compared to the saline control group. The mean logo CFU of test vaccines is compared with the negative controls and differences between groups are analyzed statistically using an appropriate test such Mann-Whitney.

Any combination of 1st and 2nd mycobacterial antigens giving a reduction in the number of viable *M. tuberculosis* that is statistically significantly (p=<0.05) lower than sham-vaccinated (saline) controls, demonstrates the protective efficacy of the antigens when co-administered.

Protective efficacy in guinea pigs is indicative of the ability of the combination vaccine to protect humans and animals from pathogenic mycobacterial infection.

Example 13—Demonstrating Vaccine Efficacy in an Experimental Model

The efficacy of vaccine candidates in guinea pigs may be assessed on the basis of reducing the bacterial burden of *M. tuberculosis* in the spleens at 4 weeks post-aerosol challenge.

The $1^{st}$ and $2^{nd}$ mycobacterial antigens are delivered as sub-unit DNA vaccines or protein in a Th1-inducing adjuvant such as DDA/MPL, or by expression vectors such as recombinant viruses or BCG (see Examples 1-4). The $1^{st}$ and $2^{nd}$ mycobacterial antigens are delivered in a manner designed to prime the immune system, which includes all of the above. At least one 'boost' to the initial prime is given through inoculation of either DNA, polypeptide or viral vector or (less commonly) recombinant BCG. Groups of six to eight guinea pigs are immunized two or three times with a 2 to 3 week rest between each immunization. Following the final inoculation, the guinea pigs are rested for 6 weeks prior to challenge.

A group of positive control animals are inoculated subcutaneously with $5\times10^4$ colony forming units (CFU) of BCG Danish (1331), and a group of negative control animals are given saline or remain unvaccinated.

Six weeks following the final vaccination, fine particle aerosols of *M. tuberculosis* (2 μm mean diameter; generated in a Collison nebuliser), are delivered directly to the animal snout using a contained Henderson apparatus. A suspension of the challenge strain, *M. tuberculosis* H37Rv (NCTC 7416), cultured under defined conditions in a chemostat is diluted to $1\times10^6$ CFU/ml in order to achieve an estimated retained, inhaled dose of approximately 10 CFU/lung.

Four weeks after aerosol challenge, the animals are humanely killed, and the spleens removed for CFU determination.

Homogenized samples are serially diluted and plated on Middlebrook 7H11 selective agar and the mean CFU for each treatment group is determined. Vaccine efficacy is assessed in terms of reduction in bacterial counts in spleens compared to the saline or unvaccinated control group. The mean $\log^{10}$ CFU of test vaccines is compared with the negative controls and differences between groups are analyzed statistically using an appropriate test such Mann-Whitney.

Any combination of 1st and $2^{nd}$ mycobacterial antigens giving a reduction in the number of viable *M. tuberculosis* that is statistically significantly (p=<0.05) lower than unvaccinated controls, demonstrates the protective efficacy of the antigens when co-administered.

Protective efficacy in guinea pigs is indicative of the ability of the combination vaccine to protect humans and animals from pathogenic mycobacterial infection.

Figure 7:
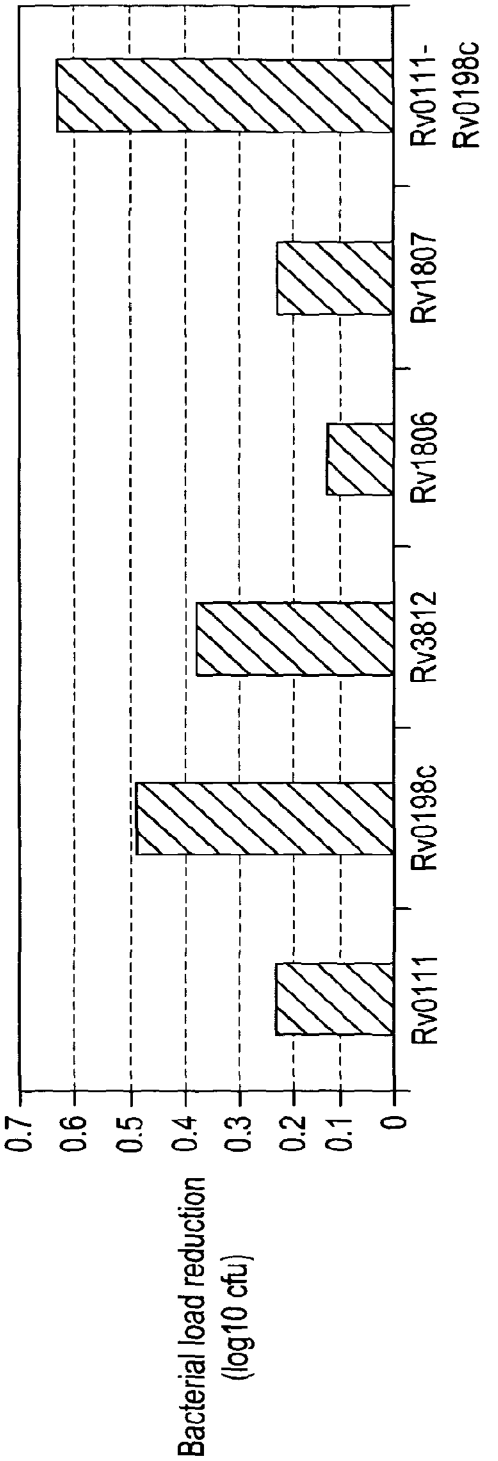
FIG. 7 illustrates the reduction in bacterial load in response to each of antigens Rv0111, Rv0198c, Rv3812, Rv1086 and Rv180 alone, and in response to a combination of antigens Rv0111 and Rv0198c.

Data generated according to this Example are illustrated in FIG. 7. FIG. 7 illustrates the reduction in bacterial load in response to each of antigens Rv0111, Rv0198c, Rv3812, Rv1806 and Rv180 alone, and in response to a combination of antigens Rv0111 and Rv0198c.

Example 14—Antigenic Activity of Multiple Antigens

Mice are immunized with at least a 1st and $2^{nd}$ mycobacterial antigen. Delivery systems include (but are not restricted to) DNA vaccines, recombinant MVA or adjuvanted protein. Delivery routes include (but are not restricted to) subcutaneous, intra-dermal or intra-muscular administration. The immunization regimen may involve heterologous prime-boosting—eg. 'priming' with a DNA vaccine followed by 'boosting' with an MVA vaccine, and/or may involve multiple doses.

After vaccination (eg. about 2 weeks later), serum are removed from the vaccinated animals and screened for the presence of antibodies. An immune response is measurable through the detection of antibodies specific for the immunising antigen—eg. as detected via ELISA.

Where an animal has been immunized with a vaccine comprising a 1st and $2^{nd}$ mycobacterial antigen, the presence in the same sample of antibodies to the $1^{st}$ and $2^{nd}$ mycobacterial antigen demonstrates immunogenicity of both antigens when co-administered. Immunogenicity is a pre-requisite for protective efficacy.

The invention claimed is:

1. A composition comprising: a) a first antibody, wherein said first antibody specifically binds a first mycobacterial antigenic polypeptide within the amino acid sequence of SEQ ID NO: 1; and (b) a second antibody, wherein said second antibody specifically binds a second mycobacterial antigenic polypeptide within the amino acid sequence of SEQ ID NO: 5; the composition further comprising an adjuvant, an antimicrobial compound, an immunoregulatory agent, or a combination thereof.

2. The composition according to claim 1, wherein the antibodies are tagged with a detectable label or a functional label.

3. The composition according to claim 1, further comprising at least one additional antibody, which binds a mycobacterial antigenic polypeptide that is different from said first and second mycobacterial antigenic polypeptides.

4. The composition according to claim 3, wherein the at least one additional antibody specifically binds within a polypeptide having an amino acid sequence selected from any of SEQ ID NOs: 3, 7, 9-20, 34-44 or 56.

5. The composition according to claim 4, wherein the at least one additional antibody is tagged with a detectable label or a functional label.

6. The composition according to claim 1, wherein the composition comprises the adjuvant, and wherein the adjuvant is selected from the group consisting of: complete Freunds adjuvant (CFA), Incomplete Freunds adjuvant (IVA), Saponin, a purified extract fraction of Saporin such as Quil A, a derivative of Saporin such as QS-21, lipid particles based on Saponin such as ISCOM/ISCOMATIX, *E. coli* heat labile toxin (LT) mutants such as LTK63 and/or LTK72, aluminium hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryl oxy)-ethylamine (CGP 19835A, referred to as MTP-PE), and RIBI, and combinations thereof.

7. A method for producing a therapeutic or prophylactic formulation, the method comprising mixing a pharmaceutically acceptable carrier and at least one component that is an adjuvant, an antimicrobial compound, or an immunoregulatory agent, with:

(a) a first antibody, wherein said first antibody specifically binds a first mycobacterial antigenic polypeptide within the amino acid sequence of SEQ ID NO: 1; and (b) a second antibody, wherein said second antibody specifically binds a second mycobacterial antigenic polypeptide within the amino acid sequence of SEQ ID NO: 5.

8. The method of claim 7, wherein the mixing comprises mixing at least two of the components with the pharmaceutically acceptable carrier and the first and the second antibody.

9. A method for producing a therapeutic or prophylactic formulation, the method comprising:

(a) mixing a pharmaceutically acceptable carrier and at least one component that is an adjuvant, an antimicrobial compound, or an immunoregulatory agent, with a first antibody to form a first mixture, wherein the first antibody specifically binds a first mycobacterial antigenic polypeptide within the amino acid sequence of SEQ ID NO: 1; and (b) mixing a pharmaceutically acceptable carrier and at least one component that is an adjuvant, an antimicrobial compound, or an immunoregulatory agent, with a second antibody to form a second mixture, wherein the second antibody specifically binds a second mycobacterial antigenic polypeptide within the amino acid sequence of SEQ ID NO: 5; and (c) combining said first mixture and said second mixture to form the therapeutic or prophylactic formulation.

* * * * *

UNITED STATES PATENT AND TRADEMARK OFFICE

CERTIFICATE OF CORRECTION

PATENT NO. : 9,982,039 B2
APPLICATION NO. : 15/098949
DATED : May 29, 2018
INVENTOR(S) : Carroll et al.

It is certified that error appears in the above-identified patent and that said Letters Patent is hereby corrected as shown below:

On the Title Page

Item (71), the Applicant should read:
--(71) Applicant: The Secretary of State for Health, London (GB)--

Signed and Sealed this
Eighth Day of January, 2019

Andrei Iancu
*Director of the United States Patent and Trademark Office*

SEQUENCE LISTING

```
<160> NUMBER OF SEQ ID NOS: 58

<210> SEQ ID NO 1
<211> LENGTH: 685
<212> TYPE: PRT
<213> ORGANISM: Mycobacterium tuberculosis

<400> SEQUENCE: 1

Val Pro Ala Arg Ser Val Pro Arg Pro Arg Trp Val Ala Pro Val Arg
1               5                   10                  15

Arg Val Gly Arg Leu Ala Val Trp Asp Arg Pro Glu Arg Arg Ser Gly
            20                  25                  30

Ile Pro Ala Leu Asp Gly Leu Arg Ala Ile Ala Val Ala Leu Val Leu
        35                  40                  45

Ala Ser His Gly Gly Ile Pro Gly Met Gly Gly Gly Phe Ile Gly Val
    50                  55                  60

Asp Ala Phe Phe Val Leu Ser Gly Phe Leu Ile Thr Ser Leu Leu Leu
65                  70                  75                  80

Asp Glu Leu Gly Arg Thr Gly Arg Ile Asp Leu Ser Gly Phe Trp Ile
                85                  90                  95

Arg Arg Ala Arg Arg Leu Leu Pro Ala Leu Val Leu Met Val Leu Thr
            100                 105                 110

Val Ser Ala Ala Arg Ala Leu Phe Pro Asp Gln Ala Leu Thr Gly Leu
        115                 120                 125

Arg Ser Asp Ala Ile Ala Ala Phe Leu Trp Thr Ala Asn Trp Arg Phe
    130                 135                 140

Val Ala Gln Asn Thr Asp Tyr Phe Thr Gln Gly Ala Pro Pro Ser Pro
145                 150                 155                 160

Leu Gln His Thr Trp Ser Leu Gly Val Glu Glu Gln Tyr Tyr Val Val
                165                 170                 175

Trp Pro Leu Leu Leu Ile Gly Ala Thr Leu Leu Leu Ala Ala Arg Ala
            180                 185                 190

Arg Arg Arg Cys Arg Arg Ala Thr Val Gly Gly Val Arg Phe Ala Ala
        195                 200                 205

Phe Leu Ile Ala Ser Leu Gly Thr Met Ala Ser Ala Thr Ala Ala Val
    210                 215                 220

Ala Phe Thr Ser Ala Ala Thr Arg Asp Arg Ile Tyr Phe Gly Thr Asp
225                 230                 235                 240

Thr Arg Ala Gln Ala Leu Leu Ile Gly Ser Ala Ala Ala Ala Leu Leu
                245                 250                 255

Val Arg Asp Trp Pro Ser Leu Asn Arg Gly Trp Cys Leu Ile Arg Thr
            260                 265                 270

Arg Trp Gly Arg Arg Ile Ala Arg Leu Leu Pro Phe Val Gly Leu Ala
        275                 280                 285

Gly Leu Ala Val Thr Thr His Val Ala Thr Gly Ser Val Gly Glu Phe
    290                 295                 300
```

```
Arg His Gly Leu Leu Ile Val Val Ala Gly Ala Ala Val Ile Val Val
305                 310                 315                 320

Ala Ser Val Ala Met Glu Gln Arg Gly Ala Val Ala Arg Ile Leu Ala
                325                 330                 335

Trp Arg Pro Leu Val Trp Leu Gly Thr Ile Ser Tyr Gly Val Tyr Leu
            340                 345                 350

Trp His Trp Pro Ile Phe Leu Ala Leu Asn Gly Gln Arg Thr Gly Trp
        355                 360                 365

Ser Gly Pro Ala Leu Phe Ala Ala Arg Cys Ala Ala Thr Val Val Leu
    370                 375                 380

Ala Gly Ala Ser Trp Trp Leu Ile Glu Gln Pro Ile Arg Arg Trp Arg
385                 390                 395                 400

Pro Ala Arg Val Pro Leu Leu Pro Leu Ala Ala Ala Thr Val Ala Ser
                405                 410                 415

Ala Ala Ala Val Thr Met Leu Val Val Pro Val Gly Ala Gly Pro Gly
            420                 425                 430

Leu Arg Glu Ile Gly Leu Pro Pro Gly Val Ser Ala Val Ala Ala Val
        435                 440                 445

Ser Pro Ser Pro Pro Glu Ala Ser Gln Pro Ala Pro Gly Pro Arg Asp
    450                 455                 460

Pro Asn Arg Pro Phe Thr Val Ser Val Phe Gly Asp Ser Ile Gly Trp
465                 470                 475                 480

Thr Leu Met His Tyr Leu Pro Pro Thr Pro Gly Phe Arg Phe Ile Asp
                485                 490                 495

His Thr Val Ile Gly Cys Ser Leu Val Arg Gly Thr Pro Tyr Arg Tyr
            500                 505                 510

Ile Gly Gln Thr Leu Glu Gln Arg Ala Glu Cys Asp Gly Trp Pro Ala
        515                 520                 525

Arg Trp Ser Ala Gln Val Asn Arg Asp Gln Pro Asp Val Ala Leu Leu
    530                 535                 540

Ile Val Gly Arg Trp Glu Thr Val Asp Arg Val Asn Glu Gly Arg Trp
545                 550                 555                 560

Thr His Ile Gly Asp Pro Thr Phe Asp Ala Tyr Leu Asn Ala Glu Leu
                565                 570                 575

Gln Arg Ala Leu Ser Ile Val Gly Ser Thr Gly Val Arg Val Met Val
            580                 585                 590

Thr Thr Val Pro Tyr Ser Arg Gly Gly Glu Lys Pro Asp Gly Arg Leu
        595                 600                 605

Tyr Pro Glu Asp Gln Pro Glu Arg Val Asn Lys Trp Asn Ala Met Leu
    610                 615                 620

His Asn Ala Ile Ser Gln His Ser Asn Val Gly Met Ile Asp Leu Asn
625                 630                 635                 640

Lys Lys Leu Cys Pro Asp Gly Val Tyr Thr Ala Lys Val Asp Gly Ile
                645                 650                 655

Lys Val Arg Ser Asp Gly Val His Leu Thr Gln Glu Gly Val Lys Trp
            660                 665                 670

Leu Ile Pro Trp Leu Glu Asp Ser Val Arg Val Ala Ser
        675                 680                 685
```

<210> SEQ ID NO 2
<211> LENGTH: 2055
<212> TYPE: DNA
<213> ORGANISM: Mycobacterium tuberculosis

<400> SEQUENCE: 2

```
gtgccggcac gttctgttcc ccggccccgt tgggtggccc cggtgcgccg ggtcggtcgg     60
ctggccgtat gggatcggcc ggagcggcgc agcggaattc cagcgttaga tggccttcgt    120
gcgatagcgg tcgcgctggt actcgccagc catggcggca tccccggtat gggcggcggg    180
ttcatcggcg tcgacgcctt cttcgtcttg agcggatttc tcatcacctc gctgctgctc    240
gacgagctgg ggcgcaccgg tcgtatcgat ctgagcgggt tctggattcg ccgtgcgcgg    300
cggctgctgc cggcgctggt gctgatggtt ctcaccgtga gcgccgcacg cgcactattt    360
cctgaccaag ctctcaccgg gctacggagc gatgcgatcg ccgcgttcct atggacggcg    420
aattggcggt ttgtggccca aaataccgat tacttcaccc agggcgctcc accctcgccc    480
ctacagcaca cctggtcgtt gggggtggag gagcagtatt acgttgtctg gccactgttg    540
ctgatcgggg cgacgctact gttggcggcc cgggcgaggc gccgttgcag acgggccacg    600
gtgggcgggg ttcggttcgc cgcgttcctg attgccagtc tcggcacgat ggcttccgcc    660
accgccgcgg tcgcatttac ctcggcggcc acccgcgacc ggatttactt cggcaccgat    720
acccgtgcgc aggcgttgct gatcggctcc gcggcagcgg ctctgctggt gcgggattgg    780
ccatcgctga accgcgggtg gtgcctgatc cggactcgct ggggacggcg gattgcccgt    840
ctgttgccgt tcgtcgggct ggctgggctg gcggtgacga ctcacgtcgc aacgggcagt    900
gtgggcgagt tccgccatgg tctgctgatc gtggtggcag gtgcggccgt catcgtggtt    960
gcctcggtag ccatggagca gcgcggagcg gtggcccgca tcctggcctg gcgaccgttg   1020
gtgtggctgg gcaccatatc gtacggcgtc tatctgtggc actggccaat ctttctggcg   1080
ctcaacggcc aacgtacggg ctggtcgggc ccggccctgt ttgccgctag gtgtgcagcc   1140
acggtggtgc tggccggtgc gtcgtggtgg ctgatcgagc aacctattcg gcgctggcga   1200
ccggcacggg ttccgctgtt gccgctggca gcggcgaccg ttgccagcgc tgccgccgtg   1260
acgatgctcg ttgttccggt cggagccgga ccggggctac gcgagatcgg ccttccgccc   1320
ggcgtttcgg cggtcgccgc ggtctcgccg tcgccgccgg aagcgagtca gcccgcgccc   1380
gggccacgag atcccaaccg gccgttcacc gtttcggtat tcggtgattc gatcgggtgg   1440
actttgatgc attacctgcc gccgactccc ggattccggt tcatcgacca caccgtcatc   1500
ggctgcagcc tggtacgcgg cacaccgtat cggtacatcg gtcaaaccct ggagcagagg   1560
gcggaatgcg acggctggcc ggccagatgg tcggcgcagg tcaaccggga ccaaccggac   1620
gttgcgttgc tgatcgtcgg ccgctgggag acggtagacc gggtcaatga ggggcggtgg   1680
acacatatcg gcgacccgac cttcgatgcg tacctcaacg ccgagctaca gcgagcgctc   1740
agcatcgttg gatccaccgg ggttcgagtg atggtcacca ccgtgcccta cagccgcggc   1800
ggcgaaaagc cggacggccg cttgtatccg gaggatcaac ccgagcgtgt gaacaaatgg   1860
aacgccatgt tacataacgc cattagccaa cactcgaacg tcggaatgat cgacctcaac   1920
aaaaagcttt gtccagacgg cgtttacacg gccaaggtcg acggcatcaa ggtccgcagt   1980
gatggtgttc atctcaccca ggaaggcgtg aagtggctga taccgtggct tgaggattcg   2040
gtgcgggtcg ccagt                                                    2055
```

<210> SEQ ID NO 3
<211> LENGTH: 99
<212> TYPE: PRT
<213> ORGANISM: Mycobacterium tuberculosis

<400> SEQUENCE: 3

```
Met Ala Phe Val Leu Val Cys Pro Asp Ala Leu Ala Ile Ala Ala Gly
1               5                   10                  15

Gln Leu Arg His Val Gly Ser Val Ile Ala Ala Arg Asn Ala Val Ala
            20                  25                  30

Ala Pro Ala Thr Ala Glu Leu Ala Pro Ala Ala Ala Asp Glu Val Ser
        35                  40                  45

Ala Leu Thr Ala Thr Gln Phe Asn Phe His Ala Ala Met Tyr Gln Ala
    50                  55                  60

Val Gly Ala Gln Ala Ile Ala Met Asn Glu Ala Phe Val Ala Met Leu
65                  70                  75                  80

Gly Ala Ser Ala Asp Ser Tyr Ala Ala Thr Glu Ala Ala Asn Ile Ile
                85                  90                  95

Ala Val Ser
```

<210> SEQ ID NO 4
<211> LENGTH: 297
<212> TYPE: DNA
<213> ORGANISM: Mycobacterium tuberculosis

<400> SEQUENCE: 4

```
atggcgtttg ttcttgtctg tccagatgcg ctggccatcg cggccggtca gttgcgccat      60

gttggatcgg tgatagccgc gcggaatgcg gtcgcggcac cggcaactgc cgaattggcc     120

ccggcggccg ctgacgaagt atcagctttg actgcaacac aattcaactt ccatgccgcc     180

atgtaccaag cggtcggcgc ccaggcgatc gccatgaatg aggcgttcgt cgcgatgttg     240

ggcgccagcg cggattctta cgcggctacc gaagccgcca acatcattgc tgtgagc        297
```

<210> SEQ ID NO 5
<211> LENGTH: 663
<212> TYPE: PRT
<213> ORGANISM: Mycobacterium tuberculosis

<400> SEQUENCE: 5

```
Val Thr Leu Ala Ile Pro Ser Gly Ile Asp Leu Ser His Ile Asp Ala
1               5                   10                  15

Asp Ala Arg Pro Gln Asp Asp Leu Phe Gly His Val Asn Gly Arg Trp
            20                  25                  30

Leu Ala Glu His Glu Ile Pro Ala Asp Arg Ala Thr Asp Gly Ala Phe
        35                  40                  45

Arg Ser Leu Phe Asp Arg Ala Glu Thr Gln Val Arg Asp Leu Ile Ile
    50                  55                  60

Gln Ala Ser Gln Ala Gly Ala Ala Val Gly Thr Asp Ala Gln Arg Ile
65                  70                  75                  80

Gly Asp Leu Tyr Ala Ser Phe Leu Asp Glu Glu Ala Val Glu Arg Ala
                85                  90                  95

Gly Val Gln Pro Leu His Asp Glu Leu Ala Thr Ile Asp Ser Ala Ala
            100                 105                 110

Asp Ala Thr Glu Leu Ala Ala Ala Leu Gly Thr Leu Gln Arg Ala Gly
        115                 120                 125

Val Gly Gly Gly Ile Gly Val Tyr Val Asp Thr Asp Ser Lys Asp Ser
    130                 135                 140

Thr Arg Tyr Leu Val His Phe Thr Gln Ser Gly Ile Gly Leu Pro Asp
145                 150                 155                 160
```

-continued

```
Glu Ser Tyr Tyr Arg Asp Glu Gln His Ala Ala Val Leu Ala Ala Tyr
                165                 170                 175

Pro Gly His Ile Ala Arg Met Phe Gly Leu Val Tyr Gly Gly Glu Ser
            180                 185                 190

Arg Asp His Ala Lys Thr Ala Asp Arg Ile Val Ala Leu Glu Thr Lys
        195                 200                 205

Leu Ala Asp Ala His Trp Asp Val Val Lys Arg Arg Asp Ala Asp Leu
    210                 215                 220

Gly Tyr Asn Leu Arg Thr Phe Ala Gln Leu Gln Thr Glu Gly Ala Gly
225                 230                 235                 240

Phe Asp Trp Val Ser Trp Val Thr Ala Leu Gly Ser Ala Pro Asp Ala
                245                 250                 255

Met Thr Glu Leu Val Val Arg Gln Pro Asp Tyr Leu Val Thr Phe Ala
            260                 265                 270

Ser Leu Trp Ala Ser Val Asn Val Glu Asp Trp Lys Cys Trp Ala Arg
        275                 280                 285

Trp Arg Leu Ile Arg Ala Arg Ala Pro Trp Leu Thr Arg Ala Leu Val
    290                 295                 300

Ala Glu Asp Phe Glu Phe Tyr Gly Arg Thr Leu Thr Gly Ala Gln Gln
305                 310                 315                 320

Leu Arg Asp Arg Trp Lys Arg Gly Val Ser Leu Val Glu Asn Leu Met
                325                 330                 335

Gly Asp Ala Val Gly Lys Leu Tyr Val Gln Arg His Phe Pro Pro Asp
            340                 345                 350

Ala Lys Ser Arg Ile Asp Thr Leu Val Asp Asn Leu Gln Glu Ala Tyr
        355                 360                 365

Arg Ile Ser Ile Ser Glu Leu Asp Trp Met Thr Pro Gln Thr Arg Gln
    370                 375                 380

Arg Ala Leu Ala Lys Leu Asn Lys Phe Thr Ala Lys Val Gly Tyr Pro
385                 390                 395                 400

Ile Lys Trp Arg Asp Tyr Ser Lys Leu Ala Ile Asp Arg Asp Asp Leu
                405                 410                 415

Tyr Gly Asn Val Gln Arg Gly Tyr Ala Val Asn His Asp Arg Glu Leu
            420                 425                 430

Ala Lys Leu Phe Gly Pro Val Asp Arg Asp Glu Trp Phe Met Thr Pro
        435                 440                 445

Gln Thr Val Asn Ala Tyr Tyr Asn Pro Gly Met Asn Glu Ile Val Phe
    450                 455                 460

Pro Ala Ala Ile Leu Gln Pro Pro Phe Phe Asp Pro Gln Ala Asp Glu
465                 470                 475                 480

Ala Ala Asn Tyr Gly Gly Ile Gly Ala Val Ile Gly His Glu Ile Gly
                485                 490                 495

His Gly Phe Asp Asp Gln Gly Ala Lys Tyr Asp Gly Asp Gly Asn Leu
            500                 505                 510

Val Asp Trp Trp Thr Asp Asp Asp Arg Thr Glu Phe Ala Ala Arg Thr
        515                 520                 525

Lys Ala Leu Ile Glu Gln Tyr His Ala Tyr Thr Pro Arg Asp Leu Val
    530                 535                 540

Asp His Pro Gly Pro Pro His Val Gln Gly Ala Phe Thr Ile Gly Glu
545                 550                 555                 560

Asn Ile Gly Asp Leu Gly Gly Leu Ser Ile Ala Leu Leu Ala Tyr Gln
                565                 570                 575
```

```
Leu Ser Leu Asn Gly Asn Pro Ala Pro Val Ile Asp Gly Leu Thr Gly
            580                 585                 590

Met Gln Arg Val Phe Phe Gly Trp Ala Gln Ile Trp Arg Thr Lys Ser
        595                 600                 605

Arg Ala Ala Glu Ala Ile Arg Arg Leu Ala Val Asp Pro His Ser Pro
    610                 615                 620

Pro Glu Phe Arg Cys Asn Gly Val Val Arg Asn Val Asp Ala Phe Tyr
625                 630                 635                 640

Gln Ala Phe Asp Val Thr Glu Asp Asp Ala Leu Phe Leu Asp Pro Gln
                645                 650                 655

Arg Arg Val Arg Ile Trp Asn
            660


<210> SEQ ID NO 6
<211> LENGTH: 1989
<212> TYPE: DNA
<213> ORGANISM: Mycobacterium tuberculosis

<400> SEQUENCE: 6

gtgacacttg ccatcccctc gggtatcgac ctgagccaca tcgacgctga tgcccgaccc      60

caagacgacc tgttcggcca cgttaacggc cgctggctgg ctgaacacga gataccagcg     120

gaccgagcga ccgacggcgc cttccgtagc ctgttcgacc gcgccgagac acaagtgcga     180

gacctgatca tccaggccag ccaagcaggt gctgcggtag gcaccgatgc gcagcgcatc     240

ggcgacctct acgccagctt cctcgacgag gaagccgtcg agcgcgcagg ggtgcaaccg     300

ctgcacgacg aattggccac gattgacagc gcggccgacg ccaccgaatt ggccgccgcc     360

cttggcactc tgcaacgtgc cggcgtgggc ggcggcatcg gagtctatgt cgataccgat     420

tccaaagact cgacccgtta cttggtgcat ttcacccaat ccggcatcgg attacccgac     480

gagtcctact accgtgacga gcaacacgcc gccgtgctag cggcctaccc ggggcacatc     540

gcccggatgt tcggcctggt gtacgggggc gagagccgtg accatgccaa aaccgcggac     600

cgcatcgtcg cgctggagac caaactcgcc gacgcgcatt gggatgtggt gaagcgccgc     660

gacgccgacc ttggctacaa cctgcgcacg tttgcccagc tgcagaccga aggggcgggt     720

ttcgactggg tcagctgggt gaccgcattg gggagcgctc cggacgccat gacggaactg     780

gttgtgcgcc aacctgatta cctcgtcacc tttgcctcgc tgtgggcgag cgttaacgtt     840

gaagactgga aatgctgggc gcgttggcgt ttgatccgcg cccgggcccc ctggctgacc     900

cgcgccctgg tcgccgagga cttcgaattc tacggccgca cgcttaccgg cgcacagcag     960

cttcgggacc gttggaagcg tggggtgtca ctggtggaga acctgatggg cgatgccgtc    1020

ggaaagctct atgtacaacg ccatttcccg ccggatgcca agtcccgcat cgacaccctg    1080

gtggacaacc tgcaggaggc gtatcggatc agcatcagcg agctggattg gatgacgccg    1140

cagacccggc aacgcgcgct agcgaagctg aacaagttca ccgccaaagt cggctatccg    1200

atcaagtggc gcgactactc gaagctggcg atcgaccgcg acgacctcta cggtaacgtc    1260

cagcgcggct acgccgtcaa ccatgaccgc gagctagcca agcttttcgg cccggtcgac    1320

cgcgacgagt ggttcatgac accacaaacc gtcaacgcct actacaaccc ggggatgaac    1380

gaaatcgtct tccccgcagc gattttacag ccaccatttt tcgatccgca ggccgacgag    1440

gccgccaact acggcgggat cggggcggtg atcgggcacg agatcgggca cggtttcgac    1500

gatcagggcg ccaaatacga cggcgacggc aatctggtcg attggtggac cgacgacgat    1560

cgcaccgagt tcgccgcccg caccaaagcg ttgatcgagc agtaccacgc ttacacgccg    1620
```

-continued

```
cgcgatctcg tcgaccaccc cggcccgcct catgtgcaag gcgcgttcac cataggcgag   1680

aacatcggcg acctgggcgg gctgtcgatc gccctgctgg cttaccagct ctcgctgaac   1740

ggcaaccccg ctccggttat cgacgggctg accggcatgc aacgggtgtt cttcggctgg   1800

gcacaaatat ggcgaaccaa atcgcgtgca gccgaagcaa tccgccggtt ggcggtcgat   1860

ccgcactccc cgccggagtt ccggtgcaac ggtgtggttc gcaacgtgga cgctttttat   1920

caggccttcg acgtcaccga ggatgacgcg ctgtttctgg acccgcagcg cagggtccgg   1980

atctggaac                                                           1989


<210> SEQ ID NO 7
<211> LENGTH: 504
<212> TYPE: PRT
<213> ORGANISM: Mycobacterium tuberculosis

<400> SEQUENCE: 7

Val Ser Phe Val Val Thr Val Pro Glu Ala Val Ala Ala Ala Ala Gly
1               5                   10                  15

Asp Leu Ala Ala Ile Gly Ser Thr Leu Arg Glu Ala Thr Ala Ala Ala
            20                  25                  30

Ala Gly Pro Thr Thr Gly Leu Ala Ala Ala Ala Ala Asp Asp Val Ser
        35                  40                  45

Ile Ala Val Ser Gln Leu Phe Gly Arg Tyr Gly Gln Glu Phe Gln Thr
    50                  55                  60

Val Ser Asn Gln Leu Ala Ala Phe His Thr Glu Phe Val Arg Thr Leu
65                  70                  75                  80

Asn Arg Gly Ala Ala Ala Tyr Leu Asn Thr Glu Ser Ala Asn Gly Gly
                85                  90                  95

Gln Leu Phe Gly Gln Ile Glu Ala Gly Gln Arg Ala Val Ser Ala Ala
            100                 105                 110

Ala Ala Ala Ala Pro Gly Gly Ala Tyr Gly Gln Leu Val Ala Asn Thr
        115                 120                 125

Ala Thr Asn Leu Glu Ser Leu Tyr Gly Ala Trp Ser Ala Asn Pro Phe
    130                 135                 140

Pro Phe Leu Arg Gln Ile Ile Ala Asn Gln Gln Val Tyr Trp Gln Gln
145                 150                 155                 160

Ile Ala Ala Ala Leu Ala Asn Ala Val Gln Asn Phe Pro Ala Leu Val
                165                 170                 175

Ala Asn Leu Pro Ala Ala Ile Asp Ala Ala Val Gln Gln Phe Leu Ala
            180                 185                 190

Phe Asn Ala Ala Tyr Tyr Ile Gln Gln Ile Ile Ser Ser Gln Ile Gly
        195                 200                 205

Phe Ala Gln Leu Phe Ala Thr Thr Val Gly Gln Gly Val Thr Ser Val
    210                 215                 220

Ile Ala Gly Trp Pro Asn Leu Ala Ala Glu Leu Gln Leu Ala Phe Gln
225                 230                 235                 240

Gln Leu Leu Val Gly Asp Tyr Asn Ala Ala Val Ala Asn Leu Gly Lys
                245                 250                 255

Ala Met Thr Asn Leu Leu Val Thr Gly Phe Asp Thr Ser Asp Val Thr
            260                 265                 270

Ile Gly Thr Met Gly Thr Thr Ile Ser Val Thr Ala Lys Pro Lys Leu
        275                 280                 285

Leu Gly Pro Leu Gly Asp Leu Phe Thr Ile Met Thr Ile Pro Ala Gln
    290                 295                 300
```

```
Glu Ala Gln Tyr Phe Thr Asn Leu Met Pro Pro Ser Ile Leu Arg Asp
305                 310                 315                 320

Met Ser Gln Asn Phe Thr Asn Val Leu Thr Thr Leu Ser Asn Pro Asn
                325                 330                 335

Ile Gln Ala Val Ala Ser Phe Asp Ile Ala Thr Thr Ala Gly Thr Leu
            340                 345                 350

Ser Thr Phe Phe Gly Val Pro Leu Val Leu Thr Tyr Ala Thr Leu Gly
        355                 360                 365

Ala Pro Phe Ala Ser Leu Asn Ala Ile Ala Thr Ser Ala Glu Thr Ile
    370                 375                 380

Glu Gln Ala Leu Leu Ala Gly Asn Tyr Leu Gly Ala Val Gly Ala Leu
385                 390                 395                 400

Ile Asp Ala Pro Ala His Ala Leu Asp Gly Phe Leu Asn Ser Ala Thr
                405                 410                 415

Val Leu Asp Thr Pro Ile Leu Val Pro Thr Gly Leu Pro Ser Pro Leu
            420                 425                 430

Pro Pro Thr Val Gly Ile Thr Leu His Leu Pro Phe Asp Gly Ile Leu
        435                 440                 445

Val Pro Pro His Pro Val Thr Ala Thr Ile Ser Phe Pro Gly Ala Pro
    450                 455                 460

Val Pro Ile Pro Gly Phe Pro Thr Thr Val Thr Val Phe Gly Thr Pro
465                 470                 475                 480

Phe Met Gly Met Ala Pro Leu Leu Ile Asn Tyr Ile Pro Gln Gln Leu
                485                 490                 495

Ala Leu Ala Ile Lys Pro Ala Ala
            500
```

<210> SEQ ID NO 8
<211> LENGTH: 1512
<212> TYPE: DNA
<213> ORGANISM: Mycobacterium tuberculosis

<400> SEQUENCE: 8

```
gtgtcgttcg tggtcacagt gccggaggcc gtggcggctg cggcgggga tttggcggcc      60

atcggctcga cgcttcggga agcgaccgct gcggcggcgg gccccacgac cgggctggcg     120

gccgcggccg ccgacgacgt gtcgatcgct gtctcgcagc tgttcggcag gtacggccag     180

gaatttcaaa ccgtgagcaa ccaactggcc gcgtttcata ccgagttcgt acgcacgttg     240

aaccgcggcg cggcggcgta tctcaacacc gaaagcgcta acggcgggca gctgttcggt     300

cagatcgagg cgggacagcg cgccgtttcc gcggccgcgg ccgccgctcc gggcggcgca     360

tacggccaac tcgttgccaa cacggccacc aacctggaat ccctctacgg cgcatggtcg     420

gccaacccgt tcccattcct ccgccagatc atcgccaacc agcaggttta ctggcagcag     480

atcgccgcgg cgctcgccaa cgccgtccag aacttccccg ccctggtggc gaatttgcca     540

gcggccatcg acgcggccgt ccagcaattc ctggccttca acgcggcgta ctacatccaa     600

cagattatta gctcgcagat cggcttcgcc cagctattcg ccacgacggt cggtcagggg     660

gtcaccagcg tcattgccgg gtggcccaac cttgcggcgg agcttcagct agcgtttcaa     720

cagcttctgg tgggtgacta caacgccgcg gtggcgaacc tgggtaaggc catgacaaac     780

cttctggtca ccgggttcga caccagcgac gtgacgatcg gcacaatggg caccaccatt     840

agtgtcaccg cgaaacccaa gctgctgggc ccgctgggag atctgttcac catcatgacc     900

atcccggcac aagaggcgca gtacttcacc aacctgatgc ccccctccat cctgcgagac     960
```

-continued

```
atgtcgcaga acttcaccaa cgtgctcacg acgctctcca acccgaacat ccaggcggtc   1020

gcttcgttcg atatcgcaac caccgccggg actttgagca ccttcttcgg ggtgccattg   1080

gtgctcactt acgccacatt gggtgcgccg ttcgcgtcac tgaacgcgat tgcgacgagc   1140

gcggaaacca tcgagcaggc cctgttggcc ggcaactacc taggggcggt gggtgcgctt   1200

atcgacgccc cggcccacgc gttagacggc ttcctcaaca gcgcaaccgt gttggatacg   1260

ccgatcctgg tgcccacggg gctcccgtcc cctctgcccc cgacggtcgg gatcacgctg   1320

cacttgcctt tcgacgggat tctcgtgccg ccgcatcccg tcaccgcgac gatcagcttc   1380

ccgggtgctc cggttcctat tcccggtttc ccaaccaccg taaccgtttt cggcacaccc   1440

ttcatgggaa tggctccgct gctgatcaac tacattcccc aacagctcgc cctggcaatc   1500

aaaccggcgg ct                                                         1512
```

<210> SEQ ID NO 9
<211> LENGTH: 338
<212> TYPE: PRT
<213> ORGANISM: Mycobacterium tuberculosis

<400> SEQUENCE: 9

```
Met Gln Leu Val Asp Arg Val Arg Gly Ala Val Thr Gly Met Ser Arg
1               5                   10                  15

Arg Leu Val Val Gly Ala Val Gly Ala Ala Leu Val Ser Gly Leu Val
            20                  25                  30

Gly Ala Val Gly Gly Thr Ala Thr Ala Gly Ala Phe Ser Arg Pro Gly
        35                  40                  45

Leu Pro Val Glu Tyr Leu Gln Val Pro Ser Pro Ser Met Gly Arg Asp
    50                  55                  60

Ile Lys Val Gln Phe Gln Ser Gly Gly Ala Asn Ser Pro Ala Leu Tyr
65                  70                  75                  80

Leu Leu Asp Gly Leu Arg Ala Gln Asp Asp Phe Ser Gly Trp Asp Ile
                85                  90                  95

Asn Thr Pro Ala Phe Glu Trp Tyr Asp Gln Ser Gly Leu Ser Val Val
            100                 105                 110

Met Pro Val Gly Gly Gln Ser Ser Phe Tyr Ser Asp Trp Tyr Gln Pro
        115                 120                 125

Ala Cys Gly Lys Ala Gly Cys Gln Thr Tyr Lys Trp Glu Thr Phe Leu
    130                 135                 140

Thr Ser Glu Leu Pro Gly Trp Leu Gln Ala Asn Arg His Val Lys Pro
145                 150                 155                 160

Thr Gly Ser Ala Val Val Gly Leu Ser Met Ala Ala Ser Ser Ala Leu
                165                 170                 175

Thr Leu Ala Ile Tyr His Pro Gln Gln Phe Val Tyr Ala Gly Ala Met
            180                 185                 190

Ser Gly Leu Leu Asp Pro Ser Gln Ala Met Gly Pro Thr Leu Ile Gly
        195                 200                 205

Leu Ala Met Gly Asp Ala Gly Gly Tyr Lys Ala Ser Asp Met Trp Gly
    210                 215                 220

Pro Lys Glu Asp Pro Ala Trp Gln Arg Asn Asp Pro Leu Leu Asn Val
225                 230                 235                 240

Gly Lys Leu Ile Ala Asn Asn Thr Arg Val Trp Val Tyr Cys Gly Asn
                245                 250                 255

Gly Lys Pro Ser Asp Leu Gly Gly Asn Asn Leu Pro Ala Lys Phe Leu
            260                 265                 270
```

```
Glu Gly Phe Val Arg Thr Ser Asn Ile Lys Phe Gln Asp Ala Tyr Asn
        275                 280                 285

Ala Gly Gly Gly His Asn Gly Val Phe Asp Phe Pro Asp Ser Gly Thr
    290                 295                 300

His Ser Trp Glu Tyr Trp Gly Ala Gln Leu Asn Ala Met Lys Pro Asp
305                 310                 315                 320

Leu Gln Arg Ala Leu Gly Ala Thr Pro Asn Thr Gly Pro Ala Pro Gln
                325                 330                 335

Gly Ala


<210> SEQ ID NO 10
<211> LENGTH: 325
<212> TYPE: PRT
<213> ORGANISM: Mycobacterium tuberculosis

<400> SEQUENCE: 10

Met Thr Asp Val Ser Arg Lys Ile Arg Ala Trp Gly Arg Arg Leu Met
1               5                   10                  15

Ile Gly Thr Ala Ala Ala Val Val Leu Pro Gly Leu Val Gly Leu Ala
            20                  25                  30

Gly Gly Ala Ala Thr Ala Gly Ala Phe Ser Arg Pro Gly Leu Pro Val
        35                  40                  45

Glu Tyr Leu Gln Val Pro Ser Pro Ser Met Gly Arg Asp Ile Lys Val
    50                  55                  60

Gln Phe Gln Ser Gly Gly Asn Asn Ser Pro Ala Val Tyr Leu Leu Asp
65                  70                  75                  80

Gly Leu Arg Ala Gln Asp Asp Tyr Asn Gly Trp Asp Ile Asn Thr Pro
                85                  90                  95

Ala Phe Glu Trp Tyr Tyr Gln Ser Gly Leu Ser Ile Val Met Pro Val
            100                 105                 110

Gly Gly Gln Ser Ser Phe Tyr Ser Asp Trp Tyr Ser Pro Ala Cys Gly
        115                 120                 125

Lys Ala Gly Cys Gln Thr Tyr Lys Trp Glu Thr Phe Leu Thr Ser Glu
    130                 135                 140

Leu Pro Gln Trp Leu Ser Ala Asn Arg Ala Val Lys Pro Thr Gly Ser
145                 150                 155                 160

Ala Ala Ile Gly Leu Ser Met Ala Gly Ser Ser Ala Met Ile Leu Ala
                165                 170                 175

Ala Tyr His Pro Gln Gln Phe Ile Tyr Ala Gly Ser Leu Ser Ala Leu
            180                 185                 190

Leu Asp Pro Ser Gln Gly Met Gly Pro Ser Leu Ile Gly Leu Ala Met
        195                 200                 205

Gly Asp Ala Gly Gly Tyr Lys Ala Ala Asp Met Trp Gly Pro Ser Ser
    210                 215                 220

Asp Pro Ala Trp Glu Arg Asn Asp Pro Thr Gln Gln Ile Pro Lys Leu
225                 230                 235                 240

Val Ala Asn Asn Thr Arg Leu Trp Val Tyr Cys Gly Asn Gly Thr Pro
                245                 250                 255

Asn Glu Leu Gly Gly Ala Asn Ile Pro Ala Glu Phe Leu Glu Asn Phe
            260                 265                 270

Val Arg Ser Ser Asn Leu Lys Phe Gln Asp Ala Tyr Asn Ala Ala Gly
        275                 280                 285

Gly His Asn Ala Val Phe Asn Phe Pro Pro Asn Gly Thr His Ser Trp
    290                 295                 300
```

```
Glu Tyr Trp Gly Ala Gln Leu Asn Ala Met Lys Gly Asp Leu Gln Ser
305                 310                 315                 320

Ser Leu Gly Ala Gly
                325


<210> SEQ ID NO 11
<211> LENGTH: 95
<212> TYPE: PRT
<213> ORGANISM: Mycobacterium tuberculosis

<400> SEQUENCE: 11

Met Thr Glu Gln Gln Trp Asn Phe Ala Gly Ile Glu Ala Ala Ala Ser
1               5                   10                  15

Ala Ile Gln Gly Asn Val Thr Ser Ile His Ser Leu Leu Asp Glu Gly
            20                  25                  30

Lys Gln Ser Leu Thr Lys Leu Ala Ala Ala Trp Gly Gly Ser Gly Ser
        35                  40                  45

Glu Ala Tyr Gln Gly Val Gln Gln Lys Trp Asp Ala Thr Ala Thr Glu
    50                  55                  60

Leu Asn Asn Ala Leu Gln Asn Leu Ala Arg Thr Ile Ser Glu Ala Gly
65                  70                  75                  80

Gln Ala Met Ala Ser Thr Glu Gly Asn Val Thr Gly Met Phe Ala
                85                  90                  95


<210> SEQ ID NO 12
<211> LENGTH: 96
<212> TYPE: PRT
<213> ORGANISM: Mycobacterium tuberculosis

<400> SEQUENCE: 12

Met Ser Gln Ile Met Tyr Asn Tyr Pro Ala Met Leu Gly His Ala Gly
1               5                   10                  15

Asp Met Ala Gly Tyr Ala Gly Thr Leu Gln Ser Leu Gly Ala Glu Ile
            20                  25                  30

Ala Val Glu Gln Ala Ala Leu Gln Ser Ala Trp Gln Gly Asp Thr Gly
        35                  40                  45

Ile Thr Tyr Gln Ala Trp Gln Ala Gln Trp Asn Gln Ala Met Glu Asp
    50                  55                  60

Leu Val Arg Ala Tyr His Ala Met Ser Ser Thr His Glu Ala Asn Thr
65                  70                  75                  80

Met Ala Met Met Ala Arg Asp Thr Ala Glu Ala Ala Lys Trp Gly Gly
                85                  90                  95


<210> SEQ ID NO 13
<211> LENGTH: 355
<212> TYPE: PRT
<213> ORGANISM: Mycobacterium tuberculosis

<400> SEQUENCE: 13

Met Ser Asn Ser Arg Arg Arg Ser Leu Arg Trp Ser Trp Leu Leu Ser
1               5                   10                  15

Val Leu Ala Ala Val Gly Leu Gly Leu Ala Thr Ala Pro Ala Gln Ala
            20                  25                  30

Ala Pro Pro Ala Leu Ser Gln Asp Arg Phe Ala Asp Phe Pro Ala Leu
        35                  40                  45

Pro Leu Asp Pro Ser Ala Met Val Ala Gln Val Gly Pro Gln Val Val
    50                  55                  60
```

Asn Ile Asn Thr Lys Leu Gly Tyr Asn Asn Ala Val Gly Ala Gly Thr
65 70 75 80

Gly Ile Val Ile Asp Pro Asn Gly Val Val Leu Thr Asn Asn His Val
85 90 95

Ile Ala Gly Ala Thr Asp Ile Asn Ala Phe Ser Val Gly Ser Gly Gln
100 105 110

Thr Tyr Gly Val Asp Val Val Gly Tyr Asp Arg Thr Gln Asp Val Ala
115 120 125

Val Leu Gln Leu Arg Gly Ala Gly Gly Leu Pro Ser Ala Ala Ile Gly
130 135 140

Gly Gly Val Ala Val Gly Glu Pro Val Val Ala Met Gly Asn Ser Gly
145 150 155 160

Gly Gln Gly Gly Thr Pro Arg Ala Val Pro Gly Arg Val Val Ala Leu
165 170 175

Gly Gln Thr Val Gln Ala Ser Asp Ser Leu Thr Gly Ala Glu Glu Thr
180 185 190

Leu Asn Gly Leu Ile Gln Phe Asp Ala Ala Ile Gln Pro Gly Asp Ser
195 200 205

Gly Gly Pro Val Val Asn Gly Leu Gly Gln Val Val Gly Met Asn Thr
210 215 220

Ala Ala Ser Asp Asn Phe Gln Leu Ser Gln Gly Gly Gln Gly Phe Ala
225 230 235 240

Ile Pro Ile Gly Gln Ala Met Ala Ile Ala Gly Gln Ile Arg Ser Gly
245 250 255

Gly Gly Ser Pro Thr Val His Ile Gly Pro Thr Ala Phe Leu Gly Leu
260 265 270

Gly Val Val Asp Asn Asn Gly Asn Gly Ala Arg Val Gln Arg Val Val
275 280 285

Gly Ser Ala Pro Ala Ala Ser Leu Gly Ile Ser Thr Gly Asp Val Ile
290 295 300

Thr Ala Val Asp Gly Ala Pro Ile Asn Ser Ala Thr Ala Met Ala Asp
305 310 315 320

Ala Leu Asn Gly His His Pro Gly Asp Val Ile Ser Val Thr Trp Gln
325 330 335

Thr Lys Ser Gly Gly Thr Arg Thr Gly Asn Val Thr Leu Ala Glu Gly
340 345 350

Pro Pro Ala
355

<210> SEQ ID NO 14
<211> LENGTH: 391
<212> TYPE: PRT
<213> ORGANISM: Mycobacterium tuberculosis

<400> SEQUENCE: 14

Met Val Asp Phe Gly Ala Leu Pro Pro Glu Ile Asn Ser Ala Arg Met
1 5 10 15

Tyr Ala Gly Pro Gly Ser Ala Ser Leu Val Ala Ala Ala Gln Met Trp
20 25 30

Asp Ser Val Ala Ser Asp Leu Phe Ser Ala Ala Ser Ala Phe Gln Ser
35 40 45

Val Val Trp Gly Leu Thr Val Gly Ser Trp Ile Gly Ser Ser Ala Gly
50 55 60

Leu Met Val Ala Ala Ala Ser Pro Tyr Val Ala Trp Met Ser Val Thr
65 70 75 80

-continued

```
Ala Gly Gln Ala Glu Leu Thr Ala Ala Gln Val Arg Val Ala Ala Ala
                85                  90                  95

Ala Tyr Glu Thr Ala Tyr Gly Leu Thr Val Pro Pro Pro Val Ile Ala
            100                 105                 110

Glu Asn Arg Ala Glu Leu Met Ile Leu Ile Ala Thr Asn Leu Leu Gly
        115                 120                 125

Gln Asn Thr Pro Ala Ile Ala Val Asn Glu Ala Glu Tyr Gly Glu Met
    130                 135                 140

Trp Ala Gln Asp Ala Ala Ala Met Phe Gly Tyr Ala Ala Ala Thr Ala
145                 150                 155                 160

Thr Ala Thr Ala Thr Leu Leu Pro Phe Glu Glu Ala Pro Glu Met Thr
                165                 170                 175

Ser Ala Gly Gly Leu Leu Glu Gln Ala Ala Ala Val Glu Glu Ala Ser
            180                 185                 190

Asp Thr Ala Ala Ala Asn Gln Leu Met Asn Asn Val Pro Gln Ala Leu
        195                 200                 205

Gln Gln Leu Ala Gln Pro Thr Gln Gly Thr Thr Pro Ser Ser Lys Leu
    210                 215                 220

Gly Gly Leu Trp Lys Thr Val Ser Pro His Arg Ser Pro Ile Ser Asn
225                 230                 235                 240

Met Val Ser Met Ala Asn Asn His Met Ser Met Thr Asn Ser Gly Val
                245                 250                 255

Ser Met Thr Asn Thr Leu Ser Ser Met Leu Lys Gly Phe Ala Pro Ala
            260                 265                 270

Ala Ala Ala Gln Ala Val Gln Thr Ala Ala Gln Asn Gly Val Arg Ala
        275                 280                 285

Met Ser Ser Leu Gly Ser Ser Leu Gly Ser Ser Gly Leu Gly Gly Gly
    290                 295                 300

Val Ala Ala Asn Leu Gly Arg Ala Ala Ser Val Gly Ser Leu Ser Val
305                 310                 315                 320

Pro Gln Ala Trp Ala Ala Ala Asn Gln Ala Val Thr Pro Ala Ala Arg
                325                 330                 335

Ala Leu Pro Leu Thr Ser Leu Thr Ser Ala Ala Glu Arg Gly Pro Gly
            340                 345                 350

Gln Met Leu Gly Gly Leu Pro Val Gly Gln Met Gly Ala Arg Ala Gly
        355                 360                 365

Gly Gly Leu Ser Gly Val Leu Arg Val Pro Pro Arg Pro Tyr Val Met
    370                 375                 380

Pro His Ser Pro Ala Ala Gly
385                 390
```

<210> SEQ ID NO 15
<211> LENGTH: 236
<212> TYPE: PRT
<213> ORGANISM: Mycobacterium tuberculosis

<400> SEQUENCE: 15

```
Met Arg Thr Pro Arg Arg His Cys Arg Arg Ile Ala Val Leu Ala Ala
1               5                   10                  15

Val Ser Ile Ala Ala Thr Val Val Ala Gly Cys Ser Ser Gly Ser Lys
            20                  25                  30

Pro Ser Gly Gly Pro Leu Pro Asp Ala Lys Pro Leu Val Glu Glu Ala
        35                  40                  45

Thr Ala Gln Thr Lys Ala Leu Lys Ser Ala His Met Val Leu Thr Val
    50                  55                  60
```

Asn Gly Lys Ile Pro Gly Leu Ser Leu Lys Thr Leu Ser Gly Asp Leu
65 70 75 80

Thr Thr Asn Pro Thr Ala Ala Thr Gly Asn Val Lys Leu Thr Leu Gly
85 90 95

Gly Ser Asp Ile Asp Ala Asp Phe Val Val Phe Asp Gly Ile Leu Tyr
100 105 110

Ala Thr Leu Thr Pro Asn Gln Trp Ser Asp Phe Gly Pro Ala Ala Asp
115 120 125

Ile Tyr Asp Pro Ala Gln Val Leu Asn Pro Asp Thr Gly Leu Ala Asn
130 135 140

Val Leu Ala Asn Phe Ala Asp Ala Lys Ala Glu Gly Arg Asp Thr Ile
145 150 155 160

Asn Gly Gln Asn Thr Ile Arg Ile Ser Gly Lys Val Ser Ala Gln Ala
165 170 175

Val Asn Gln Ile Ala Pro Pro Phe Asn Ala Thr Gln Pro Val Pro Ala
180 185 190

Thr Val Trp Ile Gln Glu Thr Gly Asp His Gln Leu Ala Gln Ala Gln
195 200 205

Leu Asp Arg Gly Ser Gly Asn Ser Val Gln Met Thr Leu Ser Lys Trp
210 215 220

Gly Glu Lys Val Gln Val Thr Lys Pro Pro Val Ser
225 230 235

<210> SEQ ID NO 16
<211> LENGTH: 540
<212> TYPE: PRT
<213> ORGANISM: Mycobacterium tuberculosis

<400> SEQUENCE: 16

Met Ala Lys Thr Ile Ala Tyr Asp Glu Glu Ala Arg Arg Gly Leu Glu
1 5 10 15

Arg Gly Leu Asn Ala Leu Ala Asp Ala Val Lys Val Thr Leu Gly Pro
20 25 30

Lys Gly Arg Asn Val Val Leu Glu Lys Lys Trp Gly Ala Pro Thr Ile
35 40 45

Thr Asn Asp Gly Val Ser Ile Ala Lys Glu Ile Glu Leu Glu Asp Pro
50 55 60

Tyr Glu Lys Ile Gly Ala Glu Leu Val Lys Glu Val Ala Lys Lys Thr
65 70 75 80

Asp Asp Val Ala Gly Asp Gly Thr Thr Thr Ala Thr Val Leu Ala Gln
85 90 95

Ala Leu Val Arg Glu Gly Leu Arg Asn Val Ala Ala Gly Ala Asn Pro
100 105 110

Leu Gly Leu Lys Arg Gly Ile Glu Lys Ala Val Glu Lys Val Thr Glu
115 120 125

Thr Leu Leu Lys Gly Ala Lys Glu Val Glu Thr Lys Glu Gln Ile Ala
130 135 140

Ala Thr Ala Ala Ile Ser Ala Gly Asp Gln Ser Ile Gly Asp Leu Ile
145 150 155 160

Ala Glu Ala Met Asp Lys Val Gly Asn Glu Gly Val Ile Thr Val Glu
165 170 175

Glu Ser Asn Thr Phe Gly Leu Gln Leu Glu Leu Thr Glu Gly Met Arg
180 185 190

Phe Asp Lys Gly Tyr Ile Ser Gly Tyr Phe Val Thr Asp Pro Glu Arg
195 200 205

Gln Glu Ala Val Leu Glu Asp Pro Tyr Ile Leu Leu Val Ser Ser Lys
    210                 215                 220

Val Ser Thr Val Lys Asp Leu Leu Pro Leu Leu Glu Lys Val Ile Gly
225                 230                 235                 240

Ala Gly Lys Pro Leu Leu Ile Ile Ala Glu Asp Val Glu Gly Glu Ala
                245                 250                 255

Leu Ser Thr Leu Val Val Asn Lys Ile Arg Gly Thr Phe Lys Ser Val
            260                 265                 270

Ala Val Lys Ala Pro Gly Phe Gly Asp Arg Arg Lys Ala Met Leu Gln
        275                 280                 285

Asp Met Ala Ile Leu Thr Gly Gly Gln Val Ile Ser Glu Glu Val Gly
    290                 295                 300

Leu Thr Leu Glu Asn Ala Asp Leu Ser Leu Leu Gly Lys Ala Arg Lys
305                 310                 315                 320

Val Val Val Thr Lys Asp Glu Thr Thr Ile Val Glu Gly Ala Gly Asp
                325                 330                 335

Thr Asp Ala Ile Ala Gly Arg Val Ala Gln Ile Arg Gln Glu Ile Glu
            340                 345                 350

Asn Ser Asp Ser Asp Tyr Asp Arg Glu Lys Leu Gln Glu Arg Leu Ala
        355                 360                 365

Lys Leu Ala Gly Gly Val Ala Val Ile Lys Ala Gly Ala Ala Thr Glu
    370                 375                 380

Val Glu Leu Lys Glu Arg Lys His Arg Ile Glu Asp Ala Val Arg Asn
385                 390                 395                 400

Ala Lys Ala Ala Val Glu Glu Gly Ile Val Ala Gly Gly Gly Val Thr
                405                 410                 415

Leu Leu Gln Ala Ala Pro Thr Leu Asp Glu Leu Lys Leu Glu Gly Asp
            420                 425                 430

Glu Ala Thr Gly Ala Asn Ile Val Lys Val Ala Leu Glu Ala Pro Leu
        435                 440                 445

Lys Gln Ile Ala Phe Asn Ser Gly Leu Glu Pro Gly Val Val Ala Glu
    450                 455                 460

Lys Val Arg Asn Leu Pro Ala Gly His Gly Leu Asn Ala Gln Thr Gly
465                 470                 475                 480

Val Tyr Glu Asp Leu Leu Ala Ala Gly Val Ala Asp Pro Val Lys Val
                485                 490                 495

Thr Arg Ser Ala Leu Gln Asn Ala Ala Ser Ile Ala Gly Leu Phe Leu
            500                 505                 510

Thr Thr Glu Ala Val Val Ala Asp Lys Pro Glu Lys Glu Lys Ala Ser
        515                 520                 525

Val Pro Gly Gly Gly Asp Met Gly Gly Met Asp Phe
    530                 535                 540

<210> SEQ ID NO 17
<211> LENGTH: 199
<212> TYPE: PRT
<213> ORGANISM: Mycobacterium tuberculosis

<400> SEQUENCE: 17

Met Ala Glu Asn Ser Asn Ile Asp Asp Ile Lys Ala Pro Leu Leu Ala
1               5                   10                  15

Ala Leu Gly Ala Ala Asp Leu Ala Leu Ala Thr Val Asn Glu Leu Ile
            20                  25                  30

Thr Asn Leu Arg Glu Arg Ala Glu Glu Thr Arg Thr Asp Thr Arg Ser
        35                  40                  45

```
Arg Val Glu Glu Ser Arg Ala Arg Leu Thr Lys Leu Gln Glu Asp Leu
    50                  55                  60

Pro Glu Gln Leu Thr Glu Leu Arg Glu Lys Phe Thr Ala Glu Glu Leu
65                  70                  75                  80

Arg Lys Ala Ala Glu Gly Tyr Leu Glu Ala Ala Thr Ser Arg Tyr Asn
                85                  90                  95

Glu Leu Val Glu Arg Gly Glu Ala Ala Leu Glu Arg Leu Arg Ser Gln
            100                 105                 110

Gln Ser Phe Glu Glu Val Ser Ala Arg Ala Glu Gly Tyr Val Asp Gln
        115                 120                 125

Ala Val Glu Leu Thr Gln Glu Ala Leu Gly Thr Val Ala Ser Gln Thr
    130                 135                 140

Arg Ala Val Gly Glu Arg Ala Ala Lys Leu Val Gly Ile Glu Leu Pro
145                 150                 155                 160

Lys Lys Ala Ala Pro Ala Lys Lys Ala Ala Pro Ala Lys Lys Ala Ala
                165                 170                 175

Pro Ala Lys Lys Ala Ala Ala Lys Lys Ala Pro Ala Lys Lys Ala Ala
            180                 185                 190

Ala Lys Lys Val Thr Gln Lys
        195


<210> SEQ ID NO 18
<211> LENGTH: 375
<212> TYPE: PRT
<213> ORGANISM: Mycobacterium tuberculosis

<400> SEQUENCE: 18

Val Thr Gln Thr Gly Lys Arg Gln Arg Arg Lys Phe Gly Arg Ile Arg
1               5                   10                  15

Gln Phe Asn Ser Gly Arg Trp Gln Ala Ser Tyr Thr Gly Pro Asp Gly
            20                  25                  30

Arg Val Tyr Ile Ala Pro Lys Thr Phe Asn Ala Lys Ile Asp Ala Glu
        35                  40                  45

Ala Trp Leu Thr Asp Arg Arg Arg Glu Ile Asp Arg Gln Leu Trp Ser
    50                  55                  60

Pro Ala Ser Gly Gln Glu Asp Arg Pro Gly Ala Pro Phe Gly Glu Tyr
65                  70                  75                  80

Ala Glu Gly Trp Leu Lys Gln Arg Gly Ile Lys Asp Arg Thr Arg Ala
                85                  90                  95

His Tyr Arg Lys Leu Leu Asp Asn His Ile Leu Ala Thr Phe Ala Asp
            100                 105                 110

Thr Asp Leu Arg Asp Ile Thr Pro Ala Ala Val Arg Arg Trp Tyr Ala
        115                 120                 125

Thr Thr Ala Val Gly Thr Pro Thr Met Arg Ala His Ser Tyr Ser Leu
    130                 135                 140

Leu Arg Ala Ile Met Gln Thr Ala Leu Ala Asp Asp Leu Ile Asp Ser
145                 150                 155                 160

Asn Pro Cys Arg Ile Ser Gly Ala Ser Thr Ala Arg Arg Val His Lys
                165                 170                 175

Ile Arg Pro Ala Thr Leu Asp Glu Leu Glu Thr Ile Thr Lys Ala Met
            180                 185                 190

Pro Asp Pro Tyr Gln Ala Phe Val Leu Met Ala Ala Trp Leu Ala Met
        195                 200                 205

Arg Tyr Gly Glu Leu Thr Glu Leu Arg Arg Lys Asp Ile Asp Leu His
    210                 215                 220
```

-continued

```
Gly Glu Val Ala Arg Val Arg Arg Ala Val Val Arg Val Gly Glu Gly
225                 230                 235                 240

Phe Lys Val Thr Thr Pro Lys Ser Asp Ala Gly Val Arg Asp Ile Ser
                245                 250                 255

Ile Pro Pro His Leu Ile Pro Ala Ile Glu Asp His Leu His Lys His
            260                 265                 270

Val Asn Pro Gly Arg Glu Ser Leu Leu Phe Pro Ser Val Asn Asp Pro
        275                 280                 285

Asn Arg His Leu Ala Pro Ser Ala Leu Tyr Arg Met Phe Tyr Lys Ala
    290                 295                 300

Arg Lys Ala Ala Gly Arg Pro Asp Leu Arg Val His Asp Leu Arg His
305                 310                 315                 320

Ser Gly Ala Val Leu Ala Ala Ser Thr Gly Ala Thr Leu Ala Glu Leu
                325                 330                 335

Met Gln Arg Leu Gly His Ser Thr Ala Gly Ala Ala Leu Arg Tyr Gln
            340                 345                 350

His Ala Ala Lys Gly Arg Asp Arg Glu Ile Ala Ala Leu Leu Ser Lys
        355                 360                 365

Leu Ala Glu Asn Gln Glu Met
    370                 375


<210> SEQ ID NO 19
<211> LENGTH: 75
<212> TYPE: PRT
<213> ORGANISM: Mycobacterium tuberculosis

<400> SEQUENCE: 19

Val Ile Ala Gly Val Asp Gln Ala Leu Ala Ala Thr Gly Gln Ala Ser
1               5                   10                  15

Gln Arg Ala Ala Gly Ala Ser Gly Gly Val Thr Val Gly Val Gly Val
            20                  25                  30

Gly Thr Glu Gln Arg Asn Leu Ser Val Val Ala Pro Ser Gln Phe Thr
        35                  40                  45

Phe Ser Ser Arg Ser Pro Asp Phe Val Asp Glu Thr Ala Gly Gln Ser
    50                  55                  60

Trp Cys Ala Ile Leu Gly Leu Asn Gln Phe His
65                  70                  75


<210> SEQ ID NO 20
<211> LENGTH: 144
<212> TYPE: PRT
<213> ORGANISM: Mycobacterium tuberculosis

<400> SEQUENCE: 20

Met Ala Thr Thr Leu Pro Val Gln Arg His Pro Arg Ser Leu Phe Pro
1               5                   10                  15

Glu Phe Ser Glu Leu Phe Ala Ala Phe Pro Ser Phe Ala Gly Leu Arg
            20                  25                  30

Pro Thr Phe Asp Thr Arg Leu Met Arg Leu Glu Asp Glu Met Lys Glu
        35                  40                  45

Gly Arg Tyr Glu Val Arg Ala Glu Leu Pro Gly Val Asp Pro Asp Lys
    50                  55                  60

Asp Val Asp Ile Met Val Arg Asp Gly Gln Leu Thr Ile Lys Ala Glu
65                  70                  75                  80

Arg Thr Glu Gln Lys Asp Phe Asp Gly Arg Ser Glu Phe Ala Tyr Gly
                85                  90                  95
```

```
Ser Phe Val Arg Thr Val Ser Leu Pro Val Gly Ala Asp Glu Asp Asp
            100                 105                 110

Ile Lys Ala Thr Tyr Asp Lys Gly Ile Leu Thr Val Ser Val Ala Val
        115                 120                 125

Ser Glu Gly Lys Pro Thr Glu Lys His Ile Gln Ile Arg Ser Thr Asn
    130                 135                 140
```

<210> SEQ ID NO 21
<211> LENGTH: 1017
<212> TYPE: DNA
<213> ORGANISM: Mycobacterium tuberculosis

<400> SEQUENCE: 21

```
atgcagcttg ttgacagggt tcgtggcgcc gtcacgggta tgtcgcgtcg actcgtggtc     60

ggggccgtcg gcgcggccct agtgtcgggt ctggtcggcg ccgtcggtgg cacggcgacc    120

gcgggggcat tttcccggcc gggcttgccg gtggagtacc tgcaggtgcc gtcgccgtcg    180

atgggccgtg acatcaaggt ccaattccaa agtggtggtg ccaactcgcc cgccctgtac    240

ctgctcgacg gcctgcgcgc gcaggacgac ttcagcggct gggacatcaa caccccggcg    300

ttcgagtggt acgaccagtc gggcctgtcg gtggtcatgc cggtgggtgg ccagtcaagc    360

ttctactccg actggtacca gcccgcctgc ggcaaggccg gttgccagac ttacaagtgg    420

gagaccttcc tgaccagcga gctgccgggg tggctgcagg ccaacaggca cgtcaagccc    480

accggaagcg ccgtcgtcgg tctttcgatg gctgcttctt cggcgctgac gctggcgatc    540

tatcaccccc agcagttcgt ctacgcggga gcgatgtcgg gcctgttgga cccctcccag    600

gcgatgggtc ccaccctgat cggcctggcg atgggtgacg ctggcggcta caaggcctcc    660

gacatgtggg gcccgaagga ggacccggcg tggcagcgca acgacccgct gttgaacgtc    720

gggaagctga tcgccaacaa cacccgcgtc tgggtgtact gcggcaacgg caagccgtcg    780

gatctgggtg gcaacaacct gccggccaag ttcctcgagg gcttcgtgcg gaccagcaac    840

atcaagttcc aagacgccta caacgccggt ggcggccaca acggcgtgtt cgacttcccg    900

gacagcggta cgcacagctg ggagtactgg ggcgcgcagc tcaacgctat gaagcccgac    960

ctgcaacggg cactgggtgc cacgcccaac accgggcccg cgccccaggg cgcctag      1017
```

<210> SEQ ID NO 22
<211> LENGTH: 978
<212> TYPE: DNA
<213> ORGANISM: Mycobacterium tuberculosis

<400> SEQUENCE: 22

```
atgacagacg tgagccgaaa gattcgagct tggggacgcc gattgatgat cggcacggca     60

gcggctgtag tccttccggg cctggtgggg cttgccggcg gagcggcaac cgcgggcgcg    120

ttctcccggc cggggctgcc ggtcgagtac ctgcaggtgc cgtcgccgtc gatgggccgc    180

gacatcaagg ttcagttcca gagcggtggg aacaactcac ctgcggttta tctgctcgac    240

ggcctgcgcg cccaagacga ctacaacggc tgggatatca acaccccggc gttcgagtgg    300

tactaccagt cgggactgtc gatagtcatg ccggtcggcg ggcagtccag cttctacagc    360

gactggtaca gcccggcctg cggtaaggct ggctgccaga cttacaagtg ggaaaccttc    420

ctgaccagcg agctgccgca atggttgtcc gccaacaggg ccgtgaagcc caccggcagc    480

gctgcaatcg gcttgtcgat ggccggctcg tcggcaatga tcttggccgc ctaccacccc    540

cagcagttca tctacgccgg ctcgctgtcg gccctgctgg acccctctca ggggatgggg    600
```

```
cctagcctga tcggcctcgc gatgggtgac gccggcggtt acaaggccgc agacatgtgg    660

ggtccctcga gtgacccggc atgggagcgc aacgacccta cgcagcagat ccccaagctg    720

gtcgcaaaca acacccggct atgggtttat tgcgggaacg gcaccccgaa cgagttgggc    780

ggtgccaaca tacccgccga gttcttggag aacttcgttc gtagcagcaa cctgaagttc    840

caggatgcgt acaacgccgc gggcgggcac aacgccgtgt tcaacttccc gcccaacggc    900

acgcacagct gggagtactg gggcgctcag ctcaacgcca tgaagggtga cctgcagagt    960

tcgttaggcg ccggctga                                                  978


<210> SEQ ID NO 23
<211> LENGTH: 288
<212> TYPE: DNA
<213> ORGANISM: Mycobacterium tuberculosis

<400> SEQUENCE: 23

atgacagagc agcagtggaa tttcgcgggt atcgaggccg cggcaagcgc aatccaggga     60

aatgtcacgt ccattcattc cctccttgac gaggggaagc agtccctgac caagctcgca    120

gcggcctggg gcggtagcgg ttcggaggcg taccagggtg tccagcaaaa atgggacgcc    180

acggctaccg agctgaacaa cgcgctgcag aacctggcgc ggacgatcag cgaagccggt    240

caggcaatgg cttcgaccga aggcaacgtc actgggatgt tcgcatag                288


<210> SEQ ID NO 24
<211> LENGTH: 291
<212> TYPE: DNA
<213> ORGANISM: Mycobacterium tuberculosis

<400> SEQUENCE: 24

atgtcgcaaa tcatgtacaa ctaccccgcg atgttgggtc acgccgggga tatggccgga     60

tatgccggca cgctgcagag cttgggtgcc gagatcgccg tggagcaggc cgcgttgcag    120

agtgcgtggc agggcgatac cgggatcacg tatcaggcgt ggcaggcaca gtggaaccag    180

gccatggaag atttggtgcg ggcctatcat gcgatgtcca gcacccatga agccaacacc    240

atggcgatga tggcccgcga cacggccgaa gccgccaaat ggggcggcta g             291


<210> SEQ ID NO 25
<211> LENGTH: 1068
<212> TYPE: DNA
<213> ORGANISM: Mycobacterium tuberculosis

<400> SEQUENCE: 25

atgagcaatt cgcgccgccg ctcactcagg tggtcatggt tgctgagcgt gctggctgcc     60

gtcgggctgg gcctggccac ggcgccggcc caggcggccc cgccggcctt gtcgcaggac    120

cggttcgccg acttccccgc gctgcccctc gacccgtccg cgatggtcgc ccaagtgggg    180

ccacaggtgg tcaacatcaa caccaaactg ggctacaaca acgccgtggg cgccgggacc    240

ggcatcgtca tcgatcccaa cggtgtcgtg ctgaccaaca accacgtgat cgcgggcgcc    300

accgacatca atgcgttcag cgtcggctcc ggccaaacct acggcgtcga tgtggtcggg    360

tatgaccgca cccaggatgt cgcggtgctg cagctgcgcg gtgccggtgg cctgccgtcg    420

gcggcgatcg gtggcggcgt cgcggttggt gagcccgtcg tcgcgatggg caacagcggt    480

gggcagggcg gaacgccccg tgcggtgcct ggcagggtgg tcgcgctcgg ccaaaccgtg    540

caggcgtcgg attcgctgac cggtgccgaa gagacattga acgggttgat ccagttcgat    600

gccgcgatcc agcccggtga ttcgggcggg cccgtcgtca acggcctagg acaggtggtc    660
```

-continued

```
ggtatgaaca cggccgcgtc cgataacttc cagctgtccc agggtgggca gggattcgcc    720

attccgatcg ggcaggcgat ggcgatcgcg ggccagatcc gatcgggtgg ggggtcaccc    780

accgttcata tcgggcctac cgccttcctc ggcttgggtg ttgtcgacaa caacggcaac    840

ggcgcacgag tccaacgcgt ggtcgggagc gctccggcgg caagtctcgg catctccacc    900

ggcgacgtga tcaccgcggt cgacggcgct ccgatcaact cggccaccgc gatggcggac    960

gcgcttaacg ggcatcatcc cggtgacgtc atctcggtga cctggcaaac caagtcgggc   1020

ggcacgcgta cagggaacgt gacattggcc gagggacccc cggcctga                1068
```

<210> SEQ ID NO 26
<211> LENGTH: 1176
<212> TYPE: DNA
<213> ORGANISM: Mycobacterium tuberculosis

<400> SEQUENCE: 26

```
atggtggatt tcggggcgtt accaccggag atcaactccg cgaggatgta cgccggcccg     60

ggttcggcct cgctggtggc cgcggctcag atgtgggaca gcgtggcgag tgacctgttt    120

tcggccgcgt cggcgtttca gtcggtggtc tggggtctga cggtggggtc gtggataggt    180

tcgtcggcgg gtctgatggt ggcggcggcc tcgccgtatg tggcgtggat gagcgtcacc    240

gcggggcagg ccgagctgac cgccgcccag gtccgggttg ctgcggcggc ctacgagacg    300

gcgtatgggc tgacggtgcc cccgccggtg atcgccgaga accgtgctga actgatgatt    360

ctgatagcga ccaacctctt ggggcaaaac accccggcga tcgcggtcaa cgaggccgaa    420

tacggcgaga tgtgggccca agacgccgcc gcgatgtttg gctacgccgc ggcgacggcg    480

acggcgacgg cgacgttgct gccgttcgag gaggcgccgg agatgaccag cgcgggtggg    540

ctcctcgagc aggccgccgc ggtcgaggag gcctccgaca ccgccgcggc gaaccagttg    600

atgaacaatg tgccccaggc gctgcaacag ctggcccagc ccacgcaggg caccacgcct    660

tcttccaagc tgggtggcct gtggaagacg gtctcgccgc atcggtcgcc gatcagcaac    720

atggtgtcga tggccaacaa ccacatgtcg atgaccaact cgggtgtgtc gatgaccaac    780

accttgagct cgatgttgaa gggctttgct ccggcggcgg ccgcccaggc cgtgcaaacc    840

gcggcgcaaa acggggtccg ggcgatgagc tcgctgggca gctcgctggg ttcttcgggt    900

ctgggcggtg gggtggccgc caacttgggt cgggcggcct cggtcggttc gttgtcggtg    960

ccgcaggcct gggccgcggc caaccaggca gtcaccccgg cggcgcgggc gctgccgctg   1020

accagcctga ccagcgccgc ggaaagaggg cccgggcaga tgctgggcgg gctgccggtg   1080

gggcagatgg gcgccagggc cggtggtggg ctcagtggtg tgctgcgtgt tccgccgcga   1140

ccctatgtga tgccgcattc tccggcggcc ggctag                             1176
```

<210> SEQ ID NO 27
<211> LENGTH: 711
<212> TYPE: DNA
<213> ORGANISM: Mycobacterium tuberculosis

<400> SEQUENCE: 27

```
atgcggaccc ccagacgcca ctgccgtcgc atcgccgtcc tcgccgccgt tagcatcgcc     60

gccactgtcg ttgccggctg ctcgtcgggc tcgaagccaa gcggcggacc acttccggac    120

gcgaagccgc tggtcgagga ggccaccgcg cagaccaagg ctctcaagag cgcgcacatg    180

gtgctgacgg tcaacggcaa gatcccggga ctgtctctga agacgctgag cggcgatctc    240

accaccaacc ccaccgccgc gacgggaaac gtcaagctca cgctgggtgg gtctgatatc    300
```

gatgccgact tcgtggtgtt cgacgggatc ctgtacgcca ccctgacgcc caaccagtgg 360
agcgatttcg gtcccgccgc cgacatctac gaccccgccc aggtgctgaa tccggatacc 420
ggcctggcca acgtgctggc gaatttcgcc gacgcaaaag ccgaagggcg ggataccatc 480
aacggccaga acaccatccg catcagcggg aaggtatcgg cacaggcggt gaaccagata 540
gcgccgccgt tcaacgcgac gcagccggtg ccggcgaccg tctggattca ggagaccggc 600
gatcatcaac tggcacaggc ccagttggac cgcggctcgg gcaattccgt ccagatgacc 660
ttgtcgaaat ggggcgagaa ggtccaggtc acgaagcccc cggtgagctg a 711

<210> SEQ ID NO 28
<211> LENGTH: 1623
<212> TYPE: DNA
<213> ORGANISM: Mycobacterium tuberculosis

<400> SEQUENCE: 28
atggccaaga caattgcgta cgacgaagag gcccgtcgcg gcctcgagcg gggcttgaac 60
gccctcgccg atgcggtaaa ggtgacattg ggccccaagg gccgcaacgt cgtcctggaa 120
aagaagtggg gtgcccccac gatcaccaac gatggtgtgt ccatcgccaa ggagatcgag 180
ctggaggatc cgtacgagaa gatcggcgcc gagctggtca aagaggtagc caagaagacc 240
gatgacgtcg ccggtgacgg caccacgacg gccaccgtgc tggcccaggc gttggttcgc 300
gagggcctgc gcaacgtcgc ggccggcgcc aacccgctcg gtctcaaacg cggcatcgaa 360
aaggccgtgg agaaggtcac cgagaccctg ctcaagggcg ccaaggaggt cgagaccaag 420
gagcagattg cggccaccgc agcgatttcg gcgggtgacc agtccatcgg tgacctgatc 480
gccgaggcga tggacaaggt gggcaacgag ggcgtcatca ccgtcgagga gtccaacacc 540
tttgggctgc agctcgagct caccgagggt atgcggttcg acaagggcta catctcgggg 600
tacttcgtga ccgacccgga gcgtcaggag gcggtcctgg aggaccccta catcctgctg 660
gtcagctcca aggtgtccac tgtcaaggat ctgctgccgc tgctcgagaa ggtcatcgga 720
gccggtaagc cgctgctgat catcgccgag gacgtcgagg gcgaggcgct gtccaccctg 780
gtcgtcaaca agatccgcgg caccttcaag tcggtggcgg tcaaggctcc cggcttcggc 840
gaccgccgca aggcgatgct gcaggatatg gccattctca ccggtggtca ggtgatcagc 900
gaagaggtcg gcctgacgct ggagaacgcc gacctgtcgc tgctaggcaa ggcccgcaag 960
gtcgtggtca ccaaggacga gaccaccatc gtcgagggcg ccggtgacac cgacgccatc 1020
gccggacgag tggcccagat ccgccaggag atcgagaaca gcgactccga ctacgaccgt 1080
gagaagctgc aggagcggct ggccaagctg gccggtggtg tcgcggtgat caaggccggt 1140
gccgccaccg aggtcgaact caaggagcgc aagcaccgca tcgaggatgc ggttcgcaat 1200
gccaaggccg ccgtcgagga gggcatcgtc gccggtgggg gtgtgacgct gttgcaagcg 1260
gccccgaccc tggacgagct gaagctcgaa ggcgacgagg cgaccggcgc caacatcgtg 1320
aaggtggcgc tggaggcccc gctgaagcag atcgccttca actccgggct ggagccgggc 1380
gtggtggccg agaaggtgcg caacctgccg gctggccacg gactgaacgc tcagaccggt 1440
gtctacgagg atctgctcgc tgccggcgtt gctgacccgg tcaaggtgac ccgttcggcg 1500
ctgcagaatg cggcgtccat cgcggggctg ttcctgacca ccgaggccgt cgttgccgac 1560
aagccggaaa aggagaaggc ttccgttccc ggtggcggcg acatgggtgg catggatttc 1620
tga 1623

<210> SEQ ID NO 29
<211> LENGTH: 600
<212> TYPE: DNA
<213> ORGANISM: Mycobacterium tuberculosis

<400> SEQUENCE: 29
atggctgaaa actcgaacat tgatgacatc aaggctccgt tgcttgccgc gcttggagcg 60
gccgacctgg ccttggccac tgtcaacgag ttgatcacga acctgcgtga gcgtgcggag 120
gagactcgta cggacacccg cagccgggtc gaggagagcc gtgctcgcct gaccaagctg 180
caggaagatc tgcccgagca gctcaccgag ctgcgtgaga agttcaccgc cgaggagctg 240
cgtaaggccg ccgagggcta cctcgaggcc gcgactagcc ggtacaacga gctggtcgag 300
cgcggtgagg ccgctctaga gcggctgcgc agccagcaga gcttcgagga agtgtcggcg 360
cgcgccgaag gctacgtgga ccaggcggtg gagttgaccc aggaggcgtt gggtacggtc 420
gcatcgcaga cccgcgcggt cggtgagcgt gccgccaagc tggtcggcat cgagctgcct 480
aagaaggctg ctccggccaa gaaggccgct ccggccaaga aggccgctcc ggccaagaag 540
gcggcggcca agaaggcgcc cgcgaagaag gcggcggcca agaaggtcac ccagaagtag 600

<210> SEQ ID NO 30
<211> LENGTH: 1128
<212> TYPE: DNA
<213> ORGANISM: Mycobacterium tuberculosis

<400> SEQUENCE: 30
gtgacgcaaa ccggcaagcg tcagagacgc aaattcggtc gcatccgaca gttcaactcc 60
ggccgctggc aagccagcta caccggcccc gacggccgcg tgtacatcgc cccccaaaacc 120 ttcaacgcca agatcgacgc cgaagcatgg ctcaccgacc gccgccgcga aatcgaccga 180
caactatggt ccccggcatc gggtcaggaa gaccgccccg gagccccatt cggtgagtac 240
gccgaaggat ggctgaagca gcgtggaatc aaggaccgca cccgcgccca ctatcgcaaa 300
ctgctggaca accacatcct ggccaccttc gctgacaccg acctacgcga catcaccccg 360
gccgccgtgc gccgctggta cgccaccacc gccgtgggca caccgaccat gcgggcacac 420
tcctacagct tgctgcgcgc aatcatgcag accgccttgg ccgacgacct gatcgactcc 480
aacccctgcc gcatctcagg cgcgtccacc gcccgccgcg tccacaagat caggcccgcc 540
accctcgacg agctggaaac catcaccaaa gccatgcccg acccctacca ggcgttcgtg 600
ctgatggcgg catggctggc catgcgctac ggcgagctga ccgaattacg ccgcaaagac 660
atcgacctgc acggcgaggt tgcgcgggtg cggcgggctg tcgttcgggt gggcgaaggc 720
ttcaaggtga cgacaccgaa aagcgatgcg ggagtgcgcg acataagtat cccgccacat 780
ctgatacccg ccatcgaaga ccaccttcac aaacacgtca accccggccg ggagtccctg 840
ctgttcccat cggtcaacga ccccaaccgt cacctagcac cctcggcgct gtaccgcatg 900
ttctacaagg cccgaaaagc cgccggccga ccagacttac gggtgcacga ccttcgacac 960
tccggcgccg tgttggctgc atccaccggc gccacactgg ccgaactgat gcagcggcta 1020
ggacacagca cagccggcgc cgcactccgc taccagcacg ccgccaaggg ccgggaccgc 1080
gaaatcgccg cactgttaag caaactggcc gagaaccagg agatgtga 1128

<210> SEQ ID NO 31
<211> LENGTH: 228
<212> TYPE: DNA
<213> ORGANISM: Mycobacterium tuberculosis

<400> SEQUENCE: 31
gtgatagcgg gcgtcgacca ggcgcttgca gcaacaggcc aggctagcca gcgggcggca 60
ggcgcatctg gtggggtcac cgtcggtgtc ggcgtgggca cggaacagag gaacctttcg 120
gtggttgcac cgagtcagtt cacatttagt tcacgcagcc cagattttgt ggatgaaacc 180
gcaggtcaat cgtggtgcgc gatactggga ttgaaccagt ttcactag 228

<210> SEQ ID NO 32
<211> LENGTH: 435
<212> TYPE: DNA
<213> ORGANISM: Mycobacterium tuberculosis

<400> SEQUENCE: 32
atggccacca cccttcccgt tcagcgccac ccgcggtccc tcttccccga gttttctgag 60
ctgttcgcgg ccttcccgtc attcgccgga ctccggccca ccttcgacac ccggttgatg 120
cggctggaag acgagatgaa agaggggcgc tacgaggtac gcgcggagct tcccggggtc 180
gaccccgaca aggacgtcga cattatggtc cgcgatggtc agctgaccat caaggccgag 240
cgcaccgagc agaaggactt cgacggtcgc tcggaattcg cgtacggttc cttcgttcgc 300
acggtgtcgc tgccggtagg tgctgacgag gacgacatta aggccaccta cgacaagggc 360
attcttactg tgtcggtggc ggtttcggaa gggaagccaa ccgaaaagca cattcagatc 420
cggtccacca actga 435

<210> SEQ ID NO 33
<211> LENGTH: 7
<212> TYPE: PRT
<213> ORGANISM: Artificial
<220> FEATURE:
<223> OTHER INFORMATION: PK tag sequence

<400> SEQUENCE: 33

Pro Asn Pro Leu Gly Leu Asp
1 5

<210> SEQ ID NO 34
<211> LENGTH: 407
<212> TYPE: PRT
<213> ORGANISM: Mycobacterium tuberculosis

<400> SEQUENCE: 34

Met Ser Gly Arg His Arg Lys Pro Thr Thr Ser Asn Val Ser Val Ala
1 5 10 15

Lys Ile Ala Phe Thr Gly Ala Val Leu Gly Gly Gly Gly Ile Ala Met
20 25 30

Ala Ala Gln Ala Thr Ala Ala Thr Asp Gly Glu Trp Asp Gln Val Ala
35 40 45

Arg Cys Glu Ser Gly Gly Asn Trp Ser Ile Asn Thr Gly Asn Gly Tyr
50 55 60

Leu Gly Gly Leu Gln Phe Thr Gln Ser Thr Trp Ala Ala His Gly Gly
65 70 75 80

Gly Glu Phe Ala Pro Ser Ala Gln Leu Ala Ser Arg Glu Gln Gln Ile
85 90 95

Ala Val Gly Glu Arg Val Leu Ala Thr Gln Gly Arg Gly Ala Trp Pro
100 105 110

Val Cys Gly Arg Gly Leu Ser Asn Ala Thr Pro Arg Glu Val Leu Pro
115 120 125

```
Ala Ser Ala Ala Met Asp Ala Pro Leu Asp Ala Ala Ala Val Asn Gly
    130                 135                 140

Glu Pro Ala Pro Leu Ala Pro Pro Pro Ala Asp Pro Ala Pro Pro Val
145                 150                 155                 160

Glu Leu Ala Ala Asn Asp Leu Pro Ala Pro Leu Gly Glu Pro Leu Pro
                165                 170                 175

Ala Ala Pro Ala Asp Pro Ala Pro Pro Ala Asp Leu Ala Pro Pro Ala
            180                 185                 190

Pro Ala Asp Val Ala Pro Pro Val Glu Leu Ala Val Asn Asp Leu Pro
        195                 200                 205

Ala Pro Leu Gly Glu Pro Leu Pro Ala Ala Pro Ala Asp Pro Ala Pro
    210                 215                 220

Pro Ala Asp Leu Ala Pro Pro Ala Pro Ala Asp Leu Ala Pro Pro Ala
225                 230                 235                 240

Pro Ala Asp Leu Ala Pro Pro Ala Pro Ala Asp Leu Ala Pro Pro Val
                245                 250                 255

Glu Leu Ala Val Asn Asp Leu Pro Ala Pro Leu Gly Glu Pro Leu Pro
            260                 265                 270

Ala Ala Pro Ala Glu Leu Ala Pro Pro Ala Asp Leu Ala Pro Ala Ser
        275                 280                 285

Ala Asp Leu Ala Pro Pro Ala Pro Ala Asp Leu Ala Pro Pro Ala Pro
    290                 295                 300

Ala Glu Leu Ala Pro Pro Ala Pro Ala Asp Leu Ala Pro Pro Ala Ala
305                 310                 315                 320

Val Asn Glu Gln Thr Ala Pro Gly Asp Gln Pro Ala Thr Ala Pro Gly
                325                 330                 335

Gly Pro Val Gly Leu Ala Thr Asp Leu Glu Leu Pro Glu Pro Asp Pro
            340                 345                 350

Gln Pro Ala Asp Ala Pro Pro Pro Gly Asp Val Thr Glu Ala Pro Ala
        355                 360                 365

Glu Thr Pro Gln Val Ser Asn Ile Ala Tyr Thr Lys Lys Leu Trp Gln
    370                 375                 380

Ala Ile Arg Ala Gln Asp Val Cys Gly Asn Asp Ala Leu Asp Ser Leu
385                 390                 395                 400

Ala Gln Pro Tyr Val Ile Gly
                405


<210> SEQ ID NO 35
<211> LENGTH: 362
<212> TYPE: PRT
<213> ORGANISM: Mycobacterium tuberculosis

<400> SEQUENCE: 35

Met Leu Arg Leu Val Val Gly Ala Leu Leu Leu Val Leu Ala Phe Ala
1               5                   10                  15

Gly Gly Tyr Ala Val Ala Ala Cys Lys Thr Val Thr Leu Thr Val Asp
            20                  25                  30

Gly Thr Ala Met Arg Val Thr Thr Met Lys Ser Arg Val Ile Asp Ile
        35                  40                  45

Val Glu Glu Asn Gly Phe Ser Val Asp Asp Arg Asp Asp Leu Tyr Pro
    50                  55                  60

Ala Ala Gly Val Gln Val His Asp Ala Asp Thr Ile Val Leu Arg Arg
65                  70                  75                  80

Ser Arg Pro Leu Gln Ile Ser Leu Asp Gly His Asp Ala Lys Gln Val
                85                  90                  95
```

-continued

```
Trp Thr Thr Ala Ser Thr Val Asp Glu Ala Leu Ala Gln Leu Ala Met
            100                 105                 110

Thr Asp Thr Ala Pro Ala Ala Ala Ser Arg Ala Ser Arg Val Pro Leu
        115                 120                 125

Ser Gly Met Ala Leu Pro Val Val Ser Ala Lys Thr Val Gln Leu Asn
    130                 135                 140

Asp Gly Gly Leu Val Arg Thr Val His Leu Pro Ala Pro Asn Val Ala
145                 150                 155                 160

Gly Leu Leu Ser Ala Ala Gly Val Pro Leu Leu Gln Ser Asp His Val
                165                 170                 175

Val Pro Ala Ala Thr Ala Pro Ile Val Glu Gly Met Gln Ile Gln Val
            180                 185                 190

Thr Arg Asn Arg Ile Lys Lys Val Thr Glu Arg Leu Pro Leu Pro Pro
        195                 200                 205

Asn Ala Arg Arg Val Glu Asp Pro Glu Met Asn Met Ser Arg Glu Val
    210                 215                 220

Val Glu Asp Pro Gly Val Pro Gly Thr Gln Asp Val Thr Phe Ala Val
225                 230                 235                 240

Ala Glu Val Asn Gly Val Glu Thr Gly Arg Leu Pro Val Ala Asn Val
                245                 250                 255

Val Val Thr Pro Ala His Glu Ala Val Val Arg Val Gly Thr Lys Pro
            260                 265                 270

Gly Thr Glu Val Pro Pro Val Ile Asp Gly Ser Ile Trp Asp Ala Ile
        275                 280                 285

Ala Gly Cys Glu Ala Gly Gly Asn Trp Ala Ile Asn Thr Gly Asn Gly
    290                 295                 300

Tyr Tyr Gly Gly Val Gln Phe Asp Gln Gly Thr Trp Glu Ala Asn Gly
305                 310                 315                 320

Gly Leu Arg Tyr Ala Pro Arg Ala Asp Leu Ala Thr Arg Glu Glu Gln
                325                 330                 335

Ile Ala Val Ala Glu Val Thr Arg Leu Arg Gln Gly Trp Gly Ala Trp
            340                 345                 350

Pro Val Cys Ala Ala Arg Ala Gly Ala Arg
        355                 360


<210> SEQ ID NO 36
<211> LENGTH: 176
<212> TYPE: PRT
<213> ORGANISM: Mycobacterium tuberculosis

<400> SEQUENCE: 36

Val His Pro Leu Pro Ala Asp His Gly Arg Ser Arg Cys Asn Arg His
1               5                   10                  15

Pro Ile Ser Pro Leu Ser Leu Ile Gly Asn Ala Ser Ala Thr Ser Gly
            20                  25                  30

Asp Met Ser Ser Met Thr Arg Ile Ala Lys Pro Leu Ile Lys Ser Ala
        35                  40                  45

Met Ala Ala Gly Leu Val Thr Ala Ser Met Ser Leu Ser Thr Ala Val
    50                  55                  60

Ala His Ala Gly Pro Ser Pro Asn Trp Asp Ala Val Ala Gln Cys Glu
65                  70                  75                  80

Ser Gly Gly Asn Trp Ala Ala Asn Thr Gly Asn Gly Lys Tyr Gly Gly
                85                  90                  95

Leu Gln Phe Lys Pro Ala Thr Trp Ala Ala Phe Gly Gly Val Gly Asn
            100                 105                 110
```

-continued

```
Pro Ala Ala Ala Ser Arg Glu Gln Gln Ile Ala Val Ala Asn Arg Val
        115                 120                 125

Leu Ala Glu Gln Gly Leu Asp Ala Trp Pro Thr Cys Gly Ala Ala Ser
    130                 135                 140

Gly Leu Pro Ile Ala Leu Trp Ser Lys Pro Ala Gln Gly Ile Lys Gln
145                 150                 155                 160

Ile Ile Asn Glu Ile Ile Trp Ala Gly Ile Gln Ala Ser Ile Pro Arg
                165                 170                 175


<210> SEQ ID NO 37
<211> LENGTH: 154
<212> TYPE: PRT
<213> ORGANISM: Mycobacterium tuberculosis

<400> SEQUENCE: 37

Met Thr Pro Gly Leu Leu Thr Thr Ala Gly Ala Gly Arg Pro Arg Asp
1               5                   10                  15

Arg Cys Ala Arg Ile Val Cys Thr Val Phe Ile Glu Thr Ala Val Val
            20                  25                  30

Ala Thr Met Phe Val Ala Leu Leu Gly Leu Ser Thr Ile Ser Ser Lys
        35                  40                  45

Ala Asp Asp Ile Asp Trp Asp Ala Ile Ala Gln Cys Glu Ser Gly Gly
    50                  55                  60

Asn Trp Ala Ala Asn Thr Gly Asn Gly Leu Tyr Gly Gly Leu Gln Ile
65                  70                  75                  80

Ser Gln Ala Thr Trp Asp Ser Asn Gly Gly Val Gly Ser Pro Ala Ala
                85                  90                  95

Ala Ser Pro Gln Gln Gln Ile Glu Val Ala Asp Asn Ile Met Lys Thr
            100                 105                 110

Gln Gly Pro Gly Ala Trp Pro Lys Cys Ser Ser Cys Ser Gln Gly Asp
        115                 120                 125

Ala Pro Leu Gly Ser Leu Thr His Ile Leu Thr Phe Leu Ala Ala Glu
    130                 135                 140

Thr Gly Gly Cys Ser Gly Ser Arg Asp Asp
145                 150


<210> SEQ ID NO 38
<211> LENGTH: 172
<212> TYPE: PRT
<213> ORGANISM: Mycobacterium tuberculosis

<400> SEQUENCE: 38

Leu Lys Asn Ala Arg Thr Thr Leu Ile Ala Ala Ala Ile Ala Gly Thr
1               5                   10                  15

Leu Val Thr Thr Ser Pro Ala Gly Ile Ala Asn Ala Asp Asp Ala Gly
            20                  25                  30

Leu Asp Pro Asn Ala Ala Ala Gly Pro Asp Ala Val Gly Phe Asp Pro
        35                  40                  45

Asn Leu Pro Pro Ala Pro Asp Ala Ala Pro Val Asp Thr Pro Pro Ala
    50                  55                  60

Pro Glu Asp Ala Gly Phe Asp Pro Asn Leu Pro Pro Pro Leu Ala Pro
65                  70                  75                  80

Asp Phe Leu Ser Pro Pro Ala Glu Glu Ala Pro Pro Val Pro Val Ala
                85                  90                  95

Tyr Ser Val Asn Trp Asp Ala Ile Ala Gln Cys Glu Ser Gly Gly Asn
            100                 105                 110
```

```
Trp Ser Ile Asn Thr Gly Asn Gly Tyr Tyr Gly Gly Leu Arg Phe Thr
        115                 120                 125

Ala Gly Thr Trp Arg Ala Asn Gly Gly Ser Gly Ser Ala Ala Asn Ala
    130                 135                 140

Ser Arg Glu Glu Gln Ile Arg Val Ala Glu Asn Val Leu Arg Ser Gln
145                 150                 155                 160

Gly Ile Arg Ala Trp Pro Val Cys Gly Arg Arg Gly
                165                 170


<210> SEQ ID NO 39
<211> LENGTH: 210
<212> TYPE: PRT
<213> ORGANISM: Mycobacterium tuberculosis

<400> SEQUENCE: 39

Met Ile Ala Thr Thr Arg Asp Arg Glu Gly Ala Thr Met Ile Thr Phe
1               5                   10                  15

Arg Leu Arg Leu Pro Cys Arg Thr Ile Leu Arg Val Phe Ser Arg Asn
            20                  25                  30

Pro Leu Val Arg Gly Thr Asp Arg Leu Glu Ala Val Val Met Leu Leu
        35                  40                  45

Ala Val Thr Val Ser Leu Leu Thr Ile Pro Phe Ala Ala Ala Ala Gly
    50                  55                  60

Thr Ala Val Gln Asp Ser Arg Ser His Val Tyr Ala His Gln Ala Gln
65                  70                  75                  80

Thr Arg His Pro Ala Thr Ala Thr Val Ile Asp His Glu Gly Val Ile
                85                  90                  95

Asp Ser Asn Thr Thr Ala Thr Ser Ala Pro Pro Arg Thr Lys Ile Thr
            100                 105                 110

Val Pro Ala Arg Trp Val Val Asn Gly Ile Glu Arg Ser Gly Glu Val
        115                 120                 125

Asn Ala Lys Pro Gly Thr Lys Ser Gly Asp Arg Val Gly Ile Trp Val
    130                 135                 140

Asp Ser Ala Gly Gln Leu Val Asp Glu Pro Ala Pro Pro Ala Arg Ala
145                 150                 155                 160

Ile Ala Asp Ala Ala Leu Ala Ala Leu Gly Leu Trp Leu Ser Val Ala
                165                 170                 175

Ala Val Ala Gly Ala Leu Leu Ala Leu Thr Arg Ala Ile Leu Ile Arg
            180                 185                 190

Val Arg Asn Ala Ser Trp Gln His Asp Ile Asp Ser Leu Phe Cys Thr
        195                 200                 205

Gln Arg
    210


<210> SEQ ID NO 40
<211> LENGTH: 339
<212> TYPE: PRT
<213> ORGANISM: Mycobacterium tuberculosis

<400> SEQUENCE: 40

Met Thr Glu Pro Ala Ala Trp Asp Glu Gly Lys Pro Arg Ile Ile Thr
1               5                   10                  15

Leu Thr Met Asn Pro Ala Leu Asp Ile Thr Thr Ser Val Asp Val Val
            20                  25                  30

Arg Pro Thr Glu Lys Met Arg Cys Gly Ala Pro Arg Tyr Asp Pro Gly
        35                  40                  45
```

Gly Gly Gly Ile Asn Val Ala Arg Ile Val His Val Leu Gly Gly Cys
50 55 60

Ser Thr Ala Leu Phe Pro Ala Gly Gly Ser Thr Gly Ser Leu Leu Met
65 70 75 80

Ala Leu Leu Gly Asp Ala Gly Val Pro Phe Arg Val Ile Pro Ile Ala
85 90 95

Ala Ser Thr Arg Glu Ser Phe Thr Val Asn Glu Ser Arg Thr Ala Lys
100 105 110

Gln Tyr Arg Phe Val Leu Pro Gly Pro Ser Leu Thr Val Ala Glu Gln
115 120 125

Glu Gln Cys Leu Asp Glu Leu Arg Gly Ala Ala Ala Ser Ala Ala Phe
130 135 140

Val Val Ala Ser Gly Ser Leu Pro Pro Gly Val Ala Ala Asp Tyr Tyr
145 150 155 160

Gln Arg Val Ala Asp Ile Cys Arg Arg Ser Ser Thr Pro Leu Ile Leu
165 170 175

Asp Thr Ser Gly Gly Gly Leu Gln His Ile Ser Ser Gly Val Phe Leu
180 185 190

Leu Lys Ala Ser Val Arg Glu Leu Arg Glu Cys Val Gly Ser Glu Leu
195 200 205

Leu Thr Glu Pro Glu Gln Leu Ala Ala Ala His Glu Leu Ile Asp Arg
210 215 220

Gly Arg Ala Glu Val Val Val Val Ser Leu Gly Ser Gln Gly Ala Leu
225 230 235 240

Leu Ala Thr Arg His Ala Ser His Arg Phe Ser Ser Ile Pro Met Thr
245 250 255

Ala Val Ser Gly Val Gly Ala Gly Asp Ala Met Val Ala Ala Ile Thr
260 265 270

Val Gly Leu Ser Arg Gly Trp Ser Leu Ile Lys Ser Val Arg Leu Gly
275 280 285

Asn Ala Ala Gly Ala Ala Met Leu Leu Thr Pro Gly Thr Ala Ala Cys
290 295 300

Asn Arg Asp Asp Val Glu Arg Phe Phe Glu Leu Ala Ala Glu Pro Thr
305 310 315 320

Glu Val Gly Gln Asp Gln Tyr Val Trp His Pro Ile Val Asn Pro Glu
325 330 335

Ala Ser Pro

<210> SEQ ID NO 41
<211> LENGTH: 331
<212> TYPE: PRT
<213> ORGANISM: Mycobacterium tuberculosis

<400> SEQUENCE: 41

Met Pro Asp Thr Met Val Thr Thr Asp Val Ile Lys Ser Ala Val Gln
1 5 10 15

Leu Ala Cys Arg Ala Pro Ser Leu His Asn Ser Gln Pro Trp Arg Trp
20 25 30

Ile Ala Glu Asp His Thr Val Ala Leu Phe Leu Asp Lys Asp Arg Val
35 40 45

Leu Tyr Ala Thr Asp His Ser Gly Arg Glu Ala Leu Leu Gly Cys Gly
50 55 60

Ala Val Leu Asp His Phe Arg Val Ala Met Ala Ala Ala Gly Thr Thr
65 70 75 80

-continued

```
Ala Asn Val Glu Arg Phe Pro Asn Pro Asn Asp Pro Leu His Leu Ala
                85                  90                  95

Ser Ile Asp Phe Ser Pro Ala Asp Phe Val Thr Glu Gly His Arg Leu
            100                 105                 110

Arg Ala Asp Ala Ile Leu Leu Arg Arg Thr Asp Arg Leu Pro Phe Ala
        115                 120                 125

Glu Pro Pro Asp Trp Asp Leu Val Glu Ser Gln Leu Arg Thr Thr Val
    130                 135                 140

Thr Ala Asp Thr Val Arg Ile Asp Val Ile Ala Asp Asp Met Arg Pro
145                 150                 155                 160

Glu Leu Ala Ala Ala Ser Lys Leu Thr Glu Ser Leu Arg Leu Tyr Asp
                165                 170                 175

Ser Ser Tyr His Ala Glu Leu Phe Trp Trp Thr Gly Ala Phe Glu Thr
            180                 185                 190

Ser Glu Gly Ile Pro His Ser Ser Leu Val Ser Ala Ala Glu Ser Asp
        195                 200                 205

Arg Val Thr Phe Gly Arg Asp Phe Pro Val Val Ala Asn Thr Asp Arg
    210                 215                 220

Arg Pro Glu Phe Gly His Asp Arg Ser Lys Val Leu Val Leu Ser Thr
225                 230                 235                 240

Tyr Asp Asn Glu Arg Ala Ser Leu Leu Arg Cys Gly Glu Met Leu Ser
                245                 250                 255

Ala Val Leu Leu Asp Ala Thr Met Ala Gly Leu Ala Thr Cys Thr Leu
            260                 265                 270

Thr His Ile Thr Glu Leu His Ala Ser Arg Asp Leu Val Ala Ala Leu
        275                 280                 285

Ile Gly Gln Pro Ala Thr Pro Gln Ala Leu Val Arg Val Gly Leu Ala
    290                 295                 300

Pro Glu Met Glu Glu Pro Pro Pro Ala Thr Pro Arg Arg Pro Ile Asp
305                 310                 315                 320

Glu Val Phe His Val Arg Ala Lys Asp His Arg
                325                 330
```

<210> SEQ ID NO 42
<211> LENGTH: 143
<212> TYPE: PRT
<213> ORGANISM: Mycobacterium tuberculosis

<400> SEQUENCE: 42

```
Met Thr Thr Ala Arg Asp Ile Met Asn Ala Gly Val Thr Cys Val Gly
1               5                   10                  15

Glu His Glu Thr Leu Thr Ala Ala Ala Gln Tyr Met Arg Glu His Asp
            20                  25                  30

Ile Gly Ala Leu Pro Ile Cys Gly Asp Asp Asp Arg Leu His Gly Met
        35                  40                  45

Leu Thr Asp Arg Asp Ile Val Ile Lys Gly Leu Ala Ala Gly Leu Asp
    50                  55                  60

Pro Asn Thr Ala Thr Ala Gly Glu Leu Ala Arg Asp Ser Ile Tyr Tyr
65                  70                  75                  80

Val Asp Ala Asn Ala Ser Ile Gln Glu Met Leu Asn Val Met Glu Glu
                85                  90                  95

His Gln Val Arg Arg Val Pro Val Ile Ser Glu His Arg Leu Val Gly
            100                 105                 110
```

```
Ile Val Thr Glu Ala Asp Ile Ala Arg His Leu Pro Glu His Ala Ile
        115                 120                 125

Val Gln Phe Val Lys Ala Ile Cys Ser Pro Met Ala Leu Ala Ser
    130                 135                 140


<210> SEQ ID NO 43
<211> LENGTH: 413
<212> TYPE: PRT
<213> ORGANISM: Mycobacterium tuberculosis

<400> SEQUENCE: 43

Met Ala Ser Ser Ala Ser Asp Gly Thr His Glu Arg Ser Ala Phe Arg
1               5                   10                  15

Leu Ser Pro Pro Val Leu Ser Gly Ala Met Gly Pro Phe Met His Thr
            20                  25                  30

Gly Leu Tyr Val Ala Gln Ser Trp Arg Asp Tyr Leu Gly Gln Gln Pro
        35                  40                  45

Asp Lys Leu Pro Ile Ala Arg Pro Thr Ile Ala Leu Ala Ala Gln Ala
    50                  55                  60

Phe Arg Asp Glu Ile Val Leu Leu Gly Leu Lys Ala Arg Arg Pro Val
65                  70                  75                  80

Ser Asn His Arg Val Phe Glu Arg Ile Ser Gln Glu Val Ala Ala Gly
                85                  90                  95

Leu Glu Phe Tyr Gly Asn Arg Arg Trp Leu Glu Lys Pro Ser Gly Phe
            100                 105                 110

Phe Ala Gln Pro Pro Pro Leu Thr Glu Val Ala Val Arg Lys Val Lys
        115                 120                 125

Asp Arg Arg Arg Ser Phe Tyr Arg Ile Phe Phe Asp Ser Gly Phe Thr
    130                 135                 140

Pro His Pro Gly Glu Pro Gly Ser Gln Arg Trp Leu Ser Tyr Thr Ala
145                 150                 155                 160

Asn Asn Arg Glu Tyr Ala Leu Leu Leu Arg His Pro Glu Pro Arg Pro
                165                 170                 175

Trp Leu Val Cys Val His Gly Thr Glu Met Gly Arg Ala Pro Leu Asp
            180                 185                 190

Leu Ala Val Phe Arg Ala Trp Lys Leu His Asp Glu Leu Gly Leu Asn
        195                 200                 205

Ile Val Met Pro Val Leu Pro Met His Gly Pro Arg Gly Gln Gly Leu
    210                 215                 220

Pro Lys Gly Ala Val Phe Pro Gly Glu Asp Val Leu Asp Asp Val His
225                 230                 235                 240

Gly Thr Ala Gln Ala Val Trp Asp Ile Arg Arg Leu Leu Ser Trp Ile
                245                 250                 255

Arg Ser Gln Glu Glu Glu Ser Leu Ile Gly Leu Asn Gly Leu Ser Leu
            260                 265                 270

Gly Gly Tyr Ile Ala Ser Leu Val Ala Ser Leu Glu Glu Gly Leu Ala
        275                 280                 285

Cys Ala Ile Leu Gly Val Pro Val Ala Asp Leu Ile Glu Leu Leu Gly
    290                 295                 300

Arg His Cys Gly Leu Arg His Lys Asp Pro Arg Arg His Thr Val Lys
305                 310                 315                 320

Met Ala Glu Pro Ile Gly Arg Met Ile Ser Pro Leu Ser Leu Thr Pro
                325                 330                 335

Leu Val Pro Met Pro Gly Arg Phe Ile Tyr Ala Gly Ile Ala Asp Arg
            340                 345                 350
```

-continued

Leu Val His Pro Arg Glu Gln Val Thr Arg Leu Trp Glu His Trp Gly
        355                 360                 365

Lys Pro Glu Ile Val Trp Tyr Pro Gly Gly His Thr Gly Phe Phe Gln
    370                 375                 380

Ser Arg Pro Val Arg Arg Phe Val Gln Ala Ala Leu Glu Gln Ser Gly
385                 390                 395                 400

Leu Leu Asp Ala Pro Arg Thr Gln Arg Asp Arg Ser Ala
                405                 410

<210> SEQ ID NO 44
<211> LENGTH: 120
<212> TYPE: PRT
<213> ORGANISM: Mycobacterium tuberculosis

<400> SEQUENCE: 44

Met Ser Thr Gln Arg Pro Arg His Ser Gly Ile Arg Ala Val Gly Pro
1               5                   10                  15

Tyr Ala Trp Ala Gly Arg Cys Gly Arg Ile Gly Arg Trp Gly Val His
            20                  25                  30

Gln Glu Ala Met Met Asn Leu Ala Ile Trp His Pro Arg Lys Val Gln
        35                  40                  45

Ser Ala Thr Ile Tyr Gln Val Thr Asp Arg Ser His Asp Gly Arg Thr
    50                  55                  60

Ala Arg Val Pro Gly Asp Glu Ile Thr Ser Thr Val Ser Gly Trp Leu
65                  70                  75                  80

Ser Glu Leu Gly Thr Gln Ser Pro Leu Ala Asp Glu Leu Ala Arg Ala
                85                  90                  95

Val Arg Ile Gly Asp Trp Pro Ala Ala Tyr Ala Ile Gly Glu His Leu
            100                 105                 110

Ser Val Glu Ile Ala Val Ala Val
        115                 120

<210> SEQ ID NO 45
<211> LENGTH: 1224
<212> TYPE: DNA
<213> ORGANISM: Mycobacterium tuberculosis

<400> SEQUENCE: 45
atgagtggac gccaccgtaa gcccaccaca tccaacgtca gcgtcgccaa gatcgccttt 60
accggcgcag tactcggtgg cggcggcatc gccatggccg ctcaggcgac cgcggccacc 120
gacggggaat gggatcaggt ggcccgctgc gagtcgggcg gcaactggtc gatcaacacc 180
ggcaacggtt acctcggtgg cttgcagttc actcaaagca cctgggccgc acatggtggc 240
ggcgagttcg ccccgtcggc tcagctggcc agccgggagc agcagattgc cgtcggtgag 300
cgggtgctgg ccacccaggg tcgcggcgcc tggccggtgt gcggccgcgg gttatcgaac 360
gcaacacccc gcgaagtgct tcccgcttcg gcagcgatgg acgctccgtt ggacgcggcc 420
gcggtcaacg gcgaaccagc accgctggcc ccgccgcccg ccgacccggc gccacccgtg 480
gaacttgccg ctaacgacct gcccgcaccg ctgggtgaac ccctcccggc agctcccgcc 540
gacccggcac cacccgccga cctggcacca cccgcgcccg ccgacgtcgc gccacccgtg 600
gaacttgccg taaacgacct gcccgcaccg ctgggtgaac ccctcccggc agctcccgcc 660
gacccggcac cacccgccga cctggcacca cccgcgcccg ccgacctggc gccacccgcg 720
cccgccgacc tggcgccacc cgcgcccgcc gacctggcac cacccgtgga acttgccgta 780
aacgacctgc ccgcgccgct gggtgaaccc ctcccggcag ctcccgccga actggcgcca 840

```
cccgccgatc tggcacccgc gtccgccgac ctggcgccac ccgcgcccgc cgacctggcg    900
ccacccgcgc ccgccgaact ggcgccaccc gcgcccgccg acctggcacc acccgctgcg    960
gtgaacgagc aaaccgcgcc gggcgatcag cccgccacag ctccaggcgg cccggttggc   1020
cttgccaccg atttggaact ccccgagccc gacccccaac cagctgacgc accgccgccc   1080
ggcgacgtca ccgaggcgcc cgccgaaacg ccccaagtct cgaacatcgc ctatacgaag   1140
aagctgtggc aggcgattcg ggcccaggac gtctgcggca acgatgcgct ggactcgctc   1200
gcacagccgt acgtcatcgg ctga                                          1224
```

<210> SEQ ID NO 46
<211> LENGTH: 1089
<212> TYPE: DNA
<213> ORGANISM: Mycobacterium tuberculosis

<400> SEQUENCE: 46

```
atgttgcgcc tggtagtcgg tgcgctgctg ctggtgttgg cgttcgccgg tggctatgcg     60
gtcgccgcat gcaaaacggt gacgttgacc gtcgacggaa ccgcgatgcg ggtgaccacg    120
atgaaatcgc gggtgatcga catcgtcgaa gagaacgggt tctcagtcga cgaccgcgac    180
gacctgtatc ccgcggccgg cgtgcaggtc catgacgccg acaccatcgt gctgcggcgt    240
agccgtccgc tgcagatctc gctggatggt cacgacgcta agcaggtgtg gacgaccgcg    300
tcgacggtgg acgaggcgct ggcccaactc gcgatgaccg acacggcgcc ggccgcggct    360
tctcgcgcca gccgcgtccc gctgtccggg atggcgctac cggtcgtcag cgccaagacg    420
gtgcagctca acgacggcgg gttggtgcgc acggtgcact tgccggcccc caatgtcgcg    480
gggctgctga gtgcggccgg cgtgccgctg ttgcaaagcg accacgtggt gcccgccgcg    540
acggccccga tcgtcgaagg catgcagatc caggtgaccc gcaatcggat caagaaggtc    600
accgagcggc tgccgctgcc gccgaacgcg cgtcgtgtcg aggacccgga gatgaacatg    660
agccgggagg tcgtcgaaga cccgggggtt ccggggaccc aggatgtgac gttcgcggta    720
gctgaggtca acggcgtcga gaccggccgt ttgcccgtcg ccaacgtcgt ggtgaccccg    780
gcccacgaag ccgtggtgcg ggtgggcacc aagcccggta ccgaggtgcc cccggtgatc    840
gacggaagca tctgggacgc gatcgccggc tgtgaggccg gtggcaactg ggcgatcaac    900
accggcaacg ggtattacgg tggtgtgcag tttgaccagg gcacctggga ggccaacggc    960
gggctgcggt atgcaccccg cgctgacctc gccacccgcg aagagcagat cgccgttgcc   1020
gaggtgaccc gactgcgtca aggttggggc gcctggccgg tatgtgctgc acgagcgggt   1080
gcgcgctga                                                           1089
```

<210> SEQ ID NO 47
<211> LENGTH: 531
<212> TYPE: DNA
<213> ORGANISM: Mycobacterium tuberculosis

<400> SEQUENCE: 47

```
gtgcatcctt tgccggccga ccacggccgg tcgcggtgca atagacaccc gatctcacca     60
ctctctctaa tcggtaacgc ttcggccact tccggcgata tgtcgagcat gacaagaatc    120
gccaagccgc tcatcaagtc cgccatggcc gcaggactcg tcacggcatc catgtcgctc    180
tccaccgccg ttgcccacgc cggtcccagc ccgaactggg acgccgtcgc gcagtgcgaa    240
tccgggggca actgggcggc caacaccgga aacggcaaat acggcggact gcagttcaag    300
ccggccacct gggccgcatt cggcggtgtc ggcaacccag cagctgcctc tcgggaacaa    360
```

caaatcgcag ttgccaatcg ggttctcgcc gaacagggat tggacgcgtg gccgacgtgc 420
ggcgccgcct ctggccttcc gatcgcactg tggtcgaaac ccgcgcaggg catcaagcaa 480
atcatcaacg agatcatttg ggcaggcatt caggcaagta ttccgcgctg a 531

<210> SEQ ID NO 48
<211> LENGTH: 465
<212> TYPE: DNA
<213> ORGANISM: Mycobacterium tuberculosis

<400> SEQUENCE: 48
atgacaccgg gtttgcttac tactgcgggt gctggccgac cacgtgacag gtgcgccagg 60
atcgtatgca cggtgttcat cgaaaccgcc gttgtcgcga ccatgtttgt cgcgttgttg 120
ggtctgtcca ccatcagctc gaaagccgac gacatcgatt gggacgccat cgcgcaatgc 180
gaatccggcg gcaattgggc ggccaacacc ggtaacgggt tatacggtgg tctgcagatc 240
agccaggcga cgtgggattc caacggtggt gtcgggtcgc cggcggccgc gagtccccag 300
caacagatcg aggtcgcaga caacattatg aaaacccaag gcccgggtgc gtggccgaaa 360
tgtagttctt gtagtcaggg agacgcaccg ctgggctcgc tcacccacat cctgacgttc 420
ctcgcggccg agactggagg ttgttcgggg agcagggacg attga 465

<210> SEQ ID NO 49
<211> LENGTH: 519
<212> TYPE: DNA
<213> ORGANISM: Mycobacterium tuberculosis

<400> SEQUENCE: 49
ttgaagaacg cccgtacgac gctcatcgcc gccgcgattg ccgggacgtt ggtgaccacg 60
tcaccagccg gtatcgccaa tgccgacgac gcgggcttgg acccaaacgc cgcagccggc 120
ccggatgccg tgggctttga cccgaacctg ccgccggccc cggacgctgc acccgtcgat 180
actccgccgg ctccggagga cgcgggcttt gatcccaacc tccccccgcc gctggccccg 240
gacttcctgt ccccgcctgc ggaggaagcg cctcccgtgc ccgtggccta cagcgtgaac 300
tgggacgcga tcgcgcagtg cgagtccggt ggaaactggt cgatcaacac cggtaacggt 360
tactacggcg gcctgcggtt caccgccggc acctggcgtg ccaacggtgg ctcggggtcc 420
gcggccaacg cgagccggga ggagcagatc cgggtggctg agaacgtgct gcgttcgcag 480
ggtatccgcg cctggccggt ctgcggccgc cgcggctga 519

<210> SEQ ID NO 50
<211> LENGTH: 633
<212> TYPE: DNA
<213> ORGANISM: Mycobacterium tuberculosis

<400> SEQUENCE: 50
atgatcgcca caacccgcga tcgtgaagga gccaccatga tcacgtttag gctgcgcttg 60
ccgtgccgga cgatactgcg ggtgttcagc cgcaatccgc tggtgcgtgg gacggatcga 120
ctcgaggcgg tcgtcatgct gctggccgtc acggtctcgc tgctgactat cccgttcgcc 180
gccgcggccg gcaccgcagt ccaggattcc cgcagccacg tctatgccca ccaggcccag 240
acccgccatc ccgcaaccgc gaccgtgatc gatcacgagg gggtgatcga cagcaacacg 300
accgccacgt cagcgccgcc gcgcacgaag atcaccgtgc ctgcccgatg ggtcgtgaac 360
ggaatagaac gcagcggtga ggtcaacgcg aagccgggaa ccaaatccgg tgaccgcgtc 420
ggcatttggg tcgacagtgc cggtcagctg gtcgatgaac cagctccgcc ggcccgtgcc 480
attgcggatg cggccctggc cgccttggga ctctggttga gcgtcgccgc ggttgcgggc 540
gccctgctgg cgctcactcg ggcgattctg atccgcgttc gcaacgccag ttggcaacac 600
gacatcgaca gcctgttctg cacgcagcgg tga 633

<210> SEQ ID NO 51
<211> LENGTH: 1020
<212> TYPE: DNA
<213> ORGANISM: Mycobacterium tuberculosis

<400> SEQUENCE: 51
atgacggagc cagcggcgtg ggacgaaggc aagccgcgaa tcatcacttt gaccatgaac 60
cccgccttgg acatcacgac gagcgtcgac gtggtgcgcc cgaccgagaa aatgcgttgt 120
ggcgcacctc gctacgatcc cggcggcggc ggtatcaatg tcgcccgcat tgtgcatgtc 180
ctcggcggtt gctcgacagc actgttcccg gccggcgggt cgaccgggag cctgctgatg 240
gcgctgctcg gtgatgcggg agtgccattt cgcgtcattc cgatcgcggc ctcgacgcgg 300
gagagcttca cggtcaacga gtccaggacc gccaagcagt atcgtttcgt gcttccgggg 360
ccgtcgctga ccgtcgcgga gcaggagcaa tgcctcgacg aactgcgcgg tgcggcggct 420
tcggccgcct ttgtggtggc cagtggcagc ctgccgccag gtgtggctgc cgactactat 480
cagcgggttg ccgacatctg ccgccgatcg agcactccgc tgatcctgga tacatctggt 540
ggcgggttgc agcacatttc gtccggggtg tttcttctca aggcgagcgt gcgggaactg 600
cgcgagtgcg tcggatccga actgctgacc gagcccgaac aactggccgc cgcacacgaa 660
ctcattgacc gtgggcgcgc cgaggtcgtg gtggtctcgc ttggatctca gggcgcgcta 720
ttggccacac gacatgcgag ccatcgattt tcgtcgattc cgatgaccgc ggttagcggt 780
gtcggcgccg gcgacgcgat ggtggccgcg attaccgtgg gcctcagccg tggctggtcg 840
ctcatcaagt ccgttcgctt gggaaacgcg gcaggtgcag ccatgctgct gacgccaggc 900
accgcggcct gcaatcgcga cgatgtggag aggttcttcg agctggcggc cgaacccacc 960
gaagtcgggc aggatcaata cgtttggcac ccgatcgtta acccggaagc ctcgccatga 1020

<210> SEQ ID NO 52
<211> LENGTH: 996
<212> TYPE: DNA
<213> ORGANISM: Mycobacterium tuberculosis

<400> SEQUENCE: 52
atgccggaca ccatggtgac caccgatgtc atcaagagcg cggtgcagtt ggcctgccgc 60
gcaccgtcgc tccacaacag ccagccctgg cgctggatag ccgaggacca cacggttgcg 120
ctgttcctcg acaaggatcg ggtgctttac gcgaccgacc actccggccg ggaagcgctg 180
ctggggtgcg gcgccgtact cgaccacttt cgggtggcga tggcggccgc gggtaccacc 240
gccaatgtgg aacggtttcc caaccccaac gatcctttgc atctggcgtc aattgacttc 300
agcccggccg atttcgtcac cgagggccac cgtctaaggg cggatgcgat cctactgcgc 360
cgtaccgacc ggctgccttt cgccgagccg ccggattggg acttggtgga gtcgcagttg 420
cgcacgaccg tcaccgccga cacggtgcgc atcgacgtca tcgccgacga tatgcgtccc 480
gaactggcgg cggcgtccaa actcaccgaa tcgctgcggc tctacgattc gtcgtatcat 540
gccgaactct tttggtggac aggggctttt gagacttctg agggcatacc gcacagttca 600
ttggtatcgg cggccgaaag tgaccgggtc accttcggac gcgacttccc ggtcgtcgcc 660
aacaccgata ggcgcccgga gtttggccac gaccgctcta aggtcctggt gctctccacc 720

```
tacgacaacg aacgcgccag cctactgcgc tgcggcgaga tgctttccgc cgtattgctt    780

gacgccacca tggctgggct tgccacctgc acgctgaccc acatcaccga actgcacgcc    840

agccgagacc tggtcgcagc gctgattggg cagcccgcaa ctccgcaagc cttggttcgc    900

gtcggtctgg ccccggagat ggaagagccg ccaccggcaa cgcctcggcg accaatcgat    960

gaagtgtttc acgttcgggc taaggatcac cggtag                              996
```

```
<210> SEQ ID NO 53
<211> LENGTH: 432
<212> TYPE: DNA
<213> ORGANISM: Mycobacterium tuberculosis

<400> SEQUENCE: 53

atgaccaccg cacgcgacat catgaacgca ggtgtgacct gtgttggcga acacgagacg     60

ctaaccgctg ccgctcaata catgcgtgag cacgacatcg gcgcgttgcc gatctgcggg    120

gacgacgacc ggctgcacgg catgctcacc gaccgcgaca ttgtgatcaa aggcctggct    180

gcgggcctag acccgaatac cgccacggct ggcgagttgg cccgggacag catctactac    240

gtcgatgcga acgcaagcat ccaggagatg ctcaacgtca tggaagaaca tcaggtccgc    300

cgtgttccgg tcatctcaga gcaccgcttg gtcggaatcg tcaccgaagc cgacatcgcc    360

cgacacctgc ccgagcacgc cattgtgcag ttcgtcaagg caatctgctc gcccatggcc    420

ctcgccagct ag                                                        432
```

```
<210> SEQ ID NO 54
<211> LENGTH: 1242
<212> TYPE: DNA
<213> ORGANISM: Mycobacterium tuberculosis

<400> SEQUENCE: 54

atggcaagtt ctgcgagcga cggcacccac gaacgctcgg cttttcgcct gagtccaccg     60

gtcttgagcg gcgccatggg accgttcatg cacaccggtc tgtacgtcgc tcaatcgtgg    120

cgcgactatc tgggtcaaca gcccgataaa ctgccgatcg cacggcccac tattgcctta    180

gcggcgcaag cctttcgaga cgaaatcgtc ctgctgggcc tcaaggcacg acgtccggtc    240

agcaatcatc gagtgttcga gcgcatcagc caagaagtgg ccgctggact ggagttctat    300

gggaatcgca gatggctgga gaagcctagc ggatttttttg cccagccccc accgctcacc    360

gaggtcgcgg tccgaaaggt caaggaccgc agacgctcct tttatcgcat cttcttcgac    420

agtgggttta cgccgcatcc gggtgaaccg ggcagccaac ggtggctctc atacactgcg    480

aacaatcgcg agtacgccct gttactgcgg cacccagagc cgcgtccctg gctggtttgt    540

gtacacggca ccgagatggg caggggcccg ttggatctcg cggtgttccg cgcctggaag    600

ctgcatgacg aactcggcct gaacattgtc atgccggttc ttccgatgca tggtccccgc    660

gggcaaggtc tgccgaaggg cgccgttttt cccggagaag atgttctcga cgatgtgcat    720

gggacggctc aagcggtgtg ggatatccgg cggctgttgt cctggatacg atcgcaggag    780

gaggagtcgc tgatcgggtt gaacggtctc tcgctgggcg gctacatcgc gtcattggtc    840

gccagcctcg aagaaggtct cgcctgcgcg attctcggtg tcccagtggc tgatctgatc    900

gagttgttgg gccgccactg cggtcttcgg cacaaagacc cccgccgcca caccgtcaag    960

atggccgaac cgatcggccg aatgatctcg ccgctctcac ttacgccact ggtgcccatg   1020

ccgggccgct ttatctacgc gggcattgcc gaccgactcg tgcatccacg cgaacaggtg   1080

actcgcctct gggagcactg gggcaaaccc gaaatcgtgt ggtatccagg cggtcacact   1140
```

```
ggcttcttcc agtcgcggcc ggtacgacgg tttgtccagg ctgcgctgga gcagtcgggc   1200

ctgttggacg cgccacggac acagcgcgac cgttccgcct aa                       1242


<210> SEQ ID NO 55
<211> LENGTH: 363
<212> TYPE: DNA
<213> ORGANISM: Mycobacterium tuberculosis

<400> SEQUENCE: 55

atgtccacgc aacgaccgag gcactccggt attcgggctg ttggccccta cgcatgggcc     60

ggccgatgtg gtcggatagg caggtggggg gtgcaccagg aggcgatgat gaatctagcg    120

atatggcacc cgcgcaaggt gcaatccgcc accatctatc aggtgaccga tcgctcgcac    180

gacgggcgca cagcacgggt gcctggtgac gagatcacta gcaccgtgtc cggttggttg    240

tcggagttgg gcacccaaag cccgttggcc gatgagcttg cgcgtgcggt gcggatcggc    300

gactggcccg ctgcgtacgc aatcggtgag cacctgtccg ttgagattgc cgttgcggtc    360

taa                                                                  363


<210> SEQ ID NO 56
<211> LENGTH: 399
<212> TYPE: PRT
<213> ORGANISM: Mycobacterium tuberculosis

<400> SEQUENCE: 56

Leu Asp Phe Ala Thr Leu Pro Pro Glu Ile Asn Ser Ala Arg Met Tyr
1               5                   10                  15

Ser Gly Ala Gly Ser Ala Pro Met Leu Ala Ala Ala Ser Ala Trp His
            20                  25                  30

Gly Leu Ser Ala Glu Leu Arg Ala Ser Ala Leu Ser Tyr Ser Ser Val
        35                  40                  45

Leu Ser Thr Leu Thr Gly Glu Glu Trp His Gly Pro Ala Ser Ala Ser
    50                  55                  60

Met Thr Ala Ala Ala Ala Pro Tyr Val Ala Trp Met Ser Val Thr Ala
65                  70                  75                  80

Val Arg Ala Glu Gln Ala Gly Ala Gln Ala Glu Ala Ala Ala Ala Ala
                85                  90                  95

Tyr Glu Ala Ala Phe Ala Ala Thr Val Pro Pro Pro Val Ile Glu Ala
            100                 105                 110

Asn Arg Ala Gln Leu Met Ala Leu Ile Ala Thr Asn Val Leu Gly Gln
        115                 120                 125

Asn Ala Pro Ala Ile Ala Ala Thr Glu Ala Gln Tyr Ala Glu Met Trp
    130                 135                 140

Ser Gln Asp Ala Met Ala Met Tyr Gly Tyr Ala Gly Ala Ser Ala Ala
145                 150                 155                 160

Ala Thr Gln Leu Thr Pro Phe Thr Glu Pro Val Gln Thr Thr Asn Ala
                165                 170                 175

Ser Gly Leu Ala Ala Gln Ser Ala Ala Ile Ala His Ala Thr Gly Ala
            180                 185                 190

Ser Ala Gly Ala Gln Gln Thr Thr Leu Ser Gln Leu Ile Ala Ala Ile
        195                 200                 205

Pro Ser Val Leu Gln Gly Leu Ser Ser Ser Thr Ala Ala Thr Phe Ala
    210                 215                 220

Ser Gly Pro Ser Gly Leu Leu Gly Ile Val Gly Ser Gly Ser Ser Trp
225                 230                 235                 240
```

```
Leu Asp Lys Leu Trp Ala Leu Leu Asp Pro Asn Ser Asn Phe Trp Asn
                245                 250                 255

Thr Ile Ala Ser Ser Gly Leu Phe Leu Pro Ser Asn Thr Ile Ala Pro
            260                 265                 270

Phe Leu Gly Leu Leu Gly Gly Val Ala Ala Ala Asp Ala Ala Gly Asp
        275                 280                 285

Val Leu Gly Glu Ala Thr Ser Gly Gly Leu Gly Gly Ala Leu Val Ala
    290                 295                 300

Pro Leu Gly Ser Ala Gly Gly Leu Gly Gly Thr Val Ala Ala Gly Leu
305                 310                 315                 320

Gly Asn Ala Ala Thr Val Gly Thr Leu Ser Val Pro Pro Ser Trp Thr
                325                 330                 335

Ala Ala Ala Pro Leu Ala Ser Pro Leu Gly Ser Ala Leu Gly Gly Thr
            340                 345                 350

Pro Met Val Ala Pro Pro Pro Ala Val Ala Ala Gly Met Pro Gly Met
        355                 360                 365

Pro Phe Gly Thr Met Gly Gly Gln Gly Phe Gly Arg Ala Val Pro Gln
    370                 375                 380

Tyr Gly Phe Arg Pro Asn Phe Val Ala Arg Pro Pro Ala Ala Gly
385                 390                 395


<210> SEQ ID NO 57
<211> LENGTH: 1197
<212> TYPE: DNA
<213> ORGANISM: Mycobacterium tuberculosis

<400> SEQUENCE: 57

cttgacttcg ccacgctacc gcccgaaatc aactcggcgc gtatgtattc cggcgcgggc     60

tcggccccga tgctggccgc agcgtcagcc tggcacggct tgtccgcaga actgcgcgcc    120

agcgcactgt catacagctc ggtgctttcg acgctgaccg gtgaagaatg gcacggtccg    180

gcgtcggcat cgatgacagc cgcggccgcc ccctacgtgg cctggatgag cgtcaccgcc    240

gtccgggccg agcaggccgg ggcacaggcg gaggctgccg ctgcagcgta cgaagccgcg    300

ttcgcagcaa cggtgccccc gccggtcatc gaggccaacc gcgcccagct catggcgctg    360

atcgccacca atgtgctagg ccaaaacgcc cccgcgatcg cggccaccga ggcccagtac    420

gccgaaatgt ggtcccagga cgcgatggcc atgtacggct acgccggcgc ctcggcagcc    480

gctacccagc tgaccccgtt caccgagccg gtgcagacta ccaacgcgtc cggcctggcg    540

gcccagtcgg ctgcgattgc ccacgccacc ggcgcctcgg ctggtgctca gcaaacgacg    600

ctgtcgcagc tgatcgccgc cataccgtct gtactgcaag gactttcgtc atcgactgca    660

gccacgttcg cgtcggggcc gtccggattg ctgggcattg tcgggtctgg atcttcctgg    720

ctcgacaaac tctgggcgtt actggacccc aactccaatt tctggaacac gatagcttcg    780

tccggactgt tcttgccgag taacacgatt gcgccctttt tgggtctact cggcggcgtg    840

gcagctgcgg atgcggccgg ggatgtgttg ggagaggcca ccagtggcgg gctcggtggc    900

gcgctggtgg cgccgcttgg ctcagcgggc gggctaggcg gcactgtcgc ggccggcctg    960

ggcaacgcgg ccaccgtcgg aaccttgtcg gtgccgccga gctggacggc ggccgcacca   1020

ctagccagcc ccttgggctc cgcgttggga ggcacaccga tggtggcacc gcccccagca   1080

gtggcggccg gcatgcccgg aatgcctttc ggcaccatgg gcggtcaagg cttcgggcgt   1140

gccgtgcccc agtatggctt ccgccccaac ttcgtcgcac gaccgcccgc cgccggg      1197
```

-continued

```
<210> SEQ ID NO 58
<211> LENGTH: 10
<212> TYPE: DNA
<213> ORGANISM: Artificial sequence
<220> FEATURE:
<223> OTHER INFORMATION: optimized Kozak sequence

<400> SEQUENCE: 58

gccaccatgg                                                     10
```